United States Patent
Natarajan et al.

(10) Patent No.: US 11,974,990 B2
(45) Date of Patent: *May 7, 2024

(54) TXNIP-TRX COMPLEX INHIBITORS AND METHODS OF USING THE SAME

(71) Applicant: City of Hope, Duarte, CA (US)

(72) Inventors: Rama Natarajan, Hacienda Heights, CA (US); Feng Miao, Alhambra, CA (US); Nagarajan Vaidehi, Arcadia, CA (US); Supriyo Bhattacharya, Monrovia, CA (US); Adrien Beau Larsen, Duarte, CA (US)

(73) Assignee: City of Hope, Duarte, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/714,569

(22) Filed: Apr. 6, 2022

(65) Prior Publication Data

US 2022/0313666 A1    Oct. 6, 2022

Related U.S. Application Data

(63) Continuation of application No. 16/570,802, filed on Sep. 13, 2019, now Pat. No. 11,324,731.

(60) Provisional application No. 62/730,988, filed on Sep. 13, 2018.

(51) Int. Cl.
| | |
|---|---|
| *A61K 31/437* | (2006.01) |
| *A61K 31/4035* | (2006.01) |
| *A61K 31/4439* | (2006.01) |
| *A61K 31/496* | (2006.01) |
| *A61K 31/5377* | (2006.01) |
| *A61P 3/10* | (2006.01) |

(52) U.S. Cl.
CPC ........ *A61K 31/437* (2013.01); *A61K 31/4035* (2013.01); *A61K 31/4439* (2013.01); *A61K 31/496* (2013.01); *A61K 31/5377* (2013.01); *A61P 3/10* (2018.01)

(58) Field of Classification Search
CPC .............. A61K 31/437; A61K 31/4035; A61K 31/4439; A61K 31/496; A61K 31/5377; A61P 3/10
See application file for complete search history.

(56) References Cited

U.S. PATENT DOCUMENTS

| | | |
|---|---|---|
| 7,973,057 B2 | 7/2011 | Greig et al. |
| 11,324,731 B2 | 5/2022 | Natarajan |
| 2013/0203811 A1 | 8/2013 | Prendergast |

FOREIGN PATENT DOCUMENTS

| | | |
|---|---|---|
| WO | WO-2007/102679 A1 | 9/2007 |
| WO | WO-2017/059062 A1 | 4/2017 |

OTHER PUBLICATIONS

Kurts et al. Nature Reviews Immunol. 2013, 13, 738-753.*
Van der Wijst et al. Physiol. Rev. 2019, 99, 1575-1653.*
Alhawiti, N.M. et al. (2017). "TXNIP in Metabolic Regulation: Physiological Role and Therapeutic Outlook," *Current Drug Targets* 18(9):1095-1103.
Bell, J.A. et al. (2012). "PrimeX and the Schrödinger computational chemistry suite of programs," vol. F, Chapter 18.10 in *International Tables for Crystallography*, pp. 534-538.
Bhattacharya, S. et al. (Jul. 15, 2014). "Differences in Allosteric Communication Pipelines in the Inactive and Active States of a GPCR," *Biophys J* 107(2):422-434.
Bhattacharya, S. et al. (Nov. 8, 2016). "Conserved Mechanism of Conformational Stability and Dynamics in G-Protein-Coupled Receptors," *J Chem Theory Comput* 12(11):5575-5584.
Chen, Z. et al. (May 24, 2016). "Epigenomic profiling reveals an association between persistence of DNA methylation and metabolic memory in the DCCT/EDIC type 1 diabetes cohort," *PNAS USA* 113(21): E3002-3011.
Chen Z. et al. (Aug. 2020). "DNA methylation mediates development of HbA1c-associated complications in type 1 diabetes," *Nature Metabolism* 2(8):744-762.
Chong, C.R. et al. (Aug. 2014). "Thioredoxin-interacting protein: pathophysiology and emerging pharmacotherapeutics in cardiovascular disease and diabetes," *Cardiovascular Drugs and Therapy* 28(4):347-360.
Halgren, T.A. et al. (Mar. 25, 2004). "Glide: a new approach for rapid, accurate docking and scoring. 2. Enrichment factors in database screening," *J Med Chem* 47(7):1750-1759.
Hwang, J. et al. (2014). The structural basis for the negative regulation of thioredoxin by thioredoxin-interacting protein. *Nat Commun* 5:2958.
Li, H. et al. (May 27, 2014). "Computational method to identify druggable binding sites that target protein-protein interactions," *J Chem Inf Model* 54(5):1391-1400.
Li, T. et al. (Jul. 2017). "W2476 ameliorates β-cell dysfunction and exerts therapeutic effects in mouse models of diabetes via modulation of the thioredoxin-interacting protein signaling pathway," *Acta Pharmacol Sin* 38(7):1024-1037.
Miao, F. et al. (Apr. 1, 2013). "RNA-sequencing analysis of high glucose-treated monocytes reveals novel transcriptome signatures and associated epigenetic profiles," *Physiol Genomics* 45(7):287-299.
Nivedha, A.K. et al. (Apr. 2018). "Identifying Functional Hotspot Residues for Biased Ligand Design in G-Protein-Coupled Receptors," *Mol Pharmacol* 93(4):288-296.
Ovalle, F. et al. (Aug. 2018). "Verapamil and beta cell function in adults with recent-onset type 1 diabetes," *Nat Med* 24(8):1108-1112.
Pai, M.Y. et al. (2015). "Drug affinity responsive target stability (DARTS) for small-molecule target identification," Chapter 22 in Methods in Molecular Biology 1263, 287-298.
Robinson, M.D. et al. (Jan. 1, 2010). "edgeR: a Bioconductor package for differential expression analysis of digital gene expression data," *Bioinformatics* 26(1):139-140.
Sastry, M. et al. (May 24, 2010). "Large-scale systematic analysis of 2D fingerprint methods and parameters to improve virtual screening enrichments," *J Chem Inf Model* 50(5):771-784.

(Continued)

*Primary Examiner* — Irina Neagu
(74) *Attorney, Agent, or Firm* — Mintz, Levin, Cohn, Ferris, Glovsky and Popeo, P.C.

(57) ABSTRACT

Disclosed herein, inter alia, are compounds and methods for inhibiting the thioredoxin-thioredoxin-interacting-protein (TXNIP-TRX) complex.

13 Claims, 17 Drawing Sheets

Specification includes a Sequence Listing.

(56) References Cited

OTHER PUBLICATIONS

Tautermann, C.S. et al. (Jan. 10, 2019). "Allosteric Activation of Striatal-Enriched Protein Tyrosine Phosphatase (STEP, PTPN5) by a Fragment-like Molecule," *J Med Chem* 62(1): 306-316.

Thielen L. et al. (Apr. 2018). "Diabetes pathogenic mechanisms and potential new therapies based upon a novel target called TXNIP," *Curr Opin Endocrinol Diabetes Obes.* 25(2):75-80.

Thielen, L.A. et al. (Sep. 1, 2020). "Identification of an Antidiabetic, Orally Available Small Molecule that Regulates TXNIP Expression and Glucagon Action," *Cell Metab* 32(3):353-365.

Vaidehi, N. et al. (Oct. 2016). "Allosteric communication pipelines in G-protein-coupled receptors," *Curr Opin Pharmacol* 30:76-83.

Waldhart, A.N. et al. (Jun. 6, 2017). "Phosphorylation of TXNIP by AKT Mediates Acute Influx of Glucose in Response to Insulin," *Cell Reports* 19(10):2005-2013.

Webb, D.R. (Jan. 1, 2014). "Animal models of human disease: inflammation," *Biochemical Pharmacology* 87(1):121-130.

Yoshihara, E. et al. (Jan. 9, 2014). "Thioredoxin/Txnip: redoxisome, as a redox switch for the pathogenesis of diseases," *Frontiers in Immunology* vol. 4, Article 514, pp. 1-9.

Huang, C. et al. (Jul. 6, 2016). "Thioredoxin interacting protein (TXNIP) regulates tubular autophagy and mitophagy in diabetic nephropathy through the mTOR signaling pathway," *Sci. Rep.* 6:29196.

Tan, S. M. et al. (Jan. 2011). "Tranilast attenuates the up-regulation of thioredoxin-interacting protein and oxidative stress in an experimental model of diabetic nephropathy," *Nephrol. Dial. Transplant.* 26(1):100-110.

* cited by examiner

Examples of $W^1$ and $W^2$

TXNIP-TRX COMPLEX INHIBITORS AND METHODS OF USING THE SAME

CROSS-REFERENCES TO RELATED APPLICATIONS

This application is a continuation of U.S. patent application Ser. No. 16/570,802, filed Sep. 13, 2019, which claims the benefit of U.S. Provisional Application No. 62/730,988, filed Sep. 13, 2018, which are incorporated herein by reference in their entirety and for all purposes.

STATEMENT AS TO RIGHTS TO INVENTIONS MADE UNDER FEDERALLY SPONSORED RESEARCH AND DEVELOPMENT

This invention was made with government support under grant number DK106917, awarded by the National Institutes of Health. The government has certain rights in the invention.

REFERENCE TO A "SEQUENCE LISTING," A TABLE, OR A COMPUTER PROGRAM LISTING APPENDIX SUBMITTED AS AN ASCII FILE

The Sequence Listing written in file 048440-711C01US_Sequence_Listing_ST25.txt, created Mar. 17, 2022, 4,880 bytes, machine format IBM-PC, MS Windows operating system, is hereby incorporated by reference.

BACKGROUND

The thioredoxin system, which includes the thioredoxin (TRX) protein, nicotinamide adenine dinucleotide phosphate (NADPH), and thioredoxin reductase (TXNRD1), is a major anti-oxidant system involved in the maintenance of cellular physiology and survival. Dysregulation in this system has been associated with metabolic and cardiovascular disorders. Thioredoxin-interacting protein (TXNIP) is an inhibitor of the redox regulator thioredoxin (TRX), an antioxidant. Increased TXNIP expression increases oxidant stress and is associated with diabetes as well as several diabetic complications, including diabetic retinopathy, diabetic nephropathy, diabetic neuropathy and cardiovascular disease. Inhibiting TXNIP levels chronically may cause unwanted side effects due to the multiple roles of TXNIP in cells. Identifying modulators of the TXNIP-TRX complex formation remains a challenge. Disclosed herein, inter alia, are solutions to these and other problems in the art.

BRIEF SUMMARY

In an aspect is provided a compound (e.g., a TXNIP-TRX complex inhibitor) having the formula:

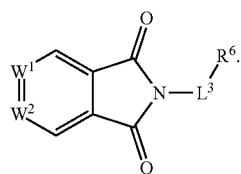

(I)

$W^1$ is $-CR^1=$, $-N=$, or $-CH=$. $W^2$ is $-CR^2=$, $-N=$, or $-CH=$. $R^1$ is independently halogen, $-CX^1_3$, $-CHX^1_2$, $-CH_2X^1$, $-OCX^1_3$, $-OCH_2X^1$, $-OCHX^1_2$, substituted or unsubstituted alkyl, or substituted or unsubstituted heteroalkyl. $R^2$ is independently halogen, $-CX^2_3$, $-CHX^2_2$, $-CH_2X^2$, $-OCX^2_3$, $-OCH_2X^2$, $-OCHX^2_2$, substituted or unsubstituted alkyl, or substituted or unsubstituted heteroalkyl. $L^3$ is a bond, $-N(R^3)-$, $-C(O)-$, $-C(O)N(R^3)-$, $-N(R^3)C(O)-$, $-N(H)-$, $-C(O)N(H)-$, $-N(H)C(O)-$, $-C(O)O-$, substituted or unsubstituted alkylene, or substituted or unsubstituted heteroalkylene. $R^3$ is independently oxo, halogen, $-CCl_3$, $-CBr_3$, $-CF_3$, $-CI_3$, $-CHCl_2$, $-CHBr_2$, $-CHF_2$, $-CHI_2$, $-CH_2Cl$, $-CH_2Br$, $-CH_2F$, $-CH_2I$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, $-N_3$, $-SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl. $R^6$ is independently hydrogen, halogen, $-CX^6_3$, $-CHX^6_2$, $-CH_2X^6$, $-OCX^6_3$, $-OCH_2X^6$, $-OCHX^6_2$, $-CN$, $-SR^{6D}$, $-SOR^{6D}$, $-SO_2R^{6D}$, $-SO_3R^{6D}$, $-SO_4R^{6D}$, $-SONR^{6A}R^{6B}$, $-SO_2NR^{6A}R^{6B}$, $-NR^{6C}C(O)NR^{6A}R^{6B}$, $-N(O)$, $-N(O)_2$, $-NR^{6A}R^{6B}$, $-C(O)R^{6C}$, $-C(O)OR^{6C}$, $-C(O)NR^{6A}R^{6B}$, $-OR^{6D}$, $-NR^{6A}SO_2R^{6D}$, $-NR^{6A}C(O)R^{6C}$, $-NR^{6A}C(O)OR^{6C}$, $-NR^{6A}OR^{6C}$, $-NR^{6C}NR^{6A}R^{6B}$, $-C(O)NR^{6C}NR^{6A}R^{6B}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl. $R^{6A}$ $R^{6B}$, $R^{6C}$, and $R^{6D}$ are each independently hydrogen, oxo, halogen, $-CCl_3$, $-CBr_3$, $-CF_3$, $-CI_3$, $-CHCl_2$, $-CHBr_2$, $-CHF_2$, $-CHI_2$, $-CH_2Cl$, $-CH_2Br$, $-CH_2F$, $-CH_2I$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, $-N_3$, $-SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl. $X^1$, $X^2$, and $X^6$ are independently $-F$, $-Cl$, $-Br$, or $-I$.

In an aspect is provided a pharmaceutical composition including a compound described herein, or pharmaceutically acceptable salt thereof, and a pharmaceutically acceptable excipient.

In an aspect is provided a method of treating a TXNIP-TRX complex-associated disease, the method including administering to a subject in need thereof an effective amount of a TXNIP-TRX complex inhibitor.

In an aspect is provided a method of treating a TXNIP-TRX complex-associated disease, the method including administering to a subject in need thereof an effective amount of a TXNIP-TRX complex inhibitor, wherein the TXNIP-TRX complex inhibitor is a compound as described herein, including embodiments. In embodiments, the compound has the formula:

(I)

wherein $W^1$, $W^2$, $L^3$, and $R^6$ are as described herein.

In an aspect is provided a method of treating a metabolic disorder, cardiovascular disease, or inflammatory disease, the method including administering to a subject in need thereof an effective amount of a compound, or pharmaceutically acceptable salt thereof, as described herein, including embodiments. In embodiments, the compound has the formula:

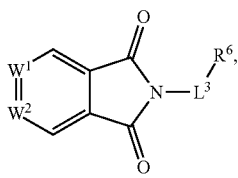

(I)

wherein $W^1$, $W^2$, $L^3$, and $R^6$ are as described herein.

In an aspect is provided a method of reducing the level of expression of TXNIP in a cell, the method including contacting the cell with a compound, or pharmaceutically acceptable salt thereof, as described herein.

In an aspect is provided a method of reducing the level of expression of TXNIP, the method including contacting TXNIP with a compound, or a pharmaceutically acceptable salt thereof, as described herein.

BRIEF DESCRIPTION OF THE DRAWINGS

FIG. 1A: TXNIP-TRX complex showing the predicted druggable allosteric sites for small molecules; FIG. 1B: Computational small molecule screening strategy. The binding sites predicted using the computational method Allosteer.

FIG. 2A. Compound 1 (C1); FIG. 2B. Additional examples of C1 analogs; FIG. 2C. Examples of substitutions at $R^1$ and $R^2$ (of the scaffold described in FIGS. 2A-2D); FIG. 2D. Examples of moieties.

FIG. 9A. C1 inhibits TXNIP mRNA expression in THP1 cells. THP1 cells were cultured in 25 mM glucose with the indicated concentrations of C1 for 72 h. Cell were collected for total RNA preparation. RT-PCR were performed and data shown are the mean+SEM from triplicates. Statistical analysis was performed using one-way ANOVA, *<0.0001. FIG. 9B. C1 inhibits TNF-α mRNA expression in THP1 cells. THP1 cells were cultured in 25 mM glucose and C1 (uM) as indicated for 72 hours and collected for total RNA preparation. RT-PCR was performed. Data shown are the mean+SEM from triplicates. Statistical analysis was performed using one-way ANOVA: *<0.02; **<0.0001.

FIG. 10A. C1 inhibits TXNIP mRNA expression in murine RAW macrophages. RAW cells were cultured in 25 mM glucose with C1 (uM) for 72 h. Total RNA was prepared. RT-PCR was performed. Data shown are the mean+SEM from triplicates. Statistical analysis was performed for each column vs. high glucose (HG) DMSO using one-way ANOVA: *<0.0001. FIG. 10B. Treatment with C1 decreased TNF-α mRNA expression in murine RAW macrophages. RAW cells were cultured in 25 mM glucose with C1 (uM) for 72 hours. Total RNA was prepared. RT-PCR was performed. Data shown are the mean+SEM from triplicates. Statistical analysis was performed for each column vs. HG DMSO using one-way ANOVA: *<0.0001.

DETAILED DESCRIPTION

I. Definitions

Figure 1A:
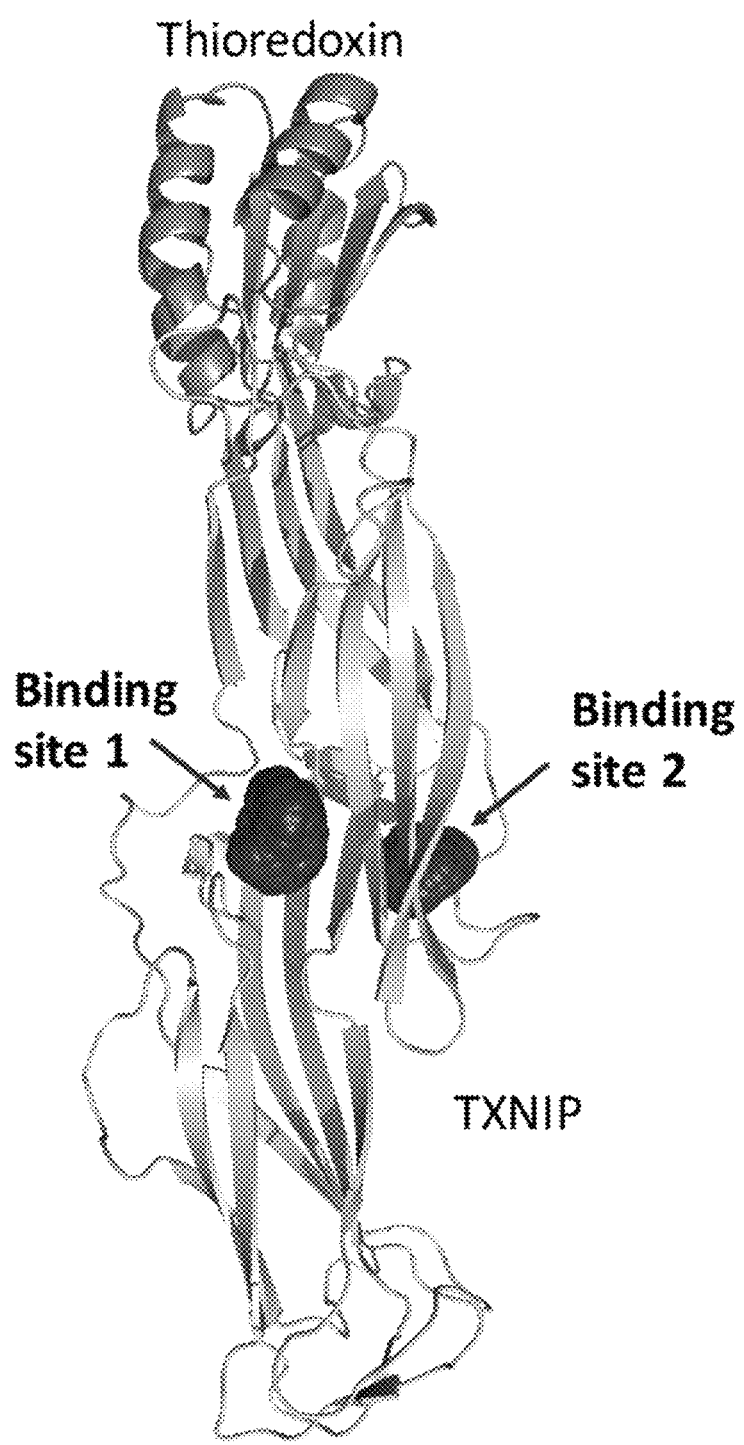
FIGS. 1A-1B.
Figure 1B:
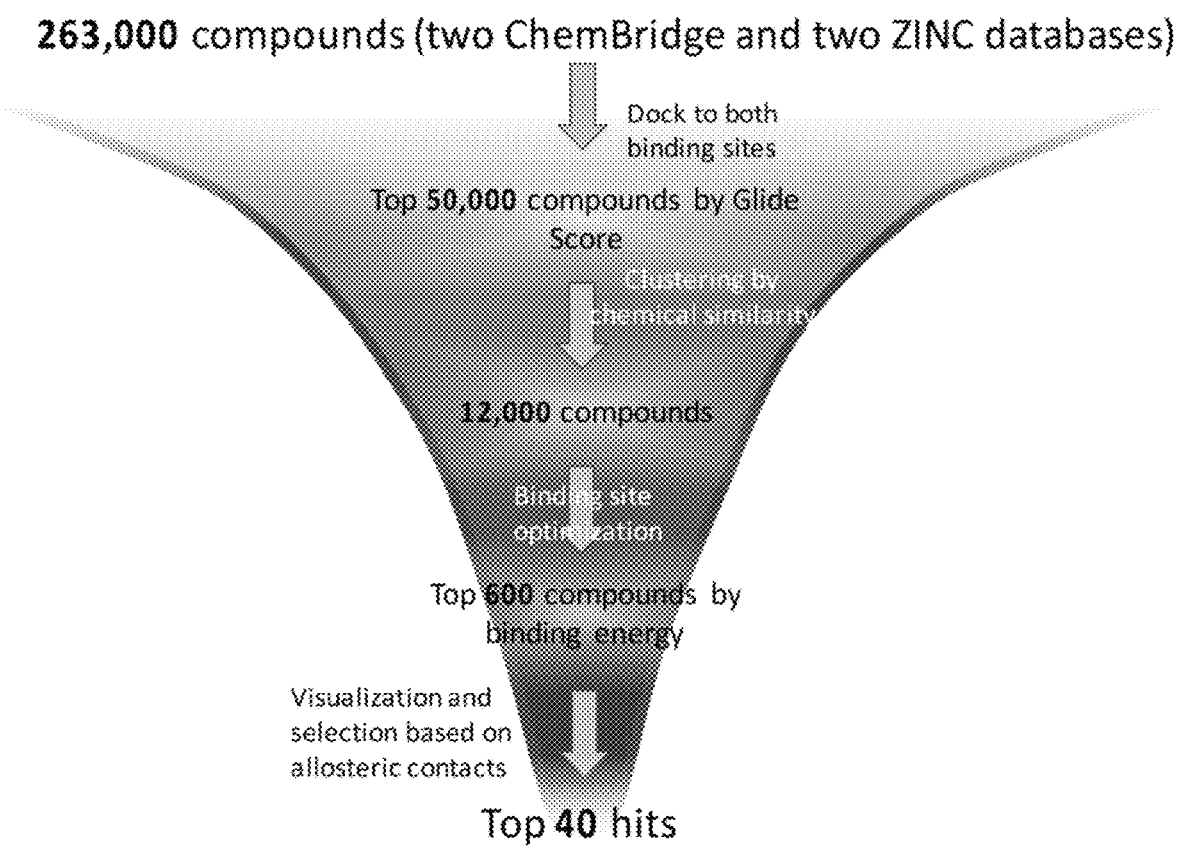

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals. The alkyl may include a designated number of carbons (e.g., $C_1$-$C_{10}$ means one to ten carbons). Alkyl is an uncyclized chain. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated. An alkenyl may include more than one double bond and/or one or more triple bonds in addition to the one or more double bonds. An alkynyl may include more than one triple bond and/or one or more double bonds in addition to the one or more triple bonds.

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms, with those groups having 10 or fewer carbon atoms being preferred herein. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom (e.g., O, N, P, Si, and S), and wherein the nitrogen and sulfur atoms may optionally be oxidized, and the nitrogen heteroatom may optionally be quaternized. The heteroatom(s) (e.g., O, N, S, Si, or P) may be placed at any interior position of the heteroalkyl group or at the position at which the alkyl group is attached to the remainder of the molecule. Heteroalkyl is an uncyclized chain. Up to two or three heteroatoms may be consecutive, such as, for example, —CH$_2$—NH—OCH$_3$ and —CH$_2$—O—Si(CH$_3$)$_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P). The term "heteroalkenyl," by itself or in combination with another term, means, unless otherwise stated, a heteroalkyl including at least one double bond. A heteroalkenyl may optionally include more than one double bond and/or one or more triple bonds in additional to the one or more double bonds. The term "heteroalkynyl," by itself or in combination with another term, means, unless otherwise stated, a heteroalkyl including at least one triple bond. A heteroalkynyl may optionally include more than one triple bond and/or one or more double bonds in additional to the one or more triple bonds.

Similarly, the term "heteroalkylene," by itself or as part of another substituent, means, unless otherwise stated, a divalent radical derived from heteroalkyl, as exemplified, but not limited by, —CH$_2$—CH$_2$—, —S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. A "cycloalkylene" and a "heterocycloalkylene," alone or as part of another substituent, means a divalent radical derived from a cycloalkyl and heterocycloalkyl, respectively.

In embodiments, the term "cycloalkyl" means a monocyclic, bicyclic, or a multicyclic cycloalkyl ring system. In embodiments, monocyclic ring systems are cyclic hydrocarbon groups containing from 3 to 8 carbon atoms, where such groups can be saturated or unsaturated, but not aromatic. In embodiments, cycloalkyl groups are fully saturated. Bicyclic cycloalkyl ring systems are bridged monocyclic rings or fused bicyclic rings. In embodiments, bridged monocyclic rings contain a monocyclic cycloalkyl ring where two non adjacent carbon atoms of the monocyclic ring are linked by an alkylene bridge of between one and three additional carbon atoms (i.e., a bridging group of the form $(CH_2)_w$, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. In embodiments, fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. In embodiments, the bridged or fused bicyclic cycloalkyl is attached to the parent molecular moiety through any carbon atom contained within the monocyclic cycloalkyl ring. In embodiments, cycloalkyl groups are optionally substituted with one or two groups which are independently oxo or thia. In embodiments, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloalkyl is optionally substituted by one or two groups which are independently oxo or thia. In embodiments, multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. In embodiments, the multicyclic cycloalkyl is attached to the parent molecular moiety through any carbon atom contained within the base ring. In embodiments, multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a monocyclic heteroaryl, a monocyclic cycloalkyl, a monocyclic cycloalkenyl, and a monocyclic heterocyclyl. Examples of multicyclic cycloalkyl groups include, but are not limited to tetradecahydrophenanthrenyl, perhydrophenothiazin-1-yl, and perhydrophenoxazin-1-yl.

In embodiments, a cycloalkyl is a cycloalkenyl. The term "cycloalkenyl" is used in accordance with its plain ordinary meaning. In embodiments, a cycloalkenyl is a monocyclic, bicyclic, or a multicyclic cycloalkenyl ring system. In embodiments, monocyclic cycloalkenyl ring systems are cyclic hydrocarbon groups containing from 3 to 8 carbon atoms, where such groups are unsaturated (i.e., containing at least one annular carbon carbon double bond), but not aromatic. Examples of monocyclic cycloalkenyl ring systems include cyclopentenyl and cyclohexenyl. In embodiments, bicyclic cycloalkenyl rings are bridged monocyclic rings or a fused bicyclic rings. In embodiments, bridged monocyclic rings contain a monocyclic cycloalkenyl ring where two non adjacent carbon atoms of the monocyclic ring are linked by an alkylene bridge of between one and three additional carbon atoms (i.e., a bridging group of the form $(CH_2)_w$, where w is 1, 2, or 3). Representative examples of bicyclic cycloalkenyls include, but are not limited to, norbornenyl and bicyclo[2.2.2]oct 2 enyl. In embodiments, fused bicyclic cycloalkenyl ring systems contain a monocyclic cycloalkenyl ring fused to either a phenyl, a monocyclic cycloalkyl, a monocyclic cycloalkenyl, a monocyclic heterocyclyl, or a monocyclic heteroaryl. In embodiments, the bridged or fused bicyclic cycloalkenyl is attached to the parent molecular moiety through any carbon atom contained within the monocyclic cycloalkenyl ring. In embodiments, cycloalkenyl groups are optionally substituted with one or two groups which are independently oxo or thia. In embodiments, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. In embodiments, the multicyclic cycloalkenyl is attached to the parent molecular moiety through any carbon atom contained within the base ring. In embodiments, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two ring systems independently selected from the group consisting of a phenyl, a monocyclic heteroaryl, a monocyclic cycloalkyl, a monocyclic cycloalkenyl, and a monocyclic heterocyclyl.

In embodiments, a heterocycloalkyl is a heterocyclyl. The term "heterocyclyl" as used herein, means a monocyclic, bicyclic, or multicyclic heterocycle. The heterocyclyl monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of O, N and S. The 5 membered ring can contain zero or one double bond and one, two or three heteroatoms selected from the group consisting of O, N and S. The 6 or 7 membered ring contains zero, one or two double bonds and one, two or three heteroatoms selected from the group consisting of O, N and S. The heterocyclyl monocyclic heterocycle is connected to the parent molecular moiety through any carbon atom or any nitrogen atom contained within the heterocyclyl monocyclic heterocycle. Representative examples of heterocyclyl monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The heterocyclyl bicyclic heterocycle is a monocyclic heterocycle fused to either a phenyl, a monocyclic cycloalkyl, a monocyclic cycloalkenyl, a monocyclic heterocycle, or a monocyclic heteroaryl. The heterocyclyl bicyclic heterocycle is connected to the parent molecular moiety through any carbon atom or any nitrogen atom contained within the monocyclic heterocycle portion of the bicyclic ring system. Representative examples of bicyclic heterocyclyls include, but are not limited to, 2,3-dihydrobenzofuran-2-yl, 2,3-dihydrobenzofuran-3-yl, indolin-1-yl, indolin-2-yl, indolin-3-yl, 2,3-dihydrobenzothien-2-yl, decahydroquinolinyl, decahydroisoquinolinyl, octahydro-1H-indolyl, and octahydrobenzofuranyl. In embodiments, heterocyclyl groups are optionally substituted with one or two groups which are independently oxo or thia. In certain embodiments, the bicyclic heterocyclyl is a 5 or 6 membered monocyclic heterocyclyl ring fused to a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the bicyclic heterocyclyl is optionally substituted by one or two groups which are independently oxo or thia. Multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. The multicyclic heterocyclyl is attached to the parent molecular moiety through any carbon atom or nitrogen atom contained within the base ring. In embodiments, multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a monocyclic heteroaryl, a monocyclic cycloalkyl, a monocyclic cycloalkenyl, and a monocyclic heterocyclyl. Examples of multicyclic heterocyclyl groups include, but are not limited to 10H-phenothiazin-10-yl, 9,10-dihydroacridin-9-yl, 9,10-dihydroacridin-10-yl, 10H-phenoxazin-10-yl, 10,11-dihydro-5H-dibenzo[b,f]azepin-5-yl, 1,2,3,4-tetrahydropyrido[4,3-g]isoquinolin-2-yl, 12H-benzo[b]phenoxazin-12-yl, and dodecahydro-1H-carbazol-9-yl.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$) alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzoxazoyl benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be —O— bonded to a ring heteroatom nitrogen.

A fused ring heterocyloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substitutents described herein.

Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g. substituents for cycloalkyl or heterocycloalkyl rings). Spirocyclic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g. all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The symbol "~~~" denotes the point of attachment of a chemical moiety to the remainder of a molecule or chemical formula.

The term "oxo," as used herein, means an oxygen that is double bonded to a carbon atom.

The term "alkylsulfonyl," as used herein, means a moiety having the formula —S(O$_2$)—R', where R' is a substituted or unsubstituted alkyl group as defined above. R' may have a specified number of carbons (e.g., "C$_1$-C$_4$ alkylsulfonyl").

Each of the above terms (e.g., "alkyl," "heteroalkyl," "cycloalkyl," "heterocycloalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C(O)NR"NR'"R"", —CN, —NO$_2$, —NR'SO$_2$R", —NR'C(O)R", —NR'C(O)—OR", —NR'OR", in a number ranging from zero to (2m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C(O)NR"NR'"R"", —CN, —NO$_2$, —R', —N$_3$, —CH(Ph)$_2$, fluoro(C$_1$-C$_4$)alkoxy, and fluoro(C$_1$-C$_4$)alkyl, —NR'SO$_2$R", —NR'C(O)R", —NR'C(O)—OR", —NR'OR", in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound described herein includes more than one R group, for example, each of the R groups is independently selected as are each R', R", R'", and R"" groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'— (C"R"R''')$_d$—, where s and d are independently integers of from 0 to 3, and X' is —O—, —NR'—, —S—, —S(O)—, —S(O)$_2$—, or —S(O)$_2$NR'—. The substituents R, R', R", and R''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), and silicon (Si).

A "substituent group," as used herein, means a group selected from the following moieties:

(A) oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (B) alkyl, heteroalkyl, cycloalkyl, heterocycloalkyl, aryl, heteroaryl, substituted with at least one substituent selected from:

(i) oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (ii) alkyl, heteroalkyl, cycloalkyl, heterocycloalkyl, aryl, heteroaryl, substituted with at least one substituent selected from:

(a) oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (b) alkyl, heteroalkyl, cycloalkyl, heterocycloalkyl, aryl, heteroaryl, substituted with at least one substituent selected from: oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, a "substituent group," as used herein, means a group selected from the following moieties:

(A) oxo, halogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and (B) alkyl (e.g., $C_1$-$C_{20}$, $C_1$-$C_{12}$, $C_1$-$C_8$, $C_1$-$C_6$, $C_1$-$C_4$, or $C_1$-$C_2$), heteroalkyl (e.g., 2 to 20 membered, 2 to 12 membered, 2 to 8 membered, 2 to 6 membered, 4 to 6 membered, 2 to 3 membered, or 4 to 5 membered), cycloalkyl (e.g., $C_3$-$C_{10}$, $C_3$-$C_8$, $C_3$-$C_6$, $C_4$-$C_6$, or $C_5$-$C_6$), heterocycloalkyl (e.g., 3 to 10 membered, 3 to 8 membered, 3 to 6 membered, 4 to 6 membered, 4 to 5 membered, or 5 to 6 membered), aryl (e.g., $C_6$-$C_{12}$, $C_6$-$C_{10}$, or phenyl), or heteroaryl (e.g., 5 to 12 membered, 5 to 10 membered, 5 to 9 membered, or 5 to 6 membered), substituted with at least one substituent selected from:

(i) oxo, halogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and (ii) alkyl (e.g., $C_1$-$C_{20}$, $C_1$-$C_{12}$, $C_1$-$C_8$, $C_1$-$C_6$, $C_1$-$C_4$, or $C_1$-$C_2$), heteroalkyl (e.g., 2 to 20 membered, 2 to 12 membered, 2 to 8 membered, 2 to 6 membered, 4 to 6 membered, 2 to 3 membered, or 4 to 5 membered), cycloalkyl (e.g., $C_3$-$C_{10}$, $C_3$-$C_8$, $C_3$-$C_6$, $C_4$-$C_6$, or $C_5$-$C_6$), heterocycloalkyl (e.g., 3 to 10 membered, 3 to 8 membered, 3 to 6 membered, 4 to 6 membered, 4 to 5 membered, or 5 to 6 membered), aryl (e.g., $C_6$-$C_{12}$, $C_6$-$C_{10}$, or phenyl), or heteroaryl (e.g., 5 to 12 membered, 5 to 10 membered, 5 to 9 membered, or 5 to 6 membered), substituted with at least one substituent selected from:

(a) oxo, halogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and (b) alkyl (e.g., $C_1$-$C_{20}$, $C_1$-$C_{12}$, $C_1$-$C_8$, $C_1$-$C_6$, $C_1$-$C_4$, or $C_1$-$C_2$), heteroalkyl (e.g., 2 to 20 membered, 2 to 12 membered, 2 to 8 membered, 2 to 6 membered, 4 to 6 membered, 2 to 3 membered, or 4 to 5 membered), cycloalkyl (e.g., $C_3$-$C_{10}$, $C_3$-$C_8$, $C_3$-$C_6$, $C_4$-$C_6$, or $C_5$-$C_6$), heterocycloalkyl (e.g., 3 to 10 membered, 3 to 8 membered, 3 to 6 membered, 4 to 6 membered, 4 to 5 membered, or 5 to 6 membered), aryl (e.g., $C_6$-$C_{12}$, $C_6$-$C_{10}$, or phenyl), or heteroaryl (e.g., 5 to 12 membered, 5 to 10 membered, 5 to 9 membered, or 5 to 6 membered), substituted with at least one substituent selected from: oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, unsubstituted alkyl (e.g., $C_1$-$C_5$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_5$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the application (e.g., Examples section, figures, or tables below).

In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is unsubstituted (e.g., is an unsubstituted alkyl, unsubstituted heteroalkyl, unsubstituted cycloalkyl, unsubstituted heterocycloalkyl, unsubstituted aryl, unsubstituted heteroaryl, unsubstituted alkylene, unsubstituted heteroalkylene, unsubstituted cycloalkylene, unsubstituted heterocycloalkylene, unsubstituted arylene, and/or unsubstituted heteroarylene, respectively). In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is substituted (e.g., is a substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene, respectively).

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, wherein if the substituted moiety is substituted with a plurality of substituent groups, each substituent group may optionally be different. In embodiments, if the substituted moiety is substituted with a plurality of substituent groups, each substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one size-limited substituent group, wherein if the substituted moiety is substituted with a plurality of size-limited substituent groups, each size-limited substituent group may optionally be different. In embodiments, if the substituted moiety is substituted with a plurality of size-limited substituent groups, each size-limited substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one lower substituent group, wherein if the substituted moiety is substituted with a plurality of lower substituent groups, each lower substituent group may optionally be different. In embodiments, if the substituted moiety is substituted with a plurality of lower substituent groups, each lower substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted moiety is substituted with a plurality of groups selected from substituent groups, size-limited substituent groups, and lower substituent groups; each substituent group, size-limited substituent group, and/or lower substituent group may optionally be different. In embodiments, if the substituted moiety is substituted with a plurality of groups selected from substituent groups, size-limited substituent groups, and lower substituent groups; each substituent group, size-limited substituent group, and/or lower substituent group is different.

Certain compounds of the present disclosure possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present disclosure. The compounds of the present disclosure do not include those that are known in art to be too unstable to synthesize and/or isolate. The present disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this disclosure may exist in tautomeric forms, all such tautomeric forms of the compounds being within the scope of the disclosure.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this disclosure.

The compounds of the present disclosure may also contain unnatural proportions of atomic isotopes at one or more of the atoms that constitute such compounds. For example, the compounds may be radiolabeled with radioactive isotopes, such as for example tritium ($^{3}$H), iodine-125 ($^{125}$I), or carbon-14 ($^{14}$C). All isotopic variations of the compounds of the present disclosure, whether radioactive or not, are encompassed within the scope of the present disclosure.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

As used herein, the term "bioconjugate reactive moiety" and "bioconjugate reactive group" refers to a moiety or group capable of forming a bioconjugate (e.g., covalent linker) as a result of the association between atoms or molecules of bioconjugate reactive groups. The association can be direct or indirect. For example, a conjugate between a first bioconjugate reactive group (e.g., —NH$_2$, —COOH, —N-hydroxysuccinimide, or -maleimide) and a second bioconjugate reactive group (e.g., sulfhydryl, sulfur-containing amino acid, amine, amine sidechain containing amino acid, or carboxylate) provided herein can be direct, e.g., by covalent bond or linker (e.g. a first linker of second linker), or indirect, e.g., by non-covalent bond (e.g. electrostatic interactions (e.g. ionic bond, hydrogen bond, halogen bond), van der Waals interactions (e.g. dipole-dipole, dipole-induced dipole, London dispersion), ring stacking (pi effects), hydrophobic interactions and the like). In embodiments, bioconjugates or bioconjugate linkers are formed using bioconjugate chemistry (i.e. the association of two bioconjugate reactive groups) including, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982. In embodiments, the first bioconjugate reactive group (e.g., maleimide moiety) is covalently attached to the second bioconjugate reactive group (e.g. a sulfhydryl). In embodiments, the first bioconjugate reactive group (e.g., haloacetyl moiety) is covalently attached to the second bioconjugate reactive group (e.g. a sulfhydryl). In embodiments, the first bioconjugate reactive group (e.g., pyridyl moiety) is covalently attached to the second bioconjugate reactive group (e.g. a sulfhydryl). In embodiments, the first bioconjugate reactive group (e.g., —N-hydroxysuccinimide moiety) is covalently attached to the second bioconjugate reactive group (e.g. an amine). In embodiments, the first bioconjugate reactive group (e.g., maleimide moiety) is covalently attached to the second bioconjugate reactive group (e.g. a sulfhydryl). In embodiments, the first bioconjugate reactive group (e.g., -sulfo-N-hydroxysuccinimide moiety) is covalently attached to the second bioconjugate reactive group (e.g. an amine).

Useful bioconjugate reactive moieties used for bioconjugate chemistries herein include, for example:
(a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters; (b) hydroxyl groups which can be converted to esters, ethers, aldehydes, etc.; (c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom; (d) dienophile groups which are capable of participating in Diels-Alder reactions such as, for example, maleimido or maleimide groups; (e) aldehyde or ketone groups such that subsequent derivatization is possible via formation of carbonyl derivatives such as, for example, imines, hydrazones, semicarbazones or oximes, or via such mechanisms as Grignard addition or alkyllithium addition; (f) sulfonyl halide groups for subsequent reaction with amines, for example, to form sulfonamides; (g) thiol groups, which can be converted to disulfides, reacted with acyl halides, or bonded to metals such as gold, or react with maleimides; (h) amine or sulfhydryl groups (e.g., present in cysteine), which can be, for example, acylated, alkylated or oxidized; (i) alkenes, which can undergo, for example, cycloadditions, acylation, Michael addition, etc; (j) epoxides, which can react with, for example, amines and hydroxyl compounds; (k) phosphoramidites and other standard functional groups useful in nucleic acid synthesis; (l) metal silicon oxide bonding; (m) metal bonding to reactive phosphorus groups (e.g. phosphines) to form, for example, phosphate diester bonds; (n) azides coupled to alkynes using copper catalyzed cycloaddition click chemistry; (o) biotin conjugate can react with avidin or strepavidin to form a avidin-biotin complex or streptavidin-biotin complex.

The bioconjugate reactive groups can be chosen such that they do not participate in, or interfere with, the chemical stability of the conjugate described herein. Alternatively, a reactive functional group can be protected from participating in the crosslinking reaction by the presence of a protecting group. In embodiments, the bioconjugate comprises a molecular entity derived from the reaction of an unsaturated bond, such as a maleimide, and a sulfhydryl group.

"Analog," or "analogue" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and appearance but not in structure or origin to a reference compound.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman alphabetic symbol may be used to distinguish each appearance of that particular R group. For example, where multiple $R^{13}$ substituents are present, each $R^{13}$ substituent may be distinguished as $R^{13A}$, $R^{13B}$, $R^{13C}$, $R^{13D}$, etc., wherein each of $R^{13A}$, $R^{13B}$, $R^{13C}$, $R^{13D}$, etc. is defined within the scope of the definition of $R^{13}$ and optionally differently.

A "detectable agent" or "detectable moiety" is a substance, element, compound, or composition; or moiety thereof, detectable by appropriate means such as spectroscopic, photochemical, biochemical, immunochemical, chemical, magnetic resonance imaging, or other physical means. For example, useful detectable agents include $^{18}$F, $^{32}$P, $^{33}$P, $^{45}$Ti, $^{47}$Sc, $^{52}$Fe, $^{59}$Fe, $^{62}$Cu, $^{64}$Cu, $^{67}$Cu, $^{67}$Ga, $^{68}$Ga, $^{77}$As, $^{86}$Y, $^{90}$Y, $^{89}$Sr, $^{89}$Zr, $^{94}$Tc, $^{94}$Tc, $^{99}$mTc, $^{99}$Mo, $^{105}$Pd, $^{105}$Rh, $^{111}$Ag, $^{111}$In, $^{123}$I, $^{124}$I, $^{125}$I, $^{131}$I, $^{142}$Pr, $^{143}$Pr, $^{149}$Pm, $^{153}$Sm, $^{154-158}$Gd, $^{161}$Tb, $^{166}$Dy, $^{166}$Ho, $^{169}$Er, $^{175}$Lu, $^{177}$Lu, $^{186}$Re, $^{188}$Re, $^{189}$Re, $^{194}$Ir, $^{198}$Au, $^{199}$Au, $^{211}$At, $^{211}$Pb, $^{212}$Bi, $^{212}$Pb, $^{213}$Bi, $^{223}$Ra, $^{225}$Ac, Cr, V, Mn, Fe, Co, Ni, Cu, La, Ce, Pr, Nd, Pm, Sm, Eu, Gd, Tb, Dy, Ho, Er, Tm, Yb, Lu, $^{32}$P, fluorophore (e.g. fluorescent dyes), electron-dense reagents, enzymes (e.g., as commonly used in an ELISA), biotin, digoxigenin, paramagnetic molecules, paramagnetic nanoparticles, ultrasmall superparamagnetic iron oxide ("USPIO") nanoparticles, USPIO nanoparticle aggregates, superparamagnetic iron oxide ("SPIO") nanoparticles, SPIO nanoparticle aggregates, monochrystalline iron oxide nanoparticles, monochrystalline iron oxide, nanoparticle contrast agents, liposomes or other delivery vehicles containing Gadolinium chelate ("Gd-chelate") molecules, Gadolinium, radioisotopes, radionuclides (e.g. carbon-11, nitrogen-13, oxygen-15, fluorine-18, rubidium-82), fluorodeoxyglucose (e.g. fluorine-18 labeled), any gamma ray emitting radionuclides, positron-emitting radionuclide, radiolabeled glucose, radiolabeled water, radiolabeled ammonia, biocolloids, microbubbles (e.g. including microbubble shells including albumin, galactose, lipid, and/or polymers; microbubble gas core including air, heavy gas(es), perfluorcarbon, nitrogen, octafluoropropane, perflexane lipid microsphere, perflutren, etc.), iodinated contrast agents (e.g. iohexol, iodixanol, ioversol, iopamidol, ioxilan, iopromide, diatrizoate, metrizoate, ioxaglate), barium sulfate, thorium dioxide, gold, gold nanoparticles, gold nanoparticle aggregates, fluorophores, two-photon fluorophores, or haptens and proteins or other entities which can be made detectable, e.g., by incorporating a radiolabel into a peptide or antibody specifically reactive with a target peptide. A detectable moiety is a monovalent detectable agent or a detectable agent capable of forming a bond with another composition.

Radioactive substances (e.g., radioisotopes) that may be used as imaging and/or labeling agents in accordance with the embodiments of the disclosure include, but are not limited to, $^{18}$F, $^{32}$P, $^{33}$P, $^{45}$Ti, $^{47}$Sc, $^{52}$Fe, $^{59}$Fe, $^{62}$Cu, $^{64}$Cu, $^{67}$Cu, $^{67}$Ga, $^{68}$Ga, $^{77}$As, $^{86}$Y, $^{90}$Y, $^{89}$Sr, $^{89}$Zr, $^{94}$Tc, $^{94}$Tc, $^{99m}$Tc, $^{99}$Mo, $^{105}$Pd, $^{105}$Rh, $^{111}$Ag, $^{111}$In, $^{123}$I, $^{124}$I, $^{125}$I, $^{131}$I, $^{142}$Pr, $^{143}$Pr, $^{149}$Pm, $^{153}$Sm, $^{154-158}$Gd, $^{161}$Tb, $^{166}$Dy, $^{166}$Ho, $^{169}$Er, $^{175}$Lu, $^{177}$Lu, $^{186}$Re, $^{188}$Re, $^{189}$Re, $^{194}$I, $^{198}$Au, $^{199}$Au, $^{211}$At, $^{211}$Pb, $^{212}$Bi, $^{212}$Pb, $^{213}$Bi, $^{223}$Ra and $^{225}$Ac. Paramagnetic ions that may be used as additional imaging agents in accordance with the embodiments of the disclosure include, but are not limited to, ions of transition and lanthanide metals (e.g. metals having atomic numbers of 21-29, 42, 43, 44, or 57-71). These metals include ions of Cr, V, Mn, Fe, Co, Ni, Cu, La, Ce, Pr, Nd, Pm, Sm, Eu, Gd, Tb, Dy, Ho, Er, Tm, Yb and Lu.

Descriptions of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

A person of ordinary skill in the art will understand when a variable (e.g., moiety or linker) of a compound or of a compound genus (e.g., a genus described herein) is described by a name or formula of a standalone compound with all valencies filled, the unfilled valence(s) of the variable will be dictated by the context in which the variable is used. For example, when a variable of a compound as described herein is connected (e.g., bonded) to the remainder of the compound through a single bond, that variable is understood to represent a monovalent form (i.e., capable of forming a single bond due to an unfilled valence) of a standalone compound (e.g., if the variable is named "methane" in an embodiment but the variable is known to be attached by a single bond to the remainder of the compound, a person of ordinary skill in the art would understand that the variable is actually a monovalent form of methane, i.e., methyl or —CH$_3$). Likewise, for a linker variable (e.g., L$^1$, L$^2$, or L$^3$ as described herein), a person of ordinary skill in the art will understand that the variable is the divalent form of a standalone compound (e.g., if the variable is assigned to "PEG" or "polyethylene glycol" in an embodiment but the variable is connected by two separate bonds to the remainder of the compound, a person of ordinary skill in the art would understand that the variable is a divalent (i.e., capable of forming two bonds through two unfilled valences) form of PEG instead of the standalone compound PEG).

As used herein, the term "salt" refers to acid or base salts of the compounds used in the methods of the present invention. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

The term "pharmaceutically acceptable salts" is meant to include salts of the active compounds that are prepared with relatively nontoxic acids or bases, depending on the particular substituents found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science*, 1977, 66, 1-19). Certain specific compounds of the present disclosure contain both basic and acidic functionalities that allow the compounds to be converted into either base or acid addition salts.

Thus, the compounds of the present disclosure may exist as salts, such as with pharmaceutically acceptable acids. The present disclosure includes such salts. Non-limiting examples of such salts include hydrochlorides, hydrobromides, phosphates, sulfates, methanesulfonates, nitrates, maleates, acetates, citrates, fumarates, proprionates, tartrates (e.g., (+)-tartrates, (−)-tartrates, or mixtures thereof including racemic mixtures), succinates, benzoates, and salts with amino acids such as glutamic acid, and quaternary ammonium salts (e.g. methyl iodide, ethyl iodide, and the like). These salts may be prepared by methods known to those skilled in the art.

The neutral forms of the compounds are preferably regenerated by contacting the salt with a base or acid and isolating the parent compound in the conventional manner. The parent form of the compound may differ from the various salt forms in certain physical properties, such as solubility in polar solvents.

In addition to salt forms, the present disclosure provides compounds, which are in a prodrug form. Prodrugs of the compounds described herein are those compounds that readily undergo chemical changes under physiological conditions to provide the compounds of the present disclosure. Prodrugs of the compounds described herein may be converted in vivo after administration. Additionally, prodrugs can be converted to the compounds of the present disclosure by chemical or biochemical methods in an ex vivo environment, such as, for example, when contacted with a suitable enzyme or chemical reagent.

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

"Pharmaceutically acceptable excipient" and "pharmaceutically acceptable carrier" refer to a substance that aids the administration of an active agent to and absorption by a subject and can be included in the compositions of the present disclosure without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the disclosure. One of skill in the art will recognize that other pharmaceutical excipients are useful in the present disclosure.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "about" means a range of values including the specified value, which a person of ordinary skill in the art would consider reasonably similar to the specified value. In embodiments, about means within a standard deviation using measurements generally acceptable in the art. In embodiments, about means a range extending to +/−10% of the specified value. In embodiments, about includes the specified value.

A "TXNIP inhibitor" refers to a compound (e.g. compounds described herein) that reduces the level of activity of TXNIP when compared to a control, such as absence of the compound or a compound with known inactivity. In embodiments, a TXNIP inhibitor reduces the activity or function (e.g., thioredoxin binding) of the TXNIP protein. In embodiments, a TXNIP inhibitor reduces the level of expression of TXNIP (e.g., in a cell).

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents that can be produced in the reaction mixture.

The term "contacting" may include allowing two species to react, interact, or physically touch, wherein the two species may be a compound as described herein and a protein or enzyme. In some embodiments, contacting includes allowing a compound described herein to interact with a protein or enzyme that is involved in a signaling pathway.

As defined herein, the term "activation", "activate", "activating", "activator" and the like in reference to a protein-inhibitor interaction means positively affecting (e.g. increasing) the activity or function of the protein relative to the activity or function of the protein in the absence of the activator. In embodiments activation means positively affecting (e.g. increasing) the concentration or levels of the protein relative to the concentration or level of the protein in the absence of the activator. The terms may reference activation, or activating, sensitizing, or up-regulating signal transduction or enzymatic activity or the amount of a protein decreased in a disease. Thus, activation may include, at least in part, partially or totally increasing stimulation, increasing or enabling activation, or activating, sensitizing, or up-regulating signal transduction or enzymatic activity or the amount of a protein associated with a disease (e.g., a protein which is decreased in a disease relative to a non-diseased control). Activation may include, at least in part, partially or totally increasing stimulation, increasing or enabling activation, or activating, sensitizing, or up-regulating signal transduction or enzymatic activity or the amount of a protein.

The terms "agonist," "activator," "upregulator," etc. refer to a substance capable of detectably increasing the expression or activity of a given gene or protein. The agonist can increase expression or activity 10%, 20%, 30%, 40%, 50%, 60%, 70%, 80%, 90% or more in comparison to a control in the absence of the agonist. In certain instances, expression or activity is 1.5-fold, 2-fold, 3-fold, 4-fold, 5-fold, 10-fold or higher than the expression or activity in the absence of the agonist.

As defined herein, the term "inhibition", "inhibit", "inhibiting" and the like in reference to a protein-inhibitor interaction means negatively affecting (e.g. decreasing) the activity or function of the protein relative to the activity or function of the protein in the absence of the inhibitor. In embodiments inhibition means negatively affecting (e.g. decreasing) the concentration or levels of the protein relative to the concentration or level of the protein in the absence of the inhibitor. In embodiments, inhibition refers to reduction of a disease or symptoms of disease. In embodiments, inhibition refers to a reduction in the activity of a particular protein target. Thus, inhibition includes, at least in part, partially or totally blocking stimulation, decreasing, preventing, or delaying activation, or inactivating, desensitizing, or down-regulating signal transduction or enzymatic activity or the amount of a protein. In embodiments, inhibition refers to a reduction of activity of a target protein resulting from a direct interaction (e.g. an inhibitor binds to the target protein). In embodiments, inhibition refers to a reduction of activity of a target protein from an indirect interaction (e.g. an inhibitor binds to a protein that activates the target protein, thereby preventing target protein activation). A "TXNIP-TRX complex inhibitor" is a compound that negatively affects (e.g. decreases) the activity or function of the TXNIP-TRX complex relative to the activity or function of TXNIP-TRX complex in the absence of the inhibitor. In embodiments, a TXNIP-TRX complex inhibitor prevents the formation of the TXNIP-TRX complex (e.g., prevents TXNIP from interacting with TRX). A "TXNIP expression inhibitor" is a compound that negatively affects (e.g. decreases) the level of expression of TXNIP relative to the level of expression of TXNIP in the absence of the inhibitor.

The terms "inhibitor," "repressor" or "antagonist" or "downregulator" interchangeably refer to a substance capable of detectably decreasing the expression or activity of a given gene or protein. The antagonist can decrease expression or activity 10%, 20%, 30%, 40%, 50%, 60%, 70%, 80%, 90% or more in comparison to a control in the absence of the antagonist. In certain instances, expression or activity is 1.5-fold, 2-fold, 3-fold, 4-fold, 5-fold, 10-fold or lower than the expression or activity in the absence of the antagonist.

The terms "thioredoxin" and "TXN" and "TRX" refer to a protein (including homologs, isoforms, and functional fragments thereof) with thioredoxin activity. The term includes any recombinant or naturally-occurring form of thioredoxin or variants thereof that maintain thioredoxin activity (e.g. within at least 30%, 40%, 50%, 60%, 70%, 80%, 90%, 95%, or 100% activity compared to wildtype thioredoxin). In embodiments, the thioredoxin protein encoded by the thioredoxin gene has the amino acid sequence set forth in or corresponding to Entrez 7295, UniProt P10599, or RefSeq (protein) NP_003320. In embodiments, the thioredoxin gene has the nucleic acid sequence set forth in RefSeq (mRNA) NM_003329. In embodiments, the amino acid sequence or nucleic acid sequence is the sequence known at the time of filing of the present application. In embodiments, the sequence corresponds to NP_003320.2. In embodiments, the sequence corresponds to NM_003329.3. In embodiments, the thioredoxin protein encoded by the thioredoxin gene has the amino acid sequence set forth in or corresponding RefSeq (protein) NP_001231867. In embodiments, the thioredoxin gene has the nucleic acid sequence set forth in RefSeq (mRNA) NM_001244938. In embodiments, the amino acid sequence or nucleic acid sequence is the sequence known at the time of filing of the present application. In embodiments, the sequence corresponds to NP_001231867.1. In embodiments, the sequence corresponds to NM_001244938.1. In embodiments, the thioredoxin is a human thioredoxin. In embodiments, the thioredoxin corresponds to the sequence:

(SEQ ID NO: 1)
MVKQIESKTAFQEALDAAGDKLVVVDFSATWCGPCKMIKPFFHSLSEKYS

NVIFLEVDVDDCQDVASECEVKCMPTFQFFKKGQKVGEFSGANKEKLEAT

INELV.

The terms "Thioredoxin-interacting protein" and "TXNIP" refer to a protein (including homologs, isoforms, and functional fragments thereof) which interacts with thioredoxin. The term includes any recombinant or naturally-occurring form of TXNIP or variants thereof that maintain TXNIP activity (e.g. within at least 30%, 40%, 50%, 60%, 70%, 80%, 90%, 95%, or 100% activity compared to wildtype TXNIP). In embodiments, the TXNIP protein encoded by the TXNIP gene has the amino acid sequence set forth in or corresponding to Entrez 10628, UniProt Q9H3M7, RefSeq (protein) NP_006463, or RefSeq (protein) NP_001300901. In embodiments, the TXNIP gene has the nucleic acid sequence set forth in RefSeq (mRNA) NM_006472. In embodiments, the TXNIP gene has the nucleic acid sequence set forth in RefSeq (mRNA) NM_001313972. In embodiments, the amino acid sequence or nucleic acid sequence is the sequence known at the time of filing of the present application. In embodiments, the sequence corresponds to NP_001300901. In embodiments, the sequence corresponds to NP_006463. In embodiments, the TXNIP protein encoded by the TXNIP gene has the amino acid sequence set forth in or corresponding RefSeq (protein) NP_00130901. In embodiments, the TXNIP gene has the nucleic acid sequence set forth in RefSeq (mRNA) NM_006472. In embodiments, the amino acid sequence or nucleic acid sequence is the sequence known at the time of filing of the present application. In embodiments, the sequence corresponds to NP_001231867.1. In embodiments, the TXNIP protein corresponds to the sequence:

(SEQ ID NO: 2)
MVMFKKIKSFEVVFNDPEKVYGSGEKVAGRVIVEVCEVTRVKAVRILACG

VAKVLWMQGSQQCKQTSEYLRYEDTLLLEDQPTGENEMVIMRPGNKYEYK

FGFELPQGPLGTSFKGKYGCVDYWVKAFLDRPSQPTQETKKNFEVVDLVD

VNTPDLMAPVSAKKEKKVSCMFIPDGRVSVSARIDRKGFCEGDEISIHAD

FENTCSRIVVPKAAIVARHTYLANGQTKVLTQKLSSVRGNHIISGTCASW

RGKSLRVQKIRPSILGCNILRVEYSLLIYVSVPGSKKVILDLPLVIGSRS

GLSSRTSSMASRTSSEMSWVDLNIPDTPEAPPCYMDVIPEDHRLESPTTP

LLDDMDGSQDSPIFMYAPEFKFMPPPTYTEVDPCILNNNNVQ.

The term "expression" includes any step involved in the production of the polypeptide including, but not limited to, transcription, post-transcriptional modification, translation, post-translational modification, and secretion. Expression can be detected using conventional techniques for detecting protein (e.g., ELISA, Western blotting, flow cytometry, immunofluorescence, immunohistochemistry, etc.).

The term "modulator" refers to a composition that increases or decreases the level of a target molecule or the function of a target molecule or the physical state of the target of the molecule relative to the absence of the modulator. The term "modulate" is used in accordance with its plain ordinary meaning and refers to the act of changing or varying one or more properties. "Modulation" refers to the process of changing or varying one or more properties. For example, as applied to the effects of a modulator on a target protein, to modulate means to change by increasing or decreasing a property or function of the target molecule or the amount of the target molecule.

The term "associated" or "associated with" in the context of a substance or substance activity or function associated with a disease (e.g. a protein associated disease, diabetes associated complication (e.g., nephropathy, retinopathy, neuropathy, cardiovascular disease, and inflammation), metabolic disorder associated disease (e.g., diabetes, inflammatory disease, or infectious disease)) means that the disease is caused by (in whole or in part), or a symptom of the disease is caused by (in whole or in part) the substance or substance activity or function. In embodiments, the TXNIP-associated disease is diabetes, diabetic retinopathy, diabetic nephropathy, diabetic neuropathy, or cardiovascular disease. In embodiments, the TXNIP-TRX-associated disease is diabetic retinopathy, diabetic nephropathy, diabetic neuropathy, or cardiovascular disease.

The term "aberrant" as used herein refers to different from normal. When used to describe enzymatic activity or protein function, aberrant refers to activity or function that is greater or less than a normal control or the average of normal non-diseased control samples. Aberrant activity may refer to an amount of activity that results in a disease, wherein returning the aberrant activity to a normal or non-disease-associated amount (e.g. by administering a compound or using a method as described herein), results in reduction of the disease or one or more disease symptoms.

The term "signaling pathway" as used herein refers to a series of interactions between cellular and optionally extracellular components (e.g. proteins, nucleic acids, small molecules, ions, lipids) that conveys a change in one component to one or more other components, which in turn may convey a change to additional components, which is optionally propogated to other signaling pathway components. For example, binding of a thioredoxin protein with a compound as described herein may reduce the interactions between the thioredoxin protein and downstream effectors or signaling pathway components, resulting in changes in cell growth, proliferation, or survival.

In this disclosure, "comprises," "comprising," "containing" and "having" and the like can have the meaning ascribed to them in U.S. Patent law and can mean "includes," "including," and the like. "Consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

The terms "disease" or "condition" refer to a state of being or health status of a patient or subject capable of being treated with the compounds or methods provided herein. The disease may be diabetes. The disease may be a metabolic disorder. The disease may be an inflammatory disease. The disease may be an infectious disease. In embodiments, the disease is diabetes (e.g., type 1 diabetes or type 2 diabetes), insulin resistance, metabolic syndrome, atherosclerosis, obesity, hyperlipidemia, hyperglycemia, high serum triglycerides, and/or high blood pressure.

Examples of inflammatory diseases include autoimmune diseases, arthritis, rheumatoid arthritis, psoriatic arthritis, juvenile idiopathic arthritis, multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, auto-immune thyroiditis, Behcet's disease, Crohn's disease, ulcerative colitis, bullous pemphigoid, sarcoidosis, ichthyosis, Graves ophthalmopathy, inflammatory bowel disease, Addison's disease, Vitiligo, asthma, allergic asthma, acne vulgaris, celiac disease, chronic prostatitis, inflammatory bowel disease, pelvic inflammatory disease, reperfusion injury, ischemia reperfusion injury, stroke, sarcoidosis, transplant rejection, interstitial cystitis, atherosclerosis, scleroderma, and atopic dermatitis.

As used herein, the term "inflammatory disease" refers to a disease or condition characterized by aberrant inflammation (e.g. an increased level of inflammation compared to a control such as a healthy person not suffering from a disease). Examples of inflammatory diseases include traumatic brain injury, arthritis, rheumatoid arthritis, psoriatic arthritis, juvenile idiopathic arthritis, multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, auto-immune thyroiditis, Behcet's disease, Crohn's disease, ulcerative colitis, bullous pemphigoid, sarcoidosis, ichthyosis, Graves ophthalmopathy, inflammatory bowel disease, Addison's disease, Vitiligo, asthma, asthma, allergic asthma, acne vulgaris, celiac disease, chronic prostatitis, inflammatory bowel disease, pelvic inflammatory disease, reperfusion injury, sarcoidosis, transplant rejection, interstitial cystitis, atherosclerosis, and atopic dermatitis. In embodiments, the inflammatory disease is inflammation.

The terms "treating", or "treatment" refers to any indicia of success in the therapy or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof, may include prevention of an injury, pathology, condition, or disease. In embodiments, treating is preventing. In embodiments, treating does not include preventing. In embodiments, treating refers to treating a subject having a disease.

"Treating" or "treatment" as used herein (and as well-understood in the art) also broadly includes any approach for obtaining beneficial or desired results in a subject's condition, including clinical results. Beneficial or desired clinical results can include, but are not limited to, alleviation or amelioration of one or more symptoms or conditions, diminishment of the extent of a disease, stabilizing (i.e., not worsening) the state of disease, prevention of a disease's transmission or spread, delay or slowing of disease progression, amelioration or palliation of the disease state, diminishment of the reoccurrence of disease, and remission, whether partial or total and whether detectable or undetectable. In other words, "treatment" as used herein includes any cure, amelioration, or prevention of a disease. Treatment may prevent the disease from occurring; inhibit the disease's spread; relieve the disease's symptoms (e.g., symptoms of diabetes, for example including increased thirst and urination, fatigue, or blurred vision), fully or partially remove the disease's underlying cause, shorten a disease's duration, or do a combination of these things.

"Treating" and "treatment" as used herein include prophylactic treatment. Treatment methods include administering to a subject a therapeutically effective amount of an active agent. The administering step may consist of a single administration or may include a series of administrations. The length of the treatment period depends on a variety of factors, such as the severity of the condition, the age of the patient, the concentration of active agent, the activity of the compositions used in the treatment, or a combination thereof. It will also be appreciated that the effective dosage of an agent used for the treatment or prophylaxis may increase or decrease over the course of a particular treatment or prophylaxis regime. Changes in dosage may result and become apparent by standard diagnostic assays known in the art. In some instances, chronic administration may be required. For example, the compositions are administered to the subject in an amount and for a duration sufficient to treat the patient. In embodiments, the treating or treatment is no prophylactic treatment.

The term "prevent" refers to a decrease in the occurrence of a disease (e.g., metabolic disorder) or disease symptoms (e.g., diabetes-associated disease symptoms) in a patient. As indicated above, the prevention may be complete (no detectable symptoms) or partial, such that fewer symptoms are observed than would likely occur absent treatment. In embodiments, the diabetes-associated disease symptom is a symptom associated with nephropathy, retinopathy, neuropathy, cardiovascular disease, or inflammation.

"Patient" or "subject in need thereof" refers to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, a patient is human.

An "effective amount" is an amount sufficient for a compound to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

The term "therapeutically effective amount," as used herein, refers to that amount of the therapeutic agent sufficient to ameliorate the disorder, as described above. For example, for the given parameter, a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control.

Dosages may be varied depending upon the requirements of the patient and the compound being employed. The dose administered to a patient, in the context of the present disclosure, should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

As used herein, the term "administering" means oral administration, administration as a suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. In embodiments, the administering does not include administration of any active agent other than the recited active agent.

"Co-administer" it is meant that a composition described herein is administered at the same time, just prior to, or just after the administration of one or more additional therapies. The compounds provided herein can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation). The compositions of the present disclosure can be delivered transdermally, by a topical route, or formulated as applicator sticks, solutions, suspensions, emulsions, gels, creams, ointments, pastes, jellies, paints, powders, and aerosols.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaroytic cells. Prokaryotic cells include but are not limited to bacteria. Eukaryotic cells include but are not limited to yeast cells and cells derived from plants and animals, for example mammalian, insect (e.g., *spodoptera*) and human cells. Cells may be useful when they are naturally nonadherent or have been treated not to adhere to surfaces, for example by trypsinization.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity of a protein in the absence of a compound as described herein (including embodiments and examples).

The terms "bind" and "bound" as used herein is used in accordance with its plain and ordinary meaning and refers to the association between atoms or molecules. The association can be direct or indirect. For example, bound atoms or molecules may be direct, e.g., by covalent bond or linker (e.g. a first linker or second linker), or indirect, e.g., by non-covalent bond (e.g. electrostatic interactions (e.g. ionic bond, hydrogen bond, halogen bond), van der Waals interactions (e.g. dipole-dipole, dipole-induced dipole, London dispersion), ring stacking (pi effects), hydrophobic interactions and the like).

The term "thioredoxin activity" as used herein refers to the biological activity of the protein. In embodiments, the thioredoxin activity may be antioxidant activity by facilitating the reduction of other proteins, for example by cysteine thiol-disulfide exchange, at a dithiol-disulfide active site. The diseases described herein (e.g., metabolic disorder, cardiovascular disease, or inflammatory disease) may be associated with aberrant (e.g., reduced) thioredoxin activity.

The term "thioredoxin interacting protein-thioredoxin protein (TXNIP-TRX) complex" as used herein refers to a thioredoxin protein bonded (e.g., covalently bonded) to a thioredoxin interacting protein. In embodiments, the TXNIP-TRX complex is detected by co-immunoprecipitation method (e.g., a method in which an antibody to TRX is used to immunoprecipitate it from cells and its association with TXNIP is detected subsequently by Western Blotting with an antibody to TXNIP).

The term "capable of binding" as used herein refers to a moiety (e.g. a compound as described herein) that is able to measurably bind to a target (e.g., a TXNIP protein or a TXNIP-TRX complex). In embodiments, where a moiety is capable of binding a target, the moiety is capable of binding with a Kd of less than about 10 μM, 5 μM, 1 μM, 500 nM, 250 nM, 100 nM, 75 nM, 50 nM, 25 nM, 15 nM, 10 nM, 5 nM, 1 nM, or about 0.1 nM.

As used herein, the term "conjugated" when referring to two moieties means the two moieties are bonded, wherein the bond or bonds connecting the two moieties may be covalent or non-covalent. In embodiments, the two moieties are covalently bonded to each other (e.g. directly or through a covalently bonded intermediary). In embodiments, the two moieties are non-covalently bonded (e.g. through ionic bond(s), van der waal's bond(s)/interactions, hydrogen bond(s), polar bond(s), or combinations or mixtures thereof).

The terms "metabolic disorder" refers to a disorder characterized by one or more abnormal metabolic processes in a subject. In embodiments, a metabolic disorder may be associated with, related to, or may be diabetes (e.g., type 1 diabetes or type 2 diabetes), insulin resistance, metabolic syndrome, obesity, hyperlipidemia, hyperglycemia, high serum triglycerides, and/or high blood pressure. In embodiments, a metabolic disorder may be associated with, related to, or may be a diabetes associated disease selected from nephropathy, retinopathy, neuropathy, cardiovascular disease, or inflammation. In embodiments, a metabolic disorder may be associated with, related to, or may be nephropathy, retinopathy, neuropathy, cardiovascular disease, or inflammation.

A "TXNIP-TRX complex-associated disease" as used herein refers to a disease associated with aberrant TXNIP-TRX complex activity. In embodiments, the TXNIP-TRX complex-associated disease is a metabolic disorder, or cardiovascular disease. The diseases described herein (e.g., metabolic disorder, cardiovascular disease, or inflammatory disease) may be associated with aberrant (e.g., reduced) thioredoxin activity.

II. Compounds

In an aspect is provided a compound (e.g., a TXNIP-TRX complex inhibitor or a TXNIP expression inhibitor) having the formula:

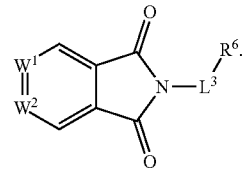

(I)

$W^1$ is —$CR^1$=, —N=, or —CH=. $W^2$ is —$CR^2$=, —N=, or —CH=. $R^1$ is independently halogen, —$CX^1_3$, —$CHX^1_2$, —$CH_2X^1$, —$OCX^1_3$, —$OCH_2X^1$, —$OCHX^1_2$, substituted or unsubstituted alkyl, or substituted or unsubstituted heteroalkyl. $R^2$ is independently halogen, —$CX^2_3$, —$CHX^2_2$, —$CH_2X^2$, —$OCX^2_3$, —$OCH_2X^2$, —$OCHX^2_2$, substituted or unsubstituted alkyl, or substituted or unsubstituted heteroalkyl. $L^3$ is a bond, —N($R^3$)—, —C(O)—, —C(O)N($R^3$)—, —N($R^3$)C(O)—, —N(H)—, —C(O)N(H)—, —N(H)C(O)—, —C(O)O—, substituted or unsubstituted alkylene, or substituted or unsubstituted heteroalkylene. $R^3$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl. $R^6$ is independently hydrogen, halogen, —$CX^6_3$, —$CHX^6_2$, —$CH_2X^6$, —$OCX^6_3$, —$OCH_2X^6$, —$OCHX^6_2$, —CN, —$SR^{6D}$, —$SOR^{6D}$, —$SO_2R^{6D}$, —$SO_3R^{6D}$, —$SO_4R^{6D}$, —$SONR^{6A}R^{6B}$, —$SO_2NR^{6A}R^{6B}$, —$NR^{6C}C(O)NR^{6A}R^{6B}$, —N(O), —N(O)$_2$, —$NR^{6A}R^{6B}$, —C(O)$R^{6C}$, —C(O)—$OR^{6C}$, —C(O)$NR^{6A}R^{6B}$, —$OR^{6D}$, —$NR^{6A}SO_2R^{6D}$, —$NR^{6A}C(O)R^{6C}$, —$NR^{6A}C(O)OR^{6C}$, —$NR^{6A}OR^{6C}$, —$NR^{6C}NR^{6A}R^{6B}$, —C(O)$NR^{6C}NR^{6A}R^{6B}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl. $R^{6A}$, $R^{6B}$, $R^{6C}$, and $R^{6D}$ are each independently hydrogen, oxo, halogen, —CCl₃, —CBr₃, —CF₃, —CI₃, —CHCl₂, —CHBr₂, —CHF₂, —CHI₂, —CH₂Cl, —CH₂Br, —CH₂F, —CH₂I, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr₃, —OCI₃, —OCHCl₂, —OCHBr₂, —OCHI₂, —OCHF₂, —OCH₂Cl, —OCH₂Br, —OCH₂I, —OCH₂F, —N₃, —SF₅, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl. $X^1$, $X^2$, and $X^6$ are independently —F, —Cl, —Br, or —I.

In embodiments, the compound has the formula:

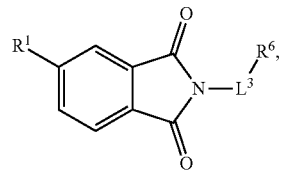

(IA)

wherein $L^3$ and $R^6$ are as described herein.

In embodiments, the compound has the formula:

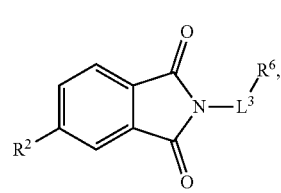

(IB)

wherein $L^3$ and $R^6$ are as described herein.

In embodiments, the compound has the formula:

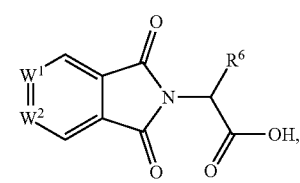

(IC)

wherein $L^3$ and $R^6$ are as described herein.

In embodiments, the compound has the formula:

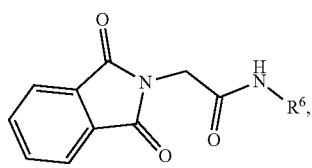

(ID)

wherein $R^1$, $R^2$, $L^3$, and $R^6$ are as described herein.

In embodiments, the compound has the formula:

(IE)

wherein $R^1$, $L^3$, and $R^6$ are as described herein.

In embodiments, the compound has the formula:

(IF)

wherein $R^2$, $L^3$, and $R^6$ are as described herein.

In embodiments, the compound has the formula:

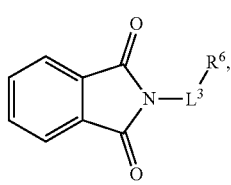

wherein $W^1$, $W^2$, and $R^6$ are as described herein.

In embodiments, the compound has the formula:

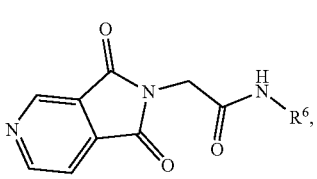

wherein $R^6$ is as described herein. In embodiments, the compound has the formula:

wherein $R^6$ is as described herein. In embodiments, the compound has the formula:

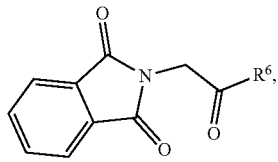

wherein $R^6$ is as described herein. In embodiments, the compound has the formula:

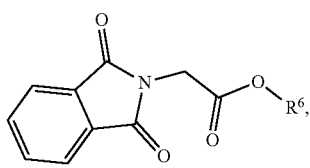

wherein $R^6$ is as described herein. In embodiments, the compound has the formula:

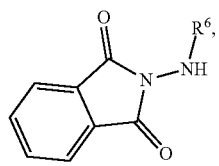

wherein $R^6$ is as described herein.

In embodiments, the compound has the formula:

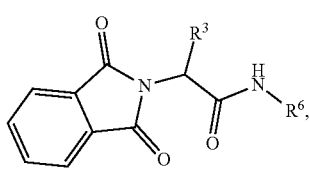

wherein $R^3$ and $R^6$ are as described herein. In embodiments, the compound has the formula:

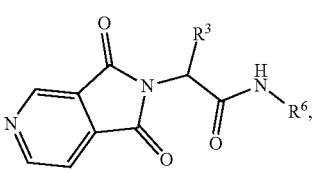

wherein $R^3$ and $R^6$ are as described herein. In embodiments, the compound has the formula:

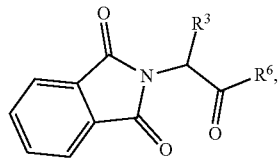

wherein $R^3$ and $R^6$ are as described herein.

In embodiments, the compound has the formula:

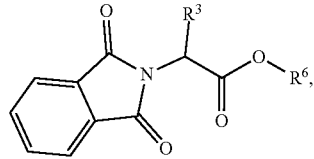

wherein $R^3$ and $R^6$ are as described herein. In embodiments, the compound has the formula:

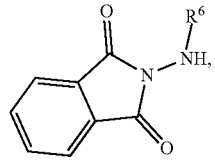

wherein $R^6$ is as described herein.

In embodiments, the compound has the formula:

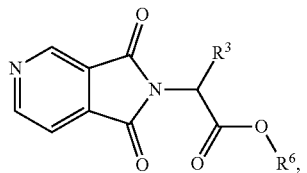

wherein $R^3$ and $R^6$ are as described herein. In embodiments, the compound has the formula:

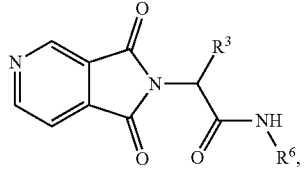

$R^6$, wherein $R^3$ and $R^6$ are as described herein. In embodiments, the compound has the formula:

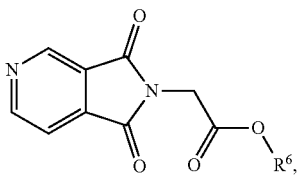

wherein $R^6$ is as described herein. In embodiments, the compound has the formula:

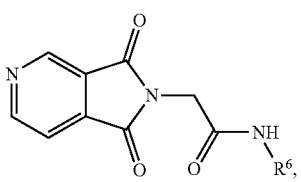

$R^6$, wherein $R^6$ is as described herein. In embodiments, the compound has the formula:

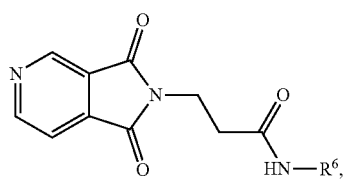

wherein $R^6$ is as described herein. In embodiments, the compound has the formula:

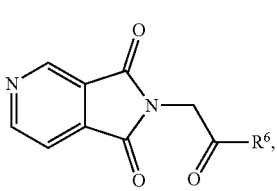

wherein $R^6$ is as described herein. In embodiments, the compound has the formula:

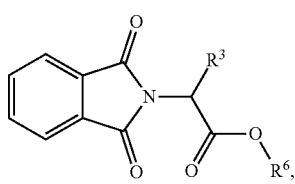

$R^6$, wherein $R^3$ and $R^6$ are as described herein. In embodiments, the compound has the formula:

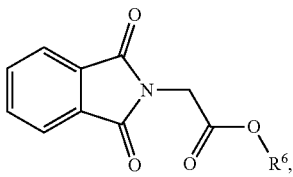

$R^6$, wherein $R^6$ is as described herein. In embodiments, the compound has the formula:

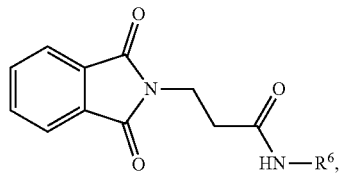

wherein $R^6$ is as described herein. In embodiments, the compound has the formula:

wherein $R^6$ is as described herein. In embodiments, the compound has the formula:

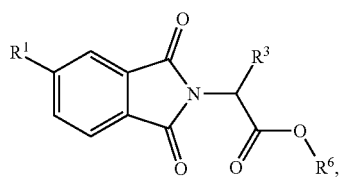

$R^6$ wherein $R^6$ is as described herein. In embodiments, the compound has the formula:

wherein $R^1$, $R^3$, and $R^6$ are as described herein. In embodiments, the compound has the formula:

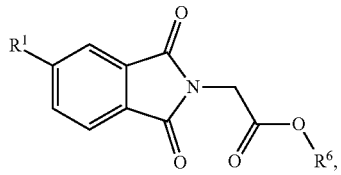

wherein $R^1$ and $R^6$ are as described herein. In embodiments, the compound has the formula:

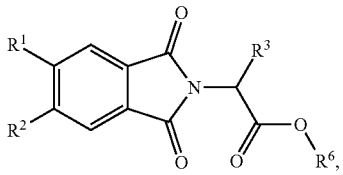

$R^6$, wherein $R^1$, $R^2$, $R^3$, and $R^6$ are as described herein. In embodiments, the compound has the formula:

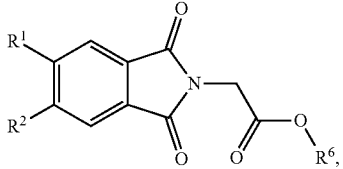

wherein $R^1$, $R^2$, and $R^6$ are as described herein. In embodiments, the compound has the formula:

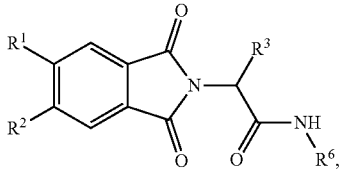

wherein $R^1$, $R^2$, $R^3$, and $R^6$ are as described herein. In embodiments, the compound has the formula:

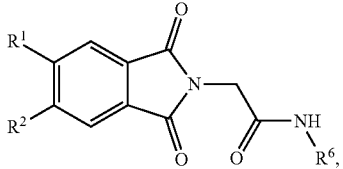

$R^6$, wherein $R^1$, $R^2$, and $R^6$ are as described herein. In embodiments, the compound has the formula

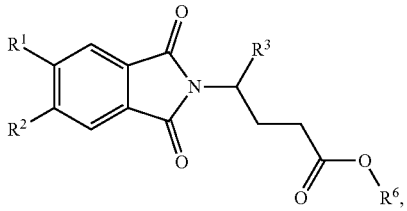

wherein $R^1$, $R^2$, $R^3$ and $R^6$ are as described herein.

In embodiments, $W^1$ is $-N=$. In embodiments, $W^1$ is $-CH=$. In embodiments, $W^1$ is $-CR^1=$, wherein $R^1$ is as described herein. In embodiments, $W^1$ is $-CX^1=$, wherein $X^1$ is a halogen. In embodiments, $W^1$ is

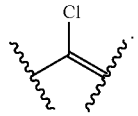 [SMILES: *C(=*)Cl]

In embodiments, $W^2$ is $-N=$. In embodiments, $W^2$ is $-CH=$. In embodiments, $W^2$ is $-CR^2=$, wherein $R^2$ is as described herein. In embodiments, $W^2$ is $-CX^2=$, wherein $X^2$ is a halogen. In embodiments, $W^2$ is

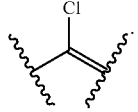 [SMILES: *C(=*)Cl]

In embodiments, $R^1$ is independently halogen, $-CX^1_3$, $-CHX^1_2$, $-CH_2X^1$, $-OCX^1_3$, $-OCH_2X^1$, $-OCHX^1_2$, substituted or unsubstituted alkyl (e.g., $C_1$-$C_8$, $C_1$-$C_6$, $C_1$-$C_4$, or $C_1$-$C_2$), or substituted or unsubstituted heteroalkyl (e.g., 2 to 8 membered, 2 to 6 membered, 4 to 6 membered, 2 to 3 membered. In embodiments, $R^1$ is independently halogen, $-CX^1_3$, $-CHX^1_2$, $-CH_2X^1$, $-OCX^1_3$, $-OCH_2X^1$, $-OCHX^1_2$, substituted (e.g., substituted with a substituent group, a size-limited substituent group, or lower substituent group) or unsubstituted alkyl, substituted (e.g., substituted with a substituent group, a size-limited substituent group, or lower substituent group) or unsubstituted heteroalkyl. In embodiments, $R^1$ is independently halogen, $-CX^1_3$, $-CHX^1_2$, $-CH_2X^1$, $-OCX^1_3$, $-OCH_2X^1$, $-OCHX^1_2$, unsubstituted alkyl (e.g., $C_1$-$C_8$, $C_1$-$C_6$, $C_1$-$C_4$, or $C_1$-$C_2$), or unsubstituted heteroalkyl (e.g., 2 to 8 membered, 2 to 6 membered, 4 to 6 membered, 2 to 3 membered, or 4 to 5 membered). In embodiments, $R^1$ is independently halogen, $-CX^1_3$, $-CHX^1_2$, $-CH_2X^1$, $-OCX^1_3$, $-OCH_2X^1$, $-OCHX^1_2$, unsubstituted $C_1$-$C_4$ alkyl, or unsubstituted 2 to 4 membered heteroalkyl.

In embodiments, a substituted $R^1$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^1$ is substituted with a plurality of groups selected from substituent groups, size-limited substituent groups, and lower substituent groups; each substituent group, size-limited substituent group, and/or lower substituent group may optionally be different. In embodiments, when $R^1$ is substituted, it is substituted with at least one substituent group. In embodiments, when $R^1$ is substituted, it is substituted with at least one size-limited substituent group. In embodiments, when $R^1$ is substituted, it is substituted with at least one lower substituent group.

In embodiments, $R^1$ is halogen. In embodiments, $R^1$ is —Cl.

In embodiments, $R^2$ is independently halogen, —$CX^2_3$, —$CHX^2_2$, —$CH_2X^2$, —$OCX^2_3$, —$OCH_2X^2$, —$OCHX^2_2$, substituted or unsubstituted alkyl (e.g., $C_1$-$C_8$, $C_1$-$C_6$, $C_1$-$C_4$, or $C_1$-$C_2$), or substituted or unsubstituted heteroalkyl (e.g., 2 to 8 membered, 2 to 6 membered, 4 to 6 membered, 2 to 3 membered. In embodiments, $R^2$ is independently halogen, —$CX^2_3$, —$CHX^2_2$, —$CH_2X^2$, —$OCX^2_3$, —$OCH_2X^2$, —$OCHX^2_2$, substituted (e.g., substituted with a substituent group, a size-limited substituent group, or lower substituent group) or unsubstituted alkyl, substituted (e.g., substituted with a substituent group, a size-limited substituent group, or lower substituent group) or unsubstituted heteroalkyl. In embodiments, $R^2$ is independently halogen, —$CX^2_3$, —$CHX^2_2$, —$CH_2X^2$, —$OCX^2_3$, —$OCH_2X^2$, —$OCHX^2_2$, unsubstituted alkyl (e.g., $C_1$-$C_8$, $C_1$-$C_6$, $C_1$-$C_4$, or $C_1$-$C_2$), or unsubstituted heteroalkyl (e.g., 2 to 8 membered, 2 to 6 membered, 4 to 6 membered, 2 to 3 membered, or 4 to 5 membered). In embodiments, $R^2$ is independently halogen, —$CX^2_3$, —$CHX^2_2$, —$CH_2X^2$, —$OCX^2_3$, —$OCH_2X^2$, —$OCHX^2_2$, unsubstituted $C_1$-$C_4$ alkyl, or unsubstituted 2 to 4 membered heteroalkyl.

In embodiments, a substituted $R^2$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^2$ is substituted with a plurality of groups selected from substituent groups, size-limited substituent groups, and lower substituent groups; each substituent group, size-limited substituent group, and/or lower substituent group may optionally be different. In embodiments, when $R^2$ is substituted, it is substituted with at least one substituent group. In embodiments, when $R^2$ is substituted, it is substituted with at least one size-limited substituent group. In embodiments, when $R^2$ is substituted, it is substituted with at least one lower substituent group.

In embodiments, $R^2$ is halogen. In embodiments, $R^2$ is —Cl.

In embodiments, $L^3$ is a bond, —N($R^3$)—, —C(O)—, —C(O)N($R^3$)—, —N($R^3$)C(O)—, —N(H)—, —C(O)N(H)—, —N(H)C(O)—, —C(O)O—, substituted or unsubstituted $C_1$-$C_6$ alkylene, or substituted or unsubstituted 2 to 6 membered heteroalkylene. In embodiments, $L^3$ is a bond, —N($R^3$)—, —C(O)—, —C(O)N($R^3$)—, —N($R^3$)C(O)—, —N(H)—, —C(O)N(H)—, —N(H)C(O)—, —C(O)O—, $R^3$-substituted or unsubstituted alkylene (e.g., $C_1$-$C_8$, $C_1$-$C_6$, $C_1$-$C_4$, or $C_1$-$C_2$), or $R^3$-substituted or unsubstituted heteroalkylene (e.g., 2 to 8 membered, 2 to 6 membered, 4 to 6 membered, 2 to 3 membered, or 4 to 5 membered). In embodiments, $L^3$ is a bond, —N($R^3$)—, —C(O)—, —C(O)N($R^3$)—, —N($R^3$)C(O)—, —N(H)—, —C(O)N(H)—, —N(H)C(O)—, —C(O)O—, unsubstituted alkylene (e.g., $C_1$-$C_8$, $C_1$-$C_6$, $C_1$-$C_4$, or $C_1$-$C_2$), or unsubstituted heteroalkylene (e.g., 2 to 8 membered, 2 to 6 membered, 4 to 6 membered, 2 to 3 membered, or 4 to 5 membered).

In embodiments, $L^3$ is a bond, —N($R^3$)—, —C(O)—, —C(O)N($R^3$)—, —N($R^3$)C(O)—, —N(H)—, —C(O)N(H)—, —N(H)C(O)—, —C(O)O—, substituted or unsubstituted $C_1$-$C_6$ alkylene, or substituted or unsubstituted 2 to 6 membered heteroalkylene. In embodiments, $L^3$ is a bond, —N($R^3$)—, —C(O)—, —C(O)N($R^3$)—, —N($R^3$)C(O)—, —N(H)—, —C(O)N(H)—, —N(H)C(O)—, —C(O)O—, $R^3$-substituted or unsubstituted $C_1$-$C_6$ alkylene, or $R^3$-substituted or unsubstituted 2 to 6 membered heteroalkylene.

In embodiments, $L^3$ is a bond, —N($R^3$)—, —C(O)—, —C(O)N($R^3$)—, —N($R^3$)C(O)—, —N(H)—, —C(O)N(H)—, —N(H)C(O)—, —C(O)O—, unsubstituted alkylene (e.g., $C_1$-$C_8$, $C_1$-$C_6$, $C_1$-$C_4$, or $C_1$-$C_2$), or unsubstituted heteroalkylene (e.g., 2 to 8 membered, 2 to 6 membered, 4 to 6 membered, 2 to 3 membered, or 4 to 5 membered).

In embodiments, $L^3$ is —N(H)— or $R^3$-substituted or unsubstituted $C_1$-$C_6$ alkylene. In embodiments, $L^3$ is —N(H)—. In embodiments, $L^3$ is $R^3$-substituted or unsubstituted $C_1$-$C_6$ alkylene.

In embodiments, $R^3$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered). In embodiments, $R^3$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

In embodiments, $R^3$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, $R^4$-substituted or unsubstituted alkyl (e.g., $C_1$-$C_8$, $C_1$-$C_6$, $C_1$-$C_4$, or $C_1$-$C_2$), $R^4$-substituted or unsubstituted heteroalkyl (e.g., 2 to 8 membered, 2 to 6 membered, 4 to 6 membered, 2 to 3 membered, or 4 to 5 membered), $R^4$-substituted or unsubstituted cycloalkyl (e.g., $C_3$-$C_8$, $C_3$-$C_6$, $C_4$-$C_6$, or $C_5$-$C_6$), $R^4$-substituted or unsubstituted heterocycloalkyl (e.g., 3 to 8 membered, 3 to 6 membered, 4 to 6 membered, 4 to 5 membered, or 5 to 6 membered), $R^4$-substituted or unsubstituted aryl (e.g., $C_6$-$C_{10}$ or phenyl), or $R^4$-substituted or unsubstituted heteroaryl (e.g., 5 to 10 membered, 5 to 9 membered, or 5 to 6 membered).

In embodiments, $R^3$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, $R^4$-substituted or unsubstituted $C_1$-$C_8$ alkyl, $R^4$-substituted or unsubstituted 2 to 8 membered heteroalkyl, $R^4$-substituted or unsubstituted $C_3$-$C_5$ cycloalkyl, $R^4$-substituted or unsubstituted 3 to 8 membered heterocycloalkyl, $R^4$-substituted or unsubstituted $C_6$-$C_{10}$ aryl, or $R^4$-substituted or unsubstituted 5 to 10 membered heteroaryl. In embodiments, $R^3$ is independently oxo. In embodiments, $R^3$ is independently unsubstituted $C_1$-$C_4$ alkyl.

In embodiments, $R^3$ is independently —COOH, —$CONH_2$, $R^4$-substituted or unsubstituted $C_1$-$C_4$ alkyl, $R^4$-substituted or unsubstituted 2 to 4 membered heteroalkyl, $R^4$-substituted or unsubstituted $C_5$-$C_6$ cycloalkyl, $R^4$-substituted or unsubstituted 5 to 6 membered heterocycloalkyl, $R^4$-substituted or unsubstituted $C_6$-$C_{10}$ aryl, or $R^4$-substituted or unsubstituted 5 to 10 membered heteroaryl. In embodiments, $R^3$ is independently —COOH. In embodiments, $R^3$ is independently unsubstituted $C_1$-$C_4$ alkyl. In embodiments, $R^3$ is unsubstituted methyl. In embodiments, $R^3$ is independently unsubstituted isopropyl. In embodiments, $R^3$ is independently unsubstituted isobutyl. In embodiments, $R^3$ is independently unsubstituted n-butyl. In embodiments, $R^3$ is independently $R^4$-substituted $C_1$-$C_4$ alkyl. In embodiments, $R^3$ is independently phenyl-substituted $C_1$ alkyl. In embodiments, $R^3$ is independently $R^4$-substituted or unsubstituted 2 to 4 membered heteroalkyl. In embodiments, $R^3$ is independently

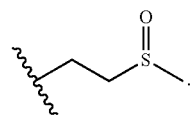 [SMILES: *CCS(C)=O]

In embodiments, $R^3$ is independently —$S(O)CH_3$. In embodiments, $R^3$ is independently $R^4$-substituted or unsubstituted $C_6$-$C_{10}$ aryl. In embodiments, $R^3$ is independently unsubstituted phenyl. In embodiments, $R^3$ is independently

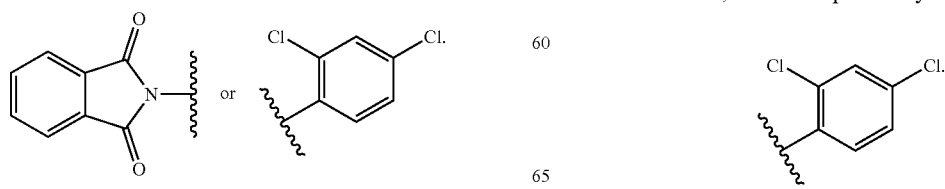

In embodiments, $R^3$ is independently

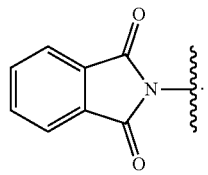 [SMILES: *N1C(=O)c2ccccc2C1=O]

In embodiments, $R^3$ is independently

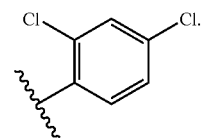 [SMILES: *c1ccc(Cl)cc1Cl]

In embodiments, $R^3$ is independently unsubstituted isopropyl.

In embodiments, $R^3$ is independently —COOH, —$CONH_2$, $R^4$-substituted or unsubstituted $C_1$-$C_4$ alkyl, $R^4$-substituted or unsubstituted 2 to 4 membered heteroalkyl, $R^4$-substituted or unsubstituted $C_5$-$C_6$ cycloalkyl, $R^4$-substituted or unsubstituted 5 to 6 membered heterocycloalkyl, $R^4$-substituted or unsubstituted $C_6$-$C_{10}$ aryl, or $R^4$-substituted or unsubstituted 5 to 10 membered heteroaryl. In embodiments, $R^3$ is independently —COOH. In embodiments, $R^3$ is independently $R^4$-substituted or unsubstituted 2 to 4 membered heteroalkyl. In embodiments, $R^3$ is independently —$S(O)CH_3$. In embodiments, $R^3$ is independently $R^4$-substituted or unsubstituted $C_6$-$C_{10}$ aryl. In embodiments, $R^3$ is independently unsubstituted phenyl. In embodiments, $R^3$ is independently

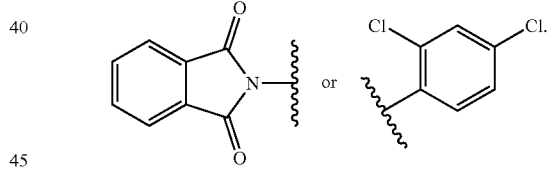

In embodiments, $R^3$ is independently

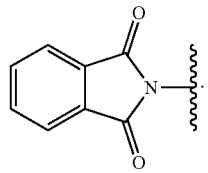 [SMILES: *N1C(=O)c2ccccc2C1=O]

In embodiments, $R^3$ is independently $R^4$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl (e.g., C$_1$-C$_8$, C$_1$-C$_6$, C$_1$-C$_4$, or C$_1$-C$_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., C$_3$-C$_8$, C$_3$-C$_6$, C$_4$-C$_6$, or C$_5$-C$_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., C$_6$-C$_{10}$ or phenyl), or substituted or unsubstituted heteroaryl (e.g., 5 to 10 membered, 5 to 9 membered, or 5 to 6 membered). In embodiments, $R^4$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 8 membered, 3 to 6 membered, 4 to 6 membered, 4 to 5 membered, or 5 to 6 membered), unsubstituted aryl (e.g., C$_6$-C$_{10}$ or phenyl), or unsubstituted heteroaryl (e.g., 5 to 10 membered, 5 to 9 membered, or 5 to 6 membered).

In embodiments, $R^4$ is independently oxo or halogen. In embodiments, $R^4$ is independently $R^5$-substituted or unsubstituted C$_6$-C$_{10}$ aryl. In embodiments, $R^4$ is independently unsubstituted phenyl.

In embodiments, $R^4$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, $R^5$-substituted or unsubstituted alkyl (e.g., C$_1$-C$_8$, C$_1$-C$_6$, C$_1$-C$_4$, or C$_1$-C$_2$), $R^5$-substituted or unsubstituted heteroalkyl (e.g., 2 to 8 membered, 2 to 6 membered, 4 to 6 membered, 2 to 3 membered, or 4 to 5 membered), $R^5$-substituted or unsubstituted cycloalkyl (e.g., C$_3$-C$_8$, C$_3$-C$_6$, C$_4$-C$_6$, or C$_5$-C$_6$), $R^5$-substituted or unsubstituted heterocycloalkyl (e.g., 3 to 8 membered, 3 to 6 membered, 4 to 6 membered, 4 to 5 membered, or 5 to 6 membered), $R^5$-substituted or unsubstituted aryl (e.g., C$_6$-C$_{10}$ or phenyl), or $R^5$-substituted or unsubstituted heteroaryl (e.g., 5 to 10 membered, 5 to 9 membered, or 5 to 6 membered).

In embodiments, $R^4$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, $R^5$-substituted or unsubstituted C$_1$-C$_8$ alkyl, $R^5$-substituted or unsubstituted 2 to 8 membered heteroalkyl, $R^5$-substituted or unsubstituted C$_3$-C$_8$ cycloalkyl, $R^5$-substituted or unsubstituted 3 to 8 membered heterocycloalkyl, $R^5$-substituted or unsubstituted C$_6$-C$_{10}$ aryl, or $R^5$-substituted or unsubstituted 5 to 10 membered heteroaryl.

$R^5$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 8 membered, 3 to 6 membered, 4 to 6 membered, 4 to 5 membered, or 5 to 6 membered), unsubstituted aryl (e.g., C$_6$-C$_{10}$ or phenyl), or unsubstituted heteroaryl (e.g., 5 to 10 membered, 5 to 9 membered, or 5 to 6 membered).

In embodiments, $R^5$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, unsubstituted C$_1$-C$_5$ alkyl, unsubstituted 2 to 8 membered heteroalkyl, unsubstituted C$_3$-C$_8$ cycloalkyl, unsubstituted 3 to 8 membered heterocycloalkyl, unsubstituted C$_6$-C$_{10}$ aryl, or unsubstituted 5 to 10 membered heteroaryl.

In embodiments, $R^6$ is independently hydrogen, halogen, —CX$^6_3$, —CHX$^6_2$, —CH$_2$X$^6$, —OCX$^6_3$, —OCH$_2$X$^6$, —OCHX$^6_2$, —CN, —SR$^{6D}$, —SOR$^{6D}$, —SO$_2$R$^{6D}$, —SO$_3$R$^{6D}$, —SO$_4$R$^{6D}$, —SONR$^{6A}$R$^{6B}$, —SO$_2$NR$^{6A}$R$^{6B}$, —NR$^{6C}$C(O)NR$^{6A}$R$^{6B}$, —N(O), —N(O)$_2$, —NR$^{6A}$R$^{6B}$, —C(O)R$^{6C}$, —C(O)—OR$^{6C}$, —C(O)NR$^{6A}$R$^{6B}$, —OR$^{6D}$, —NR$^{6A}$SO$_2$R$^{6D}$, —NR$^{6A}$C(O)R$^{6C}$, —NR$^{6A}$C(O)OR$^{6C}$, —NR$^{6A}$OR$^{6C}$, —NR$^{6C}$NR$^{6A}$R$^{6B}$, —C(O)NR$^{6C}$NR$^{6A}$R$^{6B}$, substituted or unsubstituted alkyl (e.g., C$_1$-C$_8$, C$_1$-C$_6$, C$_1$-C$_4$, or C$_1$-C$_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., C$_3$-C$_8$, C$_3$-C$_6$, C$_4$-C$_6$, or C$_5$-C$_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., C$_6$-C$_{10}$ or phenyl), or substituted or unsubstituted heteroaryl (e.g., 5 to 10 membered, 5 to 9 membered, or 5 to 6 membered).

In embodiments, $R^6$ is independently hydrogen, halogen, —CX$^6_3$, —CHX$^6_2$, —CH$_2$X$^6$, —OCX$^6_3$, —OCH$_2$X$^6$, —OCHX$^6_2$, —CN, —SH, —SOH, —SO$_2$H, —SO$_3$H, —SO$_4$H, —SONHR$^{6B}$, —SO$_2$NHR$^{6B}$, —NR$^{6C}$C(O)NHR$^{6B}$, —NHC(O)NR$^{6A}$R$^{6B}$, —N(O), —N(O)$_2$, —NHR$^{6B}$, —C(O)H, —C(O)—OH, —C(O)NHR$^{6B}$, —OH, —NHSO$_2$R$^{6D}$, —NR$^{6A}$SO$_2$H, —NR$^{6A}$C(O)H, —NHC(O)R$^{6C}$, —NHC(O)OR$^{6C}$, —NR$^{6A}$C(O)OH, —NHOR$^{6C}$, —NR$^{6A}$OH, —NHNR$^{6A}$R$^{6B}$, —NR$^{6C}$NHR$^{6B}$, —NR$^{6C}$NR$^{6A}$H, —C(O)NHNR$^{6A}$R$^{6B}$, —C(O)NR$^{6C}$NHR$^{6B}$, —C(O)NR$^{6C}$NR$^{6A}$H, substituted or unsubstituted alkyl (e.g., C$_1$-C$_8$, C$_1$-C$_6$, C$_1$-C$_4$, or C$_1$-C$_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., C$_3$-C$_8$, C$_3$-C$_6$, C$_4$-C$_6$, or C$_5$-C$_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., C$_6$-C$_{10}$ or phenyl), or substituted or unsubstituted heteroaryl (e.g., 5 to 10 membered, 5 to 9 membered, or 5 to 6 membered).

In embodiments, R$^6$ is independently hydrogen, halogen, —CX$^6_3$, —CHX$^6_2$, —CH$_2$X$^6$, —OCX$^6_3$, —OCH$_2$X$^6$, —OCHX$^6_2$, —CN, —SR$^{6D}$, —SOR$^{6D}$, —SO$_2$R$^{6D}$, —SO$_3$R$^{6D}$, —SO$_4$R$^{6D}$, —SONR$^{6A}$R$^{6B}$, —SO$_2$NR$^{6A}$R$^{6B}$, —NR$^{6C}$C(O)NR$^{6A}$R$^{6B}$, —N(O), —N(O)$_2$, —NR$^{6A}$R$^{6B}$, —C(O)R$^{6C}$, —C(O)—OR$^{6C}$, —C(O)NR$^{6A}$R$^{6B}$, —OR$^{6D}$, —NR$^{6A}$SO$_2$R$^{6D}$, —NR$^{6A}$C(O)R$^{6C}$, —NR$^{6A}$C(O)OR$^{6C}$, —NR$^{6A}$OR$^{6C}$, —NR$^{6C}$NR$^{6A}$R$^{6B}$, —C(O)NR$^{6C}$NR$^{6A}$R$^{6B}$, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 8 membered, 3 to 6 membered, 4 to 6 membered, 4 to 5 membered, or 5 to 6 membered), unsubstituted aryl (e.g., C$_6$-C$_{10}$ or phenyl), or unsubstituted heteroaryl (e.g., 5 to 10 membered, 5 to 9 membered, or 5 to 6 membered).

In embodiments, R$^6$ is independently —SOR$^{6D}$, —C(O)R$^{6C}$, —C(O)—OR$^{6C}$, —C(O)NR$^{6A}$R$^{6B}$, —NR$^{6A}$C(O)R$^{6C}$, or —C(O)NR$^{6C}$NR$^{6A}$R$^{6B}$. In embodiments, R$^6$ is independently —SOR$^{6D}$ In embodiments, R$^6$ is independently —C(O)R$^{6C}$. In embodiments, R$^6$ is independently —C(O)—OR$^{6C}$ In embodiments, R$^6$ is independently —C(O)NR$^{6A}$R$^{6B}$. In embodiments, R$^6$ is independently —NR$^{6A}$C(O)R$^{6C}$. In embodiments, R$^6$ is independently —C(O)NR$^{6C}$NR$^{6A}$R$^{6B}$ In embodiments, R$^6$ is independently —C(O)NHR$^{6B}$. In embodiments, R$^6$ is independently —NHC(O)R$^{6C}$. In embodiments, R$^6$ is independently —C(O)NHNHR$^{6B}$.

In embodiments, R$^6$ is independently an unsubstituted 3 to 8 membered heterocycloalkyl. In embodiments, R$^6$ is independently an unsubstituted 5 to 6 membered heterocycloalkyl. In embodiments, R$^6$ is independently an unsubstituted morpholinyl. In embodiments, R$^6$ is independently an R$^7$-substituted 3 to 8 membered heterocycloalkyl. In embodiments, R$^6$ is independently an R$^7$-substituted 5 to 6 membered heterocycloalkyl. In embodiments, R$^6$ is independently

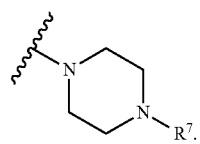

In embodiments R$^7$ is independently an R$^8$-substituted or unsubstituted C$_6$-C$_{10}$ aryl. In embodiments R$^7$ is independently an R$^8$-substituted or unsubstituted phenyl. In embodiments R$^7$ is independently an R$^8$-substituted or unsubstituted C$_6$-C$_{10}$ aryl. In embodiments R$^7$ is independently

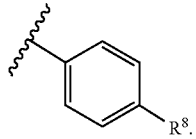

In embodiments, R$^8$ is an unsubstituted 2 to 4 membered heteroalkyl. In embodiments, R$^8$ is an unsubstituted methoxy.

In embodiments, R$^6$ is independently —C(O)NR$^{6C}$NR$^{6A}$R$^{6B}$. In embodiments, R$^{6C}$ is independently hydrogen. In embodiments, R$^{6A}$ is independently hydrogen. In embodiments, R$^{6B}$ is independently substituted C$_4$-C$_8$ alkyl. In embodiments, R$^{6B}$ is independently R$^{7B}$-substituted C$_4$-C$_8$ alkyl.

In embodiments, R$^6$ is independently hydrogen, halogen, —CX$^6_3$, —CHX$^6_2$, —CH$_2$X$^6$, —OCX$^6_3$, —OCH$_2$X$^6$, —OCHX$^6_2$, —CN, —SR$^{6D}$, —SOR$^{6D}$, —SO$_2$R$^{6D}$, —SO$_3$R$^{6D}$, —SO$_4$R$^{6D}$, —SONR$^{6A}$R$^{6B}$, —SO$_2$NR$^{6A}$R$^{6B}$, —NR$^{6C}$C(O)NR$^{6A}$R$^{6B}$, —N(O), —N(O)$_2$, —NR$^{6A}$R$^{6B}$, —C(O)R$^{6C}$, —C(O)—OR$^{6C}$, —C(O)NR$^{6A}$R$^{6B}$, —OR$^{6D}$, —N$^{6A}$SO$_2$R$^{6D}$, —NR$^{6A}$C(O)OR$^{6C}$, —NR$^{6A}$OR$^{6C}$, —NR$^{6C}$, —NR$^{6A}$R$^{6B}$, —C(O)NR$^{6C}$NR$^{6A}$R$^{6B}$, R$^7$-substituted or unsubstituted alkyl (e.g., C$_1$-C$_8$, C$_1$-C$_6$, C$_1$-C$_4$, or C$_1$-C$_2$), R$^7$-substituted or unsubstituted heteroalkyl (e.g., 2 to 8 membered, 2 to 6 membered, 4 to 6 membered, 2 to 3 membered, or 4 to 5 membered), R$^7$-substituted or unsubstituted cycloalkyl (e.g., C$_3$-C$_8$, C$_3$-C$_6$, C$_4$-C$_6$, or C$_5$-C$_6$), R$^7$-substituted or unsubstituted heterocycloalkyl (e.g., 3 to 8 membered, 3 to 6 membered, 4 to 6 membered, 4 to 5 membered, or 5 to 6 membered), R$^7$-substituted or unsubstituted aryl (e.g., C$_6$-C$_{10}$ or phenyl), or R$^7$-substituted or unsubstituted heteroaryl (e.g., 5 to 10 membered, 5 to 9 membered, or 5 to 6 membered).

In embodiments, R$^6$ is independently hydrogen, halogen, —CX$^6_3$, —CHX$^6_2$, —CH$_2$X$^6$, —OCX$^6_3$, —OCH$_2$X$^6$, —OCHX$^6_2$, —CN, —SR$^{6D}$, —SOR$^{6D}$, —SO$_2$R$^{6D}$, —SO$_3$R$^{6D}$, —SO$_4$R$^{6D}$, —SONR$^{6A}$R$^{6B}$, —SO$_2$NR$^{6A}$R$^{6B}$, —NR$^{6C}$C(O)NR$^{6A}$R$^{6B}$, —N(O), —N(O)$_2$, —NR$^{6A}$R$^{6B}$, —C(O)R$^{6C}$, —C(O)—OR$^{6C}$, —C(O)NR$^{6A}$R$^{6B}$, —OR$^{6D}$, —N$^{6A}$SO$_2$R$^{6D}$, —NR$^{6A}$C(O)R$^{6C}$, —NR$^{6A}$C(O)OR$^{6C}$, —NR$^{6A}$OR$^{6C}$, —NR$^{6C}$NR$^{6A}$R$^{6B}$, —C(O)NR$^{6C}$NR$^{6A}$R$^{6B}$, R$^7$-substituted or unsubstituted C$_1$-C$_8$ alkyl, R$^7$-substituted or unsubstituted 2 to 8 membered heteroalkyl, R$^7$-substituted or unsubstituted C$_3$-C$_8$ cycloalkyl, R$^7$-substituted or unsubstituted 3 to 8 membered heterocycloalkyl, R$^7$-substituted or unsubstituted C$_6$-C$_{10}$ aryl, or R$^7$-substituted or unsubstituted 5 to 10 membered heteroaryl.

R$^7$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl (e.g., C$_1$-C$_8$, C$_1$-C$_6$, C$_1$-C$_4$, or C$_1$-C$_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., C$_3$-C$_8$, C$_3$-C$_6$, C$_4$-C$_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered). In embodiments, $R^7$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

In embodiments, $R^7$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, R'-substituted or unsubstituted alkyl (e.g., $C_1$-$C_8$, $C_1$-$C_6$, $C_1$-$C_4$, or $C_1$-$C_2$), $R^8$-substituted or unsubstituted heteroalkyl (e.g., 2 to 8 membered, 2 to 6 membered, 4 to 6 membered, 2 to 3 membered, or 4 to 5 membered), $R^8$-substituted or unsubstituted cycloalkyl (e.g., $C_3$-$C_8$, $C_3$-$C_6$, $C_4$-$C_6$, or $C_5$-$C_6$), $R^8$-substituted or unsubstituted heterocycloalkyl (e.g., 3 to 8 membered, 3 to 6 membered, 4 to 6 membered, 4 to 5 membered, or 5 to 6 membered), $R^8$-substituted or unsubstituted aryl (e.g., $C_6$-$C_{10}$ or phenyl), or $R^8$-substituted or unsubstituted heteroaryl (e.g., 5 to 10 membered, 5 to 9 membered, or 5 to 6 membered).

In embodiments, $R^7$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, $R^8$-substituted or unsubstituted $C_1$-$C_8$ alkyl, $R^8$-substituted or unsubstituted 2 to 8 membered heteroalkyl, $R^8$-substituted or unsubstituted $C_3$-$C_8$ cycloalkyl, $R^8$-substituted or unsubstituted 3 to 8 membered heterocycloalkyl, R'-substituted or unsubstituted $C_6$-$C_{10}$ aryl, or R'-substituted or unsubstituted 5 to 10 membered heteroaryl.

$R^8$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, $R^8$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

In embodiments, $R^8$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, $R^9$-substituted or unsubstituted alkyl (e.g., $C_1$-$C_8$, $C_1$-$C_6$, $C_1$-$C_4$, or $C_1$-$C_2$), $R^9$-substituted or unsubstituted heteroalkyl (e.g., 2 to 8 membered, 2 to 6 membered, 4 to 6 membered, 2 to 3 membered, or 4 to 5 membered), $R^9$-substituted or unsubstituted cycloalkyl (e.g., $C_3$-$C_8$, $C_3$-$C_6$, $C_4$-$C_6$, or $C_5$-$C_6$), $R^9$-substituted or unsubstituted heterocycloalkyl (e.g., 3 to 8 membered, 3 to 6 membered, 4 to 6 membered, 4 to 5 membered, or 5 to 6 membered), $R^9$-substituted or unsubstituted aryl (e.g., $C_6$-$C_{10}$ or phenyl), or $R^9$-substituted or unsubstituted heteroaryl (e.g., 5 to 10 membered, 5 to 9 membered, or 5 to 6 membered).

$R^9$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

In embodiments, $R^8$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, unsubstituted $C_1$-$C_5$ alkyl, unsubstituted 2 to 8 membered heteroalkyl, unsubstituted $C_3$-$C_8$ cycloalkyl, unsubstituted 3 to 8 membered heterocycloalkyl, unsubstituted $C_6$-$C_{10}$ aryl, or unsubstituted 5 to 10 membered heteroaryl.

In embodiments, $R^{6A}$ is independently hydrogen, oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered). In embodiments, $R^{6A}$ is independently hydrogen, oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

In embodiments, $R^{6A}$ is independently hydrogen, oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, $R^{7A}$-substituted or unsubstituted alkyl (e.g., $C_1$-$C_8$, $C_1$-$C_6$, $C_1$-$C_4$, or $C_1$-$C_2$), $R^{7A}$-substituted or unsubstituted heteroalkyl (e.g., 2 to 8 membered, 2 to 6 membered, 4 to 6 membered, 2 to 3 membered, or 4 to 5 membered), $R^{7A}$-substituted or unsubstituted cycloalkyl (e.g., $C_3$-$C_8$, $C_3$-$C_6$, $C_4$-$C_6$, or $C_5$-$C_6$), $R^{7A}$-substituted or unsubstituted heterocycloalkyl (e.g., 3 to 8 membered, 3 to 6 membered, 4 to 6 membered, 4 to 5 membered, or 5 to 6 membered), $R^{7A}$-substituted or unsubstituted aryl (e.g., $C_6$-$C_{10}$ or phenyl), or $R^{7A}$-substituted or unsubstituted heteroaryl (e.g., 5 to 10 membered, 5 to 9 membered, or 5 to 6 membered).

In embodiments, $R^{6A}$ is independently hydrogen, oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, $R^{7A}$-substituted or unsubstituted $C_1$-$C_8$ alkyl, $R^{7A}$-substituted or unsubstituted 2 to 8 membered heteroalkyl, $R^{7A}$-substituted or unsubstituted $C_3$-$C_8$ cycloalkyl, $R^{7A}$-substituted or unsubstituted 3 to 8 membered heterocycloalkyl, $R^{7A}$-substituted or unsubstituted $C_6$-$C_{10}$ aryl, or $R^{7A}$-substituted or unsubstituted 5 to 10 membered heteroaryl.

$R^{7A}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, $R^{7A}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

In embodiments, $R^{7A}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, R$^{8A}$-substituted or unsubstituted alkyl (e.g., C$_1$-C$_8$, C$_1$-C$_6$, C$_1$-C$_4$, or C$_1$-C$_2$), R$^{8A}$-substituted or unsubstituted heteroalkyl (e.g., 2 to 8 membered, 2 to 6 membered, 4 to 6 membered, 2 to 3 membered, or 4 to 5 membered), R$^{8A}$-substituted or unsubstituted cycloalkyl (e.g., C$_3$-C$_8$, C$_3$-C$_6$, C$_4$-C$_6$, or C$_5$-C$_6$), R$^{8A}$-substituted or unsubstituted heterocycloalkyl (e.g., 3 to 8 membered, 3 to 6 membered, 4 to 6 membered, 4 to 5 membered, or 5 to 6 membered), R$^{8A}$-substituted or unsubstituted aryl (e.g., C$_6$-C$_{10}$ or phenyl), or R$^{9A}$-substituted or unsubstituted heteroaryl (e.g., 5 to 10 membered, 5 to 9 membered, or 5 to 6 membered).

In embodiments, R$^{7A}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, R$^{8A}$-substituted or unsubstituted C$_1$-C$_8$ alkyl, R$^{8A}$-substituted or unsubstituted 2 to 8 membered heteroalkyl, R$^{8A}$-substituted or unsubstituted C$_3$-C$_8$ cycloalkyl, R$^{8A}$-substituted or unsubstituted 3 to 8 membered heterocycloalkyl, R$^{8A}$-substituted or unsubstituted C$_6$-C$_{10}$ aryl, or R$^{8A}$-substituted or unsubstituted 5 to 10 membered heteroaryl.

R$^{8A}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl (e.g., C$_1$-C$_8$, C$_1$-C$_6$, C$_1$-C$_4$, or C$_1$-C$_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., C$_3$-C$_8$, C$_3$-C$_6$, C$_4$-C$_6$, or C$_5$-C$_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., C$_6$-C$_{10}$ or phenyl), or substituted or unsubstituted heteroaryl (e.g., 5 to 10 membered, 5 to 9 membered, or 5 to 6 membered).

In embodiments, R$^{8A}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 8 membered, 3 to 6 membered, 4 to 6 membered, 4 to 5 membered, or 5 to 6 membered), unsubstituted aryl (e.g., C$_6$-C$_{10}$ or phenyl), or unsubstituted heteroaryl (e.g., 5 to 10 membered, 5 to 9 membered, or 5 to 6 membered).

In embodiments, R$^{8A}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, unsubstituted C$_1$-C$_8$ alkyl, unsubstituted 2 to 8 membered heteroalkyl, unsubstituted C$_3$-C$_8$ cycloalkyl, unsubstituted 3 to 8 membered heterocycloalkyl, unsubstituted C$_6$-C$_{10}$ aryl, or unsubstituted 5 to 10 membered heteroaryl.

In embodiments, R$^{8A}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, R$^{9A}$-substituted or unsubstituted alkyl (e.g., C$_1$-C$_8$, C$_1$-C$_6$, C$_1$-C$_4$, or C$_1$-C$_2$), R$^{9A}$-substituted or unsubstituted heteroalkyl (e.g., 2 to 8 membered, 2 to 6 membered, 4 to 6 membered, 2 to 3 membered, or 4 to 5 membered), R$^{9A}$-substituted or unsubstituted cycloalkyl (e.g., C$_3$-C$_8$, C$_3$-C$_6$, C$_4$-C$_6$, or C$_5$-C$_6$), R$^{9A}$-substituted or unsubstituted heterocycloalkyl (e.g., 3 to 8 membered, 3 to 6 membered, 4 to 6 membered, 4 to 5 membered, or 5 to 6 membered), R$^{9A}$-substituted or unsubstituted aryl (e.g., C$_6$-C$_{10}$ or phenyl), or R$^{9A}$-substituted or unsubstituted heteroaryl (e.g., 5 to 10 membered, 5 to 9 membered, or 5 to 6 membered).

R$^{9A}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 8 membered, 3 to 6 membered, 4 to 6 membered, 4 to 5 membered, or 5 to 6 membered), unsubstituted aryl (e.g., C$_6$-C$_{10}$ or phenyl), or unsubstituted heteroaryl (e.g., 5 to 10 membered, 5 to 9 membered, or 5 to 6 membered).

In embodiments, R$^{6B}$ is independently hydrogen, oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl (e.g., C$_1$-C$_8$, C$_1$-C$_6$, C$_1$-C$_4$, or C$_1$-C$_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered). In embodiments, $R^{6B}$ is independently hydrogen, oxo, halogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

In embodiments, $R^{6B}$ is independently hydrogen, oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, $R^{7B}$-substituted or unsubstituted alkyl (e.g., $C_1$-$C_8$, $C_1$-$C_6$, $C_1$-$C_4$, or $C_1$-$C_2$), $R^{7B}$-substituted or unsubstituted heteroalkyl (e.g., 2 to 8 membered, 2 to 6 membered, 4 to 6 membered, 2 to 3 membered, or 4 to 5 membered), $R^{7B}$-substituted or unsubstituted cycloalkyl (e.g., $C_3$-$C_8$, $C_3$-$C_6$, $C_4$-$C_6$, or $C_5$-$C_6$), $R^{7B}$-substituted or unsubstituted heterocycloalkyl (e.g., 3 to 8 membered, 3 to 6 membered, 4 to 6 membered, 4 to 5 membered, or 5 to 6 membered), $R^{7B}$-substituted or unsubstituted aryl (e.g., $C_6$-$C_{10}$ or phenyl), or $R^{7B}$-substituted or unsubstituted heteroaryl (e.g., 5 to 10 membered, 5 to 9 membered, or 5 to 6 membered).

In embodiments, $R^{6B}$ is independently hydrogen, oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, $R^{7B}$-substituted or unsubstituted $C_1$-$C_8$ alkyl, $R^{7B}$-substituted or unsubstituted 2 to 8 membered heteroalkyl, $R^{7B}$-substituted or unsubstituted $C_3$-$C_8$ cycloalkyl, $R^{7B}$-substituted or unsubstituted 3 to 8 membered heterocycloalkyl, $R^{7B}$-substituted or unsubstituted $C_6$-$C_{10}$ aryl, or $R^{7B}$-substituted or unsubstituted 5 to 10 membered heteroaryl.

In embodiments, $R^{6B}$ is $R^{7B}$-substituted or unsubstituted $C_1$-$C_6$ alkyl, $R^{7B}$-substituted or unsubstituted phenyl, or $R^{7B}$-substituted or unsubstituted 5 to 6 membered heteroaryl. In embodiments, $R^{6B}$ is $R^{7B}$-substituted or unsubstituted $C_1$-$C_6$ alkyl. In embodiments, $R^{6B}$ is $R^{7B}$-substituted or unsubstituted phenyl. In embodiments, $R^{6B}$ is $R^{7B}$-substituted or unsubstituted 5 to 6 membered heteroaryl. In embodiments, $R^{6B}$ is $R^{7B}$-substituted $C_1$-$C_6$ alkyl. In embodiments, $R^{6B}$ is $R^{7B}$-substituted phenyl. In embodiments, $R^{6B}$ is $R^{7B}$-substituted 5 to 6 membered heteroaryl. In embodiments, $R^{6B}$ is unsubstituted $C_1$-$C_6$ alkyl. In embodiments, $R^{6B}$ is unsubstituted phenyl. In embodiments, $R^{6B}$ is unsubstituted 5 to 6 membered heteroaryl.

In embodiments, $R^{6B}$ is independently $R^{7B}$-substituted or unsubstituted $C_1$-$C_6$ alkyl, $R^{7B}$-substituted or unsubstituted phenyl, or $R^{7B}$-substituted or unsubstituted 5 to 6 membered heteroaryl. In embodiments, $R^{6B}$ is independently $R^{7B}$-substituted or unsubstituted $C_1$-$C_6$ alkyl. In embodiments, $R^{6B}$ is independently $R^{7B}$-substituted or unsubstituted phenyl. In embodiments, $R^{6B}$ is independently $R^{7B}$-substituted or unsubstituted 5 to 6 membered heteroaryl. In embodiments, $R^{6B}$ is independently $R^{7B}$-substituted $C_1$-$C_6$ alkyl. In embodiments, $R^{6B}$ is independently $R^{7B}$-substituted phenyl. In embodiments, $R^{6B}$ is independently $R^{7B}$-substituted 5 to 6 membered heteroaryl. In embodiments, $R^{6B}$ is independently unsubstituted $C_1$-$C_6$ alkyl. In embodiments, $R^{6B}$ is independently unsubstituted phenyl. In embodiments, $R^{6B}$ is independently unsubstituted 5 to 6 membered heteroaryl.

In embodiments, $R^{6B}$ is $R^{7B}$-substituted $C_1$-$C_6$ alkyl, $R^{7B}$-substituted phenyl, or $R^{7B}$-substituted pyridyl. In embodiments, $R^{6B}$ is $R^{7B}$-substituted $C_1$-$C_6$ alkyl. In embodiments, $R^{6B}$ is $R^{7B}$-substituted phenyl. In embodiments, $R^{6B}$ is $R^{7B}$-substituted pyridyl.

In embodiments, $R^{6B}$ is independently $R^{7B}$-substituted $C_1$-$C_6$ alkyl, $R^{7B}$-substituted phenyl, or $R^{7B}$-substituted pyridyl. In embodiments, $R^{6B}$ is independently $R^{7B}$-substituted $C_1$-$C_6$ alkyl. In embodiments, $R^{6B}$ is independently $R^{7B}$-substituted phenyl. In embodiments, $R^{6B}$ is independently $R^{7B}$-substituted pyridyl.

In embodiments, $R^{6B}$ is oxo-substituted $C_1$-$C_6$ alkyl.

In embodiments, $R^{6B}$ is independently oxo-substituted $C_1$-$C_6$ alkyl.

$R^{7B}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, $R^{7B}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

In embodiments, $R^{7B}$ is halogen, unsubstituted $C_1$-$C_3$ alkyl, $R^{8B}$-substituted or unsubstituted 2 to 4 membered heteroalkyl, or unsubstituted $C_6$-$C_{10}$ aryl. In embodiments, $R^{7B}$ is halogen. In embodiments, $R^{7B}$ is unsubstituted $C_1$-$C_3$ alkyl. In embodiments, $R^{7B}$ is $R^{8B}$-substituted or unsubstituted 2 to 4 membered heteroalkyl. In embodiments, $R^{7B}$ is $R^{8B}$-substituted 2 to 4 membered heteroalkyl. In embodiments, $R^{7B}$ is unsubstituted 2 to 4 membered heteroalkyl. In embodiments, $R^{7B}$ is unsubstituted $C_6$-$C_{10}$ aryl. In embodiments, $R^{7B}$ is unsubstituted $C_6$ aryl.

In embodiments, $R^{7B}$ is independently halogen, unsubstituted $C_1$-$C_3$ alkyl, $R^{8B}$-substituted or unsubstituted 2 to 4 membered heteroalkyl, or unsubstituted $C_6$-$C_{10}$ aryl. In embodiments, $R^{7B}$ is independently halogen. In embodiments, $R^{7B}$ is independently unsubstituted $C_1$-$C_3$ alkyl. In embodiments, $R^{7B}$ is independently $R^{8B}$-substituted or unsubstituted 2 to 4 membered heteroalkyl. In embodiments, $R^{7B}$ is independently $R^{8B}$-substituted 2 to 4 membered heteroalkyl. In embodiments, $R^{7B}$ is independently unsubstituted 2 to 4 membered heteroalkyl. In embodiments, $R^{7B}$ is independently unsubstituted $C_6$-$C_{10}$ aryl. In embodiments, $R^{7B}$ is independently unsubstituted $C_6$ aryl.

In embodiments, $R^{7B}$ is —Cl, —Br, unsubstituted methyl, unsubstituted ethyl, unsubstituted isopropyl, methoxy, $R^{8B}$-substituted 3 to 4 membered heteroalkyl, or unsubstituted phenyl. In embodiments, $R^{7B}$ is —Cl. In embodiments, $R^{7B}$ is —Br. In embodiments, $R^{7B}$ is unsubstituted methyl. In embodiments, $R^{7B}$ is unsubstituted ethyl. In embodiments, $R^{7B}$ is unsubstituted isopropyl. In embodiments, $R^{7B}$ is unsubstituted methoxy. In embodiments, $R^{7B}$ is $R^{8B}$-substituted 3 to 4 membered heteroalkyl. In embodiments, $R^{7B}$ is unsubstituted phenyl.

In embodiments, $R^{8B}$ is independently —Cl, —Br, unsubstituted methyl, unsubstituted ethyl, unsubstituted isopropyl, unsubstituted methoxy, $R^{8B}$-substituted 3 to 4 membered heteroalkyl, or unsubstituted phenyl. In embodiments, $R^{7B}$ is independently —Cl. In embodiments, $R^{7B}$ is independently —Br. In embodiments, $R^{7B}$ is independently unsubstituted methyl. In embodiments, $R^{7B}$ is independently unsubstituted ethyl. In embodiments, $R^{7B}$ is independently unsubstituted isopropyl. In embodiments, $R^{7B}$ is independently unsubstituted methoxy. In embodiments, $R^{7B}$ is independently $R^{8B}$-substituted 3 to 4 membered heteroalkyl. In embodiments, $R^{7B}$ is independently unsubstituted phenyl.

In embodiments, $R^{7B}$ is independently oxo, $R^{8B}$-substituted or unsubstituted $C_6$-$C_{10}$ aryl, or unsubstituted 5 to 10 membered heteroaryl. In embodiments, $R^{7B}$ is independently oxo. In embodiments, $R^{7B}$ is independently $R^{8B}$-substituted or unsubstituted $C_6$-$C_{10}$ aryl. In embodiments, $R^{7B}$ is independently $R^{8B}$-substituted $C_6$-$C_{10}$ aryl. In embodiments, $R^{7B}$ is independently unsubstituted $C_6$-$C_{10}$ aryl. In embodiments, $R^{7B}$ is independently $R^{8B}$-substituted $C_6$ aryl. In embodiments, $R^{7B}$ is independently unsubstituted $C_6$ aryl. In embodiments, $R^{7B}$ is independently unsubstituted 5 to 10 membered heteroaryl. In embodiments, $R^{7B}$ is independently unsubstituted 5 to 6 membered heteroaryl. In embodiments, $R^{7B}$ is independently unsubstituted 6 membered heteroaryl. In embodiments, $R^{7B}$ is independently unsubstituted pyridyl.

In embodiments, $R^{7B}$ is independently oxo,

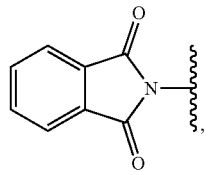 [SMILES: *N1C(=O)c2ccccc2C1=O]

or unsubstituted pyridyl. In embodiments, $R^{7B}$ is independently oxo. In embodiments, $R^{7B}$ is independently

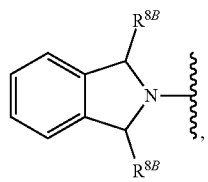

wherein each instance of $R^{8B}$ is independent and as described herein. In embodiments, $R^{7B}$ is independently

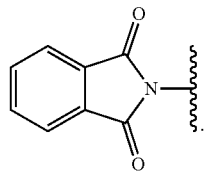 [SMILES: *N1C(=O)c2ccccc2C1=O]

In embodiments, $R^{7B}$ is independently unsubstituted pyridyl.

In embodiments, $R^{7B}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCl$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, $R^{8B}$-substituted or unsubstituted alkyl (e.g., $C_1$-$C_8$, $C_1$-$C_6$, $C_1$-$C_4$, or $C_1$-$C_2$), $R^{8B}$-substituted or unsubstituted heteroalkyl (e.g., 2 to 8 membered, 2 to 6 membered, 4 to 6 membered, 2 to 3 membered, or 4 to 5 membered), $R^{8B}$-substituted or unsubstituted cycloalkyl (e.g., $C_3$-$C_8$, $C_3$-$C_6$, $C_4$-$C_6$, or $C_5$-$C_6$), $R^{8B}$-substituted or unsubstituted heterocycloalkyl (e.g., 3 to 8 membered, 3 to 6 membered, 4 to 6 membered, 4 to 5 membered, or 5 to 6 membered), $R^{8B}$-substituted or unsubstituted aryl (e.g., $C_6$-$C_{10}$ or phenyl), or $R^{8B}$-substituted or unsubstituted heteroaryl (e.g., 5 to 10 membered, 5 to 9 membered, or 5 to 6 membered).

In embodiments, $R^{7B}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCl$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, $R^{8B}$-substituted or unsubstituted $C_1$-$C_8$ alkyl, $R^{8B}$-substituted or unsubstituted 2 to 8 membered heteroalkyl, $R^{8B}$-substituted or unsubstituted $C_3$-$C_8$ cycloalkyl, $R^{8B}$-substituted or unsubstituted 3 to 8 membered heterocycloalkyl, $R^{8B}$-substituted or unsubstituted $C_6$-$C_{10}$ aryl, or $R^{8B}$-substituted or unsubstituted 5 to 10 membered heteroaryl.

$R^{8B}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, $R^{8B}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

In embodiments, $R^{8B}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, unsubstituted $C_1$-$C_8$ alkyl, unsubstituted 2 to 8 membered heteroalkyl, unsubstituted $C_3$-$C_8$ cycloalkyl, unsubstituted 3 to 8 membered heterocycloalkyl, unsubstituted $C_6$-$C_{10}$ aryl, or unsubstituted 5 to 10 membered heteroaryl.

In embodiments, $R^{8B}$ is oxo. In embodiments, $R^{8B}$ is halogen.

In embodiments, $R^{8B}$ is independently oxo. In embodiments, $R^{8B}$ is independently halogen.

In embodiments, $R^{8B}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, $R^{9B}$-substituted or unsubstituted alkyl (e.g., $C_1$-$C_8$, $C_1$-$C_6$, $C_1$-$C_4$, or $C_1$-$C_2$), $R^{9B}$-substituted or unsubstituted heteroalkyl (e.g., 2 to 8 membered, 2 to 6 membered, 4 to 6 membered, 2 to 3 membered, or 4 to 5 membered), $R^{9B}$-substituted or unsubstituted cycloalkyl (e.g., $C_3$-$C_8$, $C_3$-$C_6$, $C_4$-$C_6$, or $C_5$-$C_6$), $R^{9B}$-substituted or unsubstituted heterocycloalkyl (e.g., 3 to 8 membered, 3 to 6 membered, 4 to 6 membered, 4 to 5 membered, or 5 to 6 membered), $R^{9B}$-substituted or unsubstituted aryl (e.g., $C_6$-$C_{10}$ or phenyl), or $R^{9B}$-substituted or unsubstituted heteroaryl (e.g., 5 to 10 membered, 5 to 9 membered, or 5 to 6 membered).

$R^{9B}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

In embodiments, $R^{6C}$ is independently hydrogen, oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered). In embodiments, $R^{6C}$ is independently hydrogen, oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

In embodiments, $R^{6C}$ is $R^{7C}$-substituted or unsubstituted $C_6$-$C_{10}$ aryl or unsubstituted 5 to 10 membered heteroaryl. In embodiments, $R^{6C}$ is $R^{7C}$-substituted $C_6$-$C_{10}$ aryl. In embodiments, $R^{6C}$ is unsubstituted $C_6$-$C_{10}$ aryl or unsubstituted 5 to 10 membered heteroaryl. In embodiments, $R^{6C}$ is unsubstituted 5 to 10 membered heteroaryl. In embodiments, $R^{6C}$ is unsubstituted 5 to 6 membered heteroaryl. In embodiments, $R^{6C}$ is unsubstituted 6 membered heteroaryl.

In embodiments, $R^{6C}$ is independently $R^{7C}$-substituted or unsubstituted $C_6$-$C_{10}$ aryl or unsubstituted 5 to 10 membered heteroaryl. In embodiments, $R^{6C}$ is independently $R^{7C}$-substituted $C_6$-$C_{10}$ aryl. In embodiments, $R^{6C}$ is independently unsubstituted $C_6$-$C_{10}$ aryl or unsubstituted 5 to 10 membered heteroaryl. In embodiments, $R^{6C}$ is independently unsubstituted 5 to 10 membered heteroaryl. In embodiments, $R^{6C}$ is independently unsubstituted 5 to 6 membered heteroaryl. In embodiments, $R^{6C}$ is independently 6 membered heteroaryl.

In embodiments, $R^{6C}$ is $R^{7C}$-substituted or unsubstituted phenyl or unsubstituted pyridyl. In embodiments, $R^{6C}$ is $R^{7C}$-substituted phenyl. In embodiments, $R^{6C}$ is unsubstituted phenyl. In embodiments, $R^{6C}$ is unsubstituted pyridyl.

In embodiments, $R^{6C}$ is independently $R^{7C}$-substituted or unsubstituted phenyl or unsubstituted pyridyl. In embodiments, $R^{6C}$ is independently $R^{7C}$-substituted phenyl. In embodiments, $R^{6C}$ is independently unsubstituted phenyl. In embodiments, $R^{6C}$ is independently unsubstituted pyridyl.

In embodiments, $R^{6C}$ is independently hydrogen, oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, $R^{7C}$-substituted or unsubstituted alkyl (e.g., $C_1$-$C_8$, $C_1$-$C_6$, $C_1$-$C_4$, or $C_1$-$C_2$), $R^{7C}$-substituted or unsubstituted heteroalkyl (e.g., 2 to 8 membered, 2 to 6 membered, 4 to 6 membered, 2 to 3 membered, or 4 to 5 membered), $R^{7C}$-substituted or unsubstituted cycloalkyl (e.g., $C_3$-$C_8$, $C_3$-$C_6$, $C_4$-$C_6$, or $C_5$-$C_6$), $R^{7C}$-substituted or unsubstituted heterocycloalkyl (e.g., 3 to 8 membered, 3 to 6 membered, 4 to 6 membered, 4 to 5 membered, or 5 to 6 membered), $R^{7C}$-substituted or unsubstituted aryl (e.g., $C_6$-$C_{10}$ or phenyl), or $R^{7C}$-substituted or unsubstituted heteroaryl (e.g., 5 to 10 membered, 5 to 9 membered, or 5 to 6 membered).

In embodiments, $R^{6C}$ is independently hydrogen, oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, $R^{7C}$-substituted or unsubstituted $C_1$-$C_8$ alkyl, $R^{7C}$-substituted or unsubstituted 2 to 8 membered heteroalkyl, $R^{7C}$-substituted or unsubstituted $C_3$-$C_8$ cycloalkyl, $R^{7C}$-substituted or unsubstituted 3 to 8 membered heterocycloalkyl, $R^{7C}$-substituted or unsubstituted $C_6$-$C_{10}$ aryl, or $R^{7C}$-substituted or unsubstituted 5 to 10 membered heteroaryl.

In embodiments, $R^{6C}$ is $R^{7C}$-substituted or unsubstituted 7 membered heterocycloalkyl. In embodiments, $R^{6C}$ is $R^{7C}$-substituted or unsubstituted 6 membered heterocycloalkyl. In embodiments, $R^{6C}$ is $R^{7C}$-substituted or unsubstituted 5 membered heterocycloalkyl. In embodiments, $R^{6C}$ is $R^{7C}$-substituted 7 membered heterocycloalkyl. In embodiments, $R^{6C}$ is $R^{7C}$-substituted 6 membered heterocycloalkyl. In embodiments, $R^{6C}$ is $R^{7C}$-substituted 5 membered heterocycloalkyl. In embodiments, $R^{6C}$ is an unsubstituted 7 membered heterocycloalkyl. In embodiments, $R^{6C}$ is an unsubstituted 6 membered heterocycloalkyl. In embodiments, $R^{6C}$ is an unsubstituted 5 membered heterocycloalkyl.

In embodiments, $R^{6C}$ is independently $R^{7C}$-substituted or unsubstituted 7 membered heterocycloalkyl. In embodiments, $R^{6C}$ is independently $R^{7C}$-substituted or unsubstituted 6 membered heterocycloalkyl. In embodiments, $R^{6C}$ is independently $R^{7C}$-substituted or unsubstituted 5 membered heterocycloalkyl. In embodiments, $R^{6C}$ is independently $R^{7C}$-substituted 7 membered heterocycloalkyl. In embodiments, $R^{6C}$ is independently $R^{7C}$-substituted 6 membered heterocycloalkyl. In embodiments, $R^{6C}$ is independently $R^{7C}$-substituted 5 membered heterocycloalkyl. In embodiments, $R^{6C}$ is independently an unsubstituted 7 membered heterocycloalkyl. In embodiments, $R^{6C}$ is independently an unsubstituted 6 membered heterocycloalkyl. In embodiments, $R^{6C}$ is independently an unsubstituted 5 membered heterocycloalkyl.

In embodiments, $R^{6C}$ is $R^{7C}$-substituted piperazinyl, $R^{7C}$-substituted piperidinyl, or unsubstituted morpholinyl. In embodiments, $R^{6C}$ is $R^{7C}$-substituted piperazinyl. In embodiments, $R^{6C}$ is $R^{7C}$-substituted piperidinyl. In embodiments, $R^{6C}$ is unsubstituted morpholinyl.

In embodiments, $R^{6C}$ is independently $R^{7C}$-substituted piperazinyl, $R^{7C}$-substituted piperidinyl, or unsubstituted morpholinyl. In embodiments, $R^{6C}$ is independently $R^{7C}$-substituted piperazinyl. In embodiments, $R^{6C}$ is independently $R^{7C}$-substituted piperidinyl. In embodiments, $R^{6C}$ is independently unsubstituted morpholinyl.

In embodiments, $R^{6C}$ is hydrogen, $R^{7C}$-substituted or unsubstituted $C_1$-$C_8$ alkyl or $R^{7C}$-substituted or unsubstituted $C_6$-$C_{10}$ aryl. In embodiments, $R^{6C}$ is hydrogen. In embodiments, $R^{6C}$ is $R^{7C}$-substituted or unsubstituted $C_1$-$C_8$ alkyl. In embodiments, $R^{6C}$ is $R^{7C}$-substituted or unsubstituted $C_6$-$C_{10}$ aryl. In embodiments, $R^{6C}$ is unsubstituted $C_1$-$C_8$ alkyl. In embodiments, $R^{6C}$ is unsubstituted $C_6$-$C_{10}$ aryl. In embodiments, $R^{6C}$ is $R^{7C}$-substituted $C_1$-$C_8$ alkyl. In embodiments, $R^{6C}$ is $R^{7C}$-substituted $C_6$-$C_{10}$ aryl.

In embodiments, $R^{6C}$ is independently hydrogen, $R^{7C}$-substituted or unsubstituted $C_1$-$C_8$ alkyl or $R^{7C}$-substituted or unsubstituted $C_6$-$C_{10}$ aryl. In embodiments, $R^{6C}$ is independently hydrogen. In embodiments, $R^{6C}$ is independently $R^{7C}$-substituted or unsubstituted $C_1$-$C_8$ alkyl. In embodiments, $R^{6C}$ is independently $R^{7C}$-substituted or unsubstituted $C_6$-$C_{10}$ aryl. In embodiments, $R^{6C}$ is independently unsubstituted $C_1$-$C_8$ alkyl. In embodiments, $R^{6C}$ is independently unsubstituted $C_6$-$C_{10}$ aryl. In embodiments, $R^{6C}$ is independently $R^{7C}$-substituted $C_1$-$C_8$ alkyl. In embodiments, $R^{6C}$ is independently $R^{7C}$-substituted $C_6$-$C_{10}$ aryl.

In embodiments, $R^{6C}$ is hydrogen, $R^{7C}$-substituted or unsubstituted ethyl or $R^{7C}$-substituted or unsubstituted phenyl. In embodiments, $R^{6C}$ is $R^{7C}$-substituted or unsubstituted ethyl. In embodiments, $R^{6C}$ is $R^{7C}$-substituted or unsubstituted phenyl. In embodiments, $R^{6C}$ is $R^{7C}$-substituted ethyl. In embodiments, $R^{6C}$ is $R^{7C}$-substituted phenyl. In embodiments, $R^{6C}$ is unsubstituted ethyl. In embodiments, $R^{6C}$ is unsubstituted phenyl.

In embodiments, $R^{6C}$ is independently hydrogen, $R^{7C}$-substituted or unsubstituted ethyl or $R^{7C}$-substituted or unsubstituted phenyl. In embodiments, $R^{6C}$ is independently $R^{7C}$-substituted or unsubstituted ethyl. In embodiments, $R^{6C}$ is independently $R^{7C}$-substituted or unsubstituted phenyl. In embodiments, $R^{6C}$ is $R^{7C}$-substituted ethyl. In embodiments, $R^{6C}$ is independently $R^{7C}$-substituted phenyl. In embodiments, $R^{6C}$ is independently unsubstituted ethyl. In embodiments, $R^{6C}$ is independently unsubstituted phenyl.

$R^{7C}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, —NHR$^{8C}$, substituted or unsubstituted alkyl (e.g., C$_1$-C$_8$, C$_1$-C$_6$, C$_1$-C$_4$, or C$_1$-C$_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., C$_3$-C$_8$, C$_3$-C$_6$, C$_4$-C$_6$, or C$_5$-C$_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., C$_6$-C$_{10}$ or phenyl), or substituted or unsubstituted heteroaryl (e.g., 5 to 10 membered, 5 to 9 membered, or 5 to 6 membered).

In embodiments, $R^{7C}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, —NHR$^{8C}$, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 8 membered, 3 to 6 membered, 4 to 6 membered, 4 to 5 membered, or 5 to 6 membered), unsubstituted aryl (e.g., C$_6$-C$_{10}$ or phenyl), or unsubstituted heteroaryl (e.g., 5 to 10 membered, 5 to 9 membered, or 5 to 6 membered).

In embodiments, $R^{7C}$ is oxo, $R^{8C}$-substituted or unsubstituted C$_1$-C$_2$ alkyl, unsubstituted 2 to 3 membered heteroalkyl, or $R^{8C}$-substituted or unsubstituted C$_6$-C$_{10}$ aryl. In embodiments, $R^{7C}$ is oxo. In embodiments, $R^{7C}$ is $R^{8C}$-substituted or unsubstituted C$_1$-C$_2$ alkyl. In embodiments, $R^{7C}$ is unsubstituted 2 to 3 membered heteroalkyl. In embodiments, $R^{7C}$ is $R^{8C}$-substituted or unsubstituted C$_6$-C$_{10}$ aryl. In embodiments, $R^{7C}$ is $R^{8C}$-substituted C$_1$-C$_2$ alkyl. In embodiments, $R^{7C}$ is unsubstituted 3 membered heteroalkyl. In embodiments, $R^{7C}$ is $R^{8C}$-substituted C$_6$-C$_{10}$ aryl. In embodiments, $R^{7C}$ is $R^{8C}$-substituted C$_6$ aryl. In embodiments, $R^{7C}$ is an unsubstituted C$_6$ aryl. In embodiments, $R^{7C}$ is an unsubstituted C$_1$-C$_2$ alkyl. In embodiments, $R^{7C}$ is unsubstituted 2 membered heteroalkyl. In embodiments, $R^{7C}$ is an unsubstituted C$_6$-C$_{10}$ aryl.

In embodiments, $R^{7C}$ is independently oxo, $R^{8C}$-substituted or unsubstituted C$_1$-C$_2$ alkyl, unsubstituted 2 to 3 membered heteroalkyl, or $R^{8C}$-substituted or unsubstituted C$_6$-C$_{10}$ aryl. In embodiments, $R^{7C}$ is independently $R^{8C}$-substituted or unsubstituted C$_1$-C$_2$ alkyl. In embodiments, $R^{7C}$ is independently unsubstituted 2 to 3 membered heteroalkyl. In embodiments, $R^{7C}$ is independently $R^{8C}$-substituted or unsubstituted C$_6$-C$_{10}$ aryl. In embodiments, $R^{7C}$ is independently $R^{8C}$-substituted C$_1$-C$_2$ alkyl. In embodiments, $R^{7C}$ is independently unsubstituted 3 membered heteroalkyl. In embodiments, $R^{7C}$ is independently $R^{8C}$-substituted C$_6$-C$_{10}$ aryl. In embodiments, $R^{7C}$ is independently $R^{8C}$-substituted C$_6$ aryl. In embodiments, $R^{7C}$ is independently an unsubstituted C$_6$ aryl. In embodiments, $R^{7C}$ is independently an unsubstituted C$_1$-C$_2$ alkyl. In embodiments, $R^{7C}$ is independently unsubstituted 2 membered heteroalkyl. In embodiments, $R^{7C}$ is independently an unsubstituted C$_6$-C$_{10}$ aryl.

In embodiments, $R^{7C}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, —NHR$^{8C}$, $R^{8C}$-substituted or unsubstituted alkyl (e.g., C$_1$-C$_8$, C$_1$-C$_6$, C$_1$-C$_4$, or C$_1$-C$_2$), $R^{8C}$-substituted or unsubstituted heteroalkyl (e.g., 2 to 8 membered, 2 to 6 membered, 4 to 6 membered, 2 to 3 membered, or 4 to 5 membered), $R^{8C}$-substituted or unsubstituted cycloalkyl (e.g., C$_3$-C$_8$, C$_3$-C$_6$, C$_4$-C$_6$, or C$_5$-C$_6$), $R^{8C}$-substituted or unsubstituted heterocycloalkyl (e.g., 3 to 8 membered, 3 to 6 membered, 4 to 6 membered, 4 to 5 membered, or 5 to 6 membered), $R^{8C}$-substituted or unsubstituted aryl (e.g., C$_6$-C$_{10}$ or phenyl), or $R^{8C}$-substituted or unsubstituted heteroaryl (e.g., 5 to 10 membered, 5 to 9 membered, or 5 to 6 membered).

In embodiments, $R^{7C}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, —NHR$^{8C}$, $R^{8C}$-substituted or unsubstituted C$_1$-C$_8$ alkyl, $R^{8C}$-substituted or unsubstituted 2 to 8 membered heteroalkyl, $R^{8C}$-substituted or unsubstituted C$_3$-C$_8$ cycloalkyl, $R^{8C}$-substituted or unsubstituted 3 to 8 membered heterocycloalkyl, $R^{8C}$-substituted or unsubstituted C$_6$-C$_{10}$ aryl, or $R^{8C}$-substituted or unsubstituted 5 to 10 membered heteroaryl.

In embodiments, $R^{7C}$ is —NHR$^{8C}$ or $R^{8C}$-substituted phenyl. In embodiments, $R^{7C}$ is —NHR$^{8C}$. In embodiments, $R^{7C}$ is $R^{8C}$-substituted phenyl.

In embodiments, $R^{7C}$ is independently —NHR$^{8C}$ or $R^{8C}$-substituted phenyl. In embodiments, $R^{7C}$ is independently —NHR$^{8C}$. In embodiments, $R^{7C}$ is independently $R^{8C}$-substituted phenyl.

In embodiments, $R^{7C}$ is $R^{8C}$-substituted C$_1$-C$_6$ alkyl. In embodiments, $R^{7C}$ is $R^{8C}$-substituted C$_1$-C$_4$ alkyl. In embodiments, $R^{7C}$ is oxo-substituted C$_1$-C$_6$ alkyl.

In embodiments, $R^{7C}$ is independently $R^{7C}$-substituted C$_1$-C$_6$ alkyl. In embodiments, $R^{7C}$ is independently $R^{8C}$-substituted C$_1$-C$_4$ alkyl. In embodiments, $R^{7C}$ is independently oxo-substituted C$_1$-C$_6$ alkyl.

$R^{8C}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl (e.g., C$_1$-C$_8$, C$_1$-C$_6$, C$_1$-C$_4$, or C$_1$-C$_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., C$_3$-C$_8$, C$_3$-C$_6$, C$_4$-C$_6$, or C$_5$-C$_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., C$_6$-C$_{10}$ or phenyl), or substituted or unsubstituted heteroaryl (e.g., 5 to 10 membered, 5 to 9 membered, or 5 to 6 membered).

In embodiments, R$^{8C}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 8 membered, 3 to 6 membered, 4 to 6 membered, 4 to 5 membered, or 5 to 6 membered), unsubstituted aryl (e.g., C$_6$-C$_{10}$ or phenyl), or unsubstituted heteroaryl (e.g., 5 to 10 membered, 5 to 9 membered, or 5 to 6 membered).

In embodiments, R$^{8C}$ is oxo, halogen, unsubstituted C$_1$-C$_4$ alkyl, or unsubstituted phenyl. In embodiments, R$^{8C}$ is oxo. In embodiments, R$^{8C}$ is halogen. In embodiments, R$^{8C}$ is unsubstituted C$_1$-C$_4$ alkyl. In embodiments, R$^{8C}$ is unsubstituted phenyl. In embodiments, R$^{8C}$ is oxo, —Cl, —Br, unsubstituted methyl, or unsubstituted phenyl. In embodiments, R$^{8C}$ is —Cl. In embodiments, R$^{8C}$ is —Br. In embodiments, R$^{8C}$ is unsubstituted methyl. In embodiments, R$^{8C}$ is unsubstituted phenyl.

In embodiments, R$^{8C}$ is independently oxo, halogen, unsubstituted C$_1$-C$_4$ alkyl, or unsubstituted phenyl. In embodiments, R$^{8C}$ is independently oxo. In embodiments, R$^{8C}$ is independently halogen. In embodiments, R$^{8C}$ is independently unsubstituted C$_1$-C$_4$ alkyl. In embodiments, R$^{8C}$ is independently unsubstituted phenyl. In embodiments, R$^{8C}$ is independently oxo, —Cl, —Br, unsubstituted methyl, or unsubstituted phenyl. In embodiments, R$^{8C}$ is independently —Cl. In embodiments, R$^{8C}$ is independently —Br. In embodiments, R$^{8C}$ is independently unsubstituted methyl. In embodiments, R$^{8C}$ is independently unsubstituted phenyl.

In embodiments, R$^{8C}$ is unsubstituted C$_1$-C$_4$ alkyl, unsubstituted 2 to 4 membered heteroalkyl, unsubstituted C$_5$-C$_6$ cycloalkyl, unsubstituted 5 to 6 membered heterocycloalkyl, R$^{9C}$-substituted or unsubstituted phenyl, or unsubstituted 5 to 6 membered heteroaryl. In embodiments, R$^{8C}$ is unsubstituted C$_1$-C$_4$ alkyl. In embodiments, R$^{8C}$ is unsubstituted 2 to 4 membered heteroalkyl. In embodiments, R$^{8C}$ is unsubstituted C$_5$-C$_6$ cycloalkyl. In embodiments, R$^{8C}$ is unsubstituted 5 to 6 membered heterocycloalkyl. In embodiments, R$^{8C}$ is R$^{9C}$-substituted or unsubstituted phenyl. In embodiments, R$^{8C}$ is R$^{9C}$-substituted phenyl. In embodiments, R$^{8C}$ is an unsubstituted phenyl. In embodiments, R$^{8C}$ is unsubstituted 5 to 6 membered heteroaryl.

In embodiments, R$^{8C}$ is independently unsubstituted C$_1$-C$_4$ alkyl, unsubstituted 2 to 4 membered heteroalkyl, unsubstituted C$_5$-C$_6$ cycloalkyl, unsubstituted 5 to 6 membered heterocycloalkyl, R$^{9C}$-substituted or unsubstituted phenyl, or unsubstituted 5 to 6 membered heteroaryl. In embodiments, R$^{8C}$ is independently unsubstituted C$_1$-C$_4$ alkyl. In embodiments, R$^{8C}$ is independently unsubstituted 2 to 4 membered heteroalkyl. In embodiments, R$^{8C}$ is independently unsubstituted C$_5$-C$_6$ cycloalkyl. In embodiments, R$^{8C}$ is independently unsubstituted 5 to 6 membered heterocycloalkyl. In embodiments, R$^{8C}$ is independently R$^{9C}$-substituted or unsubstituted phenyl. In embodiments, R$^{8C}$ is independently R$^{9C}$-substituted phenyl. In embodiments, R$^{8C}$ is independently an unsubstituted phenyl. In embodiments, R$^{8C}$ is independently unsubstituted 5 to 6 membered heteroaryl.

In embodiments, R$^{8C}$ is unsubstituted methoxy or R$^{9C}$-substituted phenyl; and R$^{9C}$ is unsubstituted isopropyl. In embodiments, R$^{8C}$ is unsubstituted ethoxy. In embodiments, R$^{8C}$ is unsubstituted methoxy. In embodiments, R$^{8C}$ is R$^{9C}$-substituted phenyl, wherein R$^{9C}$ is unsubstituted C$_1$-C$_6$ alkyl. In embodiments, R$^{8C}$ is R$^{9C}$-substituted phenyl, wherein R$^{9C}$ is unsubstituted isopropyl.

In embodiments, R$^{8C}$ is independently unsubstituted methoxy or R$^{9C}$-substituted phenyl; and R$^{9C}$ is unsubstituted isopropyl. In embodiments, R$^{8C}$ is independently unsubstituted ethoxy. In embodiments, R$^{8C}$ is independently unsubstituted methoxy. In embodiments, R$^{8C}$ is independently R$^{9C}$-substituted phenyl, wherein R$^{9C}$ is independently unsubstituted C$_1$-C$_6$ alkyl. In embodiments, R$^{8C}$ is independently R$^{9C}$-substituted phenyl, wherein R$^{9C}$ is independently unsubstituted isopropyl.

In embodiments, R$^{8C}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, R$^{9C}$-substituted or unsubstituted alkyl (e.g., C$_1$-C$_8$, C$_1$-C$_6$, C$_1$-C$_4$, or C$_1$-C$_2$), R$^{9C}$-substituted or unsubstituted heteroalkyl (e.g., 2 to 8 membered, 2 to 6 membered, 4 to 6 membered, 2 to 3 membered, or 4 to 5 membered), R$^{9C}$-substituted or unsubstituted cycloalkyl (e.g., C$_3$-C$_8$, C$_3$-C$_6$, C$_4$-C$_6$, or C$_5$-C$_6$), R$^{9C}$-substituted or unsubstituted heterocycloalkyl (e.g., 3 to 8 membered, 3 to 6 membered, 4 to 6 membered, 4 to 5 membered, or 5 to 6 membered), R$^{9C}$-substituted or unsubstituted aryl (e.g., C$_6$-C$_{10}$ or phenyl), or R$^{9C}$-substituted or unsubstituted heteroaryl (e.g., 5 to 10 membered, 5 to 9 membered, or 5 to 6 membered).

In embodiments, R$^{8C}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, R$^{9C}$-substituted or unsubstituted C$_1$-C$_8$ alkyl, R$^{9C}$-substituted or unsubstituted 2 to 8 membered heteroalkyl, R$^{9C}$-substituted or unsubstituted C$_3$-C$_8$ cycloalkyl, R$^{9C}$-substituted or unsubstituted 3 to 8 membered heterocycloalkyl, $R^{9C}$-substituted or unsubstituted $C_6$-$C_{10}$ aryl, or $R^{9C}$-substituted or unsubstituted 5 to 10 membered heteroaryl.

$R^{9C}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCl$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

In embodiments, $R^{9C}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCl$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, unsubstituted $C_1$-$C_8$ alkyl, unsubstituted 2 to 8 membered heteroalkyl, unsubstituted $C_3$-$C_8$ cycloalkyl, unsubstituted 3 to 8 membered heterocycloalkyl, unsubstituted $C_6$-$C_{10}$ aryl, or unsubstituted 5 to 10 membered heteroaryl.

In embodiments, $R^{6D}$ is independently hydrogen, oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCl$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered). In embodiments, $R^{61}$ is independently hydrogen, oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCl$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

In embodiments, $R^{6D}$ is independently hydrogen, oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCl$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, $R^{7D}$-substituted or unsubstituted alkyl (e.g., $C_1$-$C_8$, $C_1$-$C_6$, $C_1$-$C_4$, or $C_1$-$C_2$), $R^{7D}$-substituted or unsubstituted heteroalkyl (e.g., 2 to 8 membered, 2 to 6 membered, 4 to 6 membered, 2 to 3 membered, or 4 to 5 membered), $R^{7D}$-substituted or unsubstituted cycloalkyl (e.g., $C_3$-$C_8$, $C_3$-$C_6$, $C_4$-$C_6$, or $C_5$-$C_6$), $R^{7D}$-substituted or unsubstituted heterocycloalkyl (e.g., 3 to 8 membered, 3 to 6 membered, 4 to 6 membered, 4 to 5 membered, or 5 to 6 membered), $R^{7D}$-substituted or unsubstituted aryl (e.g., $C_6$-$C_{10}$ or phenyl), or $R^{7D}$-substituted or unsubstituted heteroaryl (e.g., 5 to 10 membered, 5 to 9 membered, or 5 to 6 membered).

In embodiments, $R^{6D}$ is independently hydrogen, oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCl$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, $R^{7D}$-substituted or unsubstituted $C_1$-$C_8$ alkyl, $R^{7D}$-substituted or unsubstituted 2 to 8 membered heteroalkyl, $R^{7D}$-substituted or unsubstituted $C_3$-$C_8$ cycloalkyl, $R^{7D}$-substituted or unsubstituted 3 to 8 membered heterocycloalkyl, $R^{7D}$-substituted or unsubstituted $C_6$-$C_{10}$ aryl, or $R^{7D}$-substituted or unsubstituted 5 to 10 membered heteroaryl.

In embodiments, $R^{6D}$ is $R^{7D}$-substituted or unsubstituted $C_1$-$C_4$ alkyl. In embodiments, $R^{6D}$ is $R^{7D}$-substituted $C_1$-$C_4$ alkyl. In embodiments, $R^{6D}$ is unsubstituted $C_1$-$C_4$ alkyl. In embodiments, $R^{6D}$ is unsubstituted methyl.

In embodiments, $R^{6D}$ is independently $R^{7D}$-substituted or unsubstituted $C_1$-$C_4$ alkyl. In embodiments, $R^{6D}$ is independently $R^{7D}$-substituted $C_1$-$C_4$ alkyl. In embodiments, $R^{6D}$ is independently unsubstituted $C_1$-$C_4$ alkyl. In embodiments, $R^{6D}$ is independently unsubstituted methyl.

$R^{7D}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCl$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, $R^{7D}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

In embodiments, $R^{7D}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, $R^{8D}$-substituted or unsubstituted alkyl (e.g., $C_1$-$C_8$, $C_1$-$C_6$, $C_1$-$C_4$, or $C_1$-$C_2$), $R^{8D}$-substituted or unsubstituted heteroalkyl (e.g., 2 to 8 membered, 2 to 6 membered, 4 to 6 membered, 2 to 3 membered, or 4 to 5 membered), $R^{8D}$-substituted or unsubstituted cycloalkyl (e.g., $C_3$-$C_8$, $C_3$-$C_6$, $C_4$-$C_6$, or $C_5$-$C_6$), $R^{8D}$-substituted or unsubstituted heterocycloalkyl (e.g., 3 to 8 membered, 3 to 6 membered, 4 to 6 membered, 4 to 5 membered, or 5 to 6 membered), $R^{8D}$-substituted or unsubstituted aryl (e.g., $C_6$-$C_{10}$ or phenyl), or $R^{8D}$-substituted or unsubstituted heteroaryl (e.g., 5 to 10 membered, 5 to 9 membered, or 5 to 6 membered).

In embodiments, $R^{7D}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, $R^{8D}$-substituted or unsubstituted $C_1$-$C_8$ alkyl, $R^{8D}$-substituted or unsubstituted 2 to 8 membered heteroalkyl, $R^{8D}$-substituted or unsubstituted $C_3$-$C_8$ cycloalkyl, $R^{8D}$-substituted or unsubstituted 3 to 8 membered heterocycloalkyl, $R^{8D}$-substituted or unsubstituted $C_6$-$C_{10}$ aryl, or $R^{8D}$-substituted or unsubstituted 5 to 10 membered heteroaryl.

$R^{8D}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, $R^{8D}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

In embodiments, $R^{8D}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, unsubstituted $C_1$-$C_8$ alkyl, unsubstituted 2 to 8 membered heteroalkyl, unsubstituted $C_3$-$C_8$ cycloalkyl, unsubstituted 3 to 8 membered heterocycloalkyl, unsubstituted $C_6$-$C_{10}$ aryl, or unsubstituted 5 to 10 membered heteroaryl.

In embodiments, $R^{8D}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, $R^{9D}$-substituted or unsubstituted alkyl (e.g., $C_1$-$C_5$, $C_1$-$C_6$, $C_1$-$C_4$, or $C_1$-$C_2$), R"-substituted or unsubstituted heteroalkyl (e.g., 2 to 8 membered, 2 to 6 membered, 4 to 6 membered, 2 to 3 membered, or 4 to 5 membered), $R^{9D}$-substituted or unsubstituted cycloalkyl (e.g., $C_3$-$C_8$, $C_3$-$C_6$, $C_4$-$C_6$, or $C_5$-$C_6$), $R^{9D}$-substituted or unsubstituted heterocycloalkyl (e.g., 3 to 8 membered, 3 to 6 membered, 4 to 6 membered, 4 to 5 membered, or 5 to 6 membered), $R^{9D}$-substituted or unsubstituted aryl (e.g., $C_6$-$C_{10}$ or phenyl), or $R^{9D}$-substituted or unsubstituted heteroaryl (e.g., 5 to 10 membered, 5 to 9 membered, or 5 to 6 membered).

$R^{9D}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)

—NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 8 membered, 3 to 6 membered, 4 to 6 membered, 4 to 5 membered, or 5 to 6 membered), unsubstituted aryl (e.g., C$_6$-C$_{10}$ or phenyl), or unsubstituted heteroaryl (e.g., 5 to 10 membered, 5 to 9 membered, or 5 to 6 membered).

In embodiments, X$^1$ is —F. In embodiments, X$^1$ is —Cl. In embodiments, X$^1$ is —Br. In embodiments, X$^1$ is —I. In embodiments, X$^2$ is —F. In embodiments, X$^2$ is —Cl. In embodiments, X$^2$ is —Br. In embodiments, X$^2$ is —I. In embodiments, X$^6$ is —F. In embodiments, X$^6$ is —Cl. In embodiments, X$^6$ is —Br. In embodiments, X$^6$ is —I.

In embodiments, X$^1$ is independently —F. In embodiments, X$^1$ is independently —Cl. In embodiments, X$^1$ is independently —Br. In embodiments, X$^1$ is independently —I. In embodiments, X$^2$ is independently —F. In embodiments, X$^2$ is independently —Cl. In embodiments, X$^2$ is independently —Br. In embodiments, X$^2$ is independently —I. In embodiments, X$^6$ is independently —F. In embodiments, X$^6$ is independently —Cl. In embodiments, X$^6$ is independently —Br. In embodiments, X$^6$ is independently —I.

In embodiments, R$^1$ is independently halogen, —CX$^1_3$, —CHX$^1_2$, —CH$_2$X$^1$, —OCX$^1_3$, —OCH$_2$X$^1$, —OCHX$^1_2$, unsubstituted C$_1$-C$_4$ alkyl, or unsubstituted 2 to 4 membered heteroalkyl; R$^2$ is independently halogen, —CX$^2_3$, —CHX$^2_2$, —CH$_2$X$^2$, —OCX$^2_3$, —OCH$_2$X$^2$, —OCHX$^2_2$, unsubstituted C$_1$-C$_4$ alkyl, or unsubstituted 2 to 4 membered heteroalkyl; L$^3$ is a bond, —N(R$^3$)—, —C(O)—, —C(O)N(R$^3$)—, —N(R$^3$)C(O)—, —N(H)—, —C(O)N(H)—, —N(H)C(O)—, —C(O)O—, R$^3$-substituted or unsubstituted C$_1$-C$_6$ alkylene, or R$^3$-substituted or unsubstituted 2 to 6 membered heteroalkylene; R$^3$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, R$^4$-substituted or unsubstituted C$_1$-C$_8$ alkyl, R$^4$-substituted or unsubstituted 2 to 8 membered heteroalkyl, R$^4$-substituted or unsubstituted C$_3$-C$_8$ cycloalkyl, R$^4$-substituted or unsubstituted 3 to 8 membered heterocycloalkyl, R$^4$-substituted or unsubstituted C$_6$-C$_{10}$ aryl, or R$^4$-substituted or unsubstituted 5 to 10 membered heteroaryl; R$^4$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, R$^5$-substituted or unsubstituted C$_1$-C$_8$ alkyl, R$^5$-substituted or unsubstituted 2 to 8 membered heteroalkyl, R$^5$-substituted or unsubstituted C$_3$-C$_5$ cycloalkyl, R$^5$-substituted or unsubstituted 3 to 8 membered heterocycloalkyl, R$^5$-substituted or unsubstituted C$_6$-C$_{10}$ aryl, or R$^5$-substituted or unsubstituted 5 to 10 membered heteroaryl; R$^5$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, unsubstituted C$_1$-C$_8$ alkyl, unsubstituted 2 to 8 membered heteroalkyl, unsubstituted C$_3$-C$_5$ cycloalkyl, unsubstituted 3 to 8 membered heterocycloalkyl, unsubstituted C$_6$-C$_{10}$ aryl, or unsubstituted 5 to 10 membered heteroaryl; R$^6$ is independently hydrogen, halogen, —CX$^6_3$, —CHX$^6_2$, —CH$_2$X$^6$, —OCX$^6_3$, —OCH$_2$X$^6$, —OCHX$^6_2$, —CN, —SR$^{6D}$, —SOR$^{6D}$, —SO$_2$R$^{6D}$, —SO$_3$R$^{6D}$, —SO$_4$R$^{6D}$, —SONR$^{6A}$R$^{6B}$, —SO$_2$NR$^{6A}$R$^{6B}$, —NR$^{6C}$C(O)NR$^{6A}$R$^{6B}$, —N(O), —N(O)$_2$, —NR$^{6A}$R$^{6B}$, —C(O)R$^{6C}$, —C(O)—OR$^{6C}$, —C(O)NR$^{6A}$R$^{6B}$, —OR$^{6D}$, —NR$^{6A}$SO$_2$R$^{6D}$, —NR$^{6A}$C(O)R$^{6C}$, —NR$^{6A}$C(O)OR$^{6C}$, —NR$^{6A}$OR$^{6C}$, —NR$^{6C}$NR$^{6A}$R$^{6B}$, —C(O)NR$^{6C}$NR$^{6A}$R$^{6B}$, R$^7$-substituted or unsubstituted C$_1$-C$_8$ alkyl, R$^7$-substituted or unsubstituted 2 to 8 membered heteroalkyl, R$^7$-substituted or unsubstituted C$_3$-C$_5$ cycloalkyl, R$^7$-substituted or unsubstituted 3 to 8 membered heterocycloalkyl, R$^7$-substituted or unsubstituted C$_6$-C$_{10}$ aryl, or R$^7$-substituted or unsubstituted 5 to 10 membered heteroaryl; R$^7$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, R$^8$-substituted or unsubstituted C$_1$-C$_5$ alkyl, R$^8$-substituted or unsubstituted 2 to 8 membered heteroalkyl, R$^8$-substituted or unsubstituted C$_3$-C$_5$ cycloalkyl, R$^8$-substituted or unsubstituted 3 to 8 membered heterocycloalkyl, R$^8$-substituted or unsubstituted C$_6$-C$_{10}$ aryl, or R$^8$-substituted or unsubstituted 5 to 10 membered heteroaryl; R$^8$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, R$^9$-substituted or unsubstituted C$_1$-C$_8$ alkyl, R$^9$-substituted or unsubstituted 2 to 8 membered heteroalkyl, R$^9$-substituted or unsubstituted C$_3$-C$_5$ cycloalkyl, R$^9$-substituted or unsubstituted 3 to 8 membered heterocycloalkyl, R$^9$-substituted or unsubstituted C$_6$-C$_{10}$ aryl, or R$^9$-substituted or unsubstituted 5 to 10 membered heteroaryl; R$^9$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, unsubstituted C$_1$-C$_8$ alkyl, unsubstituted 2 to 8 membered heteroalkyl, unsubstituted $C_3$-$C_5$ cycloalkyl, unsubstituted 3 to 8 membered heterocycloalkyl, unsubstituted $C_6$-$C_{10}$ aryl, or unsubstituted 5 to 10 membered heteroaryl; $R^{6A}$ is independently hydrogen, oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, $R^{7A}$-substituted or unsubstituted $C_1$-$C_8$ alkyl, $R^{7A}$-substituted or unsubstituted 2 to 8 membered heteroalkyl, $R^{7A}$-substituted or unsubstituted $C_3$-$C_8$ cycloalkyl, $R^{7A}$-substituted or unsubstituted 3 to 8 membered heterocycloalkyl, $R^{7A}$-substituted or unsubstituted $C_6$-$C_{10}$ aryl, or $R^{7A}$-substituted or unsubstituted 5 to 10 membered heteroaryl; $R^{7A}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, $R^{8A}$-substituted or unsubstituted $C_1$-$C_8$ alkyl, $R^{8A}$-substituted or unsubstituted 2 to 8 membered heteroalkyl, $R^{8A}$-substituted or unsubstituted $C_3$-$C_8$ cycloalkyl, $R^{8A}$-substituted or unsubstituted 3 to 8 membered heterocycloalkyl, $R^{8A}$-substituted or unsubstituted $C_6$-$C_{10}$ aryl, or $R^{8A}$-substituted or unsubstituted 5 to 10 membered heteroaryl; $R^{8A}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, $R^{9A}$-substituted or unsubstituted $C_1$-$C_8$ alkyl, $R^{9A}$-substituted or unsubstituted 2 to 8 membered heteroalkyl, $R^{9A}$-substituted or unsubstituted $C_3$-$C_8$ cycloalkyl, $R^{9A}$-substituted or unsubstituted 3 to 8 membered heterocycloalkyl, $R^{9A}$-substituted or unsubstituted $C_6$-$C_{10}$ aryl, or $R^{9A}$-substituted or unsubstituted 5 to 10 membered heteroaryl; $R^{9A}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, unsubstituted $C_1$-$C_8$ alkyl, unsubstituted 2 to 8 membered heteroalkyl, unsubstituted $C_3$-$C_8$ cycloalkyl, unsubstituted 3 to 8 membered heterocycloalkyl, unsubstituted $C_6$-$C_{10}$ aryl, or unsubstituted 5 to 10 membered heteroaryl; $R^{6B}$ is independently hydrogen, oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, $R^{7B}$-substituted or unsubstituted $C_1$-$C_8$ alkyl, $R^{7B}$-substituted or unsubstituted 2 to 8 membered heteroalkyl, $R^{7B}$-substituted or unsubstituted $C_3$-$C_8$ cycloalkyl, $R^{7B}$-substituted or unsubstituted 3 to 8 membered heterocycloalkyl, $R^{7B}$-substituted or unsubstituted $C_6$-$C_{10}$ aryl, or $R^{7B}$-substituted or unsubstituted 5 to 10 membered heteroaryl; $R^{7B}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, $R^{8B}$-substituted or unsubstituted $C_1$-$C_8$ alkyl, $R^{8B}$-substituted or unsubstituted 2 to 8 membered heteroalkyl, $R^{8B}$-substituted or unsubstituted $C_3$-$C_8$ cycloalkyl, $R^{8B}$-substituted or unsubstituted 3 to 8 membered heterocycloalkyl, $R^{8B}$-substituted or unsubstituted $C_6$-$C_{10}$ aryl, or $R^{8B}$-substituted or unsubstituted 5 to 10 membered heteroaryl; $R^{8B}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, $R^{9B}$-substituted or unsubstituted $C_1$-$C_8$ alkyl, $R^{9B}$-substituted or unsubstituted 2 to 8 membered heteroalkyl, $R^{9B}$-substituted or unsubstituted $C_3$-$C_8$ cycloalkyl, $R^{9B}$-substituted or unsubstituted 3 to 8 membered heterocycloalkyl, $R^{9B}$-substituted or unsubstituted $C_6$-$C_{10}$ aryl, or $R^{9B}$-substituted or unsubstituted 5 to 10 membered heteroaryl; $R^{9B}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, unsubstituted $C_1$-$C_8$ alkyl, unsubstituted 2 to 8 membered heteroalkyl, unsubstituted $C_3$-$C_8$ cycloalkyl, unsubstituted 3 to 8 membered heterocycloalkyl, unsubstituted $C_6$-$C_{10}$ aryl, or unsubstituted 5 to 10 membered heteroaryl; $R^{6C}$ is independently hydrogen, oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, $R^{7C}$-substituted or unsubstituted $C_1$-$C_8$ alkyl, $R^{7C}$-substituted or unsubstituted 2 to 8 membered heteroalkyl, $R^{7C}$-substituted or unsubstituted $C_3$-$C_8$ cycloalkyl, $R^{7C}$-substituted or unsubstituted 3 to 8 membered heterocycloalkyl, $R^{7C}$-substituted or unsubstituted $C_6$-$C_{10}$ aryl, or $R^{7C}$-substituted or unsubstituted 5 to 10 membered heteroaryl; $R^{7C}$ is independently oxo, halogen, —$CCl_3$, —$CBr_3$, —$CF_3$, —$CI_3$, —$CHCl_2$, —$CHBr_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, —NHR$^{8C}$, R$^{8C}$-substituted or unsubstituted C$_1$-C$_8$ alkyl, R$^{8C}$-substituted or unsubstituted 2 to 8 membered heteroalkyl, R$^{8C}$-substituted or unsubstituted C$_3$-C$_8$ cycloalkyl, R$^{8C}$-substituted or unsubstituted 3 to 8 membered heterocycloalkyl, R$^{8C}$-substituted or unsubstituted C$_6$-C$_{10}$ aryl, or R$^{8C}$-substituted or unsubstituted 5 to 10 membered heteroaryl; R$^{8C}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, R$^{9C}$-substituted or unsubstituted C$_1$-C$_8$ alkyl, R$^{9C}$-substituted or unsubstituted 2 to 8 membered heteroalkyl, R$^{9C}$-substituted or unsubstituted C$_3$-C$_8$ cycloalkyl, R$^{9C}$-substituted or unsubstituted 3 to 8 membered heterocycloalkyl, R$^{9C}$-substituted or unsubstituted C$_6$-C$_{10}$ aryl, or R$^{9C}$-substituted or unsubstituted 5 to 10 membered heteroaryl; R$^{9C}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, unsubstituted C$_1$-C$_8$ alkyl, unsubstituted 2 to 8 membered heteroalkyl, unsubstituted C$_3$-C$_8$ cycloalkyl, unsubstituted 3 to 8 membered heterocycloalkyl, unsubstituted C$_6$-C$_{10}$ aryl, or unsubstituted 5 to 10 membered heteroaryl; R$^{6D}$ is independently hydrogen, oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, R$^{7D}$-substituted or unsubstituted C$_1$-C$_8$ alkyl, R$^{7D}$-substituted or unsubstituted 2 to 8 membered heteroalkyl, R$^{7D}$-substituted or unsubstituted C$_3$-C$_8$ cycloalkyl, R$^{7D}$-substituted or unsubstituted 3 to 8 membered heterocycloalkyl, R$^{7D}$-substituted or unsubstituted C$_6$-C$_{10}$ aryl, or R$^{7D}$-substituted or unsubstituted 5 to 10 membered heteroaryl; R$^{7D}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, R$^{8D}$-substituted or unsubstituted C$_1$-C$_8$ alkyl, R$^{8D}$-substituted or unsubstituted 2 to 8 membered heteroalkyl, R$^{8D}$-substituted or unsubstituted C$_3$-C$_8$ cycloalkyl, R$^{8D}$-substituted or unsubstituted 3 to 8 membered heterocycloalkyl, R$^{8D}$-substituted or unsubstituted C$_6$-C$_{10}$ aryl, or R$^{8D}$-substituted or unsubstituted 5 to 10 membered heteroaryl; R$^{8D}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, R$^{9D}$-substituted or unsubstituted C$_1$-C$_8$ alkyl, R$^{9D}$-substituted or unsubstituted 2 to 8 membered heteroalkyl, R$^{9D}$-substituted or unsubstituted C$_3$-C$_8$ cycloalkyl, R$^{9D}$-substituted or unsubstituted 3 to 8 membered heterocycloalkyl, R$^{9D}$-substituted or unsubstituted C$_6$-C$_{10}$ aryl, or R$^{9D}$-substituted or unsubstituted 5 to 10 membered heteroaryl; R$^{9D}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, unsubstituted C$_1$-C$_8$ alkyl, unsubstituted 2 to 8 membered heteroalkyl, unsubstituted C$_3$-C$_8$ cycloalkyl, unsubstituted 3 to 8 membered heterocycloalkyl, unsubstituted C$_6$-C$_{10}$ aryl, or unsubstituted 5 to 10 membered heteroaryl; and X$^1$, X$^2$, and X$^6$ are independently —F, —Cl, —Br, or —I.

In embodiments, R$^1$ is independently halogen, —CX$^1_3$, —CHX$^1_2$, —CH$_2$X$^1$, —OCX$^1_3$, —OCH$_2$X$^1$, —OCHX$^1_2$, unsubstituted C$_1$-C$_4$ alkyl, or unsubstituted 2 to 4 membered heteroalkyl; R$^2$ is independently halogen, —CX$^2_3$, —CHX$^2_2$, —CH$_2$X$^2$, —OCX$^2_3$, —OCH$_2$X$^2$, —OCHX$^2_2$, unsubstituted C$_1$-C$_4$ alkyl, or unsubstituted 2 to 4 membered heteroalkyl; L$^3$ is a bond, —N(R$^3$)—, —C(O)—, —C(O)N(R$^3$)—, —N(R$^3$)C(O)—, —N(H)—, —C(O)N(H)—, —N(H)C(O)—, —C(O)O—, R$^3$-substituted or unsubstituted C$_1$-C$_6$ alkylene, or R$^3$-substituted or unsubstituted 2 to 6 membered heteroalkylene; R$^3$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, R$^4$-substituted or unsubstituted C$_1$-C$_8$ alkyl, R$^4$-substituted or unsubstituted 2 to 8 membered heteroalkyl, R$^4$-substituted or unsubstituted C$_3$-C$_8$ cycloalkyl, R$^4$-substituted or unsubstituted 3 to 8 membered heterocycloalkyl, R$^4$-substituted or unsubstituted C$_6$-C$_{10}$ aryl, or R$^4$-substituted or unsubstituted 5 to 10 membered heteroaryl; R$^4$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, R$^5$-substituted or unsubstituted C$_1$-C$_8$ alkyl, R$^5$-substituted or unsubstituted 2 to 8 membered heteroalkyl, $R^5$-substituted or unsubstituted $C_3$-$C_8$ cycloalkyl, $R^5$-substituted or unsubstituted 3 to 8 membered heterocycloalkyl, $R^5$-substituted or unsubstituted $C_6$-$C_{10}$ aryl, or $R^5$-substituted or unsubstituted 5 to 10 membered heteroaryl; $R^5$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, unsubstituted $C_1$-$C_8$ alkyl, unsubstituted 2 to 8 membered heteroalkyl, unsubstituted $C_3$-$C_8$ cycloalkyl, unsubstituted 3 to 8 membered heterocycloalkyl, unsubstituted $C_6$-$C_{10}$ aryl, or unsubstituted 5 to 10 membered heteroaryl; $R^6$ is independently hydrogen, halogen, —CX$^6_3$, —CHX$^6_2$, —CH$_2$X$^6$, —OCX$^6_3$, —OCH$_2$X$^6$, —OCHX$^6_2$, —CN, —SR$^{6D}$, —SOR$^{6D}$, —SO$_2$R$^{6D}$, —SO$_3$R$^{6D}$, —SO$_4$R$^{6D}$, —SONR$^{6A}$R$^{6B}$, —SO$_2$NR$^{6A}$R$^{6B}$, —NR$^{6C}$C(O)NR$^{6A}$R$^{6B}$, —N(O), —N(O)$_2$, —NR$^{6A}$R$^{6B}$, —C(O)R$^{6C}$, —C(O)OR$^{6C}$, —C(O)NR$^{6A}$R$^{6B}$, —OR$^{6D}$, —NR$^{6A}$SO$_2$R$^{6D}$, —NR$^{6A}$C(O)R$^{6C}$, —NR$^{6A}$C(O)OR$^{6C}$, —NR$^{6A}$OR$^{6C}$, —NR$^{6C}$NR$^{6A}$R$^{6B}$, —C(O)NR$^{6C}$NR$^{6A}$R$^{6B}$, $R^7$-substituted or unsubstituted $C_1$-$C_8$ alkyl, $R^7$-substituted or unsubstituted 2 to 8 membered heteroalkyl, $R^7$-substituted or unsubstituted $C_3$-$C_8$ cycloalkyl, $R^7$-substituted or unsubstituted 3 to 8 membered heterocycloalkyl, $R^7$-substituted or unsubstituted $C_6$-$C_{10}$ aryl, or $R^7$-substituted or unsubstituted 5 to 10 membered heteroaryl; $R^7$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, $R^8$-substituted or unsubstituted $C_1$-$C_5$ alkyl, $R^7$-substituted or unsubstituted 2 to 8 membered heteroalkyl, $R^7$-substituted or unsubstituted $C_3$-$C_8$ cycloalkyl, $R^8$-substituted or unsubstituted 3 to 8 membered heterocycloalkyl, $R^7$-substituted or unsubstituted $C_6$-$C_{10}$ aryl, or $R^8$-substituted or unsubstituted 5 to 10 membered heteroaryl; $R^7$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, unsubstituted $C_1$-$C_8$ alkyl, unsubstituted 2 to 8 membered heteroalkyl, unsubstituted $C_3$-$C_8$ cycloalkyl, unsubstituted 3 to 8 membered heterocycloalkyl, unsubstituted $C_6$-$C_{10}$ aryl, or unsubstituted 5 to 10 membered heteroaryl; $R^{6A}$ is independently hydrogen, oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, $R^{7A}$-substituted or unsubstituted $C_1$-$C_8$ alkyl, $R^{7A}$-substituted or unsubstituted 2 to 8 membered heteroalkyl, $R^{7A}$-substituted or unsubstituted $C_3$-$C_8$ cycloalkyl, $R^{7A}$-substituted or unsubstituted 3 to 8 membered heterocycloalkyl, $R^{7A}$-substituted or unsubstituted $C_6$-$C_{10}$ aryl, or $R^{7A}$-substituted or unsubstituted 5 to 10 membered heteroaryl; $R^{7A}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, $R^{8A}$-substituted or unsubstituted $C_1$-$C_8$ alkyl, $R^{8A}$-substituted or unsubstituted 2 to 8 membered heteroalkyl, $R^{8A}$-substituted or unsubstituted $C_3$-$C_8$ cycloalkyl, $R^{8A}$-substituted or unsubstituted 3 to 8 membered heterocycloalkyl, $R^{8A}$-substituted or unsubstituted $C_6$-$C_{10}$ aryl, or $R^{8A}$-substituted or unsubstituted 5 to 10 membered heteroaryl; $R^{8A}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, unsubstituted $C_1$-$C_8$ alkyl, unsubstituted 2 to 8 membered heteroalkyl, unsubstituted $C_3$-$C_8$ cycloalkyl, unsubstituted 3 to 8 membered heterocycloalkyl, unsubstituted $C_6$-$C_{10}$ aryl, or unsubstituted 5 to 10 membered heteroaryl; $R^{6B}$ is independently hydrogen, oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, $R^{7B}$-substituted or unsubstituted $C_1$-$C_8$ alkyl, $R^{7B}$-substituted or unsubstituted 2 to 8 membered heteroalkyl, $R^{7B}$-substituted or unsubstituted $C_3$-$C_8$ cycloalkyl, $R^{7B}$-substituted or unsubstituted 3 to 8 membered heterocycloalkyl, $R^{7B}$-substituted or unsubstituted $C_6$-$C_{10}$ aryl, or $R^{7B}$-substituted or unsubstituted 5 to 10 membered heteroaryl; $R^{7B}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, $R^{8B}$-substituted or unsubstituted $C_1$-$C_8$ alkyl, $R^{8B}$-substituted or unsubstituted 2 to 8 membered heteroalkyl, $R^{8B}$-substituted or unsubstituted $C_3$-$C_8$ cycloalkyl, $R^{8B}$-substituted or unsubstituted 3 to 8 membered heterocycloalkyl, $R^{8B}$-substituted or unsubstituted $C_6$-$C_{10}$ aryl, or $R^{8B}$-substituted or unsubstituted 5 to 10 membered heteroaryl; $R^{8B}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr₃, —OCI₃, —OCHCl₂, —OCHBr₂, —OCHI₂, —OCHF₂, —OCH₂Cl, —OCH₂Br, —OCH₂I, —OCH₂F, —N₃, —SF₅, unsubstituted $C_1$-$C_5$ alkyl, unsubstituted 2 to 8 membered heteroalkyl, unsubstituted $C_3$-$C_8$ cycloalkyl, unsubstituted 3 to 8 membered heterocycloalkyl, unsubstituted $C_6$-$C_{10}$ aryl, or unsubstituted 5 to 10 membered heteroaryl; $R^{6C}$ is independently hydrogen, oxo, halogen, —CCl₃, —CBr₃, —CF₃, —CI₃, —CHCl₂, —CHBr₂, —CHF₂, —CHI₂, —CH₂Cl, —CH₂Br, —CH₂F, —CH₂I, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr₃, —OCI₃, —OCHCl₂, —OCHBr₂, —OCHI₂, —OCHF₂, —OCH₂Cl, —OCH₂Br, —OCH₂I, —OCH₂F, —N₃, —SF₅, $R^{7C}$-substituted or unsubstituted $C_1$-$C_5$ alkyl, $R^{7C}$-substituted or unsubstituted 2 to 8 membered heteroalkyl, $R^{7C}$-substituted or unsubstituted $C_3$-$C_8$ cycloalkyl, $R^{7C}$-substituted or unsubstituted 3 to 8 membered heterocycloalkyl, $R^{7C}$-substituted or unsubstituted $C_6$-$C_{10}$ aryl, or $R^{7C}$-substituted or unsubstituted 5 to 10 membered heteroaryl; $R^{7C}$ is independently oxo, halogen, —CCl₃, —CBr₃, —CF₃, —CI₃, —CHCl₂, —CHBr₂, —CHF₂, —CHI₂, —CH₂Cl, —CH₂Br, —CH₂F, —CH₂I, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr₃, —OCI₃, —OCHCl₂, —OCHBr₂, —OCHI₂, —OCHF₂, —OCH₂Cl, —OCH₂Br, —OCH₂I, —OCH₂F, —N₃, —SF₅, —NHR$^{8C}$, $R^{8C}$-substituted or unsubstituted $C_1$-$C_5$ alkyl, $R^{8C}$-substituted or unsubstituted 2 to 8 membered heteroalkyl, $R^{8C}$-substituted or unsubstituted $C_3$-$C_8$ cycloalkyl, $R^{8C}$-substituted or unsubstituted 3 to 8 membered heterocycloalkyl, $R^{8C}$-substituted or unsubstituted $C_6$-$C_{10}$ aryl, or $R^{8C}$-substituted or unsubstituted 5 to 10 membered heteroaryl; $R^{8C}$ is independently oxo, halogen, —CCl₃, —CBr₃, —CF₃, —CI₃, —CHCl₂, —CHBr₂, —CHF₂, —CHI₂, —CH₂Cl, —CH₂Br, —CH₂F, —CH₂I, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr₃, —OCI₃, —OCHCl₂, —OCHBr₂, —OCHI₂, —OCHF₂, —OCH₂Cl, —OCH₂Br, —OCH₂I, —OCH₂F, —N₃, —SF₅, $R^{9C}$-substituted or unsubstituted $C_1$-$C_8$ alkyl, $R^{9C}$-substituted or unsubstituted 2 to 8 membered heteroalkyl, $R^{9C}$-substituted or unsubstituted $C_3$-$C_8$ cycloalkyl, $R^{9C}$-substituted or unsubstituted 3 to 8 membered heterocycloalkyl, $R^{9C}$-substituted or unsubstituted $C_6$-$C_{10}$ aryl, or $R^{9C}$-substituted or unsubstituted 5 to 10 membered heteroaryl; $R^{9C}$ is independently oxo, halogen, —CCl₃, —CBr₃, —CF₃, —CI₃, —CHCl₂, —CHBr₂, —CHF₂, —CHI₂, —CH₂Cl, —CH₂Br, —CH₂F, —CH₂I, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr₃, —OCI₃, —OCHCl₂, —OCHBr₂, —OCHI₂, —OCHF₂, —OCH₂Cl, —OCH₂Br, —OCH₂I, —OCH₂F, —N₃, —SF₅, unsubstituted $C_1$-$C_8$ alkyl, unsubstituted 2 to 8 membered heteroalkyl, unsubstituted $C_3$-$C_8$ cycloalkyl, unsubstituted 3 to 8 membered heterocycloalkyl, unsubstituted $C_6$-$C_{10}$ aryl, or unsubstituted 5 to 10 membered heteroaryl; $R^{6D}$ is independently hydrogen, oxo, halogen, —CCl₃, —CBr₃, —CF₃, —CI₃, —CHCl₂, —CHBr₂, —CHF₂, —CHI₂, —CH₂Cl, —CH₂Br, —CH₂F, —CH₂I, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr₃, —OCI₃, —OCHCl₂, —OCHBr₂, —OCHI₂, —OCHF₂, —OCH₂Cl, —OCH₂Br, —OCH₂I, —OCH₂F, —N₃, —SF₅, $R^{7D}$-substituted or unsubstituted $C_1$-$C_8$ alkyl, $R^{7D}$-substituted or unsubstituted 2 to 8 membered heteroalkyl, $R^{7D}$-substituted or unsubstituted $C_3$-$C_8$ cycloalkyl, $R^{7D}$-substituted or unsubstituted 3 to 8 membered heterocycloalkyl, $R^{7D}$-substituted or unsubstituted $C_6$-$C_{10}$ aryl, or $R^{7D}$-substituted or unsubstituted 5 to 10 membered heteroaryl; $R^{7D}$ is independently oxo, halogen, —CCl₃, —CBr₃, —CF₃, —CI₃, —CHCl₂, —CHBr₂, —CHF₂, —CHI₂, —CH₂Cl, —CH₂Br, —CH₂F, —CH₂I, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr₃, —OCI₃, —OCHCl₂, —OCHBr₂, —OCHI₂, —OCHF₂, —OCH₂Cl, —OCH₂Br, —OCH₂I, —OCH₂F, —N₃, —SF₅, $R^{8D}$-substituted or unsubstituted $C_1$-$C_8$ alkyl, $R^{8D}$-substituted or unsubstituted 2 to 8 membered heteroalkyl, $R^{8D}$-substituted or unsubstituted $C_3$-$C_8$ cycloalkyl, $R^{8D}$-substituted or unsubstituted 3 to 8 membered heterocycloalkyl, $R^{8D}$-substituted or unsubstituted $C_6$-$C_{10}$ aryl, or $R^{8D}$-substituted or unsubstituted 5 to 10 membered heteroaryl; $R^{8D}$ is independently oxo, halogen, —CCl₃, —CBr₃, —CF₃, —CI₃, —CHCl₂, —CHBr₂, —CHF₂, —CHI₂, —CH₂Cl, —CH₂Br, —CH₂F, —CH₂I, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr₃, —OCI₃, —OCHCl₂, —OCHBr₂, —OCHI₂, —OCHF₂, —OCH₂Cl, —OCH₂Br, —OCH₂I, —OCH₂F, —N₃, —SF₅, unsubstituted $C_1$-$C_8$ alkyl, unsubstituted 2 to 8 membered heteroalkyl, unsubstituted $C_3$-$C_8$ cycloalkyl, unsubstituted 3 to 8 membered heterocycloalkyl, unsubstituted $C_6$-$C_{10}$ aryl, or unsubstituted 5 to 10 membered heteroaryl; and $X^1$, $X^2$, and $X^6$ are independently —F, —Cl, —Br, or —I.

In embodiments, -$L^3$-$R^6$ is independently O

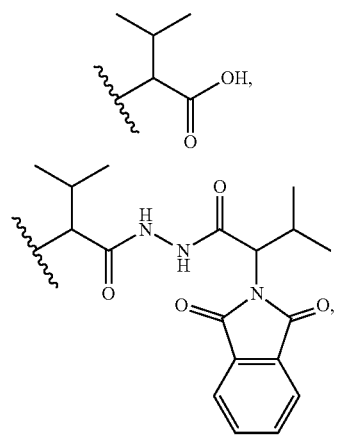

83
-continued
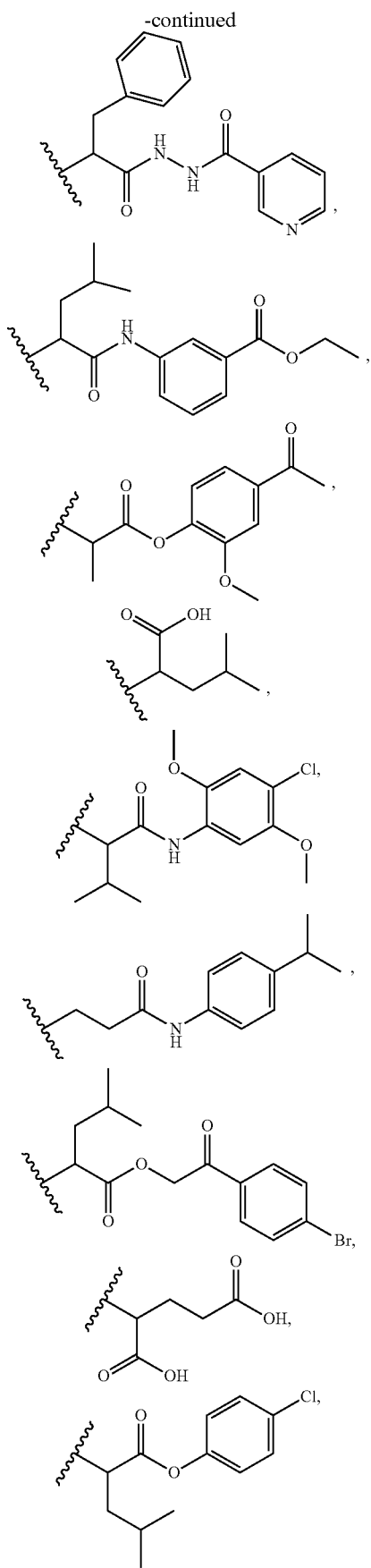
84
-continued
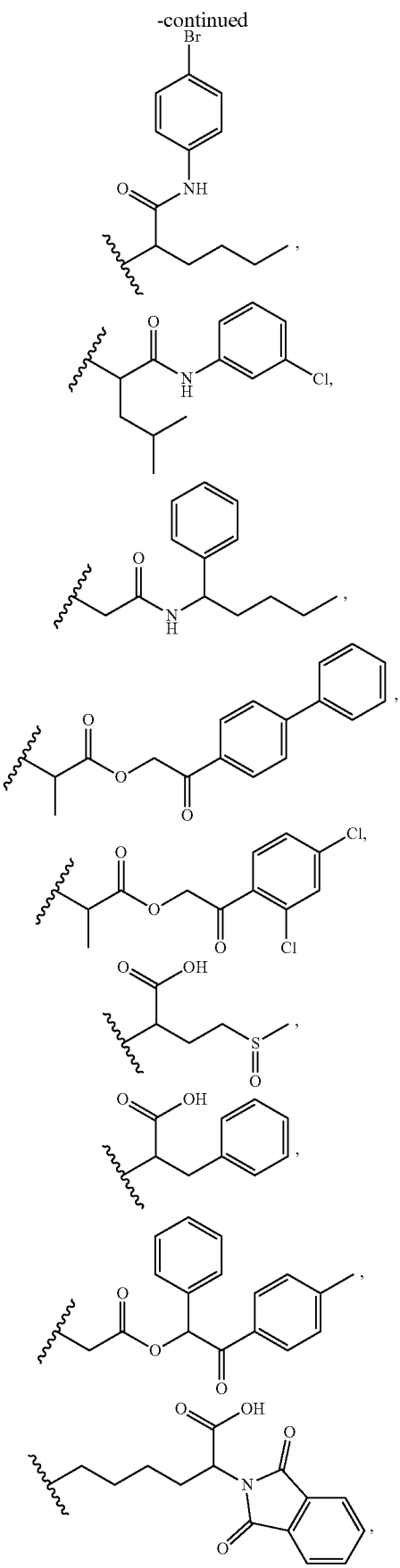

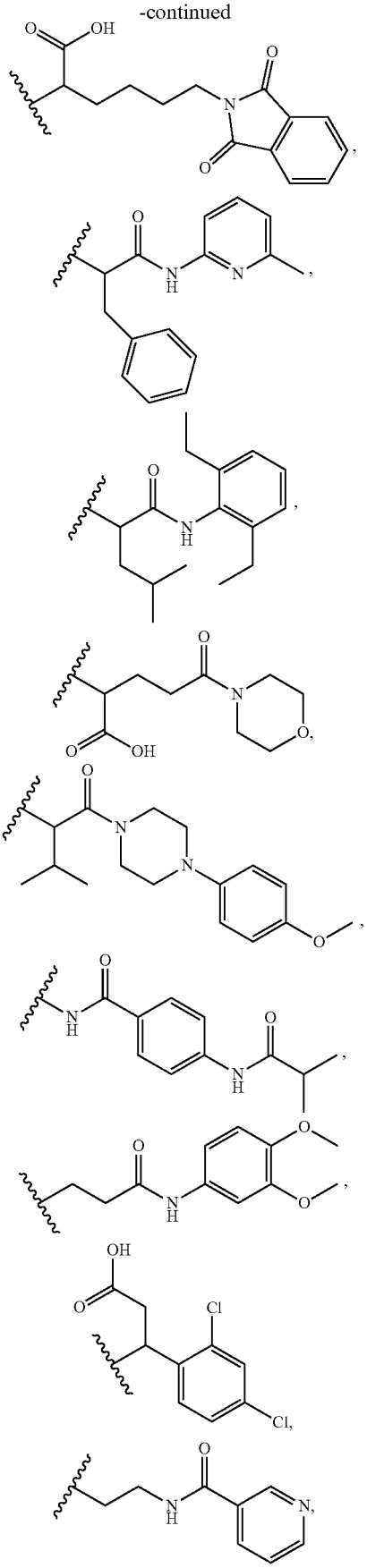
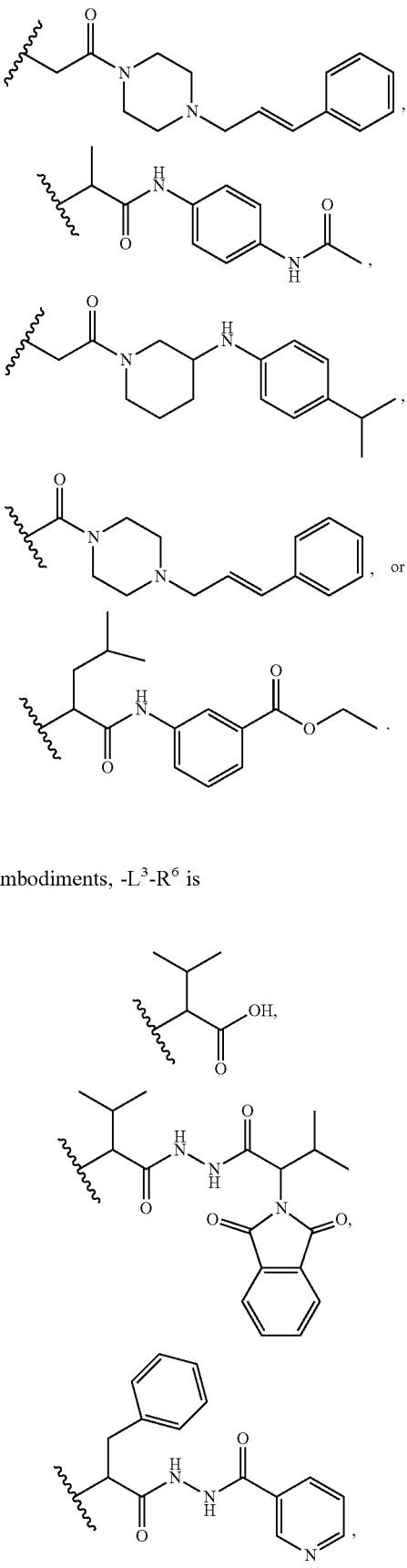
In embodiments, -L$^3$-R$^6$ is

87
-continued
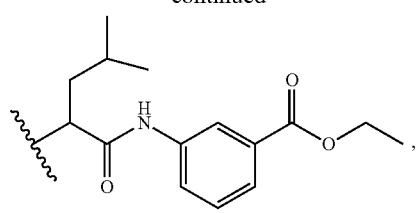
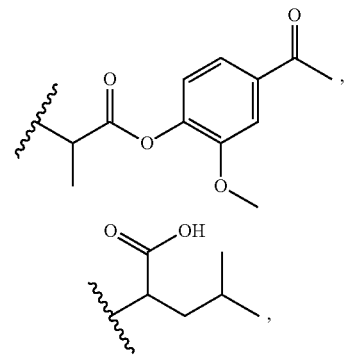
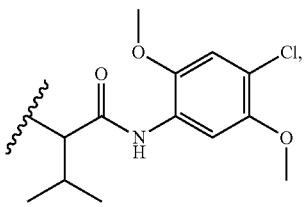
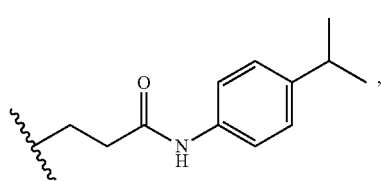
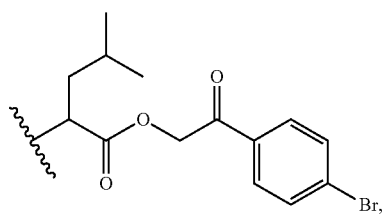
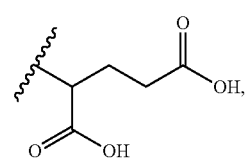
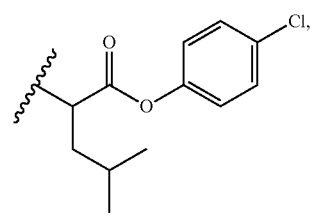
88
-continued
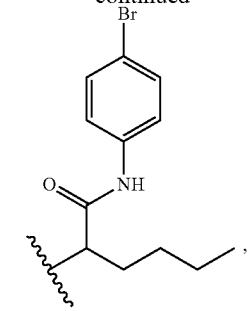
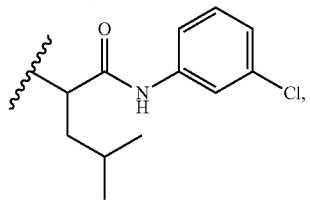
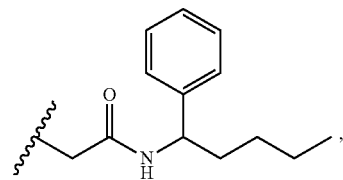
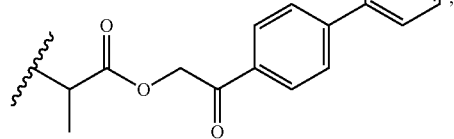
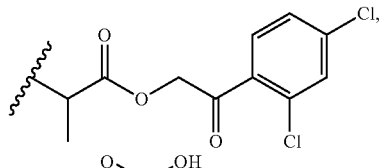
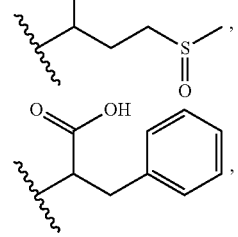
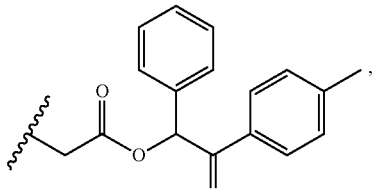
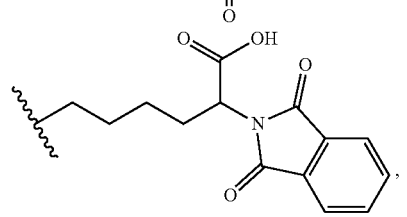

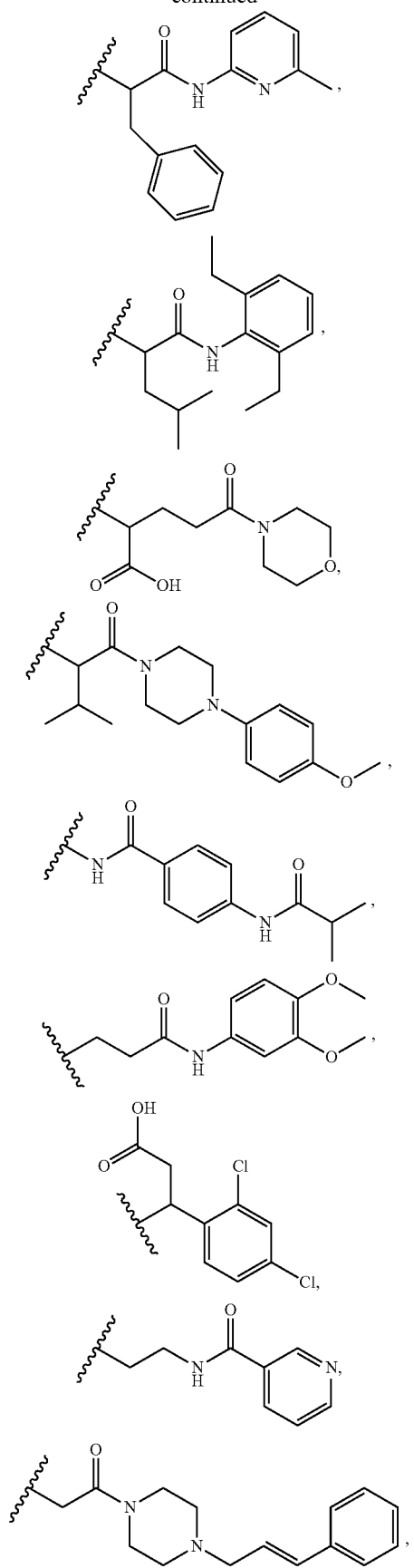
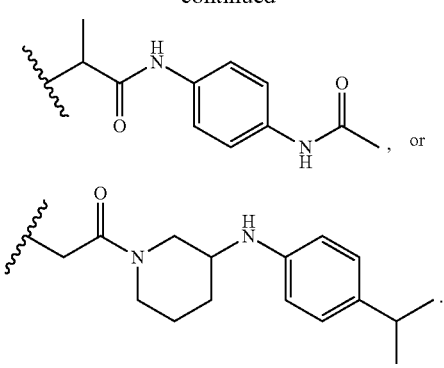
In embodiments, -L³-R⁶ is independently

91
-continued
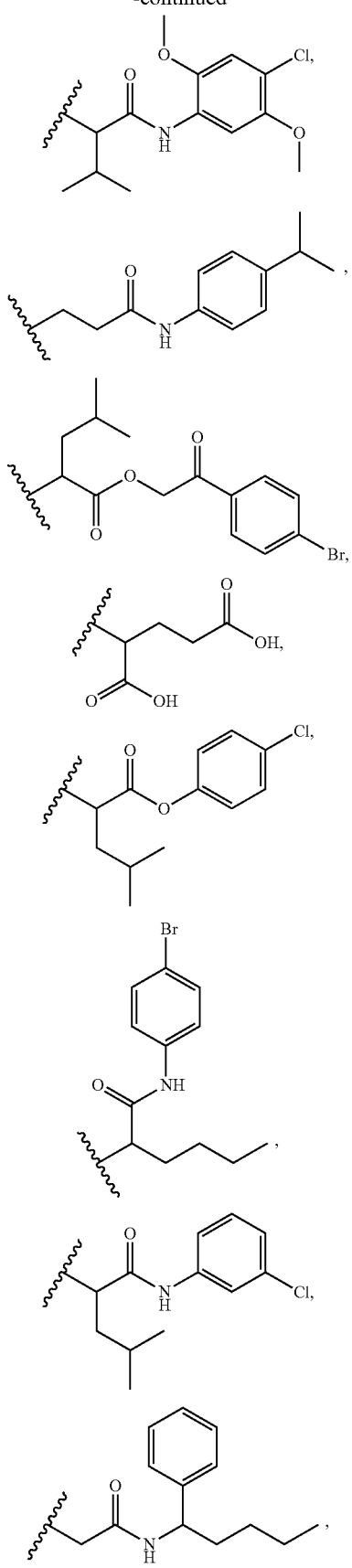
92
-continued
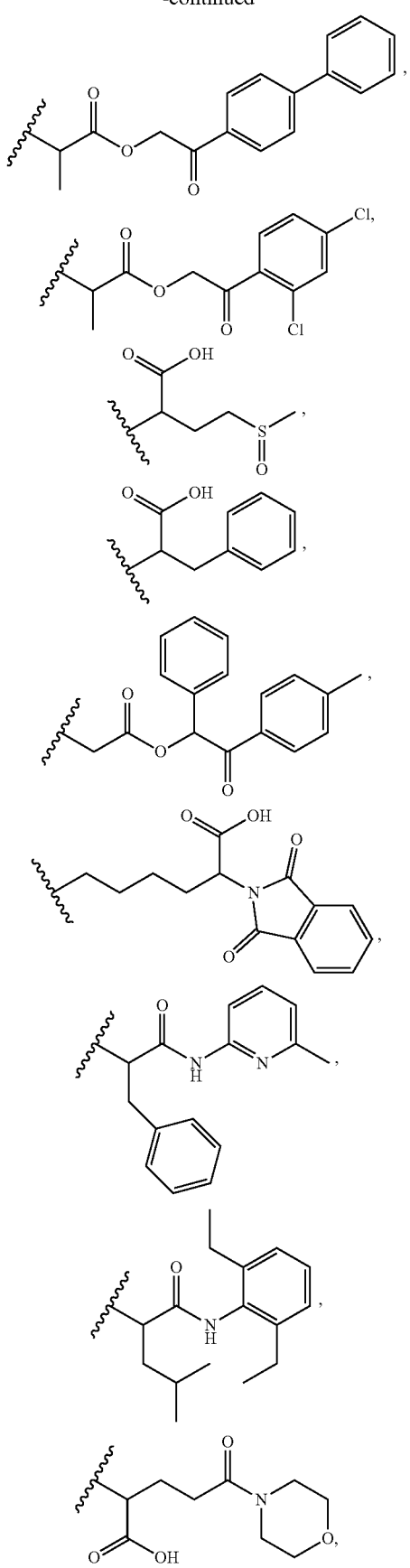

-continued
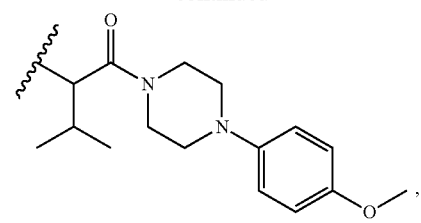
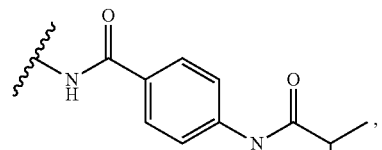
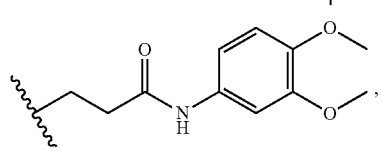
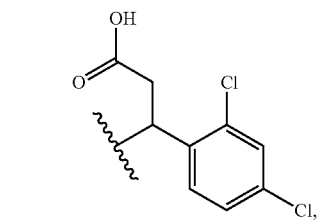
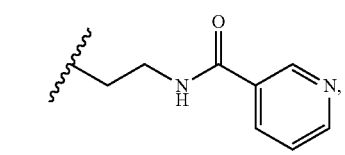
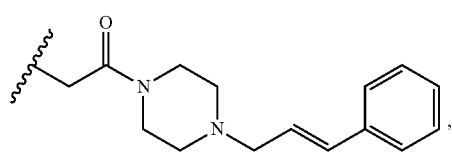
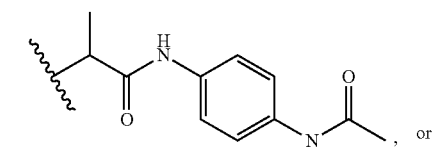
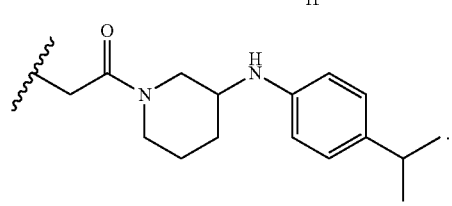
In embodiments, -L$^3$-R$^6$ is not
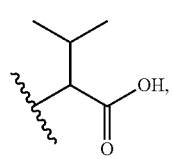
-continued
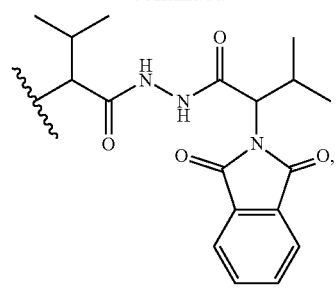
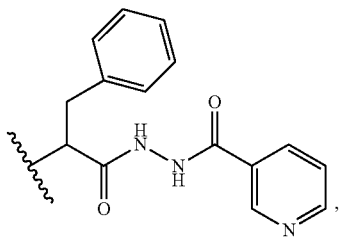
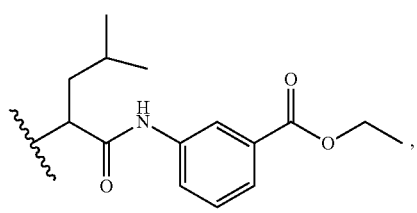
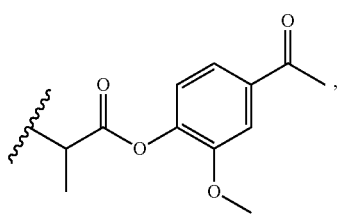
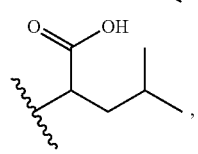
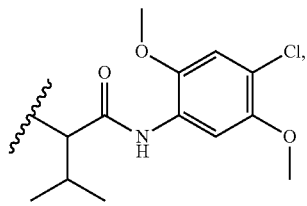
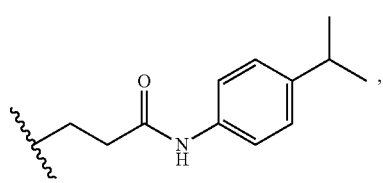
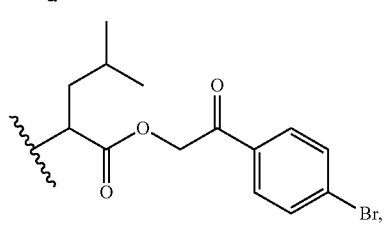

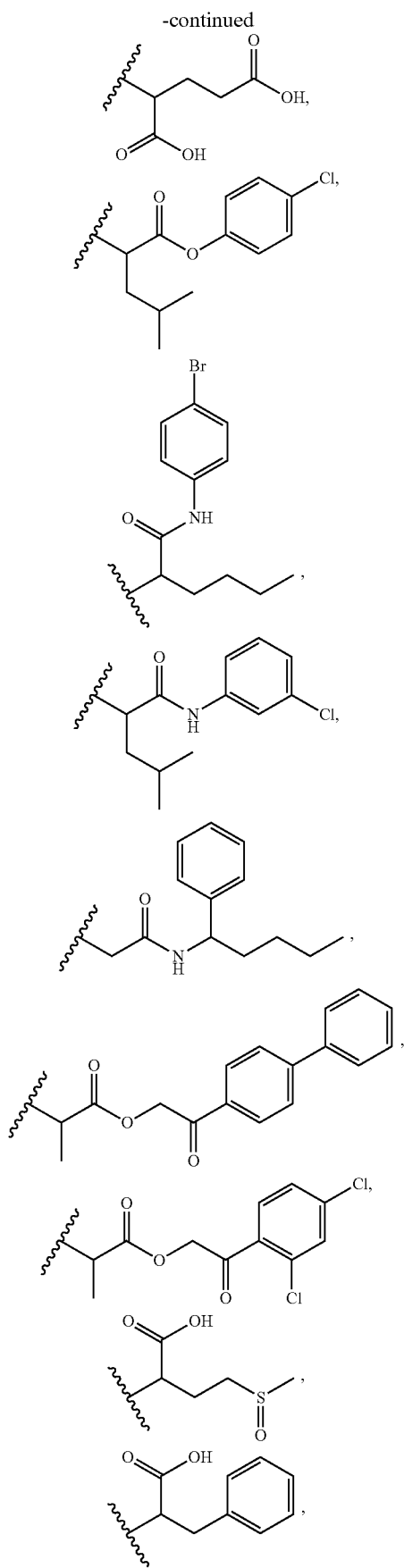
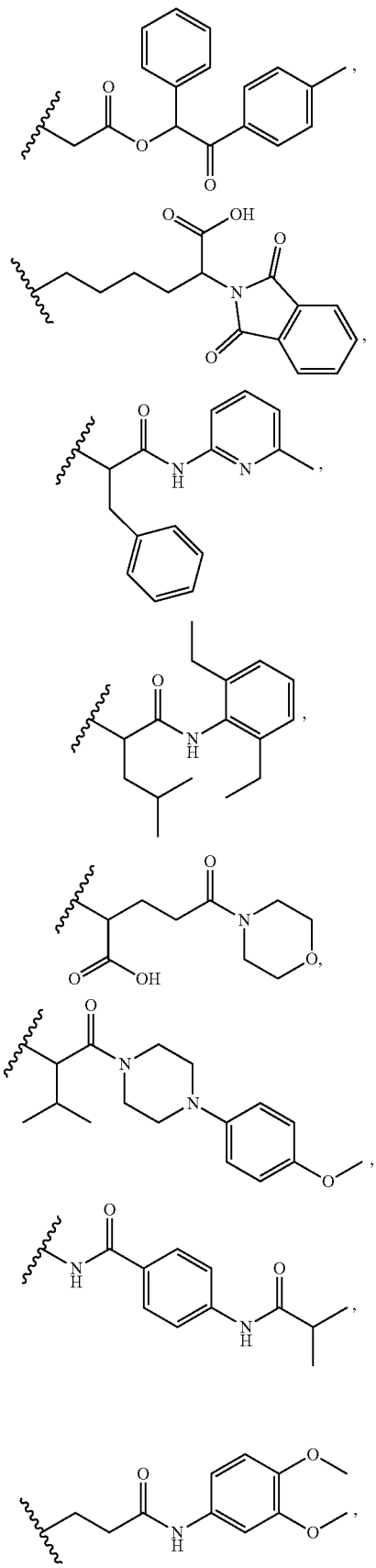

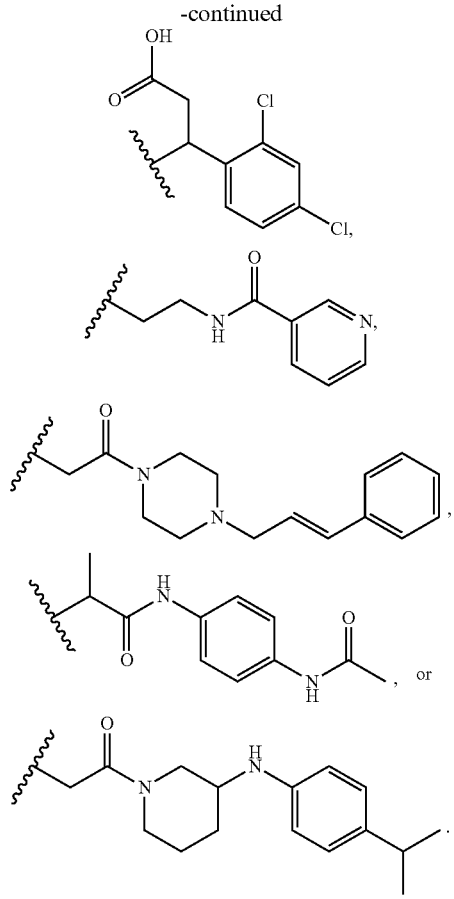
In embodiments, the compound is:
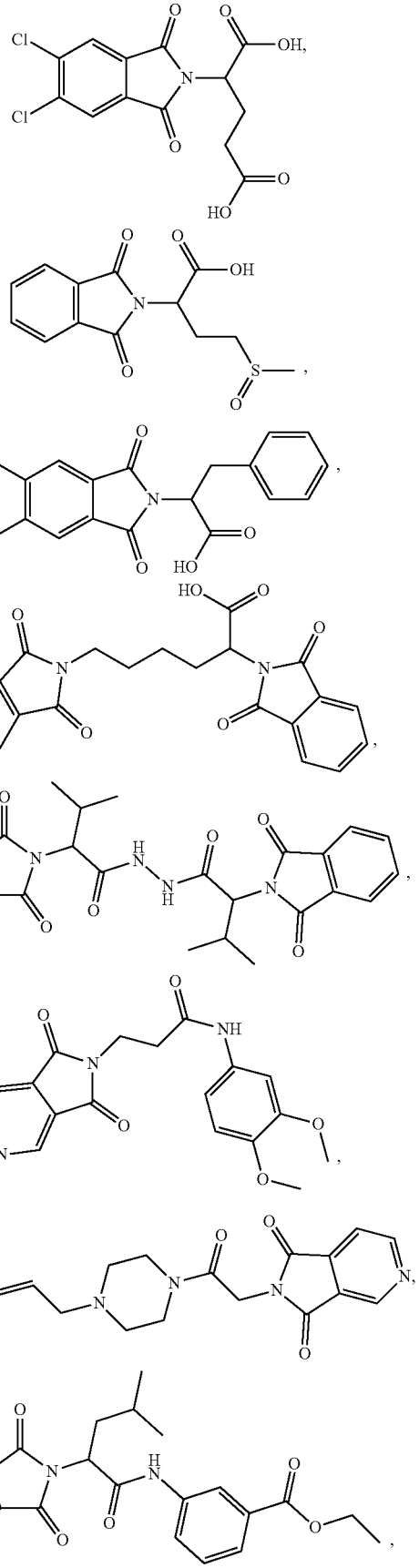

99
-continued
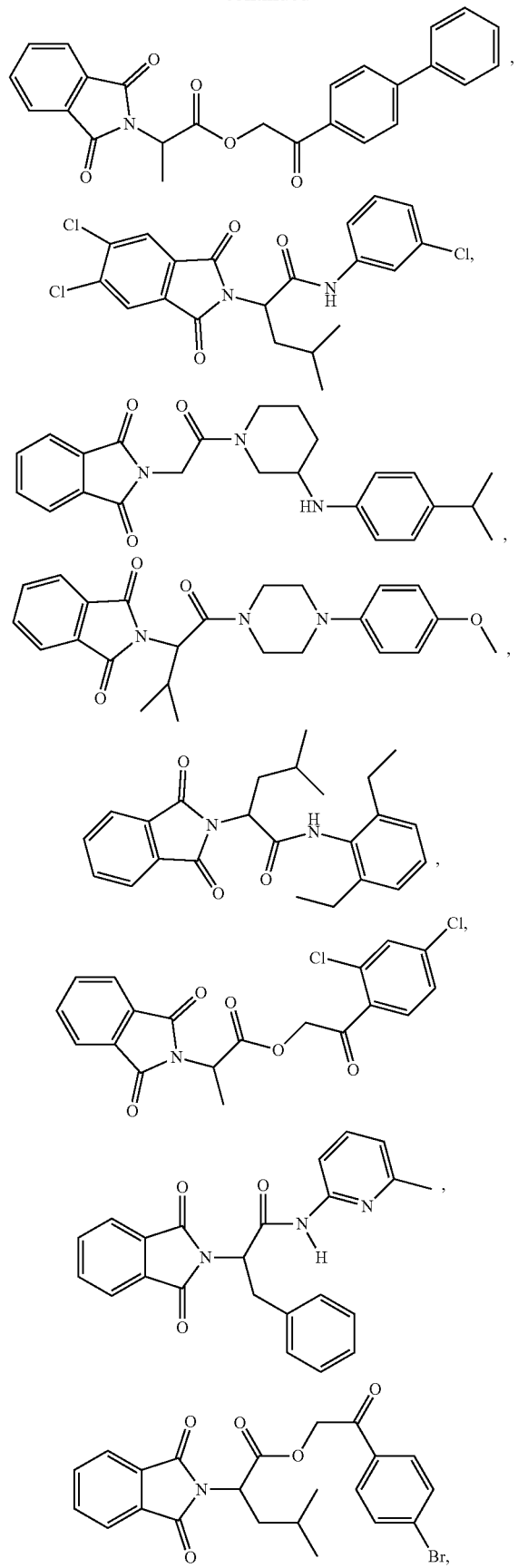
100
-continued
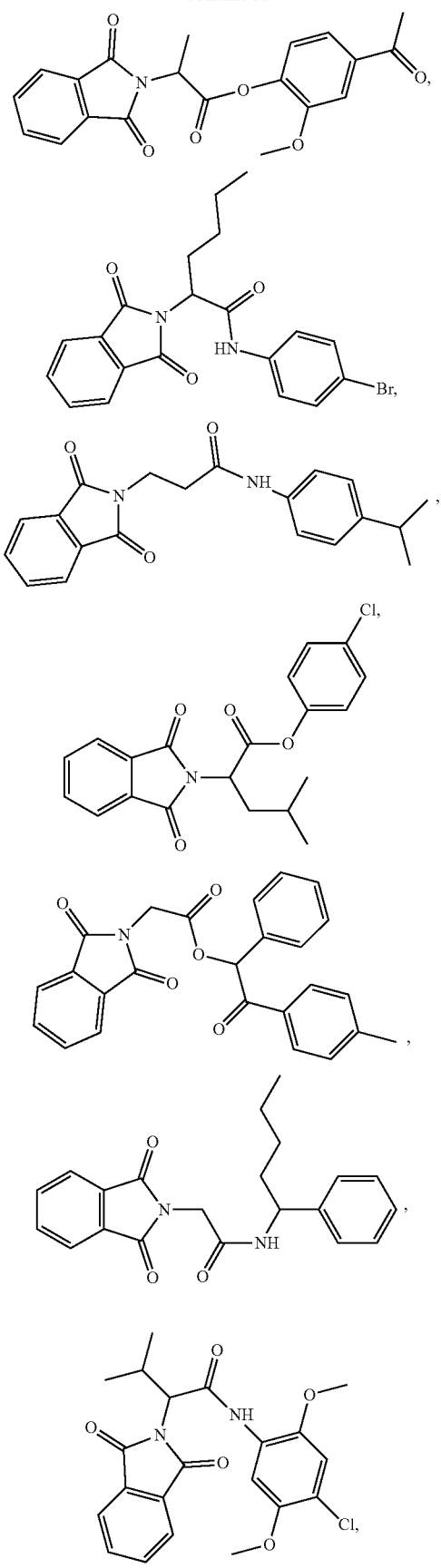

101
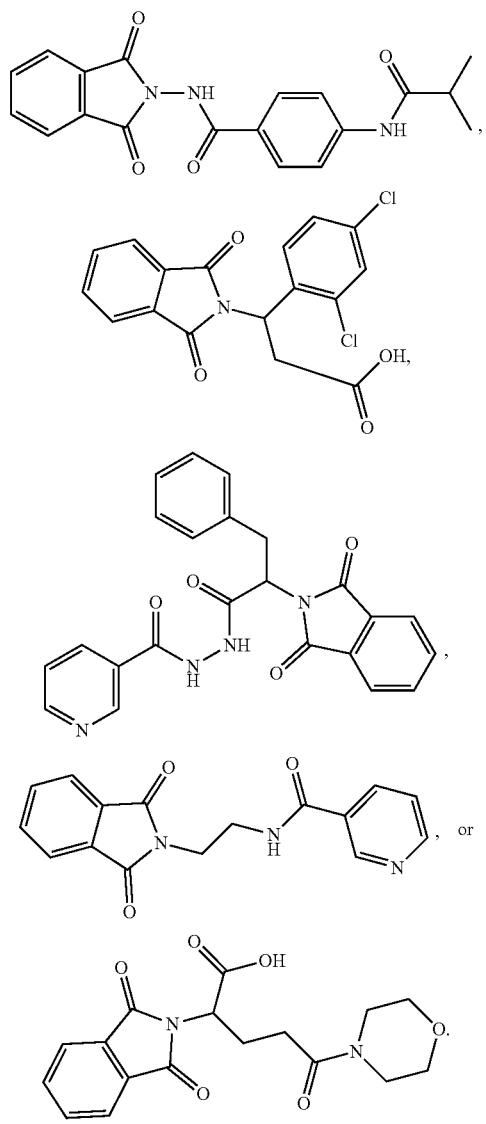
102
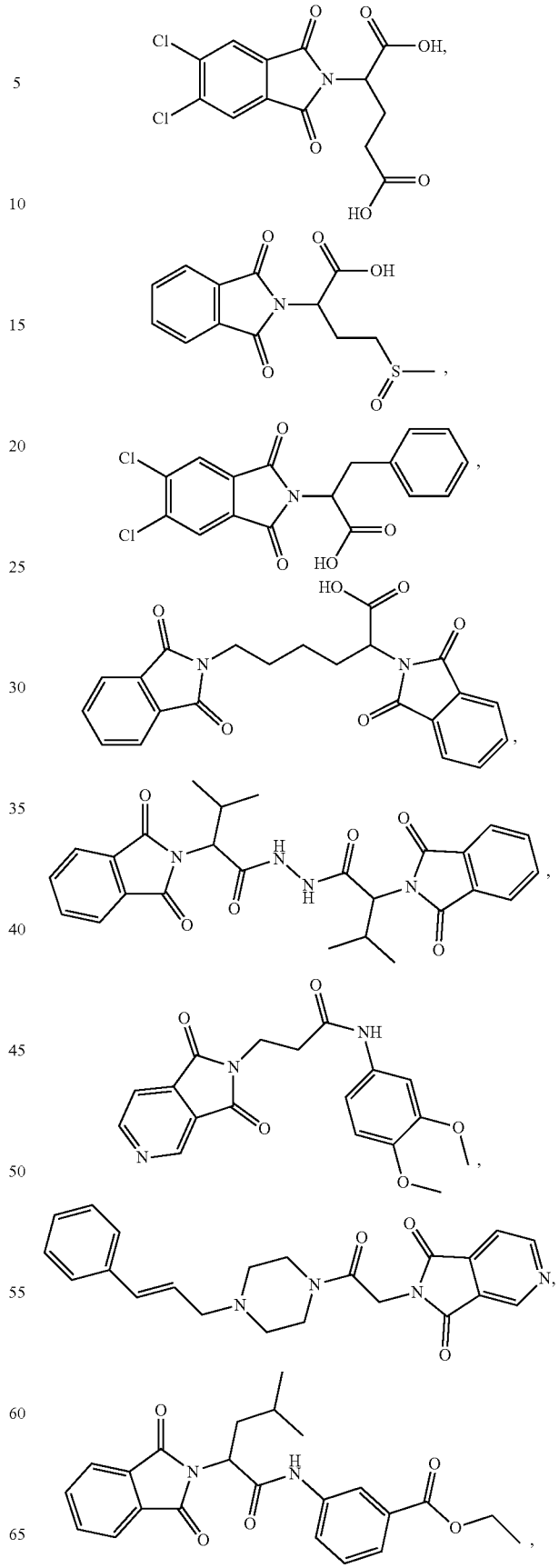
In embodiments, the compound is:
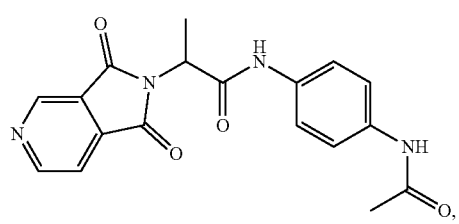
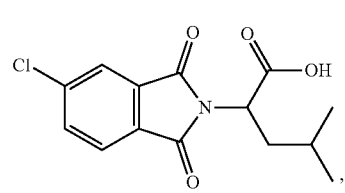

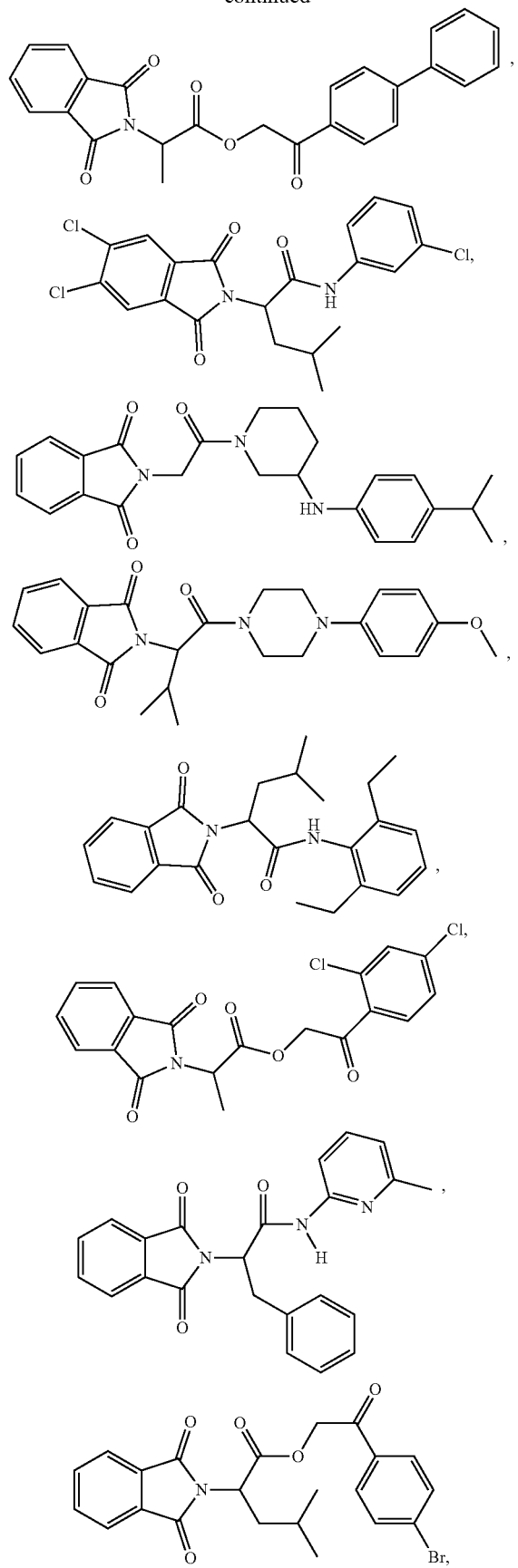
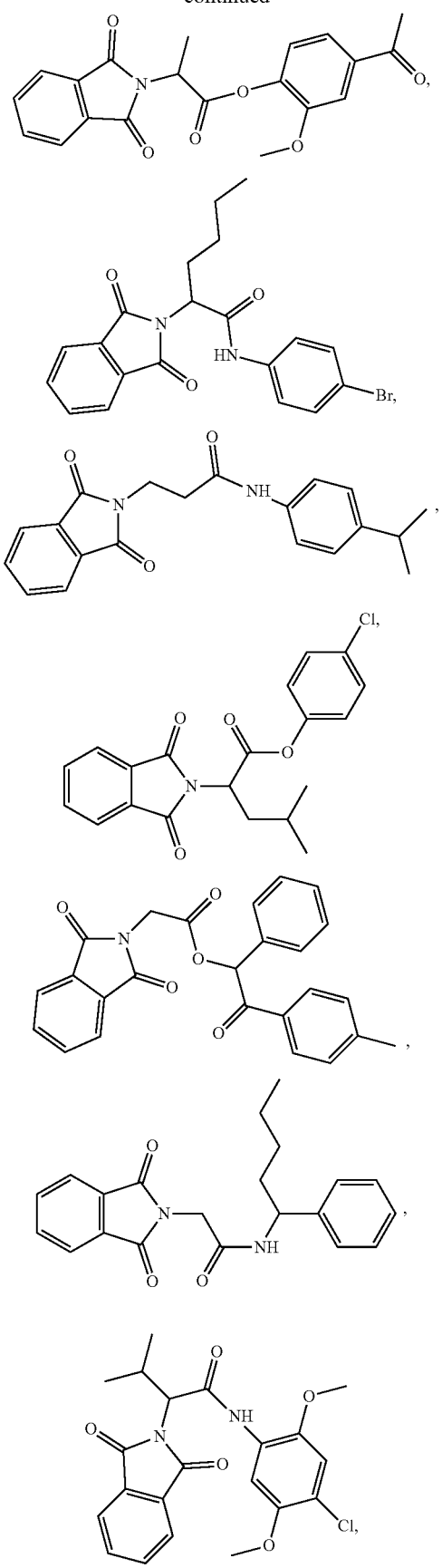

-continued
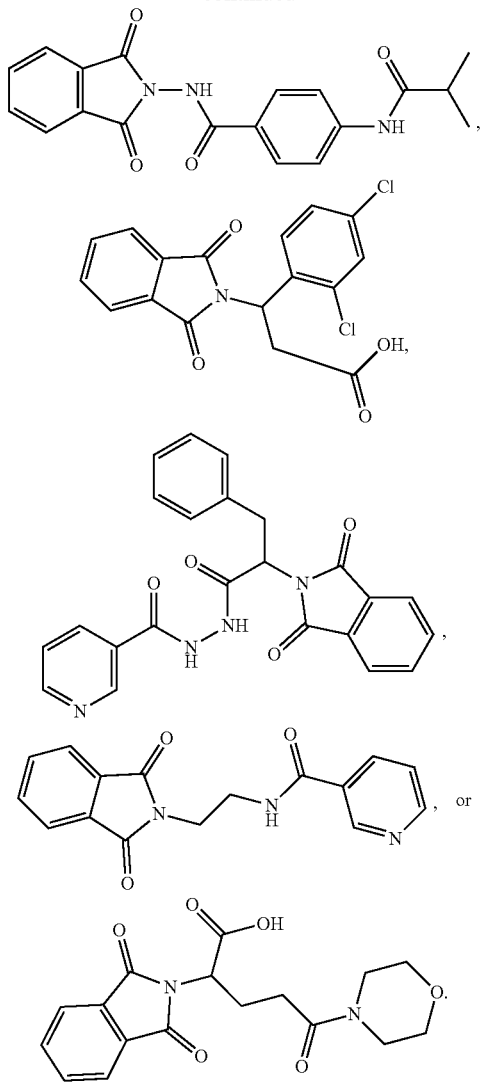
In embodiments, the compound is
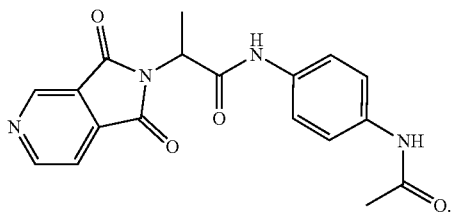 [SMILES: CC(=O)Nc1ccc(NC(=O)C(C)N2C(=O)c3ccncc3C2=O)cc1]
In embodiments, the compound is
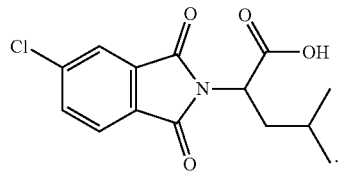 [SMILES: CC(C)CC(C(=O)O)N1C(=O)c2ccc(Cl)cc2C1=O]
In embodiments, the compound is
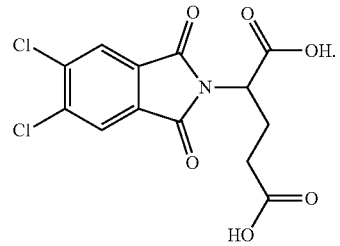 [SMILES: O=C(O)CCC(C(=O)O)N1C(=O)c2cc(Cl)c(Cl)cc2C1=O]
In embodiments, the compound is
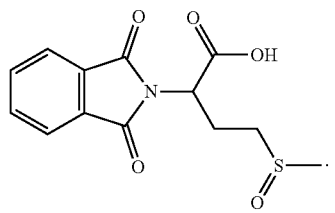 [SMILES: CS(=O)CCC(C(=O)O)N1C(=O)c2ccccc2C1=O]
In embodiments, the compound is
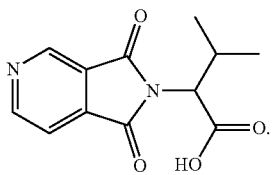
In embodiments, the compound is
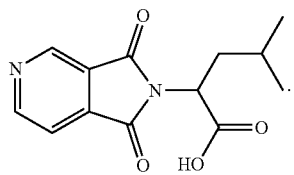
In embodiments, the compound is
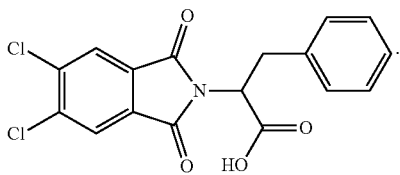 [SMILES: O=C(O)C(Cc1ccccc1)N1C(=O)c2cc(Cl)c(Cl)cc2C1=O]

In embodiments, the compound is
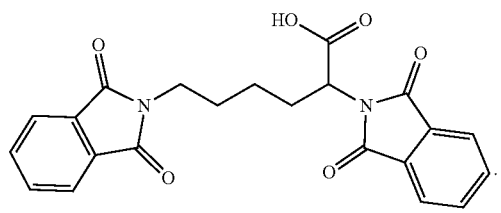 [SMILES: O=C(O)C(CCCCN1C(=O)c2ccccc2C1=O)N1C(=O)c2ccccc2C1=O]
In embodiments, the compound is
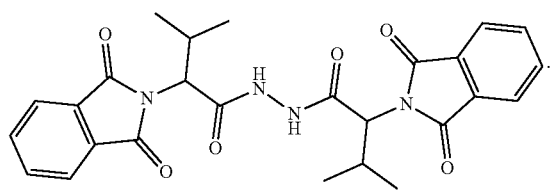 [SMILES: CC(C)C(C(=O)NNC(=O)C(C(C)C)N1C(=O)c2ccccc2C1=O)N1C(=O)c2ccccc2C1=O]
In embodiments, the compound is
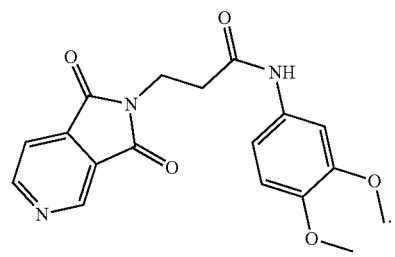 [SMILES: COc1ccc(NC(=O)CCN2C(=O)c3ccncc3C2=O)cc1OC]
The embodiments, the compound is
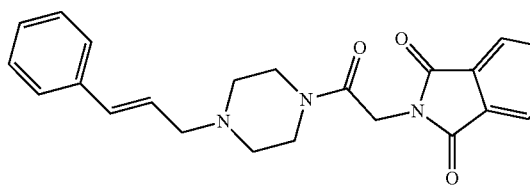
In embodiments, the compound is
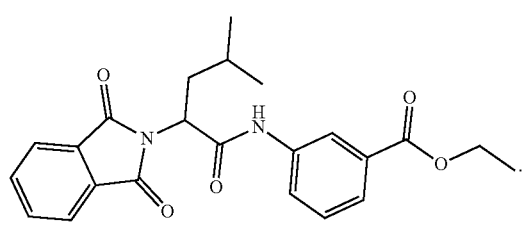 [SMILES: CCOC(=O)c1cccc(NC(=O)C(CC(C)C)N2C(=O)c3ccccc3C2=O)c1]
In embodiments, the compound is
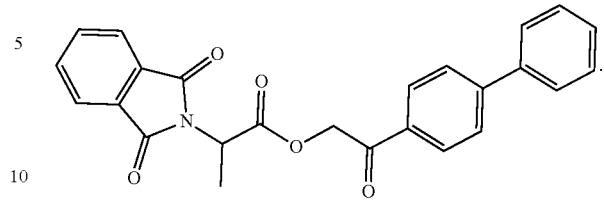
In embodiments, the compound is
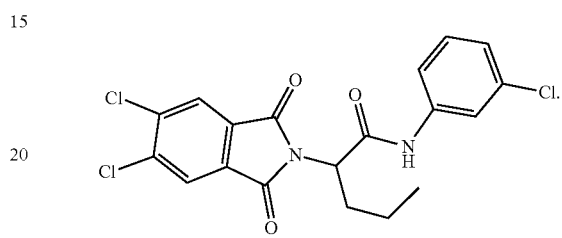
In embodiments, the compound is
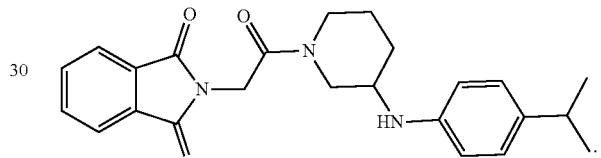
In embodiments, the compound is
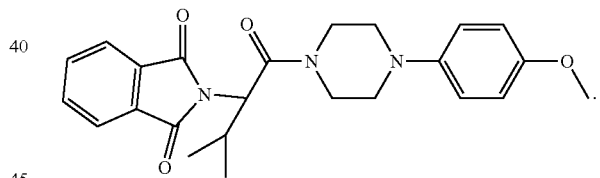
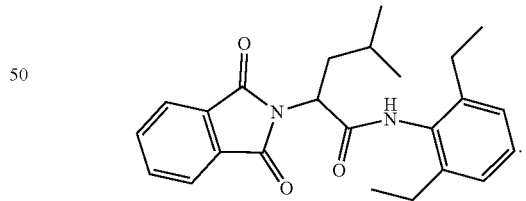
In embodiments, the compound is
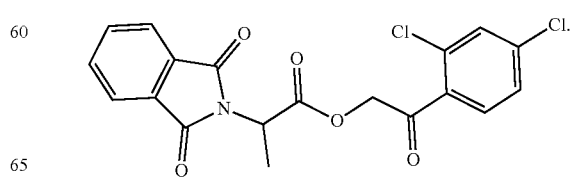

In embodiments, the compound is
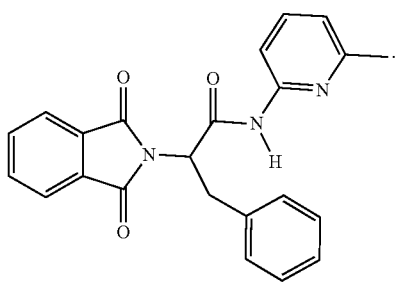 [SMILES: Cc1cccc(NC(=O)C(Cc2ccccc2)N2C(=O)c3ccccc3C2=O)n1]
In embodiments, the compound is
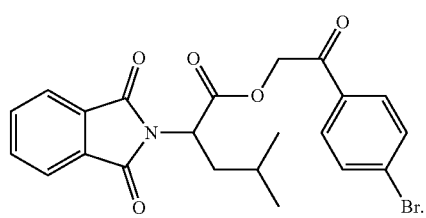 [SMILES: CC(C)CC(C(=O)OCC(=O)c1ccc(Br)cc1)N1C(=O)c2ccccc2C1=O]
In embodiments, the compound is
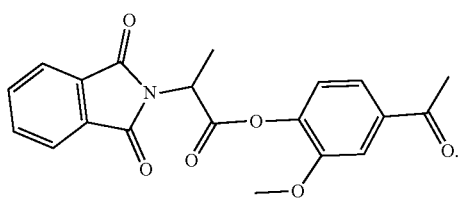 [SMILES: COc1cc(C(C)=O)ccc1OC(=O)C(C)N1C(=O)c2ccccc2C1=O]
In embodiments, the compound is
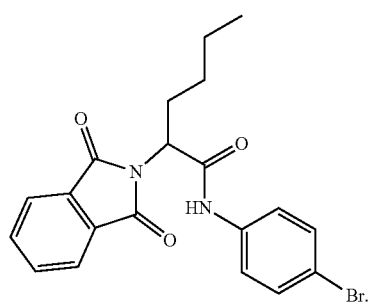 [SMILES: CCCCC(C(=O)Nc1ccc(Br)cc1)N1C(=O)c2ccccc2C1=O]
In embodiments, the compound is
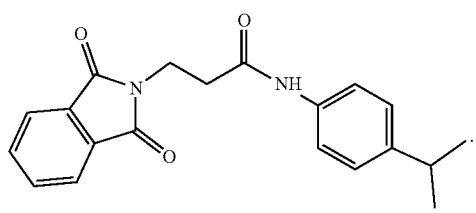 [SMILES: CC(C)c1ccc(NC(=O)CCN2C(=O)c3ccccc3C2=O)cc1]
In embodiments, the compound is
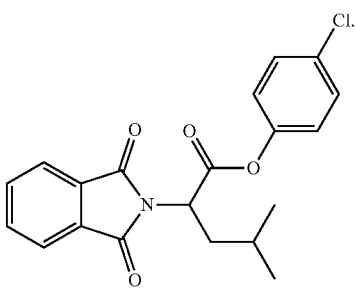 [SMILES: CC(C)CC(C(=O)Oc1ccc(Cl)cc1)N1C(=O)c2ccccc2C1=O]
In embodiments, the compound is
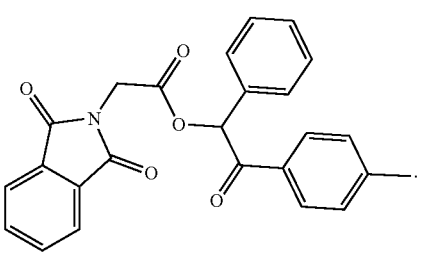 [SMILES: Cc1ccc(C(=O)C(OC(=O)CN2C(=O)c3ccccc3C2=O)c2ccccc2)cc1]
In embodiments, the compound is
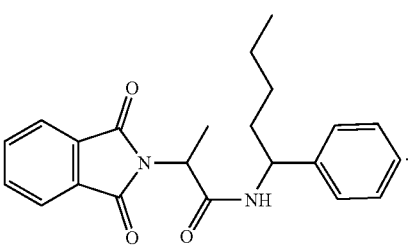 [SMILES: CCCCC(NC(=O)C(C)N1C(=O)c2ccccc2C1=O)c1ccccc1]
In embodiments, the compound is
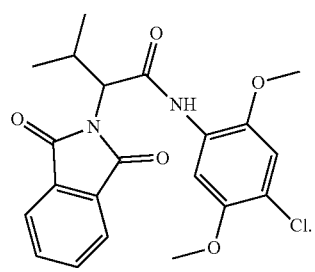 [SMILES: COc1cc(NC(=O)C(C(C)C)N2C(=O)c3ccccc3C2=O)c(OC)cc1Cl]
In embodiments, the compound is
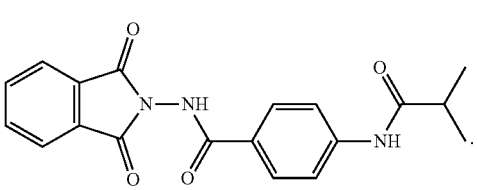

111
In embodiments, the compound is
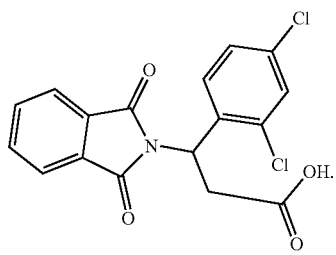 [SMILES: O=C(O)CC(c1ccc(Cl)cc1Cl)N1C(=O)c2ccccc2C1=O]
In embodiments, the compound is
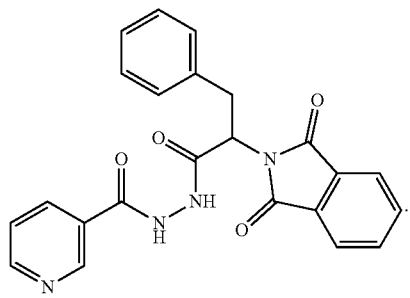 [SMILES: O=C(NNC(=O)C(Cc1ccccc1)N1C(=O)c2ccccc2C1=O)c1cccnc1]
In embodiments, the compound is
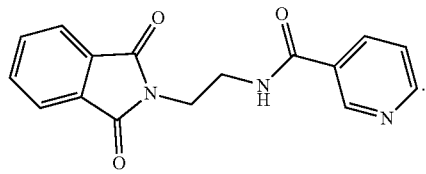 [SMILES: O=C(NCCN1C(=O)c2ccccc2C1=O)c1cccnc1]
In embodiments, the compound is
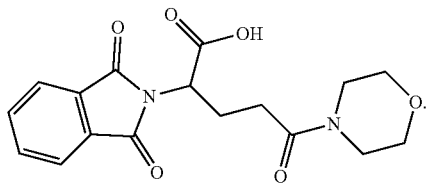 [SMILES: O=C(O)C(CCC(=O)N1CCOCC1)N1C(=O)c2ccccc2C1=O]
In embodiments, the compound is not
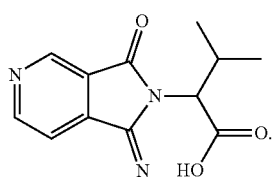 [SMILES: CC(C)C(C(=O)O)N1C(=N)c2ccncc2C1=O]
112
In embodiments, the compound is not
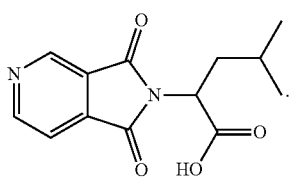 [SMILES: CC(C)CC(C(=O)O)N1C(=O)c2ccncc2C1=O]
In embodiments, the compound is not
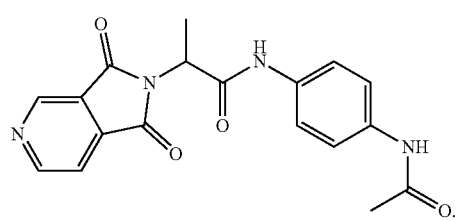 [SMILES: CC(=O)Nc1ccc(NC(=O)C(C)N2C(=O)c3ccncc3C2=O)cc1]
In embodiments, the compound is not
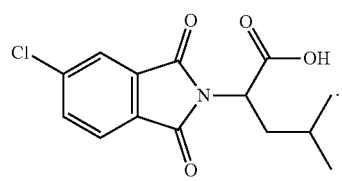 [SMILES: CC(C)CC(C(=O)O)N1C(=O)c2ccc(Cl)cc2C1=O]
In embodiments, the compound is not
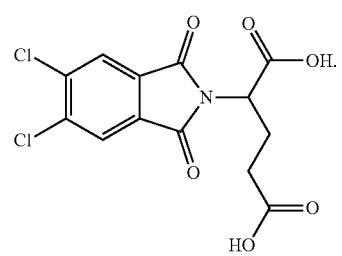 [SMILES: O=C(O)CCC(C(=O)O)N1C(=O)c2cc(Cl)c(Cl)cc2C1=O]
In embodiments, the compound is not
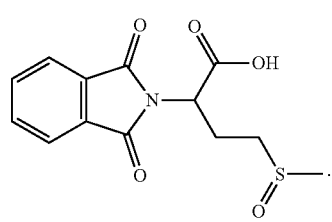 [SMILES: CS(=O)CCC(C(=O)O)N1C(=O)c2ccccc2C1=O]

In embodiments, the compound is not
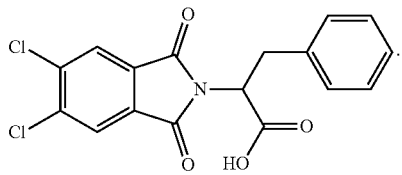 [SMILES: O=C(O)C(Cc1ccccc1)N1C(=O)c2cc(Cl)c(Cl)cc2C1=O]
In embodiments, the compound is not
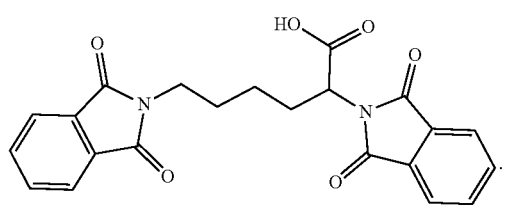 [SMILES: O=C(O)C(CCCCN1C(=O)c2ccccc2C1=O)N1C(=O)c2ccccc2C1=O]
In embodiments, the compound is not
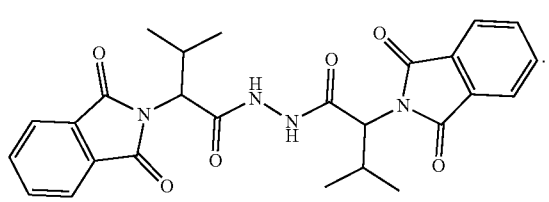 [SMILES: CC(C)C(C(=O)NNC(=O)C(C(C)C)N1C(=O)c2ccccc2C1=O)N1C(=O)c2ccccc2C1=O]
In embodiments, the compound is not
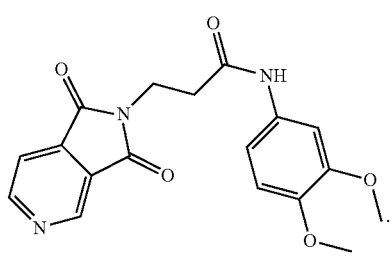 [SMILES: COc1ccc(NC(=O)CCN2C(=O)c3ccncc3C2=O)cc1OC]
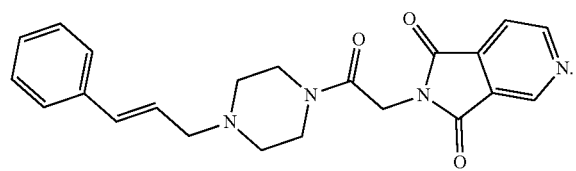 [SMILES: O=C(CN1C(=O)c2ccncc2C1=O)N1CCN(C/C=C/c2ccccc2)CC1]
In embodiments, the compound is not
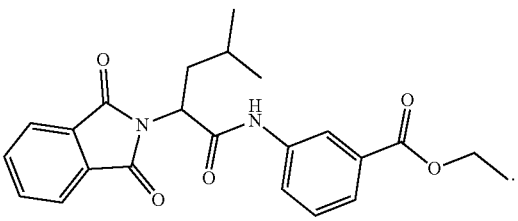 [SMILES: CCOC(=O)c1cccc(NC(=O)C(CC(C)C)N2C(=O)c3ccccc3C2=O)c1]
In embodiments, the compound is not
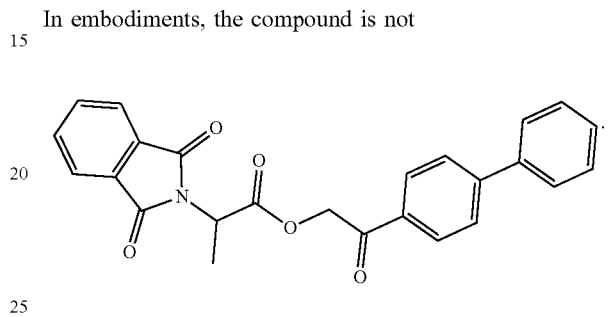
In embodiments, the compound is not
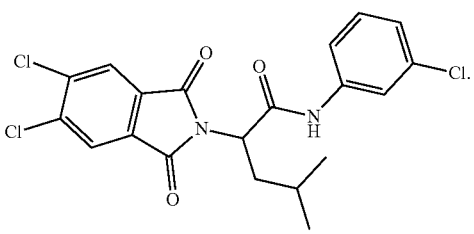 [SMILES: CC(C)CC(C(=O)Nc1cccc(Cl)c1)N1C(=O)c2cc(Cl)c(Cl)cc2C1=O]
In embodiments, the compound is not
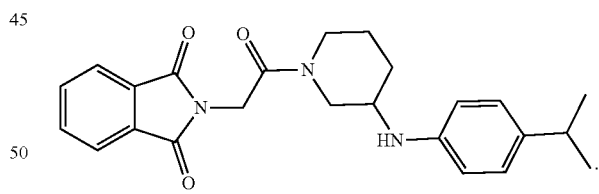
In embodiments, the compound is not
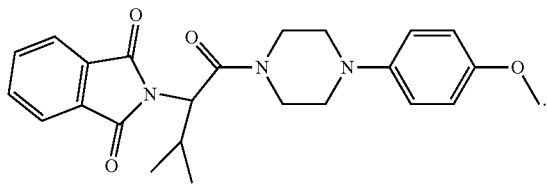 [SMILES: COc1ccc(N2CCN(C(=O)C(C(C)C)N3C(=O)c4ccccc4C3=O)CC2)cc1]

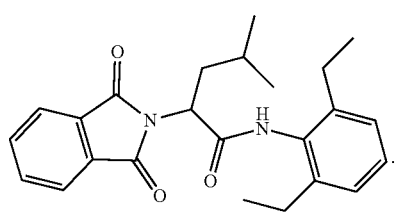 [SMILES: CCc1cccc(CC)c1NC(=O)C(CC(C)C)N1C(=O)c2ccccc2C1=O]
In embodiments, the compound is not
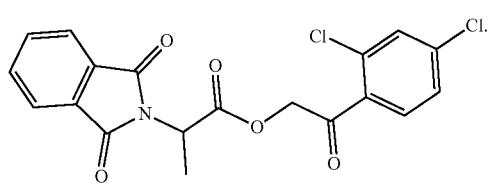 [SMILES: CC(C(=O)OCC(=O)c1ccc(Cl)cc1Cl)N1C(=O)c2ccccc2C1=O]
In embodiments, the compound is not
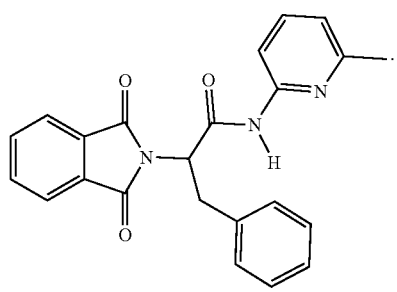 [SMILES: Cc1cccc(NC(=O)C(Cc2ccccc2)N2C(=O)c3ccccc3C2=O)n1]
In embodiments, the compound is not
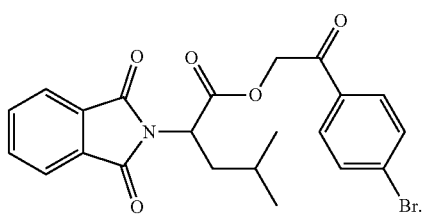 [SMILES: CC(C)CC(C(=O)OCC(=O)c1ccc(Br)cc1)N1C(=O)c2ccccc2C1=O]
In embodiments, the compound is not
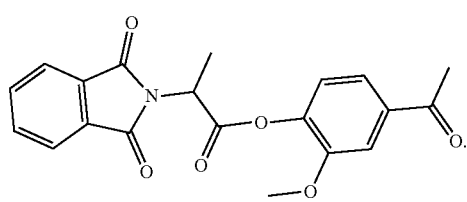 [SMILES: COc1cc(C(C)=O)ccc1OC(=O)C(C)N1C(=O)c2ccccc2C1=O]
In embodiments, the compound is not
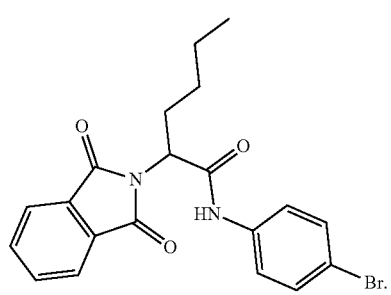 [SMILES: CCCCC(C(=O)Nc1ccc(Br)cc1)N1C(=O)c2ccccc2C1=O]
In embodiments, the compound is not
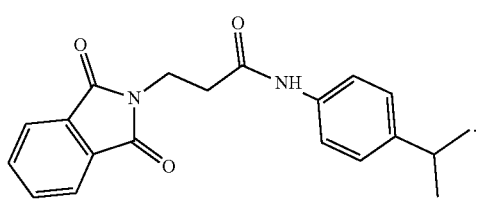 [SMILES: CC(C)c1ccc(NC(=O)CCN2C(=O)c3ccccc3C2=O)cc1]
In embodiments, the compound is not
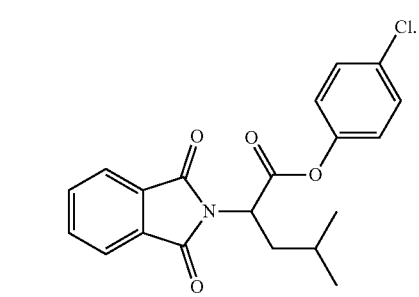 [SMILES: CC(C)CC(C(=O)Oc1ccc(Cl)cc1)N1C(=O)c2ccccc2C1=O]
In embodiments, the compound is not
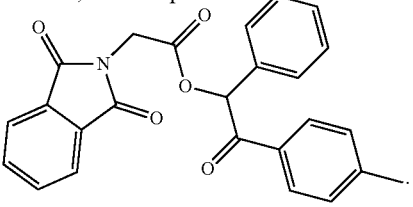
In embodiments, the compound is not
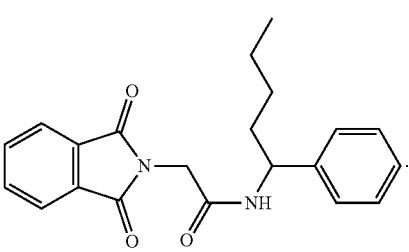 [SMILES: CCCCC(NC(=O)CN1C(=O)c2ccccc2C1=O)c1ccccc1]

In embodiments, the compound is not

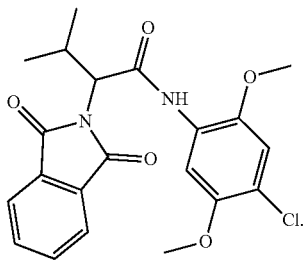 [SMILES: COc1cc(NC(=O)C(C(C)C)N2C(=O)c3ccccc3C2=O)c(OC)cc1Cl]

In embodiments, the compound is not

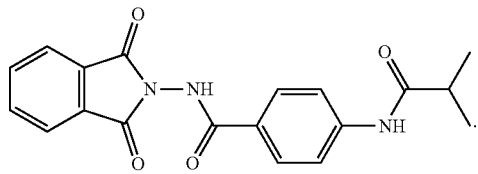 [SMILES: CC(C)C(=O)Nc1ccc(C(=O)NN2C(=O)c3ccccc3C2=O)cc1]

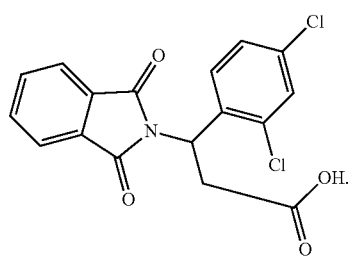 [SMILES: O=C(O)CC(c1ccc(Cl)cc1Cl)N1C(=O)c2ccccc2C1=O]

In embodiments, the compound is not

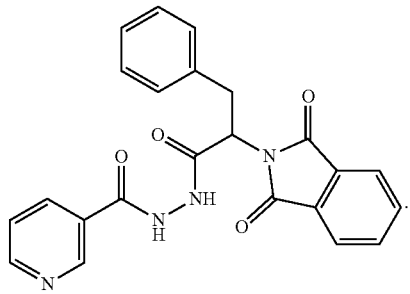 [SMILES: O=C(NNC(=O)C(Cc1ccccc1)N1C(=O)c2ccccc2C1=O)c1cccnc1]

In embodiments, the compound is not

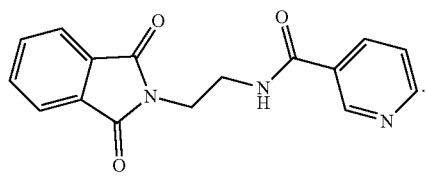 [SMILES: O=C(NCCN1C(=O)c2ccccc2C1=O)c1cccnc1]

In embodiments, the compound is not

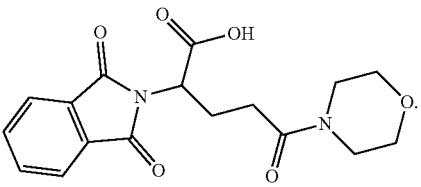 [SMILES: O=C(O)C(CCC(=O)N1CCOCC1)N1C(=O)c2ccccc2C1=O]

In embodiments, $L^3$ is a $R^3$-substituted or unsubstituted $C_1$-$C_6$ alkylene, or $R^3$-substituted or unsubstituted 2 to 6 membered heteroalkylene, wherein $R^3$ is oxo, —COOH, unsubstituted $C_1$-$C_4$ alkyl, or unsubstituted phenyl.

In embodiments, $L^3$ is independently a $R^3$-substituted or unsubstituted $C_1$-$C_6$ alkylene, or $R^3$-substituted or unsubstituted 2 to 6 membered heteroalkylene, wherein $R^3$ is oxo, —COOH, unsubstituted $C_1$-$C_4$ alkyl, or unsubstituted phenyl.

In embodiments, $L^3$ is a $R^3$-substituted or unsubstituted $C_1$-$C_6$ alkylene, or $R^3$-substituted or unsubstituted 2 to 6 membered heteroalkylene, and $R^6$ is an $R^7$-substituted phenyl.

In embodiments, $L^3$ is independently a $R^3$-substituted or unsubstituted $C_1$-$C_6$ alkylene, or $R^3$-substituted or unsubstituted 2 to 6 membered heteroalkylene, and $R^6$ is an $R^7$-substituted phenyl.

In embodiments, $L^3$ is a $R^3$-substituted or unsubstituted $C_1$-$C_6$ alkylene, or $R^3$-substituted or unsubstituted 2 to 6 membered heteroalkylene, and $R^6$ is an $R^7$-substituted heterocycloalkyl. In embodiments, $L^3$ is a $R^3$-substituted $C_1$-$C_6$ alkylene, or $R^3$-substituted 2 to 6 membered heteroalkylene, wherein $R^3$ is oxo, —COOH, unsubstituted $C_1$-$C_4$ alkyl, or unsubstituted phenyl; and $R^6$ is an $R^7$-substituted heterocycloalkyl. In embodiments, $L^3$ is a $R^3$-substituted or unsubstituted $C_1$-$C_6$ alkylene, or $R^3$-substituted or unsubstituted 2 to 6 membered heteroalkylene, and $R^6$ is an unsubstituted heterocycloalkyl.

In embodiments, $L^3$ is independently a $R^3$-substituted or unsubstituted $C_1$-$C_6$ alkylene, or $R^3$-substituted or unsubstituted 2 to 6 membered heteroalkylene, and $R^6$ is independently an $R^7$-substituted heterocycloalkyl. In embodiments, $L^3$ is independently a $R^3$-substituted $C_1$-$C_6$ alkylene, or $R^3$-substituted 2 to 6 membered heteroalkylene, wherein $R^3$ is independently oxo, —COOH, unsubstituted $C_1$-$C_4$ alkyl, or unsubstituted phenyl; and $R^6$ is independently an $R^7$-substituted heterocycloalkyl. In embodiments, $L^3$ is independently a $R^3$-substituted or unsubstituted $C_1$-$C_6$ alkylene, or $R^3$-substituted or unsubstituted 2 to 6 membered heteroalkylene, and $R^6$ is independently an unsubstituted heterocycloalkyl.

In embodiments, the compound has the formula

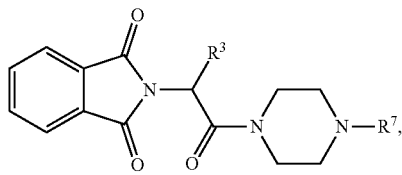

wherein $R^3$ and $R^7$ are as described herein. In embodiments, $R^7$ is independently an $R^8$-substituted phenyl. In embodiments, $R^8$ is independently unsubstituted methoxy.

In embodiments, the compound has the formula

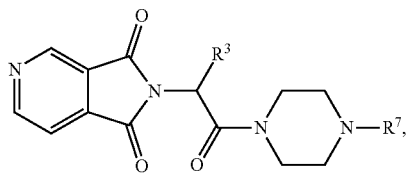

wherein R³ and R⁷ are as described herein. In embodiments, R⁷ is independently an R⁸-substituted phenyl. In embodiments, R⁸ is independently unsubstituted methoxy.

In embodiments, the compound is

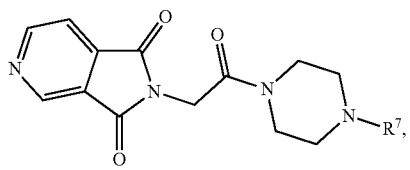

wherein R⁷ is as described herein. In embodiments, R⁷ is an R⁸-substituted C₁-C₄ alkyl. In embodiments, R⁸ is an unsubstituted phenyl.

In embodiments, the compound has the formula

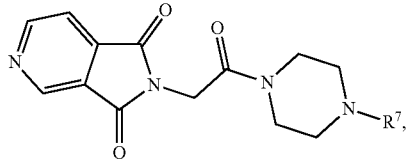

wherein R⁷ is as described herein. In embodiments, R⁷ is independently an R⁸-substituted C₁-C₄ alkyl. In embodiments, R⁸ is independently an unsubstituted phenyl.

In embodiments, the compound has the formula

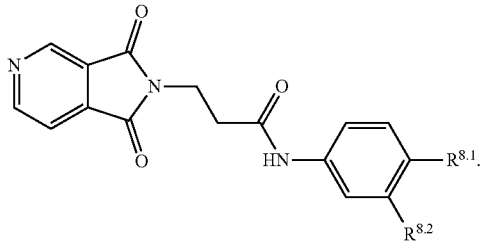

$R^{8.1}$ and $R^{8.2}$ may each independently be any value of $R^8$ as described herein, including in embodiments, or hydrogen. In embodiments, $R^{8.1}$ and $R^{8.2}$ are each independently unsubstituted methoxy.

In embodiments, the compound has the formula

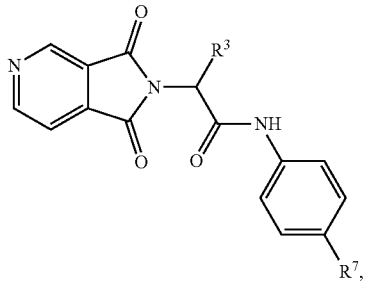

wherein R³ and R⁷ are as described herein. In embodiments, R⁷ is independently an R⁸-substituted 2 to 4 membered heteroalkyl. In embodiments, R⁷ is independently —NHC(O)CH₃.

In embodiments, the compound has the formula

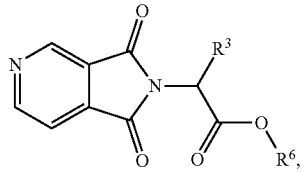

wherein R³ and R⁶ are as described herein. In embodiments, R³ is independently an unsubstituted C1-C4 alkyl. In embodiments, R³ is independently an unsubstituted isopropyl. In embodiments, R³ is independently an unsubstituted isobutyl. In embodiments, R⁶ is independently hydrogen.

In embodiments, the compound has the formula

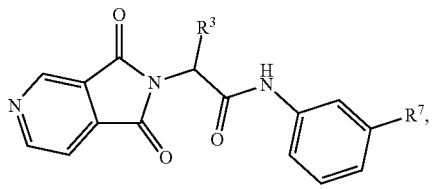

wherein R³ and R⁷ are as described herein. In embodiments, R⁷ is independently an R⁸-substituted 3 to 7 membered heteroalkyl. In embodiments, R⁸ is independently oxo.

In embodiments, the compound has the formula

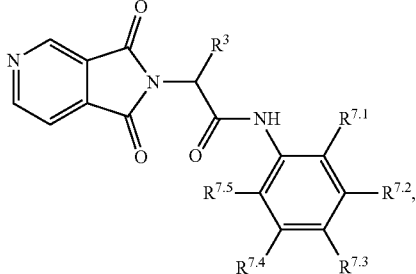

wherein R³ is as described herein. $R^{7.1}$, $R^{7.2}$, $R^{7.3}$, $R^{7.4}$, and $R^{7.5}$ may each independently be any value of $R^7$ as described herein, including in embodiments, or hydrogen. In embodiments, $R^{7.1}$ is independently unsubstituted methoxy. In embodiments, $R^7$ is independently halogen. In embodiments, $R^{7.1}$ is independently —Cl. In embodiments, $R^{7.3}$ is independently a halogen. In embodiments, $R^{7.3}$ is independently —Cl. In embodiments, $R^{7.4}$ is independently unsubstituted methoxy. In embodiments, $R^{7.1}$ and $R^{7.5}$ are each independently unsubstituted $C_1$-$C_4$ alkyl. In embodiments, $R^{7.1}$ and $R^{7.5}$ are each independently unsubstituted ethyl.

In embodiments, the compound has the formula

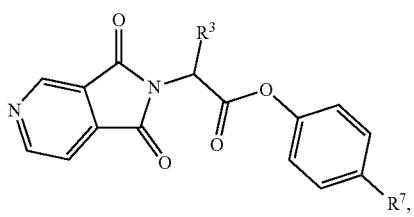

wherein $R^3$ and $R^7$ are as described herein. In embodiments, R is independently halogen. In embodiments, $R^7$ is independently —Cl.

In embodiments, the compound has the formula

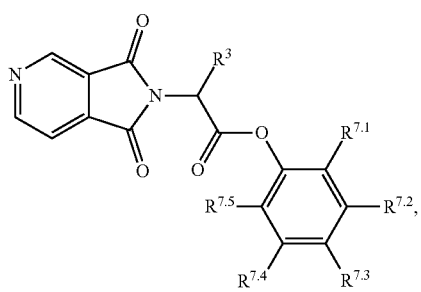

wherein $R^3$ is as described herein. $R^{7.1}$, $R^{7.2}$, $R^{7.3}$, $R^{7.4}$, and $R^{7.5}$ may each independently be any value of $R^7$ as described herein, including in embodiments, or hydrogen. In embodiments, $R^{7.1}$ is independently unsubstituted methoxy. In embodiments, $R^{7.3}$ is independently an oxo-substituted $C_1$-$C_4$ alkyl. In embodiments, $R^{7.3}$ is independently —C(O)CH$_3$.

In embodiments, the compound has the formula

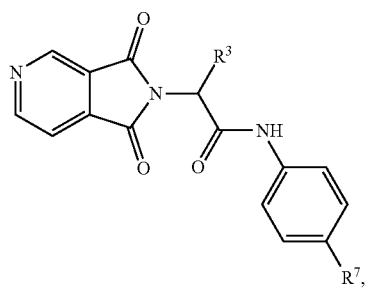

wherein $R^3$ and $R^7$ are as described herein. In embodiments, $R^3$ is independently an unsubstituted $C_1$-$C_4$ alkyl. In embodiments, $R^7$ is independently halogen. In embodiments, $R^7$ is independently —Br.

In embodiments, the compound has the formula

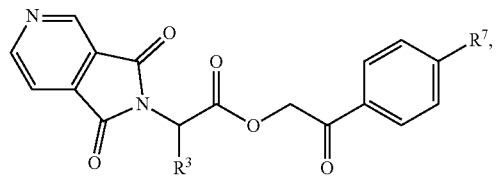

wherein $R^3$ and $R^7$ are as described herein. In embodiments, $R^7$ is independently halogen. In embodiments, $R^7$ is independently —Br.

In embodiments, the compound has the formula

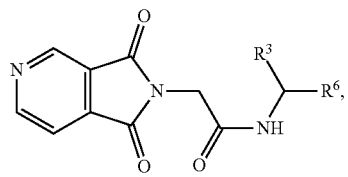

wherein $R^3$ and $R^6$ is as described herein. In embodiments, $R^6$ is independently an unsubstituted phenyl. In embodiments, $R^3$ is independently an unsubstituted $C_1$-$C_6$ alkylene.

In embodiments, the compound has the formula

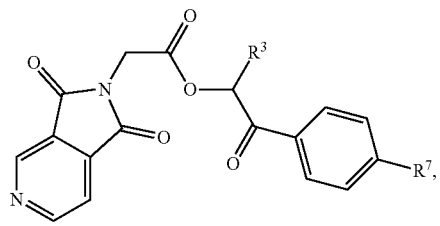

wherein $R^3$ and $R^7$ are as described herein. In embodiments, $R^3$ is independently an unsubstituted phenyl. In embodiments, $R^7$ is independently an unsubstituted $C_1$-$C_4$ alkyl. In embodiments, $R^7$ is independently unsubstituted methyl.

In embodiments, the compound has the formula

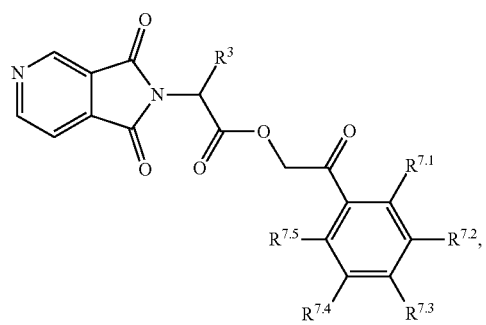

wherein $R^3$ is as described herein. $R^{7.1}$, $R^{7.2}$, $R^{7.3}$, $R^{7.4}$, and $R^{7.5}$ may each independently be any value of $R^7$ as described herein, including in embodiments, or hydrogen. In embodiments, $R^{7.3}$ is independently unsubstituted phenyl. In embodiments, $R^{7.1}$ and $R^{7.3}$ are each independently halogen. In embodiments, $R^{7.1}$ and $R^{7.3}$ are each independently —Cl.

In embodiments, the compound has the formula

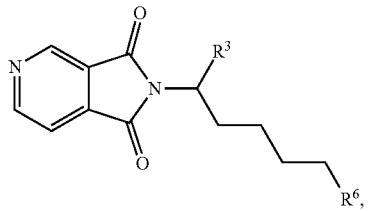

wherein $R^3$ and $R^6$ are as described herein. In embodiments, $R^3$ is independently —COOH. In embodiments, $R^6$ is independently

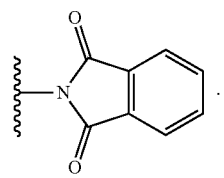

In embodiments, $R^6$ is independently

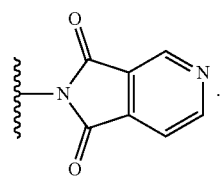

In embodiments, the compound has the formula

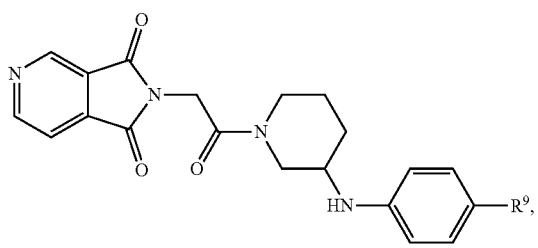

wherein $R^9$ is as described herein. In embodiments, $R^9$ is independently an unsubstituted $C_1$-$C_4$ alkyl. In embodiments, $R^9$ is independently an unsubstituted isopropyl.

In embodiments, the compound has the formula

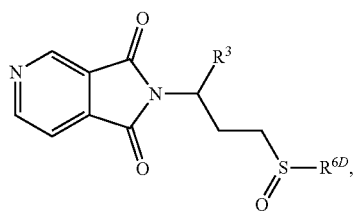

wherein $R^3$ and $R^{6D}$ are as described herein. In embodiments, $R^3$ is independently —COOH. In embodiments, $R^{6D}$ is independently unsubstituted $C_1$-$C_4$ alkyl. In embodiments, $R^{6D}$ is independently unsubstituted methyl.

In embodiments, the compound has the formula

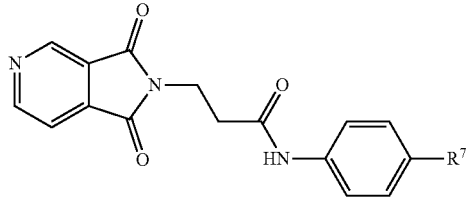

wherein $R^7$ is as described herein. In embodiments, $R^7$ is independently unsubstituted $C_1$-$C_4$ alkyl. In embodiments, $R^7$ is independently unsubstituted isopropyl.

In embodiments, the compound has the formula

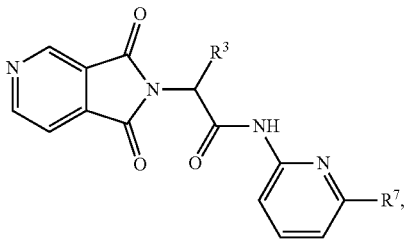

wherein $R^3$ and $R^7$ are as described herein. In embodiments, $R^7$ is independently unsubstituted $C_1$-$C_4$ alkyl. In embodiments, $R^7$ is independently unsubstituted methyl.

In embodiments, the compound has the formula

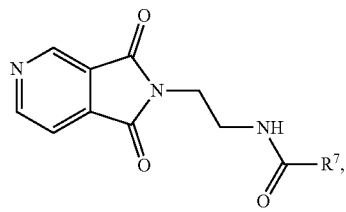

wherein $R^7$ is as described herein. In embodiments, $R^7$ is independently an unsubstituted pyridyl. In embodiments, $R^7$ is independently an unsubstituted 3-pyridyl.

In embodiments, the compound has the formula

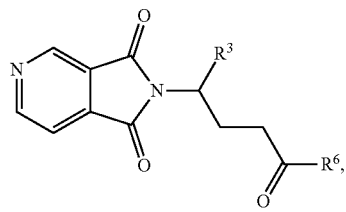

wherein $R^3$ and $R^6$ are as described herein. In embodiments, $R^3$ is independently —COOH. In embodiments, $R^6$ is independently unsubstituted morpholinyl.

In embodiments, the compound has the formula

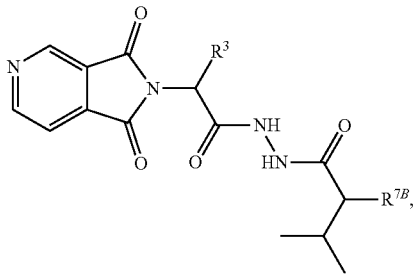

wherein $R^3$ and $R^{7B}$ are as described herein. In embodiments, $R^{7B}$ is independently

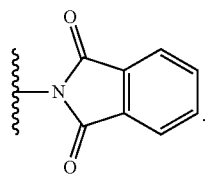 [SMILES: *N1C(=O)c2ccccc2C1=O]

In embodiments, $R^{7B}$ is independently

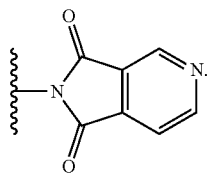 [SMILES: *N1C(=O)c2ccncc2C1=O]

In embodiments, the compound has the formula

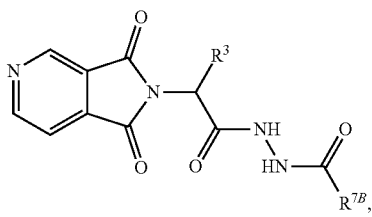

wherein $R^3$ and $R^{7B}$ are as described herein. In embodiments, $R^{7B}$ is independently an unsubstituted pyridyl. In embodiments, $R^{7B}$ is independently an unsubstituted 3-pyridyl.

In embodiments, the compound has the formula

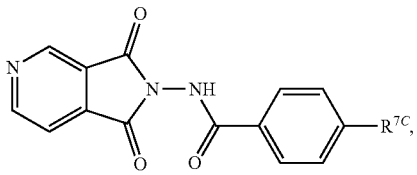

wherein $R^{7C}$ is as described herein. In embodiments, $R^{7C}$ is independently an $R^{8C}$-substituted 4 to 8 membered heteroalkyl. In embodiments, $R^{8C}$ is independently oxo.

In embodiments, the compound has the formula

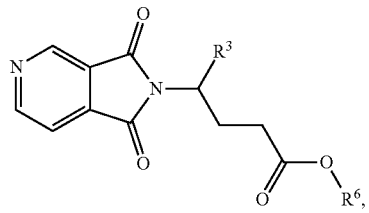

wherein $R^3$ and $R^6$ are as described herein. In embodiments, $R^3$ is independently —COOH. In embodiments, $R^6$ is independently hydrogen.

In embodiments, the compound has the formula

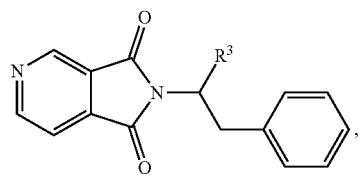

wherein $R^3$ is as described herein. In embodiments, $R^3$ is independently —COOH.

In embodiments, the compound is

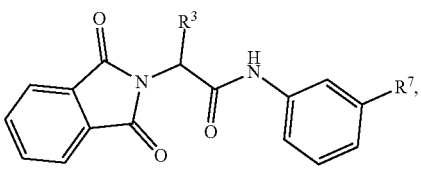

wherein $R^3$ and $R^7$ are as described herein. In embodiments, $R^7$ is independently an $R^8$-substituted 3 to 7 membered heteroalkyl. In embodiments, $R^8$ is independently oxo.

In embodiments, the compound has the formula

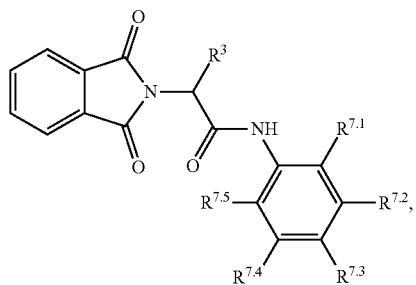

wherein $R^3$ is as described herein. $R^{7.1}$, $R^{7.2}$, $R^{7.3}$, $R^{7.4}$, and $R^{7.5}$ may each independently be any value of $R^7$ as described herein, including in embodiments, or hydrogen. In embodiments, $R^{7.1}$ is independently unsubstituted methoxy. In embodiments, $R^{7.1}$ is independently halogen. In embodiments, $R^{7.1}$ is independently —Cl. In embodiments, $R^{7.3}$ is independently a halogen. In embodiments, $R^{7.3}$ is independently —Cl. In embodiments, $R^{7.4}$ is independently unsubstituted methoxy. In embodiments, $R^{7.1}$ and $R^{7.5}$ are each independently unsubstituted $C_1$-$C_4$ alkyl. In embodiments, $R^{7.1}$ and $R^{7.5}$ are each independently unsubstituted ethyl.

In embodiments, the compound is

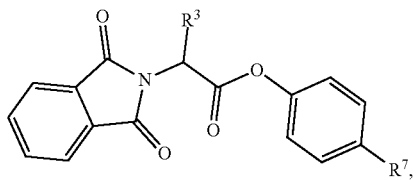

wherein $R^3$ and $R^7$ are as described herein. In embodiments, $R^7$ is independently halogen. In embodiments, $R^7$ is independently —Cl.

In embodiments, the compound has the formula

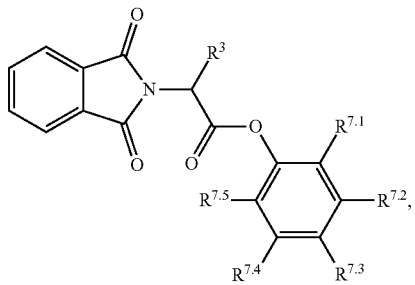

wherein $R^3$ is as described herein. $R^{7.1}$, $R^{7.2}$, $R^{7.3}$, $R^{7.4}$, and $R^{7.5}$ may each independently be any value of $R^7$ as described herein, including in embodiments, or hydrogen. In embodiments, $R^{7.1}$ is independently unsubstituted methoxy. In embodiments, $R^{7.3}$ is independently an oxo-substituted $C_1$-$C_4$ alkyl. In embodiments, $R^{7.3}$ is independently —C(O)CH$_3$.

In embodiments, the compound has the formula

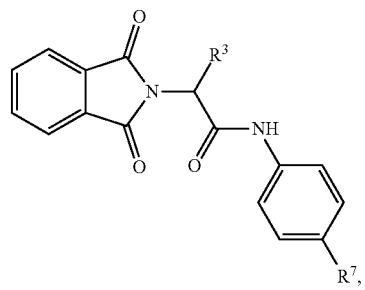

wherein $R^3$ and $R^7$ are as described herein. In embodiments, $R^3$ is independently an unsubstituted $C_1$-$C_4$ alkyl. In embodiments, $R^7$ is independently halogen. In embodiments, $R^7$ is independently —Br.

In embodiments, the compound is

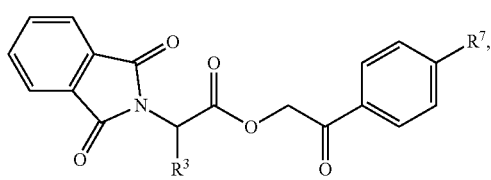

wherein $R^3$ and $R^7$ are as described herein. In embodiments, $R^7$ is halogen. In embodiments, $R^7$ is —Br.

In embodiments, the compound has the formula

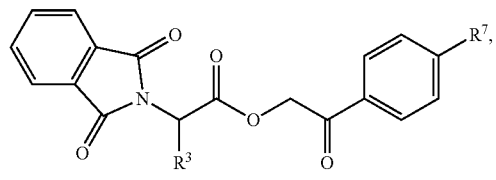

wherein $R^3$ and $R^7$ are as described herein. In embodiments, $R^7$ is independently halogen. In embodiments, $R^7$ is independently —Br.

In embodiments, the compound is

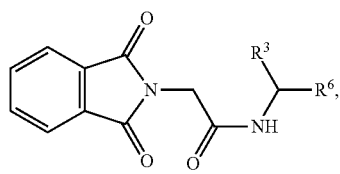

wherein $R^3$ and $R^6$ is as described herein. In embodiments, $R^6$ is an unsubstituted phenyl. In embodiments, $R^3$ is an unsubstituted $C_1$-$C_6$ alkylene.

In embodiments, the compound has the formula

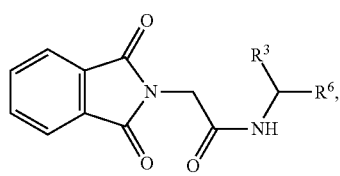

wherein $R^3$ and $R^6$ are as described herein. In embodiments, $R^6$ is independently an unsubstituted phenyl. In embodiments, $R^3$ is independently an unsubstituted $C_1$-$C_6$ alkylene.

In embodiments, the compound has the formula

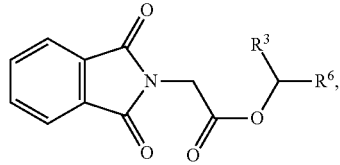

wherein $R^3$ and $R^6$ are as described herein. In embodiments, $R^6$ is independently an unsubstituted phenyl. In embodiments, $R^3$ is independently an unsubstituted $C_1$-$C_6$ alkylene.

In embodiments, the compound is

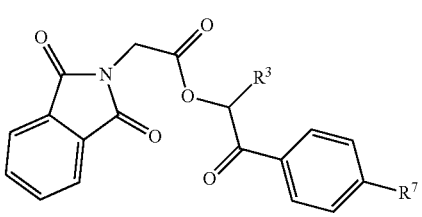

wherein $R^3$ and $R^7$ are as described herein.

In embodiments, the compound has the formula

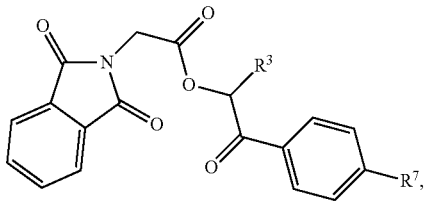

wherein R³ and R⁷ are as described herein. In embodiments, R³ is independently an unsubstituted phenyl. In embodiments, R⁸ is independently an unsubstituted $C_1$-$C_4$ alkyl. In embodiments, R⁷ is independently unsubstituted methyl.

In embodiments, the compound has the formula

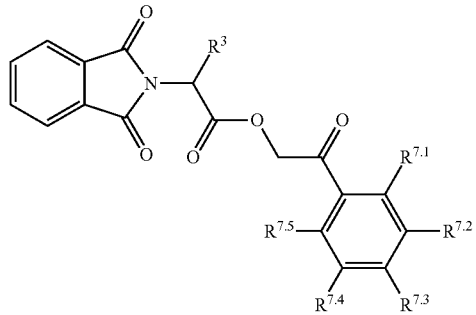

wherein R³ is as described herein. $R^{7.1}$, $R^{7.2}$, $R^{7.3}$, $R^{7.4}$, and $R^{7.5}$ may each independently be any value of R⁷ as described herein, including in embodiments, or hydrogen. In embodiments, $R^{7.3}$ is independently unsubstituted phenyl. In embodiments, $R^{7.1}$ and $R^{7.3}$ are each independently halogen. In embodiments, $R^{7.1}$ and $R^{7.3}$ are each independently —Cl.

In embodiments, the compound has the formula

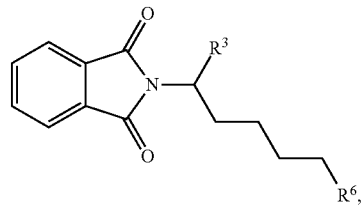

wherein R³ and R⁶ are as described herein. In embodiments, R³ is independently —COOH. In embodiments, R⁶ is independently

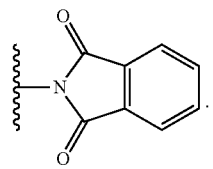 [SMILES: *N1C(=O)c2ccccc2C1=O]

In embodiments, the compound has the formula

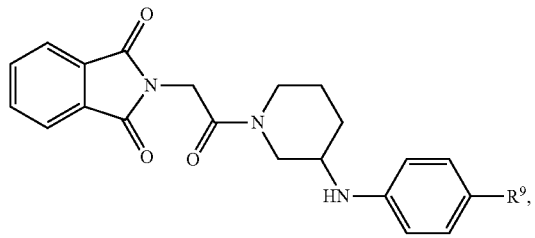

wherein R⁹ is as described herein. In embodiments, R⁹ is independently an unsubstituted $C_1$-$C_4$ alkyl. In embodiments, R⁹ is independently an unsubstituted isopropyl.

In embodiments, the compound has the formula

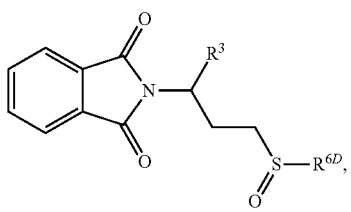

wherein R³ and $R^{6D}$ are as described herein. In embodiments, $R_3$ is independently —COOH. In embodiments, $R^{6D}$ is independently unsubstituted $C_1$-$C_4$ alkyl. In embodiments, $R^{6D}$ is independently unsubstituted methyl.

In embodiments, the compound has the formula

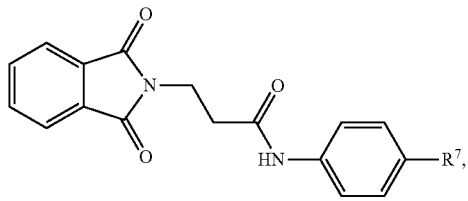

wherein R⁷ is as described herein. In embodiments, R⁷ is independently unsubstituted $C_1$-$C_4$ alkyl. In embodiments, R⁷ is independently unsubstituted isopropyl.

In embodiments, the compound has the formula

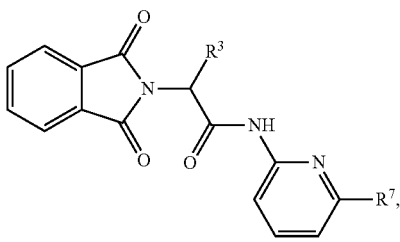

wherein R³ and R⁷ are as described herein. In embodiments, R⁷ is independently unsubstituted $C_1$-$C_4$ alkyl. In embodiments, R⁷ is independently unsubstituted methyl.

In embodiments, the compound has the formula

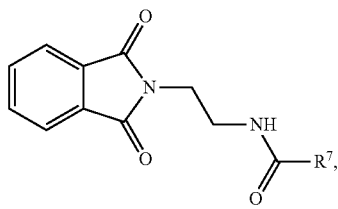

wherein R⁷ is as described herein. In embodiments, R⁷ is independently an unsubstituted pyridyl. In embodiments, R⁷ is independently an unsubstituted 3-pyridyl.

In embodiments, the compound has the formula

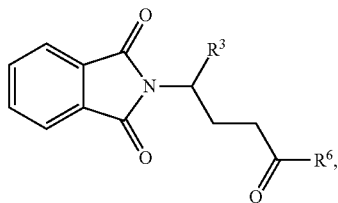

wherein $R^3$ and $R^6$ are as described herein. In embodiments, $R^3$ is independently —COOH. In embodiments, $R^6$ is independently unsubstituted morpholinyl.

In embodiments, the compound has the formula

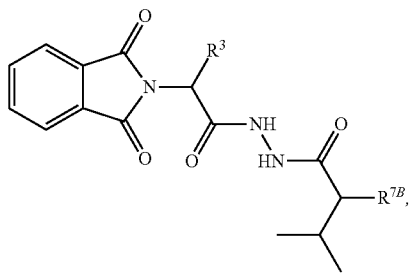

wherein $R^3$ and $R^{7B}$ are as described herein. In embodiments, $R^{7B}$ is independently

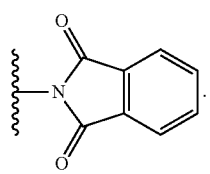 [SMILES: *N1C(=O)c2ccccc2C1=O]

In embodiments, the compound has the formula

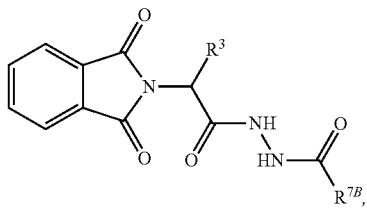

wherein $R^3$ and $R^{7B}$ are as described herein. In embodiments, $R^{7B}$ is independently an unsubstituted pyridyl. In embodiments, $R^{7B}$ is independently an unsubstituted 3-pyridyl.

In embodiments, the compound has the formula

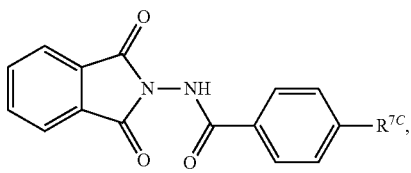

wherein $R^{7C}$ is as described herein. In embodiments, $R^{7C}$ is independently an $R^{8C}$-substituted 4 to 8 membered heteroalkyl. In embodiments, $R^{8C}$ is independently oxo.

In embodiments, the compound has the formula

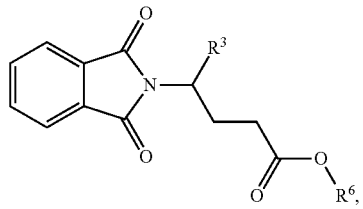

wherein $R^3$ and $R^6$ are as described herein. In embodiments, $R^3$ is independently —COOH. In embodiments, $R^6$ is independently hydrogen.

In embodiments, the compound has the formula

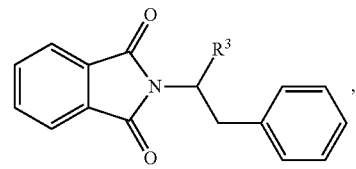

wherein $R^3$ is as described herein. In embodiments, $R^3$ is independently —COOH.

In embodiments, the compound has the formula

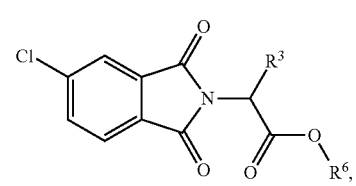

wherein $R^3$ and $R^6$ are as described herein. In embodiments, $R^3$ is independently an unsubstituted $C_1$-$C_4$ alkyl. In embodiments, $R^6$ is independently hydrogen.

In embodiments, the compound has the formula

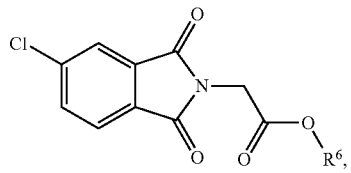

wherein $R^6$ is as described herein. In embodiments, $R^6$ is independently hydrogen.

In embodiments, the compound has the formula

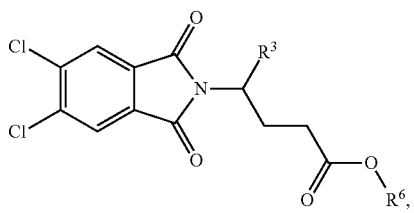

wherein $R^3$ and $R^6$ are as described herein. In embodiments, $R^3$ is independently —COOH. In embodiments, $R^6$ is independently hydrogen.

In embodiments, the compound has the formula

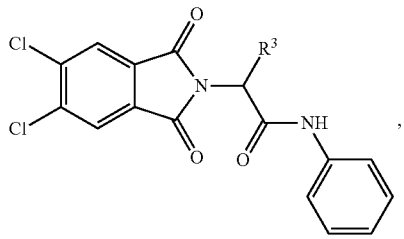

wherein $R^3$ is as described herein. In embodiments, $R^3$ is independently —COOH. In embodiments, $R^3$ is independently unsubstituted $C_1$-$C_4$ alkyl. In embodiments, $R^3$ is independently unsubstituted isobutyl.

In embodiments, the compound has the formula

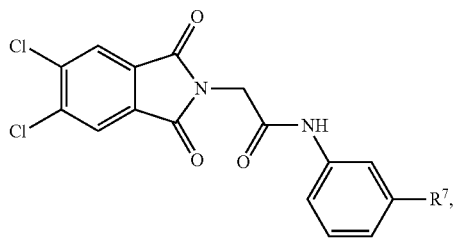

wherein is as described herein. In embodiments, $R^7$ is independently halogen. In embodiments, $R^7$ is independently —Cl.

In embodiments, the compound has the formula

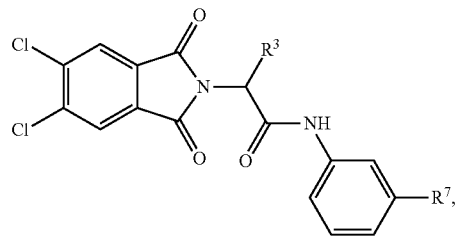

wherein $R^3$ and $R^7$ are as described herein. In embodiments, $R^3$ is independently unsubstituted $C_1$-$C_4$ alkyl. In embodiments, $R^3$ is independently unsubstituted isobutyl. In embodiments, $R^3$ is independently —COOH. In embodiments, $R^7$ is independently halogen. In embodiments, $R^7$ is independently —Cl.

In embodiments, the compound has the formula

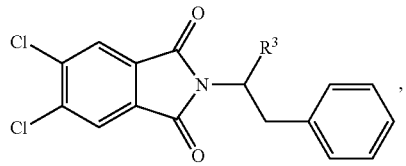

wherein $R^3$ is as described herein. In embodiments, $R^3$ is independently —COOH.

In embodiments, the compound does not have the formula

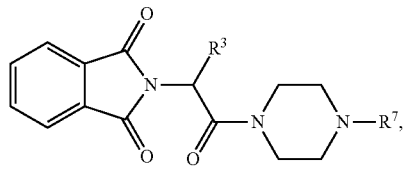

wherein $R^3$ and $R^7$ are as described herein.

In embodiments, the compound does not have the formula

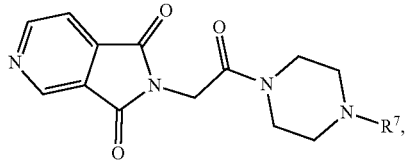

wherein $R^7$ is as described herein.

In embodiments, the compound does not have the formula

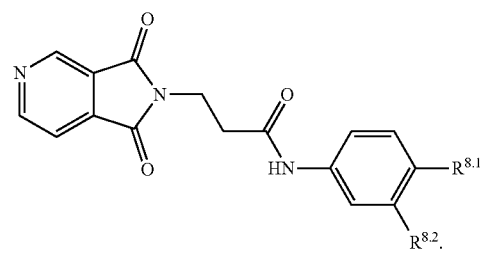

$R^{8.1}$ and $R^{8.2}$ may each independently be any value of $R^8$ as described herein, including in embodiments, or hydrogen.

In embodiments, the compound does not have the formula

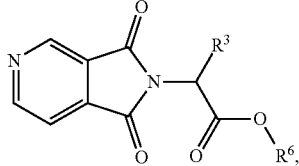

wherein $R^3$ and $R^6$ are as described herein.

In embodiments, the compound does not have the formula

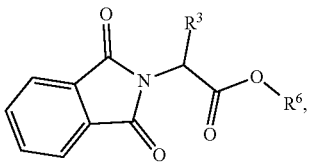

wherein $R^3$ and $R^6$ are as described herein.

In embodiments, the compound does not have the formula

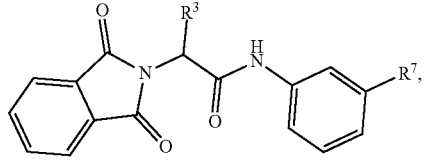

wherein $R^3$ and $R^7$ are as described herein.

In embodiments, the compound does not have the formula

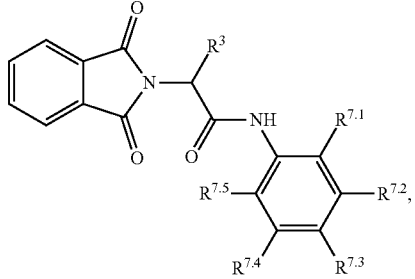

wherein $R^3$ is as described herein. $R^{7.1}$, $R^{7.2}$, $R^{7.3}$, $R^{7.4}$, and $R^{7.5}$ may each independently be any value of $R^7$ as described herein, including in embodiments, or hydrogen.

In embodiments, the compound does not have the formula

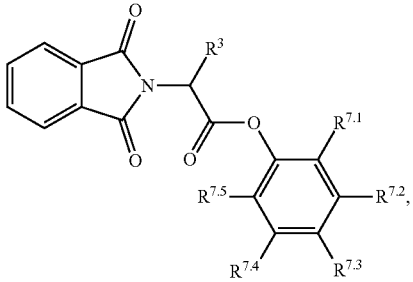

wherein $R^3$ is as described herein. $R^{7.1}$, $R^{7.2}$, $R^{7.3}$, $R^{7.4}$, and $R^{7.5}$ may each independently be any value of $R^7$ as described herein, including in embodiments, or hydrogen.

In embodiments, the compound does not have the formula

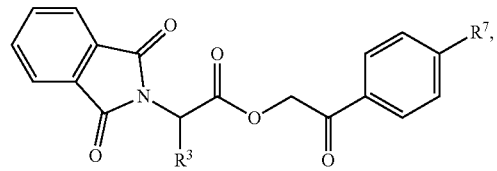

wherein $R^3$ and $R^7$ are as described herein.

In embodiments, the compound does not have the formula

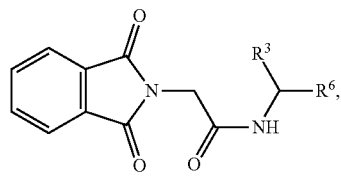

wherein $R^3$ and $R^6$ are as described herein.

In embodiments, the compound does not have the formula

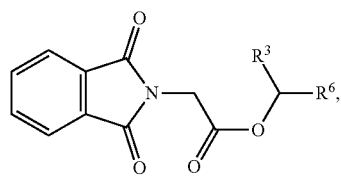

wherein $R^3$ and $R^6$ are as described herein.

In embodiments, the compound does not have the formula

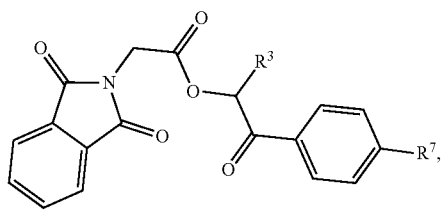

wherein $R^3$ and $R^7$ are as described herein.

In embodiments, the compound does not have the formula

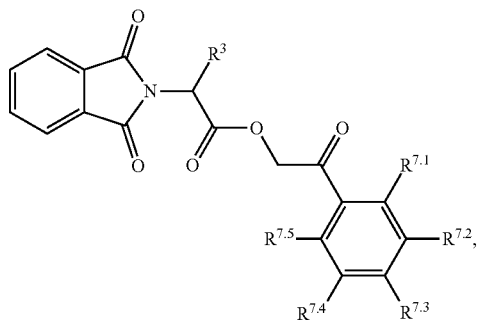

wherein $R^3$ is as described herein. $R^{7.1}$, $R^{7.2}$, $R^{7.3}$, $R^{7.4}$, and $R^{7.5}$ may each independently be any value of $R^7$ as described herein, including in embodiments, or hydrogen.

In embodiments, the compound does not have the formula

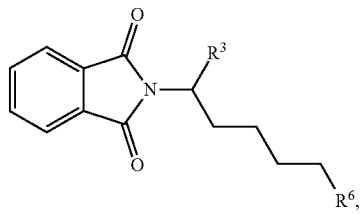

wherein $R^3$ and $R^6$ are as described herein.

In embodiments, the compound does not have the formula

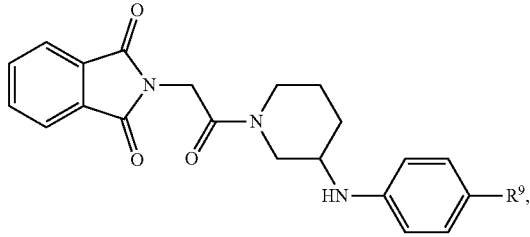

wherein $R^9$ is as described herein.

In embodiments, the compound does not have the formula

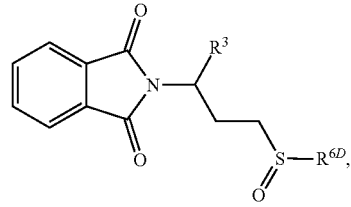

wherein $R^3$ and $R^{6D}$ are as described herein.

In embodiments, the compound does not have the formula

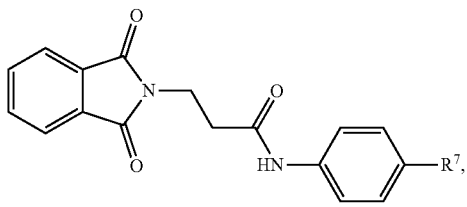

wherein $R^7$ is as described herein.

In embodiments, the compound does not have the formula

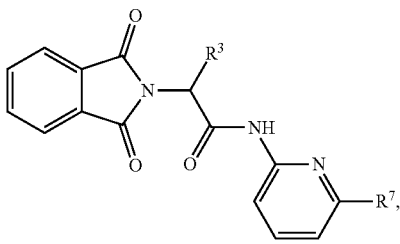

wherein $R^3$ and $R^7$ are as described herein.

In embodiments, the compound does not have the formula

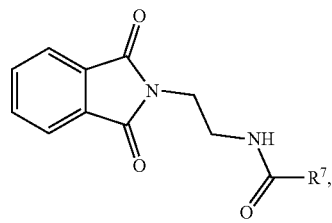

wherein $R^7$ is as described herein.

In embodiments, the compound does not have the formula

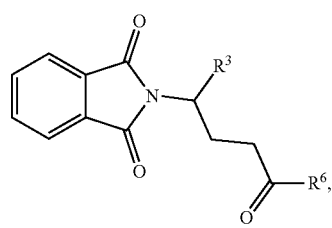

wherein $R^3$ and $R^6$ are as described herein.

In embodiments, the compound does not have the formula

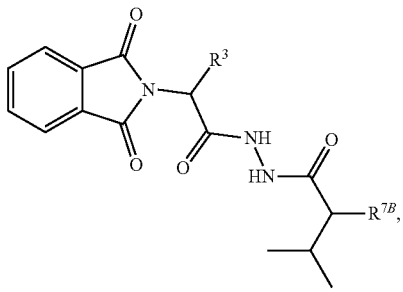

wherein $R^3$ and $R^{7B}$ are as described herein.

In embodiments, the compound does not have the formula

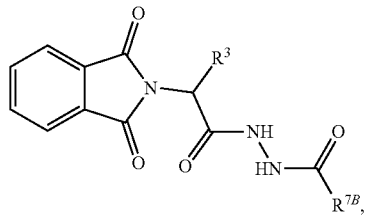

wherein $R^3$ and $R^{7B}$ are as described herein.

In embodiments, the compound does not have the formula

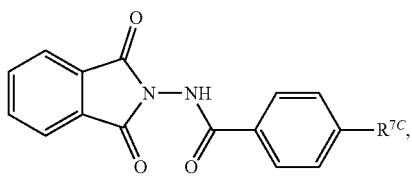

wherein $R^{7C}$ is as described herein.

In embodiments, the compound does not have the formula

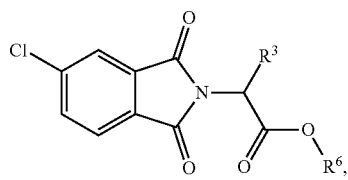

wherein $R^3$ and $R^6$ are as described herein.

In embodiments, the compound does not have the formula

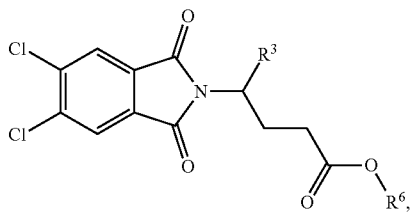

wherein $R^3$ and $R^6$ are as described herein.

In embodiments, the compound does not have the formula

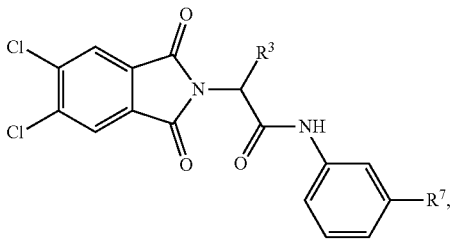

wherein $R^3$ and $R^7$ are as described herein. In embodiments, the compound does not have the formula

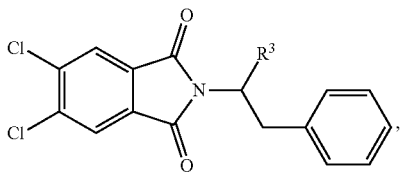

wherein $R^3$ is as described herein.

In embodiments, the compound is a compound described herein (e.g., in an aspect, embodiment, example, table, figure, or claim).

III. Pharmaceutical Compositions

In an aspect is provided a pharmaceutical composition including a compound described herein, or pharmaceutically acceptable salt thereof, and a pharmaceutically acceptable excipient.

In embodiments of the pharmaceutical compositions, the compound, or pharmaceutically acceptable salt thereof, is included in a therapeutically effective amount.

In embodiments of the pharmaceutical compositions, the pharmaceutical composition includes a second agent (e.g. therapeutic agent). In embodiments of the pharmaceutical compositions, the pharmaceutical composition includes a second agent (e.g. therapeutic agent) in a therapeutically effective amount. In embodiments of the pharmaceutical compositions, the second agent is an agent for treating inflammation. In embodiments of the pharmaceutical compositions, the second agent is an agent for treating diabetes. In embodiments, the second agent is insulin, metformin, an angiotensin converting enzyme inhibitor, or a calcium channel blocker. In embodiments, the second agent is acarbose, miglitol, bromocriptine, aloglipton, linagliptin, saxagliptin, sitagliptin, albiglutide, dulaglutide, exenatide, liraglutide, semaglutide, nateglinide, repaglinide, dapagliflozin, canagliflozin, empagliflozin, ertugliflozin, glimepiride, gliclazide, glipizide, glyburide, chlorpropamide, tolazamide, tolbutamide, rosiglitazone, or pioglitazone.

IV. Methods of Use

In an aspect is provided a method of treating a TXNIP-TRX complex-associated disease, the method including administering to a subject in need thereof an effective amount of a TXNIP-TRX complex inhibitor. In an aspect is provided a method of treating a TXNIP-TRX complex-associated disease, the method including administering to a subject in need thereof an effective amount of a TXNIP-TRX complex inhibitor, wherein the TXNIP-TRX complex inhibitor is a compound as described herein, including embodiments. In embodiments, the TXNIP-TRX complex inhibitor has the formula:

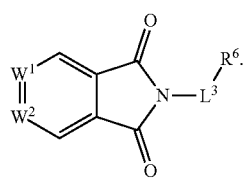

(I)

$W^1$, $W^2$, $L^3$, and $R^6$ are as described herein, including in embodiments.

$W^1$ is —$CR^1$=, —N=, or —CH=. $W^2$ is —$CR^2$=, —N=, or —CH=. $R^1$ is independently halogen, —$CX^1_3$, —$CHX^1_2$, —$CH_2X^1$, —$OCX^1_3$, —$OCH_2X^1$, —$OCHX^1_2$, substituted or unsubstituted alkyl, or substituted or unsubstituted heteroalkyl. $R^2$ is independently halogen, —$CX^2_3$, —$CHX^2_2$, —$CH_2X^2$, —$OCX^2_3$, —$OCH_2X^2$, —$OCHX^2_2$, substituted or unsubstituted alkyl, or substituted or unsubstituted heteroalkyl. $L^3$ is a bond, —$N(R^3)$—, —C(O)—, —$C(O)N(R^3)$—, —$N(R^3)C(O)$—, —N(H)—, —C(O)N(H)—, —N(H)C(O)—, —C(O)O—, substituted or unsubstituted alkylene, or substituted or unsubstituted heteroalkylene. $R^3$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl. $R^6$ is independently hydrogen, halogen, —$CX^6_3$, —$CHX^6_2$, —$CH_2X^6$, —$OCX^6_3$, —$OCH_2X^6$, —$OCHX^6_2$, —CN, —$SR^{6D}$, —$SOR^{6D}$, —$SO_2R^{6D}$, —$SO_3R^{6D}$, —$SO_4R^{6D}$, —$SONR^{6A}R^{6B}$, —$SO_2NR^{6A}R^{6B}$, —$NR^{6C}C(O)NR^{6A}R^{6B}$, —N(O), —$N(O)_2$, —$NR^{6A}R^{6B}$, —$C(O)R^{6C}$, —C(O)$OR^{6C}$, —$C(O)NR^{6A}R^{6B}$, —$OR^{6D}$, —$NR^{6A}SO_2R^{6D}$, —$NR^{6A}C(O)R^{6C}$, —$NR^{6A}C(O)OR^{6C}$, —$NR^{6A}OR^{6C}$, —$NR^{6C}NR^{6A}R^{6B}$, —$C(O)NR^{6C}NR^{6A}R^{6B}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl. $R^{6A}R^{6B}$, $R^{6C}$, and $R^{6D}$ are each independently hydrogen, oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; and $X^1$, $X^2$, and $X^6$ are independently —F, —Cl, —Br, or —I.

In embodiments, the TXNIP-TRX complex-associated disease is a metabolic disorder, cardiovascular disease, or inflammatory disease. In embodiments, the TXNIP-TRX complex-associated disease is a metabolic disorder. In embodiments, the TXNIP-TRX complex-associated disease is cardiovascular disease. In embodiments, the TXNIP-TRX complex-associated disease is inflammation.

In embodiments, the TXNIP-TRX complex-associated disease is a kidney disease or an eye disease. In embodiments, the TXNIP-TRX complex-associated disease is a kidney disease. In embodiments, the TXNIP-TRX complex-associated disease is an eye disease.

In embodiments, the compound binds (e.g., forms a covalent bond) to TXNIP.

In an aspect is provided a method of treating a metabolic disorder, cardiovascular disease, or inflammatory disease, the method including administering to a subject in need thereof an effective amount of a compound, or pharmaceutically acceptable salt thereof, as described herein, including embodiments. In embodiments, the compound has the formula:

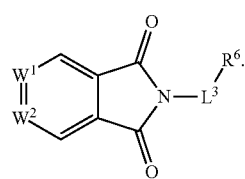

(I)

$W^1$, $W^2$, $L^3$, and $R^6$ are as described herein, including in embodiments.

$W^1$ is —$CR^1$=, —N=, or —CH=. $W^2$ is —$CR^2$=, —N=, or —CH=. $R^1$ is independently halogen, —$CX^1_3$, —$CHX^1_2$, —$CH_2X^1$, —$OCX^1_3$, —$OCH_2X^1$, —$OCHX^1_2$, substituted or unsubstituted alkyl, or substituted or unsubstituted heteroalkyl. $R^2$ is independently halogen, —$CX^2_3$, —$CHX^2_2$, —$CH_2X^2$, —$OCX^2_3$, —$OCH_2X^2$, —$OCHX^2_2$, substituted or unsubstituted alkyl, or substituted or unsubstituted heteroalkyl. $L^3$ is a bond, —$N(R^3)$—, —C(O)—, —$C(O)N(R^3)$—, —$N(R^3)C(O)$—, —N(H)—, —C(O)N(H)—, —N(H)C(O)—, —C(O)O—, substituted or unsubstituted alkylene, or substituted or unsubstituted heteroalkylene. $R^3$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl. $R^6$ is independently hydrogen, halogen, —$CX^6_3$, —$CHX^6_2$, —$CH_2X^6$, —$OCX^6_3$, —$OCH_2X^6$, —$OCHX^6_2$, —CN, —$SR^{6D}$, —$SOR^{6D}$, —$SO_2R^{6D}$, —$SO_3R^{6D}$, —$SO_4R^{6D}$, —$SONR^{6A}R^{6B}$, —$SO_2NR^{6A}R^{6B}$, —$NR^{6C}C(O)NR^{6A}R^{6B}$, —N(O), —$N(O)_2$, —$NR^{6A}R^{6B}$, —$C(O)R^{6C}$, —C(O)$OR^{6C}$, —$C(O)NR^{6A}R^{6B}$, —$OR^{6D}$, —$NR^{6A}SO_2R^{6D}$, —NR$^{6A}$C(O)R$^{6C}$, —NR$^{6A}$C(O)OR$^{6C}$, —NR$^{6A}$OR$^{6C}$, —NR$^{6C}$NR$^{6A}$R$^{6B}$, —C(O)NR$^{6C}$NR$^{6A}$R$^{6B}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl. R$^{6A}$R$^{6B}$, R$^{6C}$, and R$^{6D}$ are each independently hydrogen, oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; and X$^1$, X$^2$, and X$^6$ are independently —F, —Cl, —Br, or —I.

In embodiments, the method includes reducing side effects (e.g., lower incidences of side effects) relative to alternative forms of treatment (e.g., administering verapamil). In embodiments, the side effects include constipation, dizziness, headache, increased liver enzymes, indigestion, low blood pressure (hypotension), nausea, rash, shortness of breath, sleep disturbance, swelling (edema), or swollen gums. In embodiments, the side effect is constipation, dizziness, headache, increased liver enzymes, indigestion, low blood pressure (hypotension), nausea, rash, shortness of breath, sleep disturbance, swelling (edema), or swollen gums.

In embodiments, the compound is capable of inhibiting TXNIP protein activity or function, the method including contacting the TXNIP protein with the compound. In embodiments, the compound is capable of inhibiting TXNIP protein binding to TRX, the method including contacting the TXNIP protein with the compound. In embodiments, the compound inhibits TXNIP protein activity or function, the method including contacting the TXNIP protein with the compound. In embodiments, the compound inhibits TXNIP protein binding to TRX, the method including contacting the TXNIP protein with the compound.

In embodiments, the metabolic disorder is diabetes. In embodiments, the metabolic disorder is type 1 diabetes (T1D). In embodiments, the metabolic disorder is type 2 diabetes (T2D). In embodiments, the diabetes is associated with islet beta cell dysfunction. In embodiments, the cardiovascular disease is atherosclerosis.

In embodiments, the disease (e.g., metabolic disorder) is diabetes (e.g., type 1 diabetes or type 2 diabetes), insulin resistance, metabolic syndrome, atherosclerosis, obesity, hyperlipidemia, hyperglycemia, high serum triglycerides, and/or high blood pressure.

In embodiments, the metabolic disorder is a diabetes associated complication selected from nephropathy, retinopathy, neuropathy, cardiovascular disease, and inflammation. In embodiments, the metabolic disorder is a diabetes associated disease selected from nephropathy, retinopathy, neuropathy, cardiovascular disease, and inflammation.

In embodiments, the method does not increase the risk for an infectious disease.

In embodiments, the method inhibits high glucose-induced TXNIP-TRX co-immunoprecipitation (e.g., in cell extracts or in vivo in cells). In embodiments, the compound can bind to TXNIP and prevent its proteolysis. In embodiments, the method reduces expression of inflammatory cytokine molecules in monocytes (e.g., TNF-α, IL-1β, IL-6, or chemokines).

In an aspect is provided a method of treating a kidney disease or an eye disease, the method including administering to a subject in need thereof an effective amount of a compound, or pharmaceutically acceptable salt thereof, as described herein, including embodiments. In embodiments, the compound has the formula:

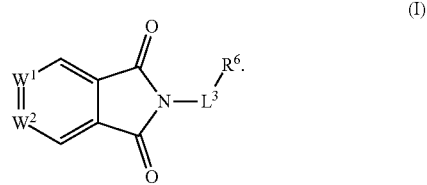

(I)

W$^1$, W$^2$, L$^3$, and R$^6$ are as described herein, including in embodiments.

In an aspect is provided a method of reducing the level of expression of TXNIP in a cell, the method including contacting the cell with a compound, or pharmaceutically acceptable salt thereof, as described herein. In embodiments, the compound has the formula:

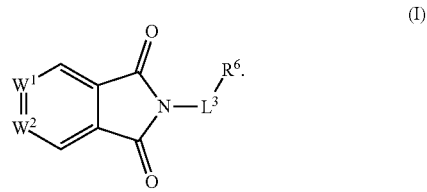

(I)

wherein W$^1$, W$^2$, L$^3$, and R$^6$ are as described herein, including in embodiments. In embodiments, the method includes reducing the level of mRNA expression of TXNIP in a cell. In embodiments, the cell is an inflammatory white cell. In embodiments, the cell is a human inflammatory cell. In embodiments, the cell is a mouse inflammatory cell. In embodiments, the cell is a pancreatic beta cell. In embodiments, the pancreatic beta cell is a mouse pancreatic beta cell. In embodiments, the pancreatic beta cell is a human pancreatic beta cell. In embodiments, the pancreatic beta cell is a primary human islet beta cell. In embodiments, the cell is a THP1 cell. In embodiments, the cell is a human monocyte THP1 cell. In embodiments, the cell is a macrophage cell.

In embodiments, the level of expression of TXNIP is reduced by greater than 10%, 20%, 30%, 40%, 50%, 60%, 70%, 80%, or greater than 90% in comparison to a control in the absence of the compound. In embodiments, the level of expression of TXNIP is reduced by about 10%, 20%, 30%, 40%, 50%, 60%, 70%, 80%, 90%, or about 100% in comparison to a control in the absence of the compound. In embodiments, the level of expression of TXNIP is reduced by 10%, 20%, 30%, 40%, 50%, 60%, 70%, 80%, 90%, or 100% in comparison to a control in the absence of the compound. In embodiments, the level of expression of TXNIP is reduced by 1.5-fold, 2-fold, 3-fold, 4-fold, 5-fold, 10-fold or lower than the expression or activity in the absence of the compound.

In an aspect is provided a method of reducing the level of expression of TNF-α in a cell, the method including contacting the cell with a compound, or pharmaceutically acceptable salt thereof, as described herein. In embodiments, the compound has the formula:

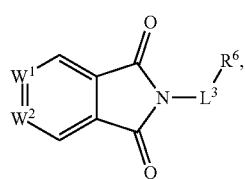
(I)

wherein $W^1$, $W^2$, $L^3$, and $R^6$ are as described herein, including in embodiments. In embodiments, the method includes reducing the level of mRNA expression of TNF-α in a cell. In embodiments, the cell is an inflammatory white cell. In embodiments, the cell is a human inflammatory cell. In embodiments, the cell is a mouse inflammatory cell. In embodiments, the cell is a pancreatic beta cell. In embodiments, the pancreatic beta cell is a mouse pancreatic beta cell. In embodiments, the pancreatic beta cell is a human pancreatic beta cell. In embodiments, the pancreatic beta cell is a primary human islet beta cell. In embodiments, the cell is a THP1 cell. In embodiments, the cell is a human monocyte THP1 cell. In embodiments, the cell is a macrophage cell.

In embodiments, the level of expression of TNF-α is reduced by greater than 10%, 20%, 30%, 40%, 50%, 60%, 70%, 80%, or greater than 90% in comparison to a control in the absence of the compound. In embodiments, the level of expression of TNF-α is reduced by about 10%, 20%, 30%, 40%, 50%, 60%, 70%, 80%, 90%, or about 100% in comparison to a control in the absence of the compound. In embodiments, the level of expression of TNF-α is reduced by 10%, 20%, 30%, 40%, 50%, 60%, 70%, 80%, 90%, or 100% in comparison to a control in the absence of the compound. In embodiments, the level of expression of TNF-α is reduced by 1.5-fold, 2-fold, 3-fold, 4-fold, 5-fold, 10-fold or lower than the expression or activity in the absence of the compound.

In an aspect is provided a method of reducing the level of expression of TXNIP, the method including contacting TXNIP with a compound, or a pharmaceutically acceptable salt thereof, as described herein. In embodiments, the compound has the formula:

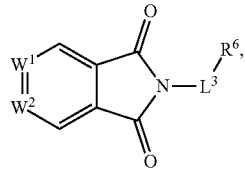
(I)

wherein $W^1$, $W^2$, $L^3$, and $R^6$ are as described herein, including in embodiments.

In embodiments, the level of expression of TXNIP is reduced by greater than 10%, 20%, 30%, 40%, 50%, 60%, 70%, 80%, or greater than 90% in comparison to a control in the absence of the compound. In embodiments, the level of expression of TXNIP is reduced by about 10%, 20%, 30%, 40%, 50%, 60%, 70%, 80%, 90%, or about 100% in comparison to a control in the absence of the compound. In embodiments, the level of expression of TXNIP is reduced by 10%, 20%, 30%, 40%, 50%, 60%, 70%, 80%, 90%, or 100% in comparison to a control in the absence of the compound. In embodiments, the level of expression of TXNIP is reduced by 1.5-fold, 2-fold, 3-fold, 4-fold, 5-fold, 10-fold or lower than the expression or activity in the absence of the compound.

In embodiments, the compound modulates (e.g., inhibits) the level of expression of FLNA. In embodiments, the compound modulates (e.g., inhibits) the level of expression of MPEG1. In embodiments, the compound modulates (e.g., inhibits) the level of expression of TKTL1. In embodiments, the compound modulates (e.g., inhibits) the level of expression of NATD1. In embodiments, the compound modulates (e.g., inhibits) the level of expression of TXNIP. In embodiments, the compound modulates (e.g., inhibits) the level of expression of KLF10. In embodiments, the compound modulates (e.g., inhibits) the level of expression of KLF2. In embodiments, the compound modulates (e.g., inhibits) the level of expression of CD52. In embodiments, the compound modulates (e.g., inhibits) the level of expression of TNF. In embodiments, the compound modulates (e.g., inhibits) the level of expression of ARRDC4. In embodiments, the compound modulates (e.g., inhibits) the level of expression of JMJ1C-AS1. In embodiments, the compound modulates (e.g., inhibits) the level of expression of RGMA. In embodiments, the compound modulates (e.g., inhibits) the level of expression of EGR1. In embodiments, the compound modulates (e.g., inhibits) the level of expression of NPIPA1. In embodiments, the compound modulates (e.g., inhibits) the level of expression of G0S2. In embodiments, the compound modulates (e.g., inhibits) the level of expression of EPHB1. In embodiments, the compound modulates (e.g., inhibits) the level of expression of VSIG4. In embodiments, the compound modulates (e.g., inhibits) the level of expression of CFP. In embodiments, the compound modulates (e.g., inhibits) the level of expression of CAPS. In embodiments, the compound modulates (e.g., inhibits) the level of expression of GLUD1P3. In embodiments, the compound modulates (e.g., inhibits) the level of expression of PCDHB14. In embodiments, the compound modulates (e.g., inhibits) the level of expression of CCDC153. In embodiments, the compound modulates (e.g., inhibits) the level of expression of FAM229A. In embodiments, the compound modulates (e.g., inhibits) the level of expression of SMURF2. In embodiments, the compound modulates (e.g., activates) the level of expression of PDE9A. In embodiments, the compound modulates (e.g., activates) the level of expression of SLC44A2. In embodiments, the compound modulates (e.g., activates) the level of expression of ARHGEF25. In embodiments, the compound modulates (e.g., activates) the level of expression of APBB1. In embodiments, the compound modulates (e.g., activates) the level of expression of GTF2IRD1. In embodiments, the compound modulates (e.g., activates) the level of expression of LOC100506688. In embodiments, the compound modulates (e.g., activates) the level of expression of PPM1K. In embodiments, the compound modulates (e.g., activates) the level of expression of SLC16A2. In embodiments, the compound modulates (e.g., activates) the level of expression of PCGF2. In embodiments, the compound modulates (e.g., activates) the level of expression of HK2. In embodiments, the compound modulates (e.g., activates) the level of expression of TSPAN2. In embodiments, the compound modulates (e.g., activates) the level of expression of S1PR5. In embodiments, the compound modulates (e.g., activates) the level of expression of EFCAB7. In embodiments, the compound modulates (e.g., activates) the level of expression of MACROD1. In embodiments, the compound modulates (e.g., activates) the level of expression of GBP5. In embodiments, the compound modulates (e.g., activates) the level of expression of KIAA1147. In embodiments, the compound modulates (e.g., activates) the level of expression of ADGRE4P. In embodiments, the compound modulates (e.g., activates) the level of expression of UQCRHL. In embodiments, the compound modulates (e.g., activates) the level of expression of DICER1-AS1. In embodiments, the compound modulates (e.g., activates) the level of expression of PDIA3P1.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

V. Embodiments

Embodiment P1. A method of treating a TXNIP-TRX complex-associated disease, said method comprising administering to a subject in need thereof an effective amount of a TXNIP-TRX complex inhibitor, wherein said TXNIP-TRX complex inhibitor has the formula:

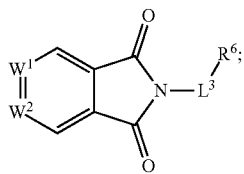

(I)

wherein
W$^1$ is —CR$^1$═, —N═, or —CH═;
W$^2$ is —CR$^2$═, —N═, or —CH═;
R$^1$ is independently halogen, —CX$^1_3$, —CHX$^1_2$, —CH$_2$X$^1$, —OCX$^1_3$, —OCH$_2$X$^1$, —OCHX$^1_2$, substituted or unsubstituted alkyl, or substituted or unsubstituted heteroalkyl;
R$^2$ is independently halogen, —CX$^2_3$, —CHX$^2_2$, —CH$_2$X$^2$, —OCX$^2_3$, —OCH$_2$X$^2$, —OCHX$^2_2$, substituted or unsubstituted alkyl, or substituted or unsubstituted heteroalkyl;
L$^3$ is a bond, —N(R$^3$)—, —C(O)—, —C(O)N(R$^3$)—, —N(R$^3$)C(O)—, —N(H)—, —C(O)N(H)—, —N(H)C(O)—, —C(O)O—, substituted or unsubstituted alkylene, or substituted or unsubstituted heteroalkylene;
R$^3$ is independently oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;
R$^6$ is independently hydrogen, halogen, —CX$^6_3$, —CHX$^6_2$, —CH$_2$X$^6$, —OCX$^6_3$, —OCH$_2$X$^6$, —OCHX$^6_2$, —CN, —SR$^{6D}$, —SOR$^{6D}$, —SO$_2$R$^{6D}$, —SO$_3$R$^{6D}$, —SO$_4$R$^{6D}$, —SONR$^{6A}$R$^{6B}$, —SO$_2$NR$^{6A}$R$^{6B}$, —NR$^{6C}$C(O)NR$^{6A}$R$^{6B}$, —N(O), —N(O)$_2$, —NR$^{6A}$R$^{6B}$, —C(O)R$^{6C}$, —C(O)OR$^{6C}$, —C(O)NR$^{6A}$R$^{6B}$, —OR$^{6D}$, —NR$^{6A}$SO$_2$R$^{6D}$, —NR$^{6A}$C(O)R$^{6C}$, —NR$^{6A}$C(O)OR$^{6C}$, —NR$^{6A}$OR$^{6C}$, —NR$^{6C}$NR$^{6A}$R$^{6B}$, C(O)NR$^{6C}$NR$^{6A}$R$^{6B}$ substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; R$^{6A}$, R$^{6B}$, R$^{6C}$, and R$^{6D}$ are each independently hydrogen, oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; and
X$^1$, X$^2$, and X$^6$ are independently —F, —Cl, —Br, or —I.

Embodiment P2. A method of treating a metabolic disorder, cardiovascular disease, or inflammatory disease, said method comprising administering to a subject in need thereof an effective amount of a compound, or pharmaceutically acceptable salt thereof, having the formula.

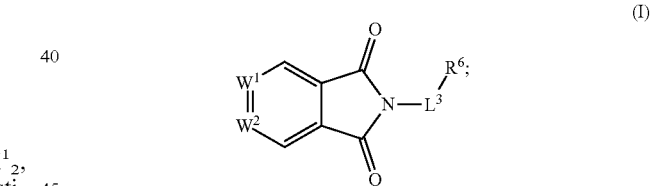

(I)

wherein
W$^1$ is —CR$^1$═, —N═, or —CH═;
W$^2$ is —CR$^2$═, —N═, or —CH═;
R$^1$ is independently halogen, —CX$^1_3$, —CHX$^1_2$, —CH$_2$X$^1$, —OCX$^1_3$, —OCH$_2$X$^1$, —OCHX$^1_2$, substituted or unsubstituted alkyl, or substituted or unsubstituted heteroalkyl;
R$^2$ is independently halogen, —CX$^2_3$, —CHX$^2_2$, —CH$_2$X$^2$, —OCX$^2_3$, —OCH$_2$X$^2$, —OCHX$^2_2$, substituted or unsubstituted alkyl, or substituted or unsubstituted heteroalkyl;
L$^3$ is a bond, —N(R$^3$)—, —C(O)—, —C(O)N(R$^3$)—, —N(R$^3$)C(O)—, —N(H)—, —C(O)N(H)—, —N(H)C(O)—, —C(O)O—, substituted or unsubstituted alkylene, or substituted or unsubstituted heteroalkylene;
R$^3$ is independently oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC (O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;

R$^6$ is independently hydrogen, halogen, —CX$^6_3$, —CHX$^6_2$, —CH$_2$X$^6$, —OCX$^6_3$, —OCH$_2$X$^6$, —OCHX$^6_2$, —CN, —SR$^{6D}$, —SOR$^{6D}$, —SO$_2$R$^{6D}$, —SO$_3$R$^{6D}$, —SO$_4$R$^{6D}$, —SONR$^{6A}$R$^{6B}$, —SO$_2$NR$^{6A}$R$^{6B}$, —NR$^{6C}$C(O)NR$^{6A}$R$^{6B}$, —N(O), —N(O)$_2$, —NR$^{6A}$R$^{6B}$, —C(O)R$^{6C}$, —C(O)—OR$^{6C}$, —C(O)NR$^{6A}$R$^{6B}$, —OR$^{6D}$, —NR$^{6A}$SO$_2$R$^{6D}$, —NR$^{6A}$C(O)R$^{6C}$, —NR$^{6A}$C(O)OR$^{6C}$, —NR$^{6A}$OR$^{6C}$, —NR$^{6C}$NR$^{6A}$R$^{6B}$, —C(O)NR$^{6C}$NR$^{6A}$R$^{6B}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;

R$^{6A}$, R$^{6B}$, R$^{6C}$, and R$^{6D}$ are each independently hydrogen, oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; and X$^1$, X$^2$, and X$^6$ are independently —F, —Cl, —Br, or —I.

Embodiment P3. The method of embodiment P1 or embodiment P2, wherein

R$^1$ is independently halogen, —CX$^1_3$, —CHX$^1_2$, —CH$_2$X$^1$, —OCX$^1_3$, —OCH$_2$X$^1$, —OCHX$^1_2$, unsubstituted C$_1$-C$_4$ alkyl, or unsubstituted 2 to 4 membered heteroalkyl;

R$^2$ is independently halogen, —CX$^2_3$, —CHX$^2_2$, —CH$_2$X$^2$, —OCX$^2_3$, —OCH$_2$X$^2$, —OCHX$^2_2$, unsubstituted C$_1$-C$_4$ alkyl, or unsubstituted 2 to 4 membered heteroalkyl;

L$^3$ is a bond, —N(R$^3$)—, —C(O)—, —C(O)N(R$^3$)—, —N(R$^3$)C(O)—, —N(H)—, —C(O)N(H)—, —N(H)C(O)—, —C(O)O—, R$^3$-substituted or unsubstituted C$_1$-C$_6$ alkylene, or R$^3$-substituted or unsubstituted 2 to 6 membered heteroalkylene;

R$^3$ is independently oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, R$^4$-substituted or unsubstituted C$_1$-C$_5$ alkyl, R$^4$-substituted or unsubstituted 2 to 8 membered heteroalkyl, R$^4$-substituted or unsubstituted C$_3$-C$_8$ cycloalkyl, R$^4$-substituted or unsubstituted 3 to 8 membered heterocycloalkyl, R$^4$-substituted or unsubstituted C$_6$-C$_{10}$ aryl, or R$^4$-substituted or unsubstituted 5 to 10 membered heteroaryl;

R$^4$ is independently oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, R$^5$-substituted or unsubstituted C$_1$-C$_8$ alkyl, R$^5$-substituted or unsubstituted 2 to 8 membered heteroalkyl, R$^5$-substituted or unsubstituted C$_3$-C$_8$ cycloalkyl, R$^5$-substituted or unsubstituted 3 to 8 membered heterocycloalkyl, R$^5$-substituted or unsubstituted C$_6$-C$_{10}$ aryl, or R$^5$-substituted or unsubstituted 5 to 10 membered heteroaryl;

R$^5$ is independently oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, unsubstituted C$_1$-C$_8$ alkyl, unsubstituted 2 to 8 membered heteroalkyl, unsubstituted C$_3$-C$_8$ cycloalkyl, unsubstituted 3 to 8 membered heterocycloalkyl, unsubstituted C$_6$-C$_{10}$ aryl, or unsubstituted 5 to 10 membered heteroaryl;

R$^6$ is independently hydrogen, halogen, —CX$^6_3$, —CHX$^6_2$, —CH$_2$X$^6$, —OCX$^6_3$, —OCH$_2$X$^6$, —OCHX$^6_2$, —CN, —SR$^{6D}$, —SOR$^{6D}$, —SO$_2$R$^{6D}$, —SO$_3$R$^{6D}$, —SO$_4$R$^{6D}$, —SONR$^{6A}$R$^{6B}$, —SO$_2$NR$^{6A}$R$^{6B}$, —NR$^{6C}$C(O)NR$^{6A}$R$^{6B}$, —N(O), —N(O)$_2$, —NR$^{6A}$R$^{6B}$, —C(O)R$^{6C}$, —C(O)—OR$^{6C}$, —C(O)NR$^{6A}$R$^{6B}$, —OR$^{6D}$, —NR$^{6A}$SO$_2$R$^{6D}$, —NR$^{6A}$C(O)R$^{6C}$, —NR$^{6A}$C(O)OR$^{6C}$, —NR$^{6A}$OR$^{6C}$, —NR$^{6C}$NR$^{6A}$R$^{6B}$, —C(O)NR$^{6C}$NR$^{6A}$R$^{6B}$, R$^7$-substituted or unsubstituted C$_1$-C$_8$ alkyl, R$^7$-substituted or unsubstituted 2 to 8 membered heteroalkyl, R$^7$-substituted or unsubstituted C$_3$-C$_8$ cycloalkyl, R$^7$-substituted or unsubstituted 3 to 8 membered heterocycloalkyl, R$^7$-substituted or unsubstituted C$_6$-C$_{10}$ aryl, or R$^7$-substituted or unsubstituted 5 to 10 membered heteroaryl;

R$^7$ is independently oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, R$^8$-substituted or unsubstituted C$_1$-C$_8$ alkyl, R$^8$-substituted or unsubstituted 2 to 8 membered heteroalkyl, R$^8$-substituted or unsubstituted C$_3$-C$_8$ cycloalkyl, R$^8$-substituted or unsubstituted 3 to 8 membered heterocycloalkyl, R$^8$-substituted or unsubstituted C$_6$-C$_{10}$ aryl, or R$^8$-substituted or unsubstituted 5 to 10 membered heteroaryl;

R$^8$ is independently oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, unsubstituted C$_1$-C$_8$ alkyl, unsubstituted 2 to 8 membered heteroalkyl, unsubstituted C$_3$-C$_8$ cycloalkyl, unsubstituted 3 to 8 membered heterocycloalkyl, unsubstituted C$_6$-C$_{10}$ aryl, or unsubstituted 5 to 10 membered heteroaryl;

$R^{6A}$ is independently hydrogen, oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, $R^{7A}$-substituted or unsubstituted C$_1$-C$_8$ alkyl, $R^{7A}$-substituted or unsubstituted 2 to 8 membered heteroalkyl, $R^{7A}$-substituted or unsubstituted C$_3$-C$_8$ cycloalkyl, $R^{7A}$-substituted or unsubstituted 3 to 8 membered heterocycloalkyl, $R^{7A}$-substituted or unsubstituted C$_6$-C$_{10}$ aryl, or $R^{7A}$-substituted or unsubstituted 5 to 10 membered heteroaryl;

$R^{7A}$ is independently oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, $R^{8A}$-substituted or unsubstituted C$_1$-C$_8$ alkyl, $R^{8A}$-substituted or unsubstituted 2 to 8 membered heteroalkyl, $R^{8A}$-substituted or unsubstituted C$_3$-C$_8$ cycloalkyl, $R^{8A}$-substituted or unsubstituted 3 to 8 membered heterocycloalkyl, $R^{8A}$-substituted or unsubstituted C$_6$-C$_{10}$ aryl, or $R^{8A}$-substituted or unsubstituted 5 to 10 membered heteroaryl;

$R^{8A}$ is independently oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, unsubstituted C$_1$-C$_8$ alkyl, unsubstituted 2 to 8 membered heteroalkyl, unsubstituted C$_3$-C$_8$ cycloalkyl, unsubstituted 3 to 8 membered heterocycloalkyl, unsubstituted C$_6$-C$_{10}$ aryl, or unsubstituted 5 to 10 membered heteroaryl;

$R^{6B}$ is independently hydrogen, oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, $R^{7B}$-substituted or unsubstituted C$_1$-C$_8$ alkyl, $R^{7B}$-substituted or unsubstituted 2 to 8 membered heteroalkyl, $R^{7B}$-substituted or unsubstituted C$_3$-C$_8$ cycloalkyl, $R^{7B}$-substituted or unsubstituted 3 to 8 membered heterocycloalkyl, $R^{7B}$-substituted or unsubstituted C$_6$-C$_{10}$ aryl, or $R^{7B}$-substituted or unsubstituted 5 to 10 membered heteroaryl;

$R^{7B}$ is independently oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, $R^{8B}$-substituted or unsubstituted C$_1$-C$_8$ alkyl, $R^{8B}$-substituted or unsubstituted 2 to 8 membered heteroalkyl, $R^{8B}$-substituted or unsubstituted C$_3$-C$_8$ cycloalkyl, $R^{8B}$-substituted or unsubstituted 3 to 8 membered heterocycloalkyl, $R^{8B}$-substituted or unsubstituted C$_6$-C$_{10}$ aryl, or $R^{8B}$-substituted or unsubstituted 5 to 10 membered heteroaryl;

$R^{8B}$ is independently oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, unsubstituted C$_1$-C$_8$ alkyl, unsubstituted 2 to 8 membered heteroalkyl, unsubstituted C$_3$-C$_8$ cycloalkyl, unsubstituted 3 to 8 membered heterocycloalkyl, unsubstituted C$_6$-C$_{10}$ aryl, or unsubstituted 5 to 10 membered heteroaryl;

$R^{6C}$ is independently hydrogen, oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, $R^{7C}$-substituted or unsubstituted C$_1$-C$_8$ alkyl, $R^{7C}$-substituted or unsubstituted 2 to 8 membered heteroalkyl, $R^{7C}$-substituted or unsubstituted C$_3$-C$_8$ cycloalkyl, $R^{7C}$-substituted or unsubstituted 3 to 8 membered heterocycloalkyl, $R^{7C}$-substituted or unsubstituted C$_6$-C$_{10}$ aryl, or $R^{7C}$-substituted or unsubstituted 5 to 10 membered heteroaryl;

$R^{7C}$ is independently oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, —NHR$^{8C}$, $R^{8C}$-substituted or unsubstituted C$_1$-C$_8$ alkyl, $R^{8C}$-substituted or unsubstituted 2 to 8 membered heteroalkyl, $R^{8C}$-substituted or unsubstituted C$_3$-C$_8$ cycloalkyl, $R^{8C}$-substituted or unsubstituted 3 to 8 membered heterocycloalkyl, $R^{8C}$- substituted or unsubstituted $C_6$-$C_{10}$ aryl, or $R^{8C}$-substituted or unsubstituted 5 to 10 membered heteroaryl;

$R^{8C}$ is independently oxo, halogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, $R^{9C}$-substituted or unsubstituted $C_1$-$C_8$ alkyl, $R^{9C}$-substituted or unsubstituted 2 to 8 membered heteroalkyl, $R^{9C}$-substituted or unsubstituted $C_3$-$C_8$ cycloalkyl, $R^{9C}$-substituted or unsubstituted 3 to 8 membered heterocycloalkyl, $R^{9C}$-substituted or unsubstituted $C_6$-$C_{10}$ aryl, or $R^{9C}$-substituted or unsubstituted 5 to 10 membered heteroaryl;

$R^{9C}$ is independently oxo, halogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, unsubstituted $C_1$-$C_8$ alkyl, unsubstituted 2 to 8 membered heteroalkyl, unsubstituted $C_3$-$C_8$ cycloalkyl, unsubstituted 3 to 8 membered heterocycloalkyl, unsubstituted $C_6$-$C_{10}$ aryl, or unsubstituted 5 to 10 membered heteroaryl;

$R^{6D}$ is independently hydrogen, oxo, halogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, $R^{7D}$-substituted or unsubstituted $C_1$-$C_8$ alkyl, $R^{7D}$-substituted or unsubstituted 2 to 8 membered heteroalkyl, $R^{7D}$-substituted or unsubstituted $C_3$-$C_8$ cycloalkyl, $R^{7D}$-substituted or unsubstituted 3 to 8 membered heterocycloalkyl, $R^{7D}$-substituted or unsubstituted $C_6$-$C_{10}$ aryl, or $R^{7D}$-substituted or unsubstituted 5 to 10 membered heteroaryl;

$R^{7D}$ is independently oxo, halogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, $R^{8D}$-substituted or unsubstituted $C_1$-$C_8$ alkyl, $R^{8D}$-substituted or unsubstituted 2 to 8 membered heteroalkyl, $R^{8D}$-substituted or unsubstituted $C_3$-$C_8$ cycloalkyl, $R^{8D}$-substituted or unsubstituted 3 to 8 membered heterocycloalkyl, $R^{8D}$-substituted or unsubstituted $C_6$-$C_{10}$ aryl, or $R^{8D}$-substituted or unsubstituted 5 to 10 membered heteroaryl;

$R^{8D}$ is independently oxo, halogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, unsubstituted $C_1$-$C_8$ alkyl, unsubstituted 2 to 8 membered heteroalkyl, unsubstituted $C_3$-$C_8$ cycloalkyl, unsubstituted 3 to 8 membered heterocycloalkyl, unsubstituted $C_6$-$C_{10}$ aryl, or unsubstituted 5 to 10 membered heteroaryl;

$X^1$, $X^2$, and $X^6$ are independently —F, —Cl, —Br, or —I.

Embodiment P4. The method of any one of embodiments P1 to P3, wherein $W^1$ is —N=.

Embodiment P5. The method of any one of embodiments P1 to P3, wherein $W^1$ is —CH=.

Embodiment P6. The method of any one of embodiments P1 to P3, wherein $W^1$ is —$CR^1$=.

Embodiment P7. The method of any one of embodiments P1 to P6, wherein $R^1$ is halogen.

Embodiment P8. The method of any one of embodiments P1 to P6, wherein $R^1$ is —Cl.

Embodiment P9. The method of one of embodiments P1 to P8, wherein $W^2$ is —N=.

Embodiment P10. The method of one of embodiments P1 to P8, wherein $W^2$ is —CH=.

Embodiment P11. The method of one of embodiments P1 to P8, wherein $W^2$ is —$CR^2$=.

Embodiment P12. The method of one of embodiments P1 to P11, wherein $R^2$ is halogen.

Embodiment P13. The method of one of embodiments P1 to P11, wherein $R^2$ is —Cl.

Embodiment P14. The method of one of embodiments P1 to P13, wherein $L^3$ is —N(H)— or $R^3$-substituted or unsubstituted $C_1$-$C_6$ alkylene.

Embodiment P15. The method of one of embodiments P1 to P13, wherein $L^3$ is —N(H)—.

Embodiment P16. The method of one of embodiments P1 to P13, wherein $L^3$ is $R^3$-substituted or unsubstituted $C_1$-$C_6$ alkylene.

Embodiment P17. The method of one of embodiments P1 to P16, wherein $R^3$ is independently —COOH, —$CONH_2$, $R^4$-substituted or unsubstituted $C_1$-$C_4$ alkyl, $R^4$-substituted or unsubstituted 2 to 4 membered heteroalkyl, $R^4$-substituted or unsubstituted $C_5$-$C_6$ cycloalkyl, $R^4$-substituted or unsubstituted 5 to 6 membered heterocycloalkyl, $R^4$-substituted or unsubstituted $C_6$-$C_{10}$ aryl, or $R^4$-substituted or unsubstituted 5 to 10 membered heteroaryl.

Embodiment P18. The method of one of embodiments P1 to P16, wherein $R^3$ is independently —COOH.

Embodiment P19. The method of one of embodiments P1 to P16, wherein $R^3$ is independently $R^4$-substituted or unsubstituted 2 to 4 membered heteroalkyl.

Embodiment P20. The method of one of embodiments P1 to P16, wherein $R^3$ is independently —S(O)$CH_3$.

Embodiment P21. The method of one of embodiments P1 to P16, wherein $R^3$ is independently $R^4$-substituted or unsubstituted $C_6$-$C_{10}$ aryl.

Embodiment P22. The method of embodiment P21, wherein $R^4$ is independently oxo or halogen.

Embodiment P23. The method of one of embodiments P1 to P16, wherein $R^3$ is independently unsubstituted phenyl.

Embodiment P24. The method of one of embodiments P1 to P16, wherein $R^3$ is independently

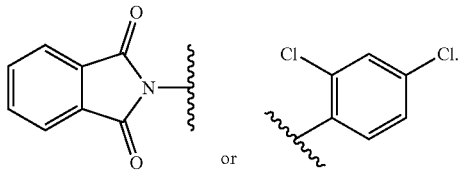 [SMILES: *N1C(=O)c2ccccc2C1=O ; *c1ccc(Cl)cc1Cl]

or

Embodiment P25. The method of one of embodiments P1 to P24, wherein $R^6$ is independently —$SOR^{6D}$, —$C(O)R^{6C}$, —$C(O)$—$OR^{6C}$, —$C(O)NR^{6A}R^{6B}$, —$NR^{6A}C(O)R^{6C}$ or —$C(O)NR^{6C}NR^{6A}R^{6B}$.

Embodiment P26. The method of one of embodiments P1 to P24, wherein $R^6$ is —$SOR^{6D}$.

Embodiment P27. The method of embodiment P26, wherein $R^{6D}$ is $R^{7D}$-substituted or unsubstituted $C_1$-$C_4$ alkyl.

Embodiment P28. The method of embodiment P26, wherein $R^{6D}$ is unsubstituted methyl.

Embodiment P29. The method of one of embodiments P1 to P24, wherein $R^6$ is —$C(O)R^{6C}$.

Embodiment P30. The method of embodiment P29, wherein $R^{6C}$ is $R^{7C}$-substituted or unsubstituted 6 membered heterocycloalkyl.

Embodiment P31. The method of embodiment P29, wherein $R^{6C}$ is $R^{7C}$-substituted piperazinyl, $R^{7C}$-substituted piperidinyl, or unsubstituted morpholinyl.

Embodiment P32. The method of embodiment P31, wherein $R^{7C}$ is —$NHR^{8C}$ or $R^{8C}$-substituted phenyl.

Embodiment P33. The method of embodiment P32, wherein $R^{8C}$ is unsubstituted $C_1$-$C_4$ alkyl, unsubstituted 2 to 4 membered heteroalkyl, unsubstituted $C_5$-$C_6$ cycloalkyl, unsubstituted 5 to 6 membered heterocycloalkyl, $R^{9C}$-substituted or unsubstituted phenyl, or unsubstituted 5 to 6 membered heteroaryl.

Embodiment P34. The method of embodiment P32, wherein $R^{8C}$ is unsubstituted methoxy or $R^{9C}$-substituted phenyl; and $R^{9C}$ is unsubstituted isopropyl.

Embodiment P35. The method of one of embodiments P1 to P24, wherein $R^6$ is —$C(O)$—$OR^{6C}$.

Embodiment P36. The method of embodiment P35, wherein $R^{6C}$ is hydrogen, $R^{7C}$-substituted or unsubstituted $C_1$-$C_5$ alkyl or $R^{7C}$-substituted or unsubstituted $C_6$-$C_{10}$ aryl.

Embodiment P37. The method of embodiment P35, wherein $R^{6C}$ is hydrogen, $R^{7C}$-substituted or unsubstituted ethyl or $R^{7C}$-substituted or unsubstituted phenyl.

Embodiment P38. The method of embodiment P37, wherein $R^{7C}$ is oxo, $R^{8C}$-substituted or unsubstituted $C_1$-$C_2$ alkyl, unsubstituted 2 to 3 membered heteroalkyl, or $R^{8C}$-substituted or unsubstituted $C_6$-$C_{10}$ aryl.

Embodiment P39. The method of embodiment P38, wherein $R^{8C}$ is oxo, halogen, unsubstituted $C_1$-$C_4$ alkyl, or unsubstituted phenyl.

Embodiment P40. The method of embodiment P38, wherein $R^{8C}$ is oxo, —Cl, —Br, unsubstituted methyl, or unsubstituted phenyl.

Embodiment P41. The method of embodiment P35, wherein $R^{6C}$ is hydrogen.

Embodiment P42. The method of one of embodiments P1 to P24, wherein $R^6$ is —$C(O)NR^{6A}R^{6B}$.

Embodiment P43. The method of embodiment P42, wherein $R^{6A}$ is hydrogen.

Embodiment P44. The method of one of embodiments P42 to P43, wherein $R^{6B}$ is $R^{7B}$-substituted or unsubstituted $C_1$-$C_6$ alkyl, $R^{7B}$-substituted or unsubstituted phenyl, or $R^{7B}$-substituted or unsubstituted 5 to 6 membered heteroaryl.

Embodiment P45. The method of one of embodiments P42 to P43, wherein $R^{6B}$ is $R^{7B}$-substituted $C_1$-$C_6$ alkyl, $R^{7B}$-substituted phenyl, or $R^{7B}$-substituted pyridyl.

Embodiment P46. The method of one of embodiments P44 to P42, wherein $R^{7B}$ is halogen, unsubstituted $C_1$-$C_3$ alkyl, $R^{8B}$-substituted or unsubstituted 2 to 4 membered heteroalkyl, or unsubstituted $C_6$-$C_{10}$ aryl.

Embodiment P47. The method of one of embodiments P41 to P45, wherein $R^{7B}$ is —Cl, —Br, unsubstituted methyl, unsubstituted ethyl, unsubstituted isopropyl, unsubstituted methoxy, $R^{8B}$-substituted 3 to 4 membered heteroalkyl, or unsubstituted phenyl.

Embodiment P48. The method of one of embodiments P46 to P47, wherein $R^{8B}$ is oxo.

Embodiment P49. The method of one of embodiments P1 to P24, wherein $R^6$ is —$NR^{6A}C(O)R^{6C}$.

Embodiment P50. The method of embodiment P49, wherein $R^{6A}$ is hydrogen.

Embodiment P51. The method of one of embodiments P49 to P50, wherein $R^{6C}$ is $R^{7C}$-substituted or unsubstituted $C_6$-$C_{10}$ aryl or unsubstituted 5 to 10 membered heteroaryl.

Embodiment P52. The method of one of embodiments P49 to P50, wherein $R^{6C}$ is $R^{7C}$-substituted or unsubstituted phenyl or unsubstituted pyridyl.

Embodiment P53. The method of one of embodiments P51 to P52, wherein $R^{7C}$ is $R^{8C}$-substituted $C_1$-$C_6$ alkyl.

Embodiment P54. The method of embodiment P53, wherein $R^{8C}$ is oxo.

Embodiment P55. The method of one of embodiments P1 to P24, wherein $R^6$ is —$C(O)NR^{6C}NR^{6A}R^{6B}$.

Embodiment P56. The method of embodiment P55, wherein $R^{6A}$ and $R^{6C}$ are hydrogen.

Embodiment P57. The method of one of embodiments P55 to P56, wherein $R^{6B}$ is $R^{7B}$-substituted $C_1$-$C_6$ alkyl.

Embodiment P58. The method of embodiment P57, wherein $R^{7B}$ is independently oxo, $R^{8B}$-substituted or unsubstituted $C_6$-$C_{10}$ aryl, or unsubstituted 5 to 10 membered heteroaryl.

Embodiment P59. The method of embodiment P57, wherein $R^{7B}$ is independently oxo, $R^{8B}$-substituted $C_6$-$C_{10}$ aryl, or unsubstituted pyridyl.

Embodiment P60. The method of one of embodiments P58 to P59, wherein $R^{8B}$ is oxo.

Embodiment P61. The method of embodiment P57, wherein $R^{7B}$ is independently oxo,

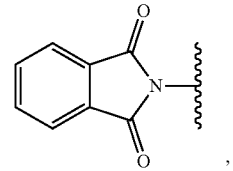 [SMILES: *N1C(=O)c2ccccc2C1=O]

, or unsubstituted pyridyl.

Embodiment P62. The method of one of embodiments P1 to P61, wherein the compound is capable of inhibiting TXNIP protein activity or function, said method comprising contacting the TXNIP protein with the compound.

Embodiment P63. The method of one of embodiments P1 to P61, wherein the compound is capable of inhibiting TXNIP protein binding to TRX, said method comprising contacting the TXNIP protein with the compound.

Embodiment P64. The method of one of embodiments P1 to P61, wherein the metabolic disorder is diabetes.

Embodiment P65. The method of embodiment P64, wherein the diabetes is T1D.

Embodiment P66. The method of embodiment P64, wherein the diabetes is T2D.

Embodiment P67. The method of embodiment P64, wherein the diabetes is associated with islet beta cell dysfunction.

Embodiment P68. The method of one of embodiments P1 to P61, wherein the cardiovascular disease is atherosclerosis.

Embodiment P69. The method of one of embodiments P1 to P61, wherein the metabolic disorder is a diabetes associated complication selected from nephropathy, retinopathy, neuropathy, cardiovascular disease, and inflammation.

Embodiment P70. The method of one of embodiments P1 to P61, wherein the method does not increase the risk for an infectious disease.

Embodiment P71. A pharmaceutical composition comprising a compound, or pharmaceutically acceptable salt thereof, and a pharmaceutically acceptable excipient, wherein the compound has the formula:

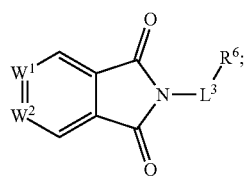

(I)

wherein
$W^1$ is $-CR^1=$, $-N=$, or $-CH=$;
$W^2$ is $-CR^2=$, $-N=$, or $-CH=$;
$R^1$ is independently halogen, $-CX^1_3$, $-CHX^1_2$, $-CH_2X^1$, $-OCX^1_3$, $-OCH_2X^1$, $-OCHX^1_2$, substituted or unsubstituted alkyl, or substituted or unsubstituted heteroalkyl;
$R^2$ is independently halogen, $-CX^2_3$, $-CHX^2_2$, $-CH_2X^2$, $-OCX^2_3$, $-OCH_2X^2$, $-OCHX^2_2$, substituted or unsubstituted alkyl, or substituted or unsubstituted heteroalkyl;
$L^3$ is a bond, $-N(R^3)-$, $-C(O)-$, $-C(O)N(R^3)-$, $-N(R^3)C(O)-$, $-N(H)-$, $-C(O)N(H)-$, $-N(H)C(O)-$, $-C(O)O-$, substituted or unsubstituted alkylene, or substituted or unsubstituted heteroalkylene;
$R^3$ is independently oxo, halogen, $-CCl_3$, $-CBr_3$, $-CF_3$, $-CI_3$, $CHCl_2$, $-CHBr_2$, $-CHF_2$, $-CHI_2$, $-CH_2Cl$, $-CH_2Br$, $-CH_2F$, $-CH_2I$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, $-N_3$, $-SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^6$ is independently hydrogen, halogen, $-CX^6_3$, $-CHX^6_2$, $-CH_2X^6$, $-OCX^6_3$, $-OCH_2X^6$, $-OCHX^6_2$, $-CN$, $-SR^{6D}$, $-SOR^{6D}$, $-SO_2R^{6D}$, $-SO_3R^{6D}$, $-SO_4R^{6D}$, $-SONR^{6A}R^{6B}$, $-SO_2NR^{6A}R^{6B}$, $-NR^{6C}C(O)NR^{6A}R^{6B}$, $-N(O)$, $-N(O)_2$, $-NR^{6A}R^{6B}$, $-C(O)R^{6C}$, $-C(O)-OR^{6C}$, $-C(O)NR^{6A}R^{6B}$, $-OR^{6D}$, $-NR^{6A}SO_2R^{6D}$, $-NR^{6A}C(O)R^{6C}$, $-NR^{6A}C(O)OR^{6C}$, $-NR^{6A}OR^{6C}$, $-NR^{6C}NR^{6A}R^{6B}$, $-C(O)NR^{6C}NR^{6A}R^{6B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^{6A}$, $R^{6B}$, $R^{6C}$, and $R^{6D}$ are each independently hydrogen, oxo, halogen, $-CCl_3$, $-CBr_3$, $-CF_3$, $-CI_3$, $CHCl_2$, $-CHBr_2$, $-CHF_2$, $-CHI_2$, $-CH_2Cl$, $-CH_2Br$, $-CH_2F$, $-CH_2I$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, $-N_3$, $-SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; and
$X^1$, $X^2$, and $X^6$ are independently $-F$, $-Cl$, $-Br$, or $-I$.

VI. Additional Embodiments

Embodiment 1. A method of treating a TXNIP-TRX complex-associated disease, said method comprising administering to a subject in need thereof an effective amount of a TXNIP-TRX complex inhibitor, wherein said TXNIP-TRX complex inhibitor has the formula:

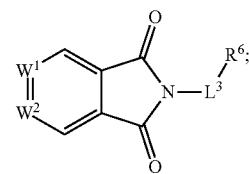

(I)

wherein
$W^1$ is $-CR^1=$, $-N=$, or $-CH=$;
$W^2$ is $-CR^2=$, $-N=$, or $-CH=$;
$R^1$ is independently halogen, $-CX^1_3$, $-CHX^1_2$, $-CH_2X^1$, $-OCX^1_3$, $-OCH_2X^1$, $-OCHX^1_2$, substituted or unsubstituted alkyl, or substituted or unsubstituted heteroalkyl;
$R^2$ is independently halogen, $-CX^2_3$, $-CHX^2_2$, $-CH_2X^2$, $-OCX^2_3$, $-OCH_2X^2$, $-OCHX^2_2$, substituted or unsubstituted alkyl, or substituted or unsubstituted heteroalkyl;
$L^3$ is a bond, $-N(R^3)-$, $-C(O)-$, $-C(O)N(R^3)-$, $-N(R^3)C(O)-$, $-N(H)-$, $-C(O)N(H)-$, $-N(H)C(O)-$, $-C(O)O-$, substituted or unsubstituted alkylene, or substituted or unsubstituted heteroalkylene;
$R^3$ is independently oxo, halogen, $-CCl_3$, $-CBr_3$, $-CF_3$, $-CI_3$, $-CHCl_2$, $-CHBr_2$, $-CHF_2$, $-CHI_2$, $-CH_2Cl$, $-CH_2Br$, $-CH_2F$, $-CH_2I$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)

H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;

R$^6$ is independently hydrogen, halogen, —CX$^6_3$, —CHX$^6_2$, —CH$_2$X$^6$, —OCX$^6_3$, —OCH$_2$X$^6$, —OCHX$^6_2$, —CN, —SR$^{6D}$, —SOR$^{6D}$, —SO$_2$R$^{6D}$, —SO$_3$R$^{6D}$, —SO$_4$R$^{6D}$, —SONR$^{6A}$R$^{6B}$, —SO$_2$NR$^{6A}$R$^{6B}$, —NR$^{6C}$C(O)NR$^{6A}$R$^{6B}$, —N(O), —N(O)$_2$, —NR$^{6A}$R$^{6B}$, —C(O)R$^{6C}$, —C(O)—OR$^{6C}$, —C(O)NR$^{6A}$R$^{6B}$, —OR$^{6D}$, —NR$^{6A}$SO$_2$R$^{6D}$, —NR$^{6A}$C(O)R$^{6C}$, —NR$^{6A}$C(O)OR$^{6C}$, —NR$^{6A}$OR$^{6C}$, —NR$^{6C}$NR$^{6A}$R$^{6B}$, —C(O)NR$^{6C}$NR$^{6A}$R$^{6B}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;

R$^{6A}$, R$^{6B}$, R$^{6C}$, and R$^{6D}$ are each independently hydrogen, oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; and X$^1$, X$^2$, and X$^6$ are independently —F, —Cl, —Br, or —I.

Embodiment 2. A method of treating a metabolic disorder, cardiovascular disease, or inflammatory disease, said method comprising administering to a subject in need thereof an effective amount of a compound, or pharmaceutically acceptable salt thereof, having the formula.

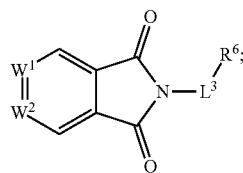

(I)

wherein
W$^1$ is —CR$^1$=, —N=, or —CH=;
W$^2$ is —CR$^2$=, —N=, or —CH=;
R$^1$ is independently halogen, —CX$^1_3$, —CHX$^1_2$, —CH$_2$X$^1$, —OCX$^1_3$, —OCH$_2$X$^1$, —OCHX$^1_2$, substituted or unsubstituted alkyl, or substituted or unsubstituted heteroalkyl;
R$^2$ is independently halogen, —CX$^2_3$, —CHX$^2_2$, —CH$_2$X$^2$, —OCX$^2_3$, —OCH$_2$X$^2$, —OCHX$^2_2$, substituted or unsubstituted alkyl, or substituted or unsubstituted heteroalkyl;
L$^3$ is a bond, —N(R$^3$)—, —C(O)—, —C(O)N(R$^3$)—, —N(R$^3$)C(O)—, —N(H)—, —C(O)N(H)—, —N(H)C(O)—, —C(O)O—, substituted or unsubstituted alkylene, or substituted or unsubstituted heteroalkylene;

R$^3$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;

R$^6$ is independently hydrogen, halogen, —CX$^6_3$, —CHX$^6_2$, —CH$_2$X$^6$, —OCX$^6_3$, —OCH$_2$X$^6$, —OCHX$^6_2$, —CN, —SR$^{6D}$, —SOR$^{6D}$, —SO$_2$R$^{6D}$, —SO$_3$R$^{6D}$, —SO$_4$R$^{6D}$, —SONR$^{6A}$R$^{6B}$, —SO$_2$NR$^{6A}$R$^{6B}$, —NR$^{6C}$C(O)NR$^{6A}$R$^{6B}$, —N(O), —N(O)$_2$, —NR$^{6A}$R$^{6B}$, —C(O)R$^{6C}$, —C(O)—OR$^{6C}$, —C(O)NR$^{6A}$R$^{6B}$, —OR$^{6D}$, —NR$^{6A}$SO$_2$R$^{6D}$, —NR$^{6A}$C(O)R$^{6C}$, —NR$^{6A}$C(O)OR$^{6C}$, —NR$^{6A}$OR$^{6C}$, —NR$^{6C}$NR$^{6A}$R$^{6B}$, —C(O)NR$^{6C}$NR$^{6A}$R$^{6B}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;

R$^{6A}$, R$^{6B}$, R$^{6C}$, and R$^{6D}$ are each independently hydrogen, oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; and X$^1$, X$^2$, and X$^6$ are independently —F, —Cl, —Br, or —I.

Embodiment 3. The method of embodiment 1 or embodiment 2, wherein

R$^1$ is independently halogen, —CX$^1_3$, —CHX$^1_2$, —CH$_2$X$^1$, —OCX$^1_3$, —OCH$_2$X$^1$, —OCHX$^1_2$, unsubstituted C$_1$-C$_4$ alkyl, or unsubstituted 2 to 4 membered heteroalkyl;

R$^2$ is independently halogen, —CX$^2_3$, —CHX$^2_2$, —CH$_2$X$^2$, —OCX$^2_3$, —OCH$_2$X$^2$, —OCHX$^2_2$, unsubstituted C$_1$-C$_4$ alkyl, or unsubstituted 2 to 4 membered heteroalkyl;

L$^3$ is a bond, —N(R$^3$)—, —C(O)—, —C(O)N(R$^3$)—, —N(R$^3$)C(O)—, —N(H)—, —C(O)N(H)—, —N(H)C(O)—, —C(O)O—, R$^3$-substituted or unsubstituted C$_1$-C$_6$ alkylene, or R$^3$-substituted or unsubstituted 2 to 6 membered heteroalkylene;

R$^3$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC (O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, R$^4$-substituted or unsubstituted C$_1$-C$_8$ alkyl, R$^4$-substituted or unsubstituted 2 to 8 membered heteroalkyl, R$^4$-substituted or unsubstituted C$_3$-C$_8$ cycloalkyl, R$^4$-substituted or unsubstituted 3 to 8 membered heterocycloalkyl, R$^4$-substituted or unsubstituted C$_6$-C$_{10}$ aryl, or R$^4$-substituted or unsubstituted 5 to 10 membered heteroaryl;

R$^4$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, R$^5$-substituted or unsubstituted C$_1$-C$_8$ alkyl, R$^5$-substituted or unsubstituted 2 to 8 membered heteroalkyl, R$^5$-substituted or unsubstituted C$_3$-C$_8$ cycloalkyl, R$^5$-substituted or unsubstituted 3 to 8 membered heterocycloalkyl, R$^5$-substituted or unsubstituted C$_6$-C$_{10}$ aryl, or R$^5$-substituted or unsubstituted 5 to 10 membered heteroaryl;

R$^5$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, unsubstituted C$_1$-C$_5$ alkyl, unsubstituted 2 to 8 membered heteroalkyl, unsubstituted C$_3$-C$_8$ cycloalkyl, unsubstituted 3 to 8 membered heterocycloalkyl, unsubstituted C$_6$-C$_{10}$ aryl, or unsubstituted 5 to 10 membered heteroaryl;

R$^6$ is independently hydrogen, halogen, —CX$^6{}_3$, —CHX$^6{}_2$, —CH$_2$X$^6$, —OCX$^6{}_3$, —OCH$_2$X$^6$, —OCHX$^6{}_2$, —CN, —SR$^{6D}$, —SOR$^{6D}$, —SO$_2$R$^{6D}$, —SO$_3$R$^{6D}$, —SO$_4$R$^{6D}$, —SONR$^{6A}$R$^{6B}$, —SO$_2$NR$^{6A}$R$^{6B}$, —NR$^{6C}$C(O)NR$^{6A}$R$^{6B}$, —N(O), —N(O)$_2$, —NR$^{6A}$R$^{6B}$, —C(O)R$^{6C}$, —C(O)—OR$^{6C}$, —C(O)NR$^{6A}$R$^{6B}$, —OR$^{6D}$, —NR$^{6A}$SO$_2$R$^{6D}$, —NR$^{6A}$C(O)R$^{6C}$, —NR$^{6A}$C(O)OR$^{6C}$, —NR$^{6A}$OR$^{6C}$, —NR$^{6C}$NR$^{6A}$R$^{6B}$, —C(O)NR$^{6C}$NR$^{6A}$R$^{6B}$, R$^7$-substituted or unsubstituted C$_1$-C$_8$ alkyl, R$^7$-substituted or unsubstituted 2 to 8 membered heteroalkyl, R$^7$-substituted or unsubstituted C$_3$-C$_8$ cycloalkyl, R$^7$-substituted or unsubstituted 3 to 8 membered heterocycloalkyl, R$^7$-substituted or unsubstituted C$_6$-C$_{10}$ aryl, or R$^7$-substituted or unsubstituted 5 to 10 membered heteroaryl;

R$^7$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, R$^8$-substituted or unsubstituted C$_1$-C$_8$ alkyl, R$^8$-substituted or unsubstituted 2 to 8 membered heteroalkyl, R$^8$-substituted or unsubstituted C$_3$-C$_8$ cycloalkyl, R$^8$-substituted or unsubstituted 3 to 8 membered heterocycloalkyl, R$^8$-substituted or unsubstituted C$_6$-C$_{10}$ aryl, or R$^8$-substituted or unsubstituted 5 to 10 membered heteroaryl;

R$^8$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, unsubstituted C$_1$-C$_5$ alkyl, unsubstituted 2 to 8 membered heteroalkyl, unsubstituted C$_3$-C$_8$ cycloalkyl, unsubstituted 3 to 8 membered heterocycloalkyl, unsubstituted C$_6$-C$_{10}$ aryl, or unsubstituted 5 to 10 membered heteroaryl;

R$^{6A}$ is independently hydrogen, oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, R$^{7A}$-substituted or unsubstituted C$_1$-C$_8$ alkyl, R$^{7A}$-substituted or unsubstituted 2 to 8 membered heteroalkyl, R$^{7A}$-substituted or unsubstituted C$_3$-C$_8$ cycloalkyl, R$^{7A}$-substituted or unsubstituted 3 to 8 membered heterocycloalkyl, R$^{7A}$-substituted or unsubstituted C$_6$-C$_{10}$ aryl, or R$^{7A}$-substituted or unsubstituted 5 to 10 membered heteroaryl;

R$^{7A}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, R$^{8A}$-substituted or unsubstituted C$_1$-C$_8$ alkyl, R$^{8A}$-substituted or unsubstituted 2 to 8 membered heteroalkyl, R$^{8A}$-substituted or unsubstituted C$_3$-C$_8$ cycloalkyl, R$^{8A}$-substituted or unsubstituted 3 to 8 membered heterocycloalkyl, R$^{8A}$-substituted or unsubstituted C$_6$-C$_{10}$ aryl, or R$^{8A}$-substituted or unsubstituted 5 to 10 membered heteroaryl;

R$^{8A}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, unsubstituted C$_1$-C$_8$ alkyl, unsubstituted 2 to 8 membered heteroalkyl, unsubstituted C$_3$-C$_8$ cycloalkyl, unsubstituted 3 to 8 membered heterocycloalkyl, unsubstituted C$_6$-C$_{10}$ aryl, or unsubstituted 5 to 10 membered heteroaryl;

R$^{6B}$ is independently hydrogen, oxo, halogen, —CCl$_3$, —CBr$_3$, —CF$_3$, —CI$_3$, —CHCl$_2$, —CHBr$_2$, —CHF$_2$, —CHI₂, —CH₂Cl, —CH₂Br, —CH₂F, —CH₂I, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr₃, —OCI₃, —OCHCl₂, —OCHBr₂, —OCHI₂, —OCHF₂, —OCH₂Cl, —OCH₂Br, —OCH₂I, —OCH₂F, —N₃, —SF₅, $R^{7B}$-substituted or unsubstituted $C_1$-$C_8$ alkyl, $R^{7B}$-substituted or unsubstituted 2 to 8 membered heteroalkyl, $R^{7B}$-substituted or unsubstituted $C_3$-$C_8$ cycloalkyl, $R^{7B}$-substituted or unsubstituted 3 to 8 membered heterocycloalkyl, $R^{7B}$-substituted or unsubstituted $C_6$-$C_{10}$ aryl, or $R^{7B}$-substituted or unsubstituted 5 to 10 membered heteroaryl;

$R^{7B}$ is independently oxo, halogen, —CCl₃, —CBr₃, —CF₃, —CI₃, —CHCl₂, —CHBr₂, —CHF₂, —CHI₂, —CH₂Cl, —CH₂Br, —CH₂F, —CH₂I, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr₃, —OCI₃, —OCHCl₂, —OCHBr₂, —OCHI₂, —OCHF₂, —OCH₂Cl, —OCH₂Br, —OCH₂I, —OCH₂F, —N₃, —SF₅, $R^{8B}$-substituted or unsubstituted $C_1$-$C_8$ alkyl, $R^{8B}$-substituted or unsubstituted 2 to 8 membered heteroalkyl, $R^{8B}$-substituted or unsubstituted $C_3$-$C_8$ cycloalkyl, $R^{8B}$-substituted or unsubstituted 3 to 8 membered heterocycloalkyl, $R^{8B}$-substituted or unsubstituted $C_6$-$C_{10}$ aryl, or $R^{8B}$-substituted or unsubstituted 5 to 10 membered heteroaryl;

$R^{8B}$ is independently oxo, halogen, —CCl₃, —CBr₃, —CF₃, —CI₃, —CHCl₂, —CHBr₂, —CHF₂, —CHI₂, —CH₂Cl, —CH₂Br, —CH₂F, —CH₂I, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr₃, —OCI₃, —OCHCl₂, —OCHBr₂, —OCHI₂, —OCHF₂, —OCH₂Cl, —OCH₂Br, —OCH₂I, —OCH₂F, —N₃, —SF₅, unsubstituted $C_1$-$C_5$ alkyl, unsubstituted 2 to 8 membered heteroalkyl, unsubstituted $C_3$-$C_8$ cycloalkyl, unsubstituted 3 to 8 membered heterocycloalkyl, unsubstituted $C_6$-$C_{10}$ aryl, or unsubstituted 5 to 10 membered heteroaryl;

$R^{6C}$ is independently hydrogen, oxo, halogen, —CCl₃, —CBr₃, —CF₃, —CI₃, —CHCl₂, —CHBr₂, —CHF₂, —CHI₂, —CH₂Cl, —CH₂Br, —CH₂F, —CH₂I, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr₃, —OCI₃, —OCHCl₂, —OCHBr₂, —OCHI₂, —OCHF₂, —OCH₂Cl, —OCH₂Br, —OCH₂I, —OCH₂F, —N₃, —SF₅, $R^{7C}$-substituted or unsubstituted $C_1$-$C_8$ alkyl, $R^{7C}$-substituted or unsubstituted 2 to 8 membered heteroalkyl, $R^{7C}$-substituted or unsubstituted $C_3$-$C_8$ cycloalkyl, $R^{7C}$-substituted or unsubstituted 3 to 8 membered heterocycloalkyl, $R^{7C}$-substituted or unsubstituted $C_6$-$C_{10}$ aryl, or $R^{7C}$-substituted or unsubstituted 5 to 10 membered heteroaryl;

$R^{7C}$ is independently oxo, halogen, —CCl₃, —CBr₃, —CF₃, —CI₃, —CHCl₂, —CHBr₂, —CHF₂, —CHI₂, —CH₂Cl, —CH₂Br, —CH₂F, —CH₂I, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr₃, —OCI₃, —OCHCl₂, —OCHBr₂, —OCHI₂, —OCHF₂, —OCH₂Cl, —OCH₂Br, —OCH₂I, —OCH₂F, —N₃, —SF₅, —NHR$^{8C}$, $R^{8C}$-substituted or unsubstituted $C_1$-$C_8$ alkyl, $R^{8C}$-substituted or unsubstituted 2 to 8 membered heteroalkyl, $R^{8C}$-substituted or unsubstituted $C_3$-$C_8$ cycloalkyl, $R^{8C}$-substituted or unsubstituted 3 to 8 membered heterocycloalkyl, $R^{8C}$-substituted or unsubstituted $C_6$-$C_{10}$ aryl, or $R^{8C}$-substituted or unsubstituted 5 to 10 membered heteroaryl;

$R^{8C}$ is independently oxo, halogen, —CCl₃, —CBr₃, —CF₃, —CI₃, —CHCl₂, —CHBr₂, —CHF₂, —CHI₂, —CH₂Cl, —CH₂Br, —CH₂F, —CH₂I, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr₃, —OCI₃, —OCHCl₂, —OCHBr₂, —OCHI₂, —OCHF₂, —OCH₂Cl, —OCH₂Br, —OCH₂I, —OCH₂F, —N₃, —SF₅, R'C-substituted or unsubstituted $C_1$-$C_8$ alkyl, $R^{9C}$-substituted or unsubstituted 2 to 8 membered heteroalkyl, $R^{9C}$-substituted or unsubstituted $C_3$-$C_8$ cycloalkyl, $R^{9C}$-substituted or unsubstituted 3 to 8 membered heterocycloalkyl, $R^{9C}$-substituted or unsubstituted $C_6$-$C_{10}$ aryl, or $R^{9C}$-substituted or unsubstituted 5 to 10 membered heteroaryl;

$R^{9C}$ is independently oxo, halogen, —CCl₃, —CBr₃, —CF₃, —CI₃, —CHCl₂, —CHBr₂, —CHF₂, —CHI₂, —CH₂Cl, —CH₂Br, —CH₂F, —CH₂I, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr₃, —OCI₃, —OCHCl₂, —OCHBr₂, —OCHI₂, —OCHF₂, —OCH₂Cl, —OCH₂Br, —OCH₂I, —OCH₂F, —N₃, —SF₅, unsubstituted $C_1$-$C_5$ alkyl, unsubstituted 2 to 8 membered heteroalkyl, unsubstituted $C_3$-$C_8$ cycloalkyl, unsubstituted 3 to 8 membered heterocycloalkyl, unsubstituted $C_6$-$C_{10}$ aryl, or unsubstituted 5 to 10 membered heteroaryl;

$R^{6D}$ is independently hydrogen, oxo, halogen, —CCl₃, —CBr₃, —CF₃, —CI₃, —CHCl₂, —CHBr₂, —CHF₂, —CHI₂, —CH₂Cl, —CH₂Br, —CH₂F, —CH₂I, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr₃, —OCI₃, —OCHCl₂, —OCHBr₂, —OCHI₂, —OCHF₂, —OCH₂Cl, —OCH₂Br, —OCH₂I, —OCH₂F, —N₃, —SF₅, $R^{7D}$-substituted or unsubstituted $C_1$-$C_8$ alkyl, $R^{7D}$-substituted or unsubstituted 2 to 8 membered heteroalkyl, $R^{7D}$-substituted or unsubstituted $C_3$-$C_8$ cycloalkyl, $R^{7D}$-substituted or unsubstituted 3 to 8 membered heterocycloalkyl, $R^{7D}$-substituted or unsubstituted $C_6$-$C_{10}$ aryl, or $R^{7D}$-substituted or unsubstituted 5 to 10 membered heteroaryl;

$R^{7D}$ is independently oxo, halogen, —CCl₃, —CBr₃, —CF₃, —CI₃, —CHCl₂, —CHBr₂, —CHF₂, —CHI₂, —CH₂Cl, —CH₂Br, —CH₂F, —CH₂I, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr₃, —OCI₃, —OCHCl₂, —OCHBr₂, —OCHI₂, —OCHF₂, —OCH₂Cl, —OCH₂Br, —OCH₂I, —OCH₂F, —N₃, —SF₅, $R^{8D}$-substituted or unsubstituted $C_1$-$C_8$ alkyl, $R^{8D}$-substituted or unsubstituted 2 to 8 membered heteroalkyl, $R^{8D}$-substituted or unsubstituted $C_3$-$C_8$ cycloalkyl, $R^{8D}$-substituted or unsubstituted 3 to 8 membered heterocycloalkyl, R"D-substituted or unsubstituted $C_6$-$C_{10}$ aryl, or R"D-substituted or unsubstituted 5 to 10 membered heteroaryl;

$R^{8D}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, unsubstituted $C_1$-$C_5$ alkyl, unsubstituted 2 to 8 membered heteroalkyl, unsubstituted $C_3$-$C_8$ cycloalkyl, unsubstituted 3 to 8 membered heterocycloalkyl, unsubstituted $C_6$-$C_{10}$ aryl, or unsubstituted 5 to 10 membered heteroaryl;

$X^1$, $X^2$, and $X^6$ are independently —F, —Cl, —Br, or —I.

Embodiment 4. The method of one of embodiments 1 to 3, wherein $W^1$ is —N=.

Embodiment 5. The method of one of embodiments 1 to 3, wherein $W^1$ is —CH=.

Embodiment 6. The method of one of embodiments 1 to 3, wherein $W^1$ is —$CR^1$=.

Embodiment 7. The method of one of embodiments 1 to 6, wherein $R^1$ is halogen.

Embodiment 8. The method of one of embodiments 1 to 6, wherein $R^1$ is —Cl.

Embodiment 9. The method of one of embodiments 1 to 8, wherein $W^2$ is —N=.

Embodiment 10. The method of one of embodiments 1 to 8, wherein $W^2$ is —CH=.

Embodiment 11. The method of one of embodiments 1 to 8, wherein $W^2$ is —$CR^2$=.

Embodiment 12. The method of one of embodiments 1 to 11, wherein $R^2$ is halogen.

Embodiment 13. The method of one of embodiments 1 to 11, wherein $R^2$ is —Cl.

Embodiment 14. The method of one of embodiments 1 to 13, wherein $L^3$ is —N(H)— or $R^3$-substituted or unsubstituted $C_1$-$C_6$ alkylene.

Embodiment 15. The method of one of embodiments 1 to 13, wherein $L^3$ is —N(H)—.

Embodiment 16. The method of one of embodiments 1 to 13, wherein $L^3$ is $R^3$-substituted or unsubstituted $C_1$-$C_6$ alkylene.

Embodiment 17. The method of one of embodiments 1 to 16, wherein $R^3$ is independently —COOH, —$CONH_2$, $R^4$-substituted or unsubstituted $C_1$-$C_4$ alkyl, $R^4$-substituted or unsubstituted 2 to 4 membered heteroalkyl, $R^4$-substituted or unsubstituted $C_5$-$C_6$ cycloalkyl, $R^4$-substituted or unsubstituted 5 to 6 membered heterocycloalkyl, $R^4$-substituted or unsubstituted $C_6$-$C_{10}$ aryl, or $R^4$-substituted or unsubstituted 5 to 10 membered heteroaryl.

Embodiment 18. The method of one of embodiments 1 to 16, wherein $R^3$ is independently —COOH.

Embodiment 19. The method of one of embodiments 1 to 16, wherein $R^3$ is independently $R^4$-substituted or unsubstituted 2 to 4 membered heteroalkyl.

Embodiment 20. The method of one of embodiments 1 to 16, wherein $R^3$ is independently —S(O)$CH_3$.

Embodiment 21. The method of one of embodiments 1 to 16, wherein $R^3$ is independently $R^4$-substituted or unsubstituted $C_6$-$C_{10}$ aryl.

Embodiment 22. The method of embodiment 21, wherein $R^4$ is independently oxo or halogen.

Embodiment 23. The method of one of embodiments 1 to 16, wherein $R^3$ is independently unsubstituted phenyl.

Embodiment 24. The method of one of embodiments 1 to 16, wherein $R^3$ is independently

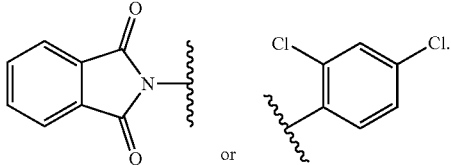 [SMILES: *N1C(=O)c2ccccc2C1=O ; *c1ccc(Cl)cc1Cl]

Embodiment 25. The method of one of embodiments 1 to 24, wherein $R^6$ is independently —$SOR^{6D}$, —C(O)$R^{6C}$, —C(O)—$OR^{6C}$, —C(O)$NR^{6A}R^{6B}$, —$NR^{6A}$C(O)$R^{6C}$ or —C(O)$NR^{6C}NR^{6A}R^{6B}$.

Embodiment 26. The method of one of embodiments 1 to 24, wherein $R^6$ is —$SOR^{6D}$.

Embodiment 27. The method of embodiment 26, wherein $R^{6D}$ is R'-substituted or unsubstituted $C_1$-$C_4$ alkyl.

Embodiment 28. The method of embodiment 26, wherein $R^{6D}$ is unsubstituted methyl.

Embodiment 29. The method of one of embodiments 1 to 24, wherein $R^6$ is —C(O)$R^{6C}$.

Embodiment 30. The method of embodiment 29, wherein $R^{6C}$ is $R^{7C}$-substituted or unsubstituted 6 membered heterocycloalkyl.

Embodiment 31. The method of embodiment 29, wherein $R^{6C}$ is $R^{7C}$-substituted piperazinyl, $R^{7C}$-substituted piperidinyl, or unsubstituted morpholinyl.

Embodiment 32. The method of embodiment 31, wherein $R^{7C}$ is —$NHR^{8C}$ or $R^{8C}$-substituted phenyl.

Embodiment 33. The method of embodiment 32, wherein $R^{8C}$ is unsubstituted $C_1$-$C_4$ alkyl, unsubstituted 2 to 4 membered heteroalkyl, unsubstituted $C_5$-$C_6$ cycloalkyl, unsubstituted 5 to 6 membered heterocycloalkyl, $R^{9C}$-substituted or unsubstituted phenyl, or unsubstituted 5 to 6 membered heteroaryl.

Embodiment 34. The method of embodiment 32, wherein $R^{8C}$ is unsubstituted methoxy or $R^{9C}$-substituted phenyl; and $R^{9C}$ is unsubstituted isopropyl.

Embodiment 35. The method of one of embodiments 1 to 24, wherein $R^6$ is —C(O)—$OR^{6C}$.

Embodiment 36. The method of embodiment 35, wherein $R^{6C}$ is hydrogen, $R^{7C}$-substituted or unsubstituted $C_1$-$C_5$ alkyl or $R^{7C}$-substituted or unsubstituted $C_6$-$C_{10}$ aryl.

Embodiment 37. The method of embodiment 35, wherein $R^{6C}$ is hydrogen, $R^{7C}$-substituted or unsubstituted ethyl or $R^{7C}$-substituted or unsubstituted phenyl.

Embodiment 38. The method of embodiment 37, wherein $R^{7C}$ is oxo, $R^{8C}$-substituted or unsubstituted $C_1$-$C_2$ alkyl, unsubstituted 2 to 3 membered heteroalkyl, or $R^{8C}$-substituted or unsubstituted $C_6$-$C_{10}$ aryl.

Embodiment 39. The method of embodiment 38, wherein $R^{8C}$ is oxo, halogen, unsubstituted $C_1$-$C_4$ alkyl, or unsubstituted phenyl.

Embodiment 40. The method of embodiment 38, wherein $R^{8C}$ is oxo, —Cl, —Br, unsubstituted methyl, or unsubstituted phenyl.

Embodiment 41. The method of embodiment 35, wherein $R^{6C}$ is hydrogen.

Embodiment 42. The method of one of embodiments 1 to 24, wherein $R^6$ is —C(O)$NR^{6A}R^{6B}$.

Embodiment 43. The method of embodiment 42, wherein $R^{6A}$ is hydrogen.

Embodiment 44. The method of one of embodiments 42 to 43, wherein $R^{6B}$ is $R^{7B}$-substituted or unsubstituted $C_1$-$C_6$ alkyl, $R^{7B}$-substituted or unsubstituted phenyl, or $R^{7B}$-substituted or unsubstituted 5 to 6 membered heteroaryl.

Embodiment 45. The method of one of embodiments 42 to 43, wherein $R^{6B}$ is $R^{7B}$-substituted $C_1$-$C_6$ alkyl, $R^{7B}$-substituted phenyl, or $R^{7B}$-substituted pyridyl.

Embodiment 46. The method of one of embodiments 44 to 45, wherein $R^{7B}$ is halogen, unsubstituted $C_1$-$C_3$ alkyl, $R^{8B}$-substituted or unsubstituted 2 to 4 membered heteroalkyl, or unsubstituted $C_6$-$C_{10}$ aryl.

Embodiment 47. The method of one of embodiments 41 to 45, wherein $R^{7B}$ is —Cl, —Br, unsubstituted methyl, unsubstituted ethyl, unsubstituted isopropyl, unsubstituted methoxy, $R^{8B}$-substituted 3 to 4 membered heteroalkyl, or unsubstituted phenyl.

Embodiment 48. The method of one of embodiments 46 to 47, wherein $R^{8B}$ is oxo.

Embodiment 49. The method of one of embodiments 1 to 24, wherein $R^6$ is —$NR^{6A}C(O)R^{6C}$.

Embodiment 50. The method of embodiment 49, wherein $R^{6A}$ is hydrogen.

Embodiment 51. The method of one of embodiments 49 to 50, wherein $R^{6C}$ is $R^{7C}$-substituted or unsubstituted $C_6$-$C_{10}$ aryl or unsubstituted 5 to 10 membered heteroaryl.

Embodiment 52. The method of one of embodiments 49 to 50, wherein $R^{6C}$ is $R^{7C}$-substituted or unsubstituted phenyl or unsubstituted pyridyl.

Embodiment 53. The method of one of embodiments 51 to 52, wherein $R^{7C}$ is $R^{8C}$-substituted $C_1$-$C_6$ alkyl.

Embodiment 54. The method of embodiment 53, wherein $R^{8C}$ is oxo.

Embodiment 55. The method of one of embodiments 1 to 24, wherein $R^6$ is —$C(O)NR^{6C}NR^{6A}R^{6B}$.

Embodiment 56. The method of embodiment 55, wherein $R^{6A}$ and $R^{6C}$ are hydrogen.

Embodiment 57. The method of one of embodiments 55 to 56, wherein $R^{6B}$ is $R^{7B}$-substituted $C_1$-$C_6$ alkyl.

Embodiment 58. The method of embodiment 57, wherein $R^{7B}$ is independently oxo, $R^{8B}$-substituted or unsubstituted $C_6$-$C_{10}$ aryl, or unsubstituted 5 to 10 membered heteroaryl.

Embodiment 59. The method of embodiment 57, wherein $R^{7B}$ is independently oxo, $R^{8B}$-substituted $C_6$-$C_{10}$ aryl, or unsubstituted pyridyl.

Embodiment 60. The method of one of embodiments 58 to 59, wherein $R^{8B}$ is oxo.

Embodiment 61. The method of embodiment 57, wherein $R^{7B}$ is independently oxo, or unsubstituted pyridyl.

Embodiment 62. The method of one of embodiments 1 to 3, wherein the compound is

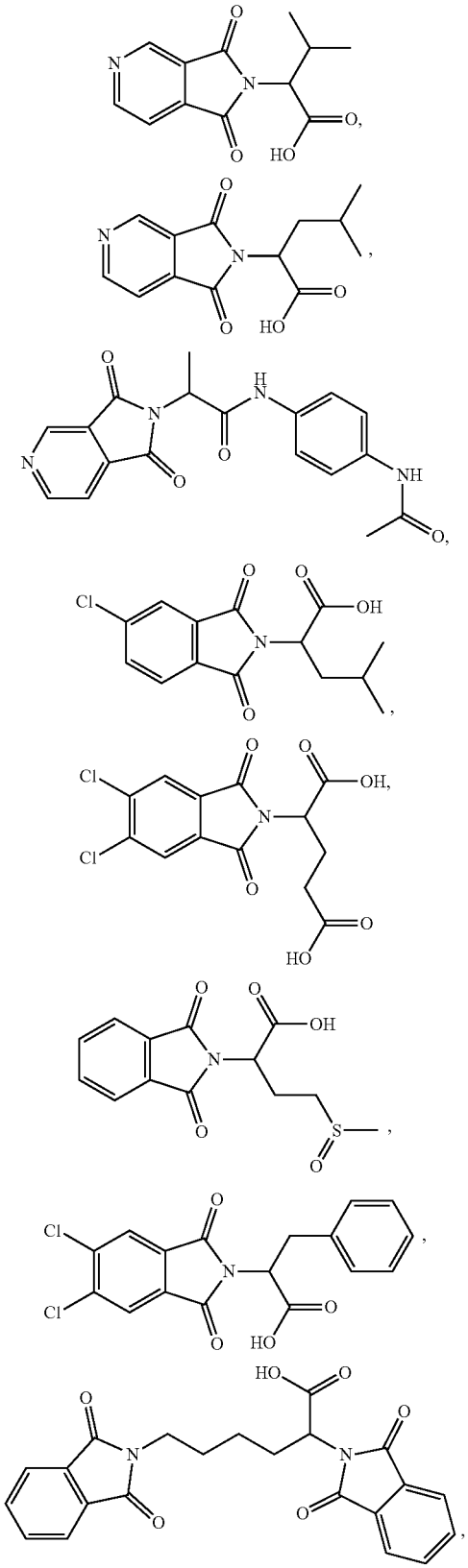

169
-continued
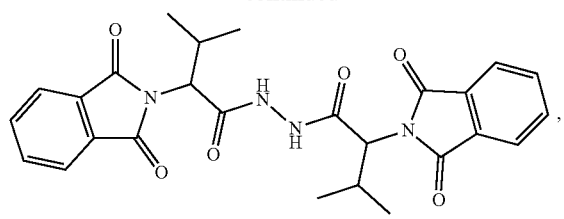
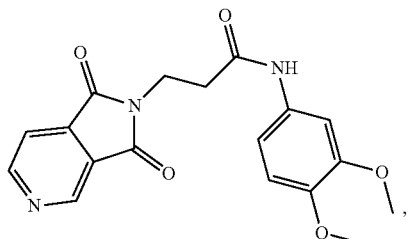
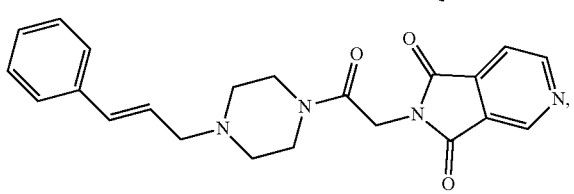
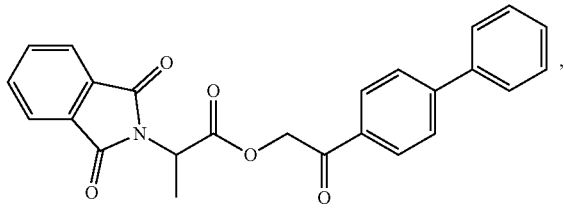
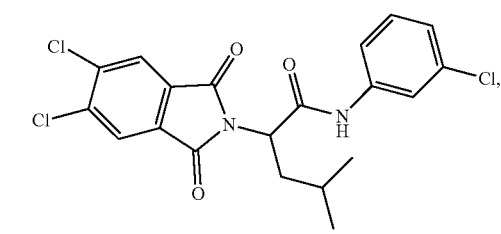
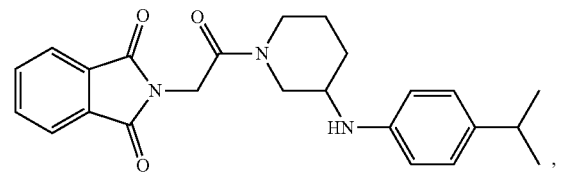
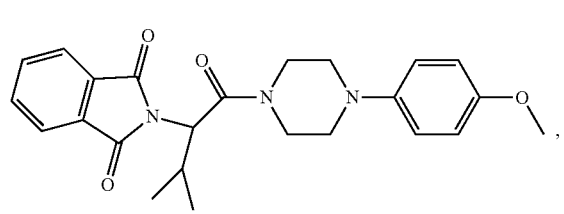
170
-continued
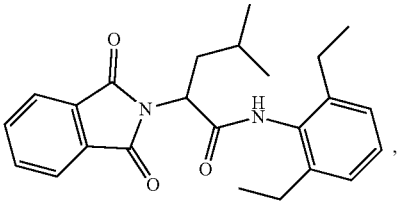
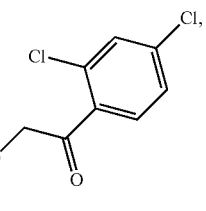
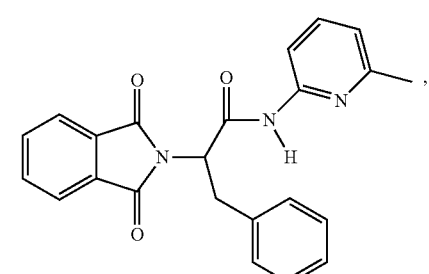
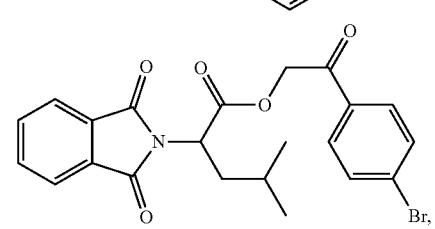
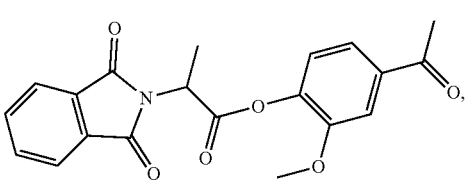
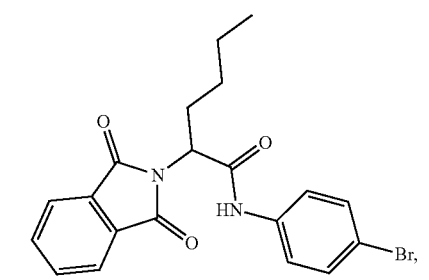
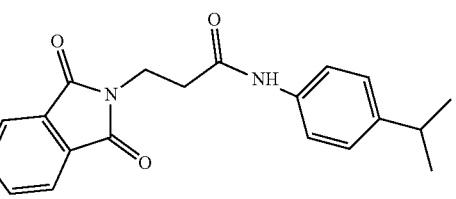

171
-continued

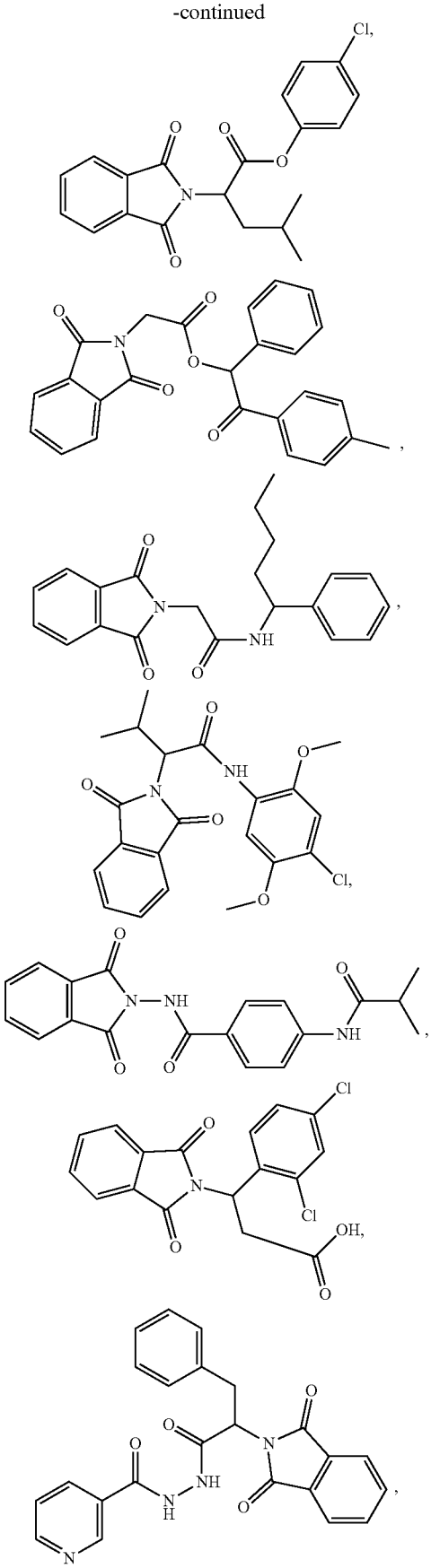

172
-continued

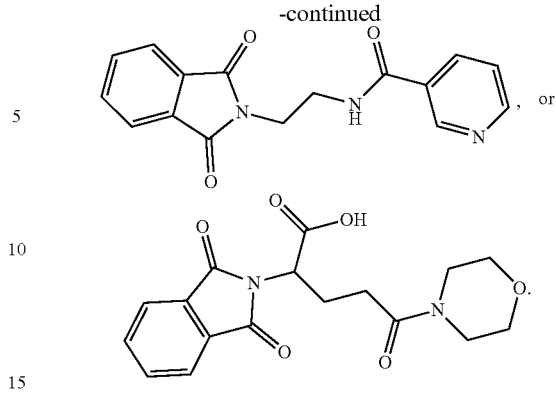

Embodiment 63. The method of one of embodiments 1 to 3, wherein the compound is

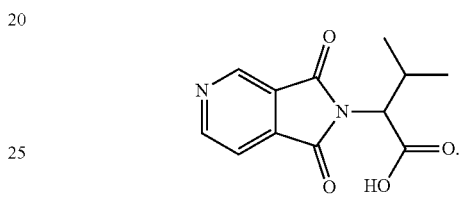

Embodiment 64. The method of one of embodiments 1 to 63, wherein the compound is capable of inhibiting TXNIP protein activity or function, said method comprising contacting the TXNIP protein with the compound.

Embodiment 65. The method of one of embodiments 1 to 63, wherein the compound is capable of inhibiting TXNIP protein binding to TRX, said method comprising contacting the TXNIP protein with the compound.

Embodiment 66. The method of one of embodiments 1 to 63, wherein the metabolic disorder is diabetes.

Embodiment 67. The method of embodiment 66, wherein the diabetes is T1D.

Embodiment 68. The method of embodiment 66, wherein the diabetes is T2D.

Embodiment 69. The method of embodiment 66, wherein the diabetes is associated with islet beta cell dysfunction.

Embodiment 70. The method of one of embodiments 1 to 63, wherein the cardiovascular disease is atherosclerosis.

Embodiment 71. The method of one of embodiments 1 to 63, wherein the metabolic disorder is a diabetes associated disease selected from nephropathy, retinopathy, neuropathy, cardiovascular disease, and inflammation.

Embodiment 72. The method of one of embodiments 1 to 63, wherein the method does not increase the risk for an infectious disease.

Embodiment 73. A pharmaceutical composition comprising a compound, or pharmaceutically acceptable salt thereof, and a pharmaceutically acceptable excipient, wherein the compound has the formula:

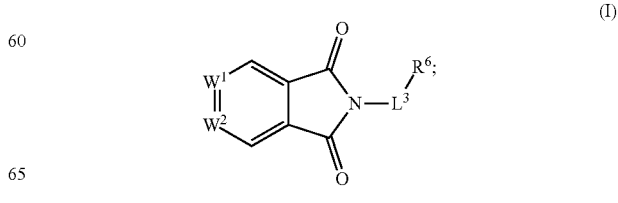

(I)

wherein
W$^1$ is —CR$^1$=, —N=, or —CH=;
W$^2$ is —CR$^2$=, —N=, or —CH=;
R$^1$ is independently halogen, —CX$^1_3$, —CHX$^1_2$, —CH$_2$X$^1$, —OCX$^1_3$, —OCH$_2$X$^1$, —OCHX$^1_2$, substituted or unsubstituted alkyl, or substituted or unsubstituted heteroalkyl;
R$^2$ is independently halogen, —CX$^2_3$, —CHX$^2_2$, —CH$_2$X$^2$, —OCX$^2_3$, —OCH$_2$X$^2$, —OCHX$^2_2$, substituted or unsubstituted alkyl, or substituted or unsubstituted heteroalkyl;
L$^3$ is a bond, —N(R$^3$)—, —C(O)—, —C(O)N(R$^3$)—, —N(R$^3$)C(O)—, —N(H)—, —C(O)N(H)—, —N(H)C(O)—, —C(O)O—, substituted or unsubstituted alkylene, or substituted or unsubstituted heteroalkylene;
R$^3$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;
R$^6$ is independently hydrogen, halogen, —CX$^6_3$, —CHX$^6_2$, —CH$_2$X$^6$, —OCX$^6_3$, —OCH$_2$X$^6$, —OCHX$^6_2$, —CN, —SR$^{6D}$, —SOR$^{6D}$, —SO$_2$R$^{6D}$, —SO$_3$R$^{6D}$, —SO$_4$R$^{6D}$, —SONR$^{6A}$R$^{6B}$, —SO$_2$NR$^{6A}$R$^{6B}$, —NR$^{6C}$C(O)NR$^{6A}$R$^{6B}$, —N(O), —N(O)$_2$, —NR$^{6A}$R$^{6B}$, —C(O)R$^{6C}$, —C(O)—OR$^{6C}$, —C(O)NR$^{6A}$R$^{6B}$, —OR$^{6D}$, —NR$^{6A}$SO$_2$R$^{6D}$, —NR$^{6A}$C(O)R$^{6C}$, —NR$^{6A}$C(O)OR$^{6C}$, —NR$^{6A}$OR$^{6C}$, —NR$^{6C}$NR$^{6A}$R$^{6B}$, —C(O)NR$^{6C}$NR$^{6A}$R$^{6B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
R$^{6A}$, R$^{6B}$, R$^{6C}$, and R$^{6D}$ are each independently hydrogen, oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; and
X$^1$, X$^2$, and X$^6$ are independently —F, —Cl, —Br, or —I.

EXAMPLES

Example 1: Inhibitors of TXNIP Action to Target Oxidant Stress, Inflammation, Diabetes, its Complications and Metabolic Memory The thioredoxin system, which includes thioredoxin (TRX), nicotinamide adenine dinucleotide phosphate (NADPH) and thioredoxin reductase (TXNRD1), is a major anti-oxidant system involved in the maintenance of cellular physiology and survival. Dysregulation in this system has been associated with metabolic and cardiovascular disorders. Thioredoxin-interacting protein (TXNIP) was first identified as an inhibitor of the redox regulator thioredoxin (TRX), an antioxidant. TXNIP functions as an inhibitor of TRX, and pathological suppression of TRX by TXNIP (which leads to oxidant stress) has been demonstrated in diabetes and cardiovascular diseases.

In cells, TXNIP expression is modulated by redox stress, glucose levels, hypoxia and inflammatory activators etc. and is highly sensitive to glucose. High glucose [HG] greatly increases TXNIP expression. TXNIP expression is greatly increased in pancreatic beta cells and is associated with beta cell dysfunction and diabetes development. Furthermore, increased TXNIP expression is associated with several diabetic complications, including diabetic retinopathy, diabetic nephropathy, diabetic neuropathy, and cardiovascular disease. Evidence shows that clinically used therapeutic agents for diabetes including insulin, metformin, angiotensin converting enzyme inhibitors and calcium channel blockers reduce TXNIP expression. Verapamil, a clinically used compound for hypertension was recently shown (Nature Med. 2018) to inhibit the expression of TXNIP and improve beta cell function in subjects with type 1 diabetes (Nat Med 2018). This provides strong evidence for the proof of concept that inhibition of TXNIP is clinically viable therapeutic strategy in treatment of T1D and T2D.

Recent studies from our laboratory (Zhen et al., PNAS 2016) have demonstrated a novel connection between epigenetic modification (DNA methylation) of TXNIP and Metabolic Memory, in which prior episodes of hyperglycemia can lead to the continued development of diabetic complications in certain diabetic patients despite subsequent glucose control: a major challenge in the clinical management of diabetes. Our data from that study, as well as our recent data from a much bigger cohort, shows TXNIP is highly induced by HG and inflammatory cytokines, and TXNIP molecule depicts the most significant changes in epigenetic DNA methylation in patients with metabolic memory of diabetic complications. Notably, we found that this alteration in TXNIP DNA methylation remained sustained in the same patient at two different time points 17 years apart (i.e. it depicts epigenetic memory). Furthermore, our data suggests that the known connections between HbA1c and diabetic complications can also be explained by epigenetic changes at TXNIP and other genomic loci.

A similar memory effect has also been documented in type 2 diabetes (T2D), referred as "legacy effect". Interestingly, studies from other groups have recently shown that a similar epigenetic modification of TXNIP (as that noted by us) is also seen in patients with type 2 diabetes, insulin resistance (obesity) and dyslipidemia.

Taken together the data from our lab show strong connections between TXNIP and its epigenetic modifications in inflammation, diabetic complications, metabolic memory and hyperglycemia. Data from others have also shown its pathological role in beta cell function, in both T1D and T2D. Thus our objective is to identify small molecules that can inactivate TXNIP functions by directly binding/interacting with it in a way that will disrupt its interaction with TRX. This approach is different from how some of the known compounds that target the expression of TXNIP. The TXNIP inhibitors available to date, target the expression of TXNIP. Such a strategy could cause side effects since TXNIP has multiple functionalities in the cell. The strategy described herein is to specifically downregulate TXNIP functions by targeting the TXNIP-TRX complex formation. The levels of the TXNIP-TRX complex are increased under certain diseases (e.g., diabetic conditions). Such a strategy could reduce the number of adverse side effects caused during treatment. We believe that given the importance of epigenetic modification of TXNIP, that targeting the interaction of TXNIP with TRX would be a more effective therapeutic strategy.

Computational Screening of small molecule TXNIP inhibitors: To find small molecule inhibitors of TXNIP we collaborated with the Computational Therapeutics Core (CTC). The TXNIP-TRX protein-protein complex is a challenging target because TXNIP interacts with TRX through a covalent disulfide bond that requires more energy to break. Therefore, the direct interacting interface of the TXNIP-TRX complex is difficult to be targeted for small molecules. There is no known small molecule binding site in TXNIP. This posed a challenge to identify and target an allosteric small molecule binding site to screen for candidate molecules. An innovative computational method and software called Allosteer to identify allosteric binding sites that are effective in allosteric inhibition (Bhattacharya 2014, 2016, Vaidehi 2016) was used. Using Allosteer we identified two putative binding sites as shown in FIG. 1A. We subsequently used a virtual ligand screening protocol d to screen 263,000 small molecules from four small molecule databases in two putative binding sites predicted using Allosteer. The virtual screening of 263,000 compounds, generated a list of 40 compounds, which was then trimmed to 26 for further experimental testing.

Experimental testing of small molecules: We developed three different bench based assays to perform rigorous and reproducible tests for the predicted hit molecules. These assays include testing direct binding to TXNIP as well as functional assays including under diabetic high glucose conditions. The assays are: (1) drug affinity responsive target stability test that tests the direct binding of the compounds. In this assay, when a compound binds to its target molecule, it can reduce the rate of its proteolytic digestion. (2) This assay looks for compounds that can interfere with the interaction between TXNIP and TRX in THP-1 monocytes treated with high glucose. TXNIP is already highly expressed because the cells are treated with high glucose, and therefore would have high concentration of TXNIP/TRX complexes in the cell extract Co-immunoprecipitation was done in these extracts through adding TRX antibody and the test compounds. If a compound can break the pre-formed TXNIP/TRX complex, there will be a reduced signal (band intensity) in the assay. (3) The third assay is designed to test the effects of compounds on high glucose-induced effects in target cells.

Testing of 26 compounds were performed rigorously using the experimental assays described above have led to the initial identification of a putative lead small molecule inhibitor of TXNIP, namely Compound C1, which can inhibit high glucose-induced TXNIP-TRX co-immunoprecipitation in cell extracts, in vivo in cells, can bind to TXNIP and prevent its proteolysis, and also attenuate high glucose induced expression of inflammatory cytokine molecules and TXNIP in monocytes.

Figure 2A:
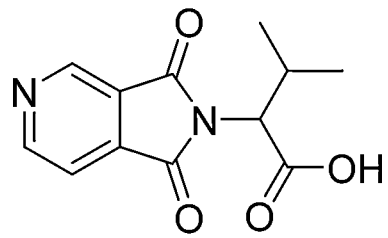
FIGS. 2A-2D.
Figure 2B:
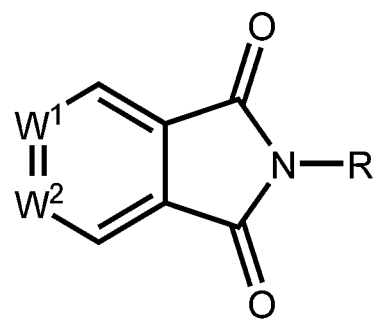
Figure 2C:
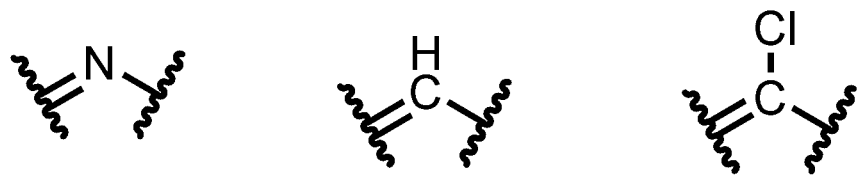
Figure 2D:
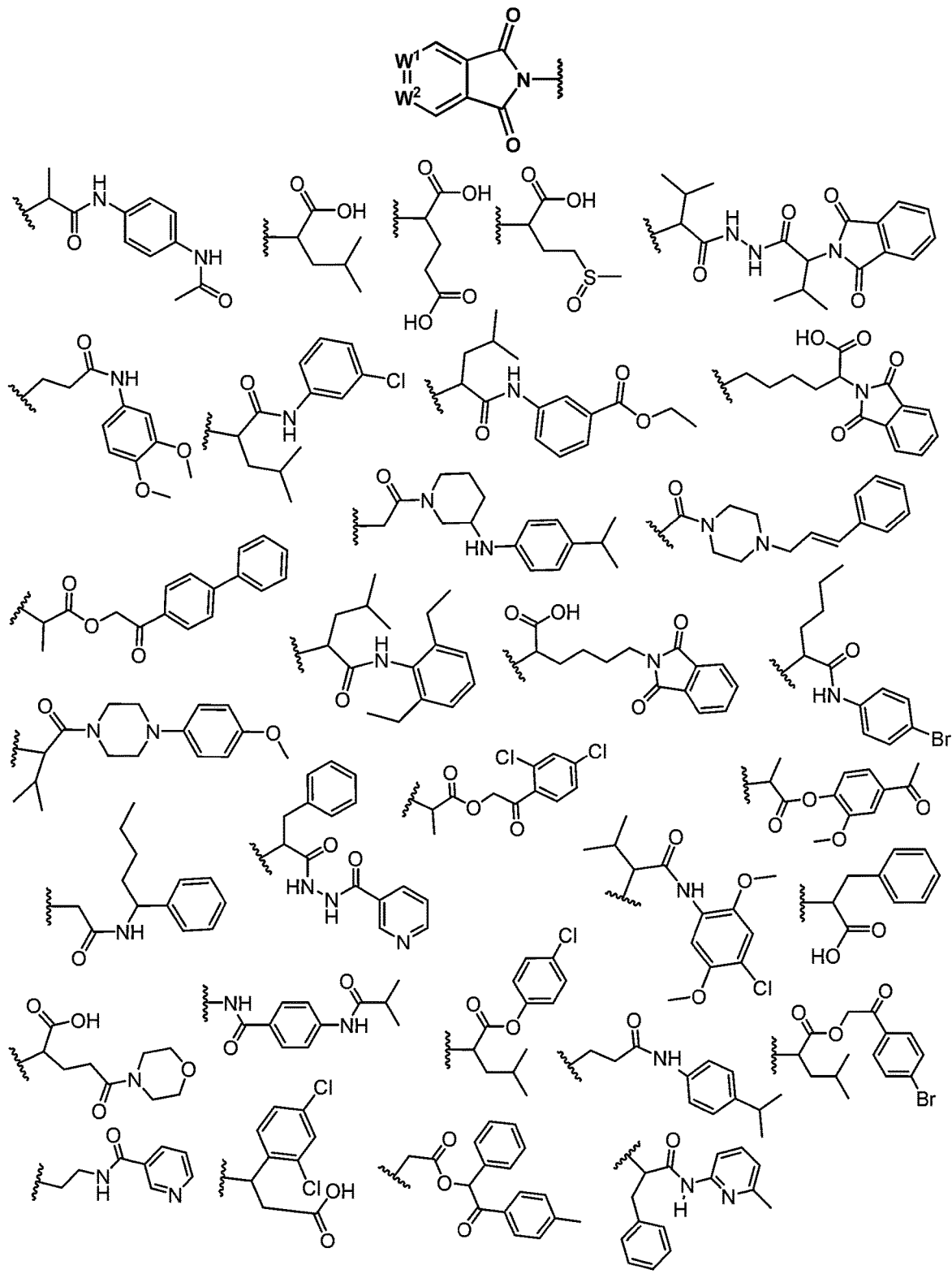

The compound C1 (shown in FIG. 2A) works at micromolar concentrations. To find C1 analogs that work at nM concentrations, evaluation of analogs of C1 (FIG. 2B) that are predicted to have better affinity than C1 is in progress.

Compound C1 and analogs with substitutions at various positions in the primary template (e.g., shown in FIGS. 2A-2D) with similar or better affinity are being developed as effective drug candidates for a) preventing complications of diabetes (nephropathy, retinopathy, neuropathy, cardiovascular, inflammation; b) diabetes itself (reduce oxidative stress to protect against type 1 and type 2 diabetes caused by oxidant stress and inflammation induced islet beta cell dysfunction); and c) for patients depicting metabolic memory (blocking oxidant stress, may reduce the epigenetic modification of TXNIP).

Example 2. Computational Screening and Experimental Results

As indicated in Example 1, the data from our lab show strong connections between TXNIP and its epigenetic modifications in inflammation, diabetic complications, metabolic memory and hyperglycemia. Data from others have also shown its pathological role in beta cell function, in both T1D and T2D. Thus our objective is to identify small molecules that can inactivate TXNIP functions by directly binding/interacting with it in a way that will disrupt its interaction with TRX. This approach is different from how some of the known compounds that target the expression of TXNIP. We believe that given the importance of epigenetic modification of TXNIP, that targeting the interaction of TXNIP with TRX would be a more effective therapeutic strategy especially for complications and metabolic memory.

We therefore adopted a Computational modeling approach in collaboration with our Computational Therapeutics Core (CTC) to screen candidate molecules from large databases We then established a series of experimental assays to screen these candidates and identify lead compounds. 40 hits were initially identified and 26 of these evaluated by 3 different assays.

Computational Screening of small molecule TXNIP inhibitors: A virtual ligand screening protocol was developed in Computational Therapeutics Core at City of Hope, to screen 263,000 small molecules from four small molecule databases in two putative binding sites predicted using Allosteer. After the virtual screening of 263,000 compounds, the CTC gave us a list of 40 compounds, which was then trimmed to 26 for further experimental testing.

Experimental testing of small molecules: We developed three different bench based assays to perform rigorous and reproducible tests for the predicted hit molecules. These assays include testing direct binding to TXNIP as well as functional assays including under diabetic high glucose conditions. The assays are: (1) drug affinity responsive target stability test that tests the direct binding of the compounds. In this assay, when a compound binds to its target molecule, it can reduce the rate of its proteolytic digestion. (2) This assay looks for compounds that can interfere with the interaction between TXNIP and TRX in THP-1 monocytes treated with high glucose. TXNIP is already highly expressed because the cells are treated with high glucose, and therefore would have high concentration of TXNIP/TRX complexes in the cell extract. Co-immunopreciation is done in these extracts through adding TRX antibody and the test compounds. If a compound can break the pre-formed TXNIP/TRX complex, there will be a reduced signal (band intensity) in the assay. (3) The third assay is designed to test the effects of compounds on high glucose-induced effects in target cells.

Small molecules were screened generated using the computer modeling approach shown below (done by the core). The first batch 26 compounds (selected from 40 based on availability) have been tested using 3 different assays.

Figure 4A:
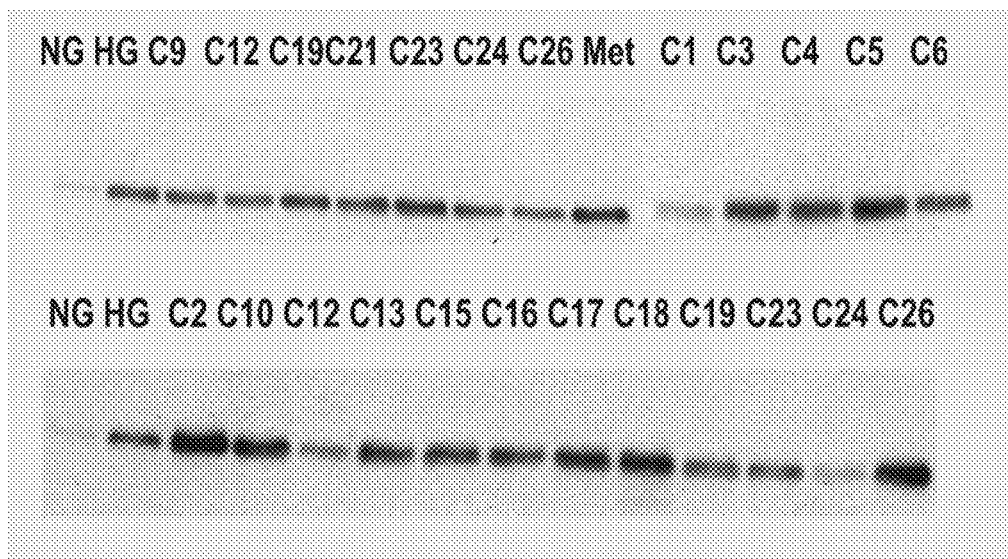
FIGS. 4A-4B. Co-IP with anti-TRX in THP 1 cells treated with compounds under high glucose condition. THP1 cells were treated by 10 uM compounds over night, then glucose was added up to 25 mM. The cells were cultured for 72-96 h. Cell extracts were prepared using cell extract buffer (Thermo Fisher Scientific) and Co-IP were performed with mouse anti-TRX (abcam).
Figure 4B:
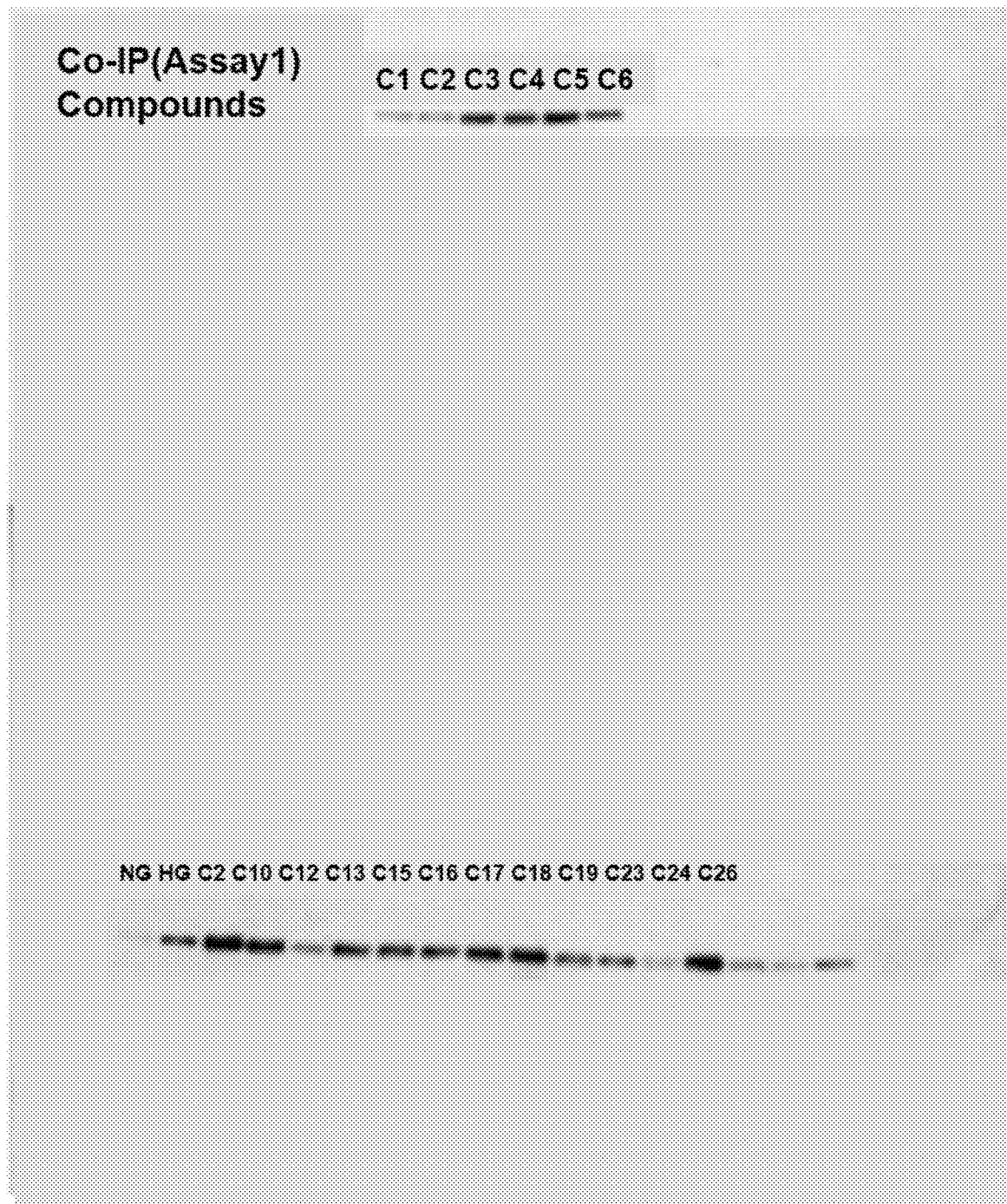
Figure 5:
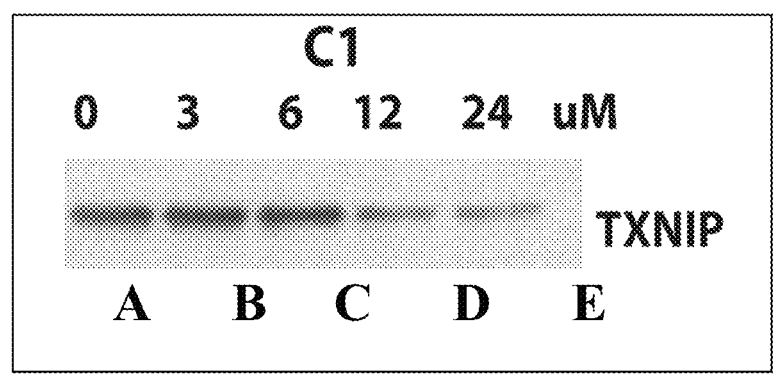
FIG. 5. Co-IP with anti-TRX in THP 1 cells treated with compound 1 under high glucose. A: HG no compound 1; B: HG, 3 uM compound 1; C: HG, 6 uM compound 1; D: HG, 12 uM compound 1; E: HG, 24 uM compound 1.

Assay 1: Co-immunoprecipitation (Co-IP) of TXNIP with TRX in THP 1 monocytes cells treated with compounds under high glucose condition. In this assay, we looked for compounds that can interfere with the interaction between TXNIP and TRX in THP-1 monocytes treated with HG. So here compounds are added to cells in culture. We found that in general, in this assay, the results are not very stable, and the false positive rate is high. However, the good part is that a positive control (metformin, a drug currently used to treat diabetes) works every time (ie it reduces the intensity of the band showing TXNIP-TRX binding in cells treated with HG). So we picked the candidates only if the results are repeatable. FIGS. 4A-4B shows representative results: As seen in FIGS. 4A-4B, we observed that compound 1 (C1) reproducibly shows a reduction in the HG-induced band.

Assay 2: Co-IP using extracts from THP 1 cells treated high glucose and in the presence of compounds. In this assay, TXNIP is already highly expressed (because the cells are treated with HG), we assume there is high concentration of TXNIP/TRX complexes in the cell extract. Co-IPs were done in these extracts through adding TRX antibody and compounds. If a compound is able to break the (pre-formed) TXNIP/TRX complex, there will be a reduced signal (band intensity) in the assay.

In this type of assay, we see C1 reproducibly can affect TXNIP/TRX complex. Moreover, in this assay, Metformin (widely used drug for diabetes) does not have any effect on TXNIP/TRX complex. This is because it is known that Metformin can reduce the expression of TXNIP through the AMPK pathway, and most likely not through interfering with the TXNIP/TRX complex.

Figure 6A:
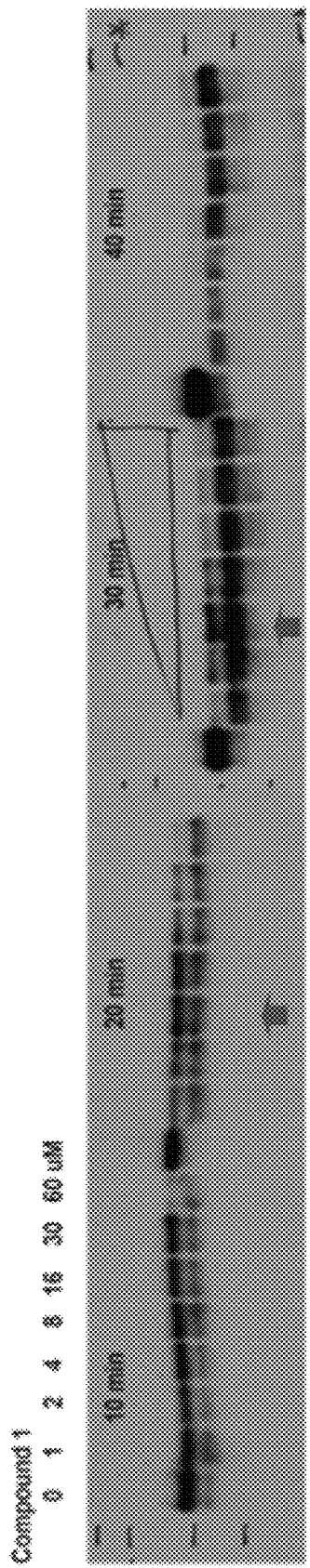
FIGS. 6A-6B. DARTS Assay results. See Example 2 for additional details.
Figure 6B:
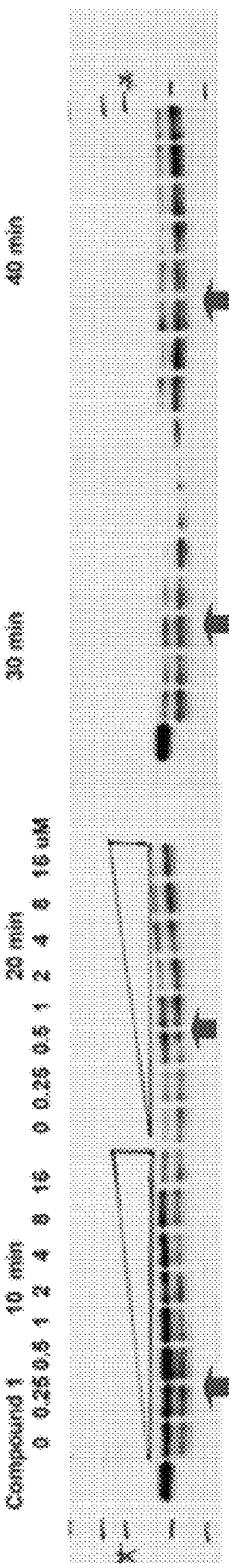
Figure 7:
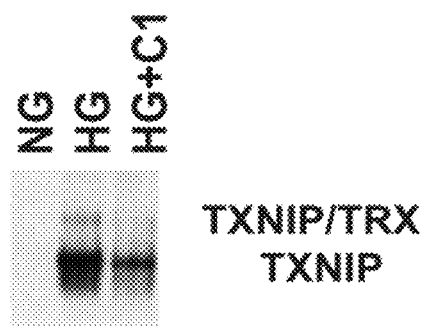
FIG. 7. C1 blocks High glucose (HG induced) TXNIP-TRX complex formation. We use nondenaturing gel to detect TXNIP-s-s-TRX complex. Under HG condition, we are able to detect the TXNIP-s-s-TRX complex Adding Compound 1 reduced the detected signal.
Figure 8:
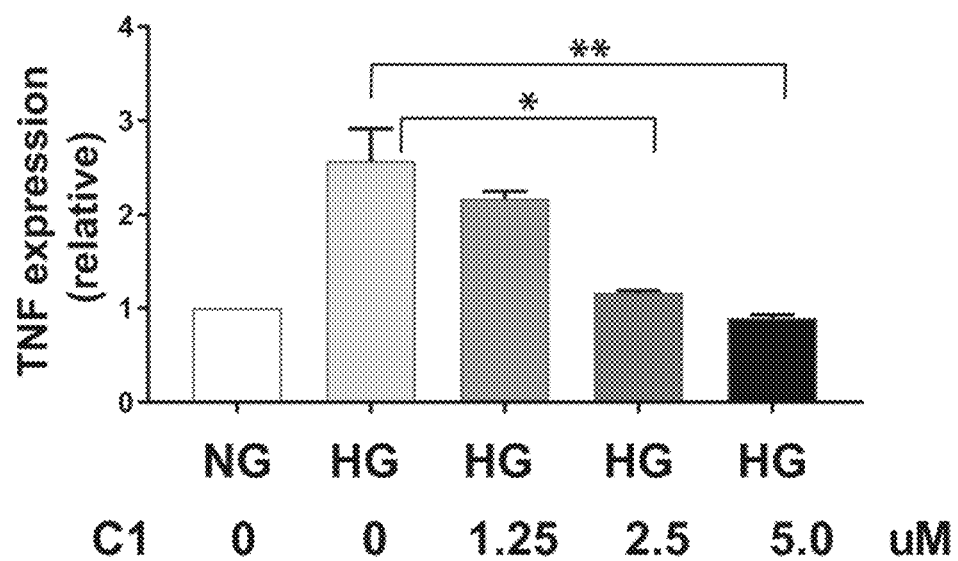
FIG. 8. Compound 1 reduces HG-induced expression of TNF (an inflammatory molecule) in monocytes. High glucose induced TNF expression in THP1 cells. This HG induced TNF increase is alleviated by C1 in dose manner (1.25, 2.5 and 5 uM). Results shown are means±SE of triplet real-time PCRs. *:P=0.002 vs. HG only, by t tests; **:P=0.001 vs. HG only, by t tests.

Assay 3: DARTS Assay (drug affinity responsive target stability). We adopted the DARTS assay because it is a straightforward method to check if a compound interacts with TXNIP. In this assay, when a compound binds to its target molecule, it can reduce the rate of its proteolytic digestion. FIG. 6A shows that compound 1 (C1) is able to protect TXNIP from being proteolytically digested (20 min and 30 min panels, indicated by arrows) at the concentration of 2 to 8 uM range. Further experiments indicates that the protection can be seen with as low as 0.5 to 4 uM (FIG. 6B indicated by arrows).

Compound 1, ID 9264548 in ChemBridge EXP, appears promising as a TXNIP-TXR complex inhibitor. The compound has a molecular weight of 248 and its chemical name is 2-(1,3-dioxo-1,3-dihydro-2H-pyrrolo[3,4-c]pyridin-2-yl)-3-methylbutanoic acid.

Western blotting. Lysis buffer (25 mM Tris-HCl pH 7.5, 100 mM NaCl, 2.5 mM EDTA and EGTA, 20 mM NaF, 1 mM Na3VO4, 20 mM Na b-glycerophosphate, 10 mM Na pyrophosphate, 0.5% Triton X-100, 0.1% b-mercaptoethanol and protease inhibitor cocktail [Roche]) was used to lyse the cells after various treatments. SDS-PAGE-resolved proteins were transferred to nitrocellulose membrane. Antibodies used were rabbit anti-TXNIP (Cell Signaling) and mouse anti-TRX (abcam ab16965).

RNA extraction and quantitative RT-PCR. RNA was extracted using the Direct-zol™ RNA MiniPrep Plus (Zymo Research). Reverse transcription of RNA samples into cDNA was performed using GeneAmp RNA PCR Kit (Applied Biosystems), dNTP (from Roche Applied Science), Rnase inhibitor, MULV Reverse Transcriptase and Random hexamers reagent (all from Invitrogen). Diluted cDNA was quantified using real-time PCR performed with Power SYBR Green qPCR MasterMix (Applied Biosystem) and 7500 real-time PCR system (Applied Biosystems). The HPRT1 gene was used as an internal control.

Co-IP with compounds treated THP1 under high glucose condition. THP1 cells were treated with compounds (2.5 uM) overnight and glucose was add to 25 mM and culture for 3-5 days, then coIP were carried using co-IP protocol.

Co-IP with THP1 high glucose treated extract in the presence of the compounds. THP1 cells were treated with 25 mM glucose for 3 days, the cell extract were prepared. Them 300 ul extract were used for TP. Compounds were added to 5 uM Co-IP were followed according to the Co-IP protocol.

Co-IP Protocol

Harvest and Wash Cells

1. Transfer the cultured cells from the culture dish to a 15-mL conical tube. 2. Centrifuge at 500×g for 2 min at 4° C. and remove the supernatant. 3. Wash with ice-cold PBS and centrifuge at 500×g for 2 min at 4° C. Remove the supernatant. 4. Repeat Step 3 twice.

Cell Lysates Preparation

5. Resuspend the cell pellet in ice-cold cell lysis buffer (1 mL per 1×10$^7$ cells) and incubate on ice for 10 min. 6. Sonicate cells in ice bath three times for 5 second pulses each. 7. Centrifuge at 13,000×g at 4° C. for 10 min, and transfer the supernatant to a fresh tube. Store the tube on ice for further use, or for long storage at −80° C.

Pre-Wash the Magnetic Beads

8. Resuspend the magnetic beads by pipetting up and down for several times. 9. Transfer 20 μL of bead slurry to a fresh tube. Place the tube in a magnetic separation rack for seconds. Carefully remove the supernatant once the solution is clear. 10. Add 200 μL of cell lysis buffer (without protease inhibitor) to wash the magnetic bead pellet, pipette up and down for several seconds. Place the tube back in magnetic separation rack. Magnetize beads and remove the supernatant as dry as possible. 11. Repeat Step 10 twice.

Pre-Clear the Lysate (Optional)

Note: Pre-clearing the lysate is recommended to reduce the non-specific binding. However, if the protein is detected by western blotting, pre-clearing may not be necessary unless a contaminating protein is interfering with visualization of the protein of interest. 12. Add 200 L cell lysate to 20 μL of pre-washed magnetic beads. Note: The volume of cell lysate depends on the expression level of the protein of interest. A starting concentration between 250 μg/mL-1.0 mg/mL is recommended. 13. Incubate for 20 min at room temperature with gentle agitation. 14. Pellet beads out from the lysate by a magnetic separation rack, carefully collect the pre-cleared cell lysate, and discard the magnetic bead pellet.

Immunoprecipitation

15. Add relevant antibody to the pre-cleared cell lysate. Incubate for 30 min at room temperature or overnight at 4° C. with gentle agitation to form the immunocomplex. 16. Pre-wash the magnetic beads as described in Pre-wash the Magnetic Beads (Step 8 to Step 11). 17.

Transfer the lysate and antibody solution (immunocomplex) obtained in Step 15 to the tube containing the pre-washed magnetic bead pellet. 18. Incubate for 30 min at room temperature keeping gentle agitation. 19. Pellet beads using magnetic separation rack and discard the supernatant. 20. Wash pellet with 500 uL cell lysis buffer (without protease inhibitor). Magnetize beads and remove the supernatant as dry as possible. 21. Repeat Step 20 four times.

Elution

Note: There are three methods that can be used to elute the protein from the beads: SDS buffer elution, glycine buffer elution and urea buffer elution. Each of them have their own advantages. Here we describe an elution method based on SDS buffer, which is highly efficient. 22. Resuspend the pellet with 50 μL SDS buffer, pipette up and down for several times to mix the sample. 23. Boil the sample for 5 min. 24. Pellet beads using magnetic separation rack. Transfer the supernatant to a fresh tube for further analysis.

DARTS ASSAY. This assay was completed according to known methods in the art, namely: PNAS Dec. 22, 2009. 106 (51) 21984-21989; Methods Mol Biol. 2015; 1263: 287-298.

Example 3: Screening TXNIP-Targeting Small Molecules in Murine and Human Cells

Thioredoxin interacting protein (TXNIP) is a glucose-response protein and a major regulator of cellular redox signaling. It promotes oxidative stress in the pancreas and other organs, and is emerging as a key therapeutic target in diabetes and its complications and metabolic memory (Alhawiti et al., 2017; Chen et al., 2016; Chong et al., 2014; Shalev, 2014). Glucose induced overexpression of TXNIP results in increased interaction with its partner thioredoxin, an antioxidant. This reduces the activity of thioredoxin and raises oxidative stress leading to pancreatic beta cell death as well as dysfunction of several target organs (like kidneys, eyes, heart). Therefore, inhibiting TXNIP expression and its interaction with thioredoxin (TRX) is a promising therapeutic route towards protecting islet beta cells against diabetes-induced attrition and diabetic complications. We report novel small molecule inhibitors of TXNIP that reduce TXNIP and TNF-α expression in glucose-stimulated human monocytes and human pancreatic islet cells. Our evidence suggests these compounds disrupt the interaction between TXNIP and its partner thioredoxin by binding to TXNIP. The compounds were discovered through screening of small molecule databases. The compounds may have therapeutic potential in type I and type II diabetes.

Initial screening identified a leading TXNIP-targeting compound, referred to herein as C1. In support of the invention, data is presented that demonstrates the effects this compound upon TXNIP signaling in a range of cell types (inflammatory white cells and pancreatic beta cells) including THP1 cells (a human monocyte cell line), mouse RAW264.7 macrophage cells, MIN6 mouse pancreas beta cells and 1.1 B4 human pancreas beta cell line as well as primary human pancreatic islets. Each cell type was treated with the lead compound and changes in TXNIP, TNF-α (as a marker of cell activation) quantified and other assays performed. Results obtained in cell experiments will inform in vivo animal studies.

Figure 9A:
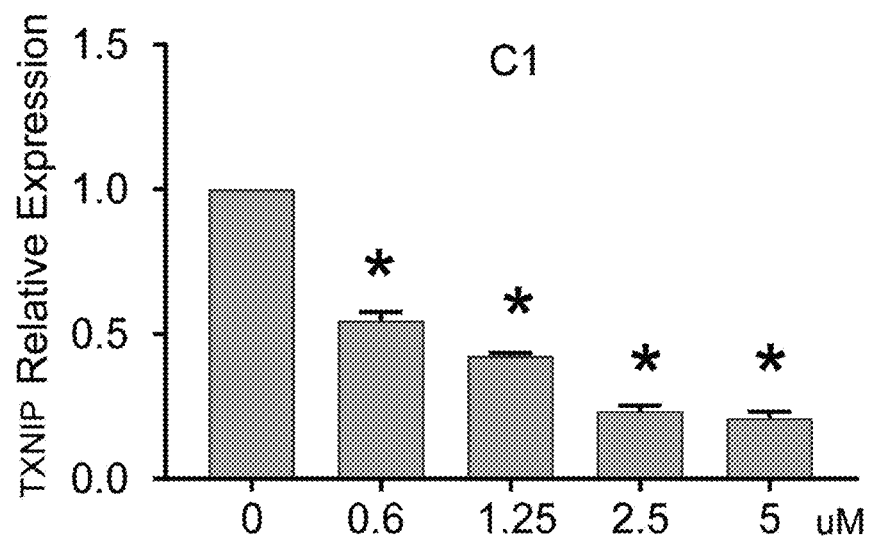
FIGS. 9A-9B.

C1 inhibited TXNIP mRNA expression in THP1 cells. FIG. 9A shows the effects of concentration ranges of C1 on TXNIP mRNA expression in THP1 human monocyte cell line. These results confirmed that C1 inhibit TXNIP expression in a dose-dependent manner.

Figure 9B:
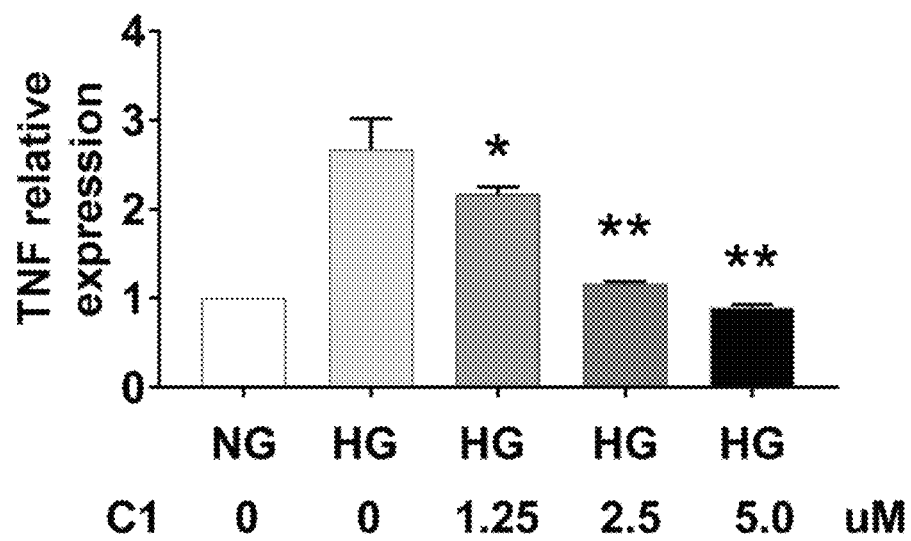

C1 treatment also reduced TNF-α expression in THP1 cells. FIG. 9B shows the effects of treatment with the lead compound C1 on mRNA levels of the proinflammatory cytokine TNF-α. Treatment with this agent lead to lower levels of TNF-α mRNA, although this required higher concentrations compared to those that suppressed TXNIP mRNA (FIG. 9A).

Figure 10A:
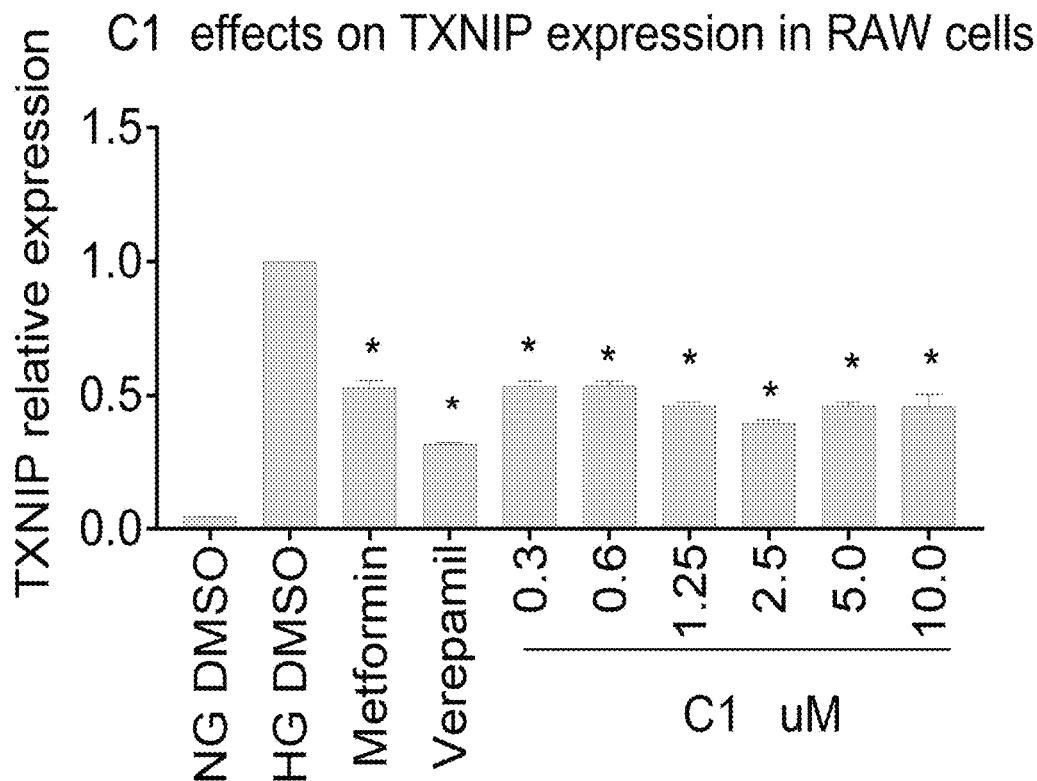
FIGS. 10A-10B.
Figure 10B:
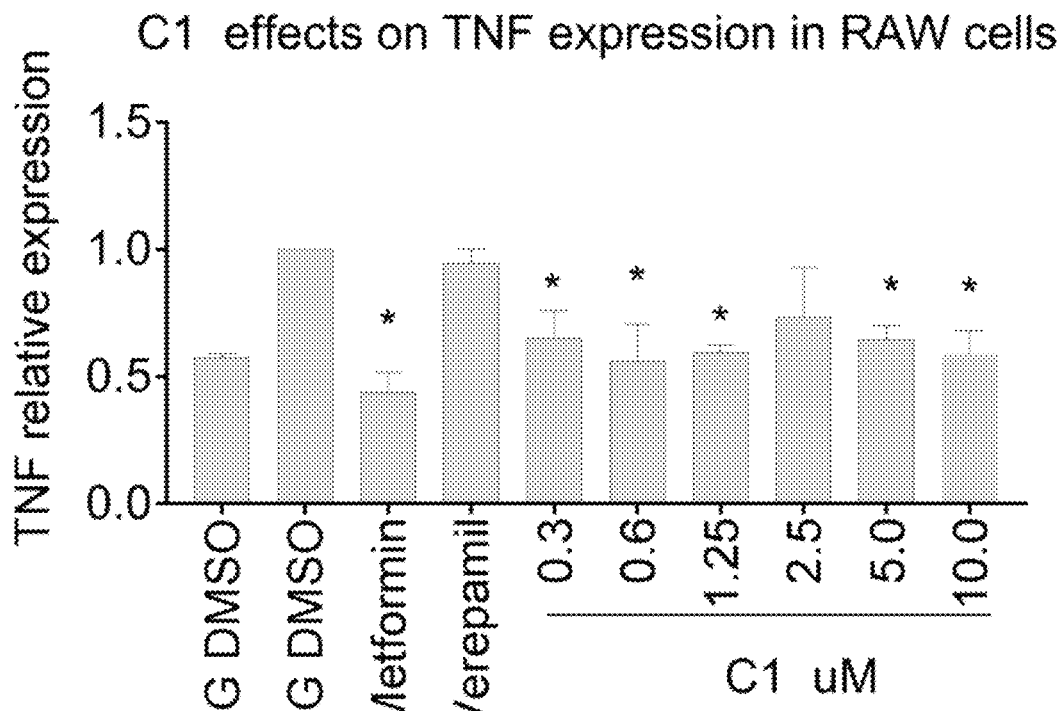

Treatment of murine RAW macrophages with C1 decreased TXNIP and TNF-α. It was not clear if C1 altered TXNIP and TNF-α mRNA levels in mouse cells other than THP1 cells. To test this, we have tested the effects of C1 in murine RAW macrophages. As in human THP1 cells, C1 inhibited TXNIP and TNF-α mRNA expression in mouse RAW cells (FIG. 10A and FIG. 10B). Thus, C1 alters mRNA levels in human and mouse inflammatory cells.

Figure 11:
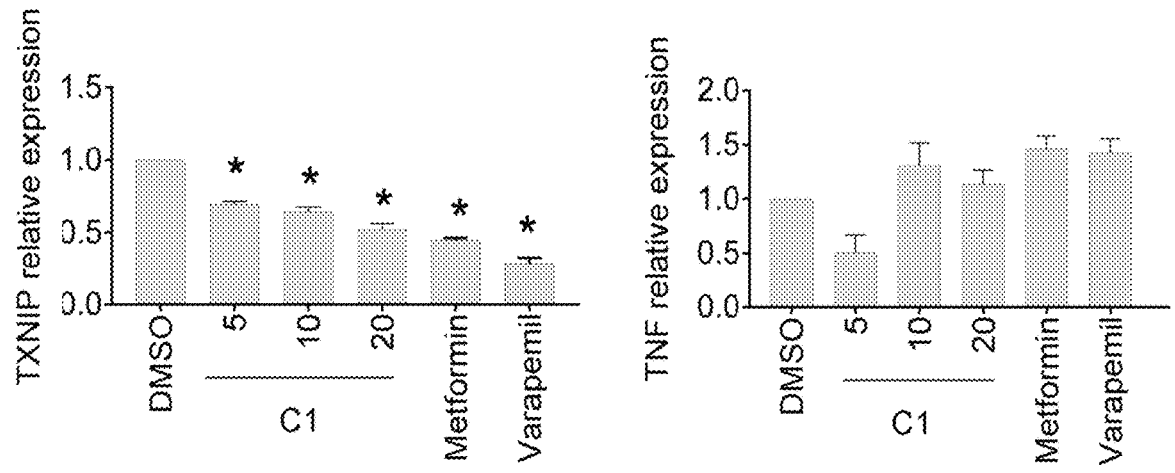
FIG. 11. Treatment of murine MIN6 cells with C1 decreased TXNIP but not TNF-α mRNA levels. MIN6 cells were cultured in 25 mM glucose with C1 at uM concentrations for 72 h. Total RNA was prepared. RT-PCR was performed. Data shown are the mean+SEM from triplicates. Statistical analysis was performed for each column vs. HG DMSO using one-way ANOVA: *<0.0001.

Treating murine MIN6 cells with C1 showed varying effects on key mRNA levels. To ascertain the relevance of these effects upon pancreatic beta cells, we tested C1 treatment on key target gene mRNA levels in murine MIN6 pancreatic beta cells. Interestingly, C1 decreased TXNIP (FIG. 11, left), but these murine MIN6 cells appeared to be less sensitive to C1. Also, C1 did not decrease TNF-α levels (FIG. 11, right panel). These data are important in looking at the effects of C1 upon a range of cells types. They may also be of use in our in vivo mouse studies.

Figure 12:
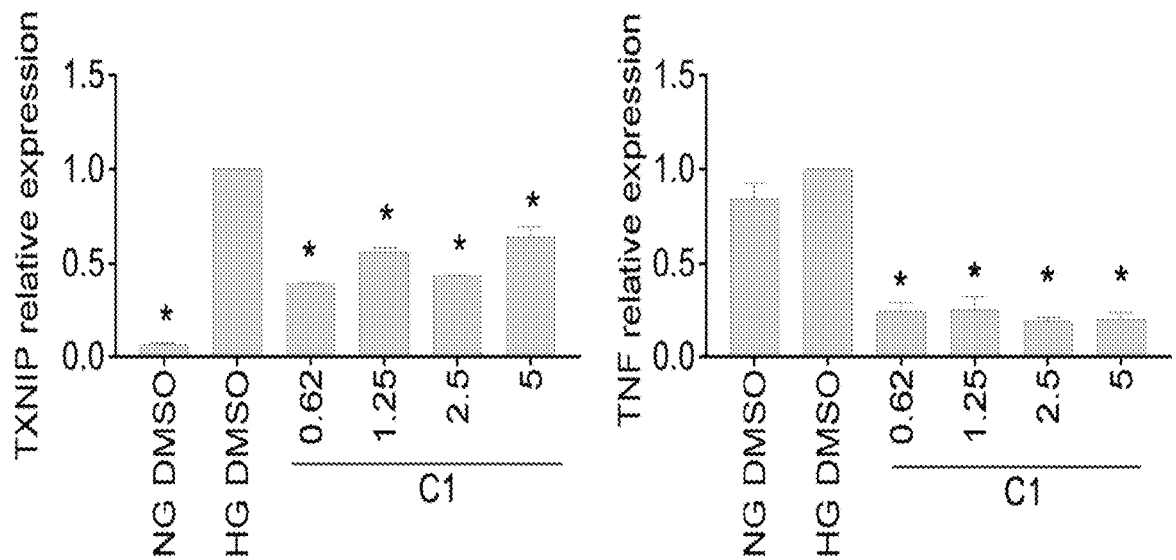
FIG. 12. C1 affects TXNIP and TNF-α mRNA expression in human pancreas 1.1B4 β cells. Human 1.1B4 β cells were cultured in 25 mM glucose with C1 (uM) for 72 h. Total RNA was prepared. RT-PCR was performed. Data shown are the mean+SEM from triplicates. Statistical analysis was performed for each column vs. HG DMSO using one-way ANOVA: *<0.0001.

Treating human 1.1 B4 β cells with the lead compounds decreased TXNIP and TNF-α mRNA levels. We tested the effects of C1 in the human 1.1 B4 pancreatic β cell line. The lead compound C1 strongly inhibited TXNIP mRNA expression (FIG. 12, left). Also, the compounds decreased TNF-α expression (FIG. 12, right). Overall, human 1.1B4 ρ cells were found to be sensitive to the lead compound. Together these data suggest that human cells are more sensitive to the effects of C1 compared to murine cells. This is relevant as C1 is being pursued for development for the clinic.

Figure 13:
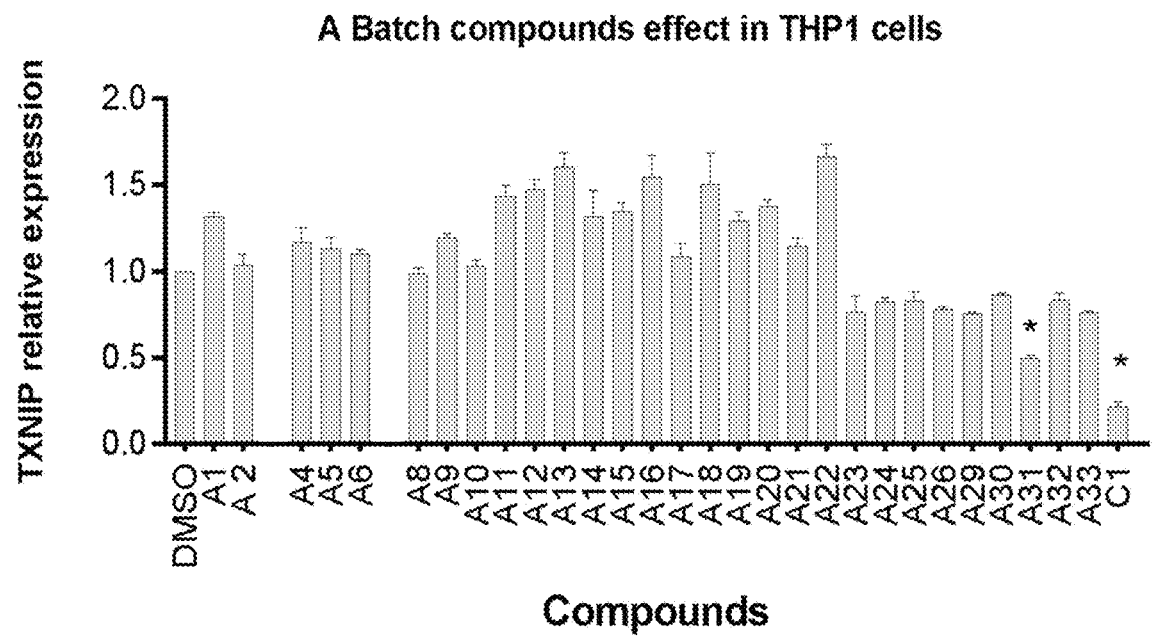
FIG. 13. C1 analogs affects TXNIP mRNA expression in THP1 cells. THP1 cells were cultured in 25 mM glucose with 5 uM of compounds for 72 h. Total RNA was collected and RT-PCR was performed in triplicate and data shown are the mean+SEM. Statistical analysis was performed using one-way ANOVA: *<0.0001.

Discovery of lead compound analogues. A search of chemical libraries was performed in the interest of identifying possible analogues of lead compound C1. Analogues to C1 were identified. They are named "A" batch compounds (Table 1). To determine the properties of these C1 analogues, we treated THP1 cells with "A" batch compounds (5 uM) for three days, prepared RNA and measured TXNIP mRNA levels. None of the A batch C1 analogues (except A31) displayed significant inhibitory effects on TXNIP mRNA expression in the assays employed (FIG. 13).

Figure 14:
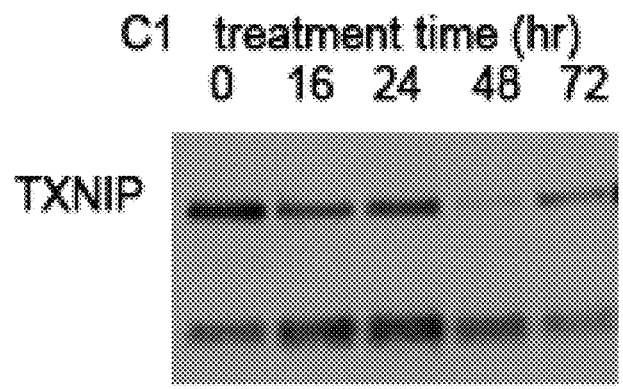
FIG. 14. Inhibition of TXNIP-TRX interaction by THP1 cells were cultured in 25 mM glucose with 5 uM C1 for 16-72 h. Aliquots were taken at indicated time points and nuclear cell extracts prepared. Standard co-IP was performed with mouse anti-TRX antibody overnight. Beads were washed with buffer and blots treated with rabbit anti-TXNIP antibody.

TXNIP interaction/binding with TRX is inhibited by C1. A primary goal of this research is to identify chemical compounds that block TXNIP interactions with the target thioredoxin (TRX). To confirm such activity in our lead compound, we employed the well-established technique of co-immunoprecipitation (co-IP). Our results indicated that basal TXNIP association/interaction with TRX (upper band, w. blot with TXNIP antibody) was significantly reduced at 48 h by treatment with C1 (FIG. 14).

Figure 15:
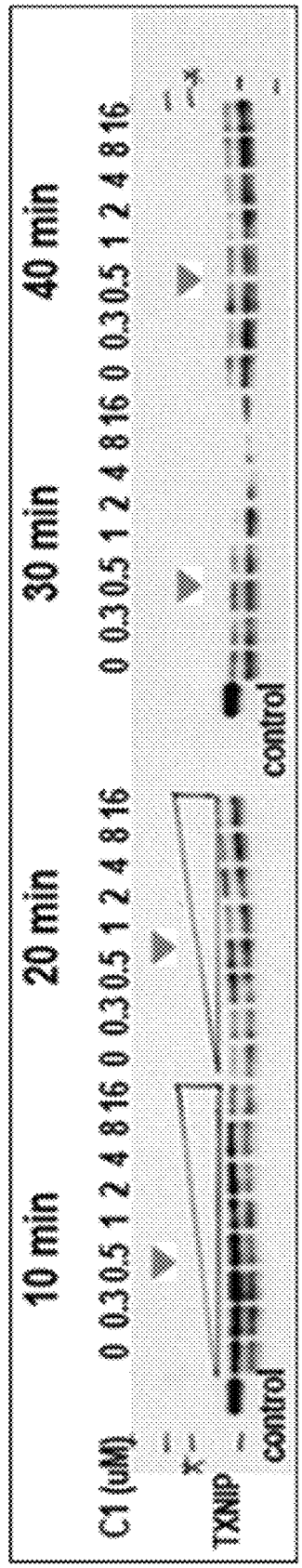
FIG. 15. C1 stabilizes TXNIP by binding to it in DARTS assay. THP1 cell were cultured in RPMI 1640 medium in 25 mM glucose for 72 hours. Cell extracts were prepared. C1 was added at the indicated concentrations and protease was added except in control cells. Aliquots were withdrawn at 10, 20, 30 and 40 minutes and loaded onto 10% SDS gels. C1: compound 1; control: without protease.

Treatment with C1 protects TXNIP from proteolysis. The drug affinity response target stability assay (DARTS assay) is a method to identify potential protein targets (binders) of small molecules. The advantage of this method is being able to use the native small molecule without having to immobilize or modify the protein (e.g., by incorporation of biotin, fluorescent molecules, radioisotope, or photo-affinity labels). In this case, it relies on the protection against proteolysis conferred on TXNIP by interaction with a small molecule (lead compound). FIG. 15 shows that C1 protects TXNIP from proteolysis at 10 and 20 minutes (between 0.5 and 4 uM lanes).

Figure 16:
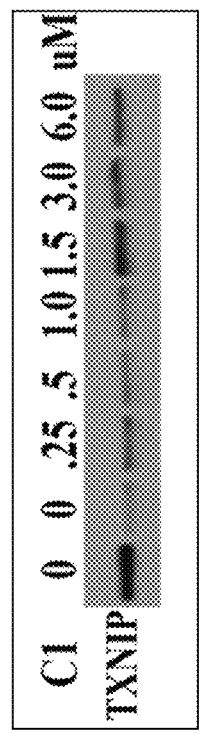
FIG. 16. C1 protects purified TXNIP from proteolysis in a DARTS assay. Purified TRX and TXNIP proteins and C1 (at the indicated concentrations) were mixed together. Protease was added. Aliquots were withdrawn at 7 minutes and loaded on 10% SDS gels. C1: compound 1; control: without protease.

To further confirm that C1 is able to protect TXNIP from proteolysis in the presence of TXNIP+TRX1, we performed DARTS assay using pure TXNIP protein (LSBio) and TRX1 protein (Sigma). The TRX1 protein we employed is also usually used for TRX1 activity assays. In contrast, the TXNIP protein is generated by E. coli and might not be in the active form. Therefore, we re-natured the protein prior to use in the DARTS assay. FIG. 16 demonstrates that C1 protects purified TXNIP from proteolysis.

Figure 17:
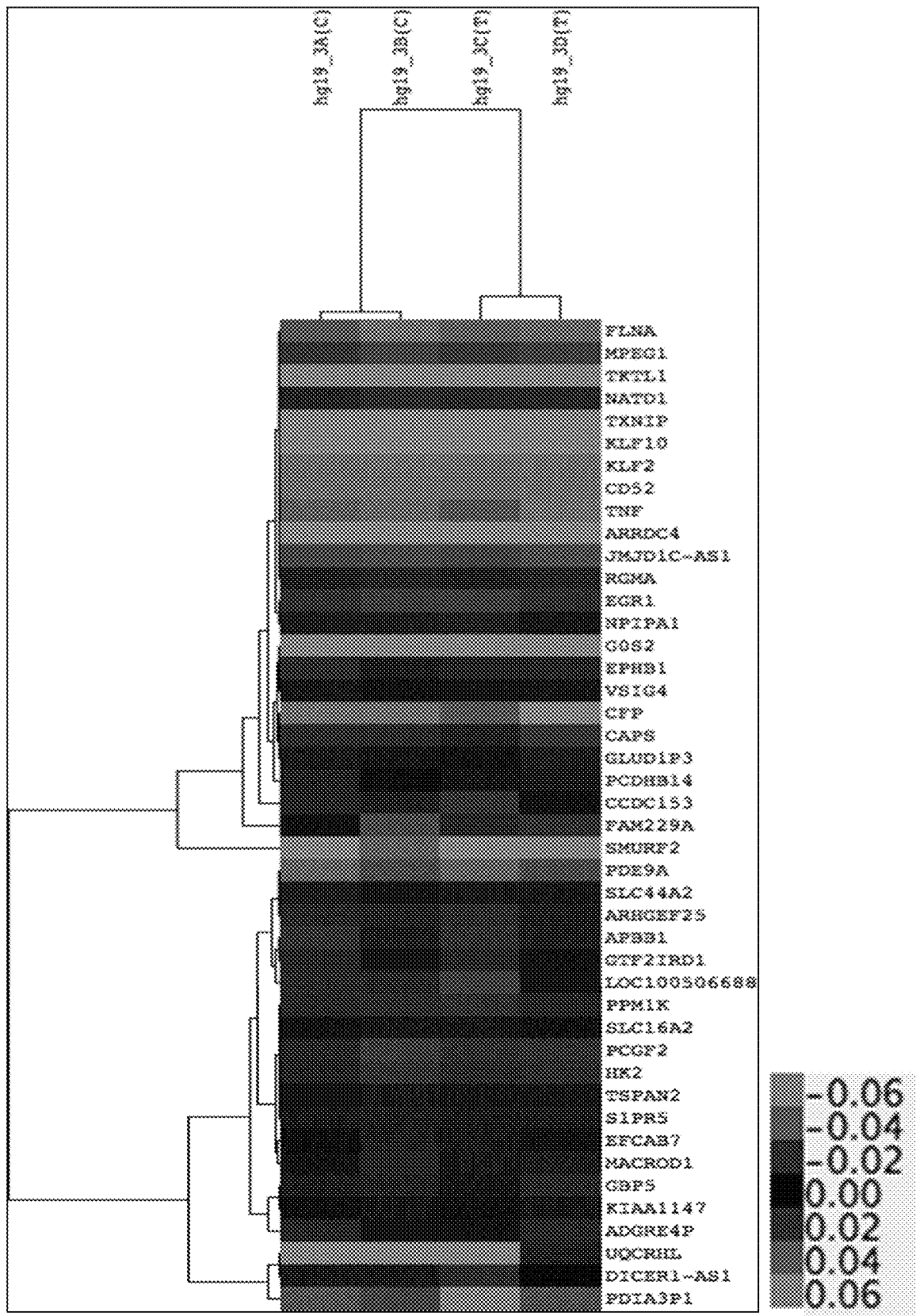
FIG. 17. Hierarchical Clustering using differential expressed genes. Differential expression was calculated using these counts with edgeR (5, 6) version 3.0. After correcting for differences in library sizes, a fold change of >1.5 and a p-value of <0.05 were applied to select expressed genes. The corrected measures of the latter were further processed using Cluster3.0 (7) to generate a heatmap using Java TreeView. C=HG treated THP-1 cells (A, B are replicates); T=HG+C1 5 uM (C, D are replicates). From top to bottom: FLNA, MPEG1, TKTL1, NATD1, TXNIP, KLF10, KLF2, CD52, TNF, ARRDC4, JMJ1C-AS1, RGMA, EGR1, NPIPA1, G0S2, EPHB1, VSIG4, CFP, CAPS, GLUD1P3, PCDHB14, CCDC153, FAM229A, SMURF2, PDE9A, SLC44A2, ARHGEF25, APBB1, GTF2IRD1, LOC100506688, PPM1K, SLC16A2, PCGF2, HK2, TSPAN2, S1PR5, EFCAB7, MACROD1, GBP5, KIAA1147, ADGRE4P, UQCRHL, DICER1-AS1, PDIA3P1.

Treatment with C1 alters expression of a limited number of genes including TXNIP and TNFα. THP1 Cells were treated with or without C1 under HG treated conditions, and gene differential analysis with RNA-seq was performed and identified 20 up- and 24 down-regulated genes (FIG. 17). We found that C1 treatment suppressed TXNIP and TNF-α, and that overall C1 alters the expression of only a limited number of genes. These data suggest that C1 may have less off-target effects with lower toxicity. This is supported by preliminary cell toxicity study in THP1 cells showing IC50 of 450 uM for C1.

Figure 18:
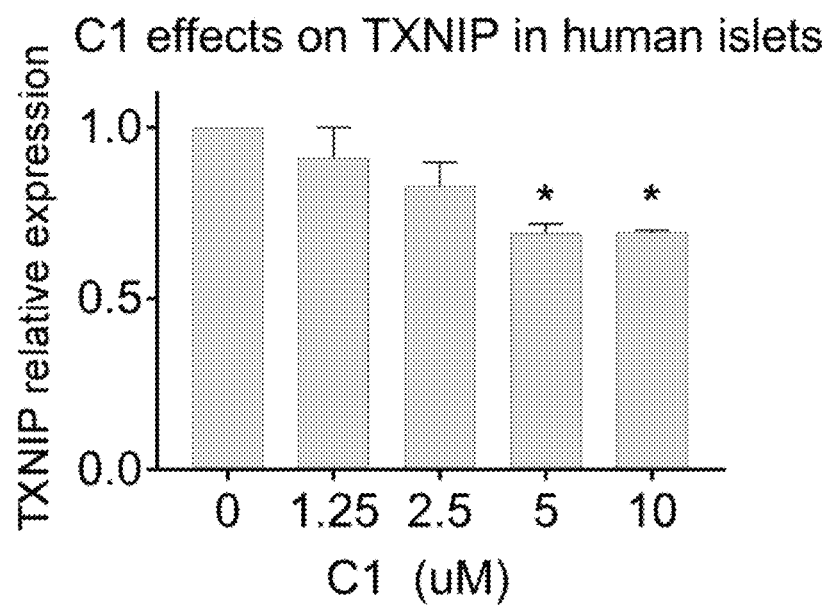
FIG. 18. C1 targets TXNIP mRNA in human pancreatic islets. Human pancreatic islets (500 IEQ) were cultured with PIM(R) (Prodo Labs) in 25 mM glucose with C1 as indicated for 48 h. Total RNA was collected. RT-PCR was performed in triplicate and data shown are the mean+SEM. Statistical analysis was performed using one-way ANOVA: *<0.0001.

Testing lead compounds in human pancreatic islets. To further explore the effects of C1 as a possible therapy in diabetes, we conducted initial translational studies in fresh primary human pancreatic islets. Results indicated C1 also efficiently inhibited TXNIP mRNA in isolated human islets (FIG. 18). Further studies will explore a dose effect of C1 upon these and other targets in human islets. We will also conduct studies to determine whether C1 can also improve islet functions.

TABLE 1

Structures of lead compounds and analogs.

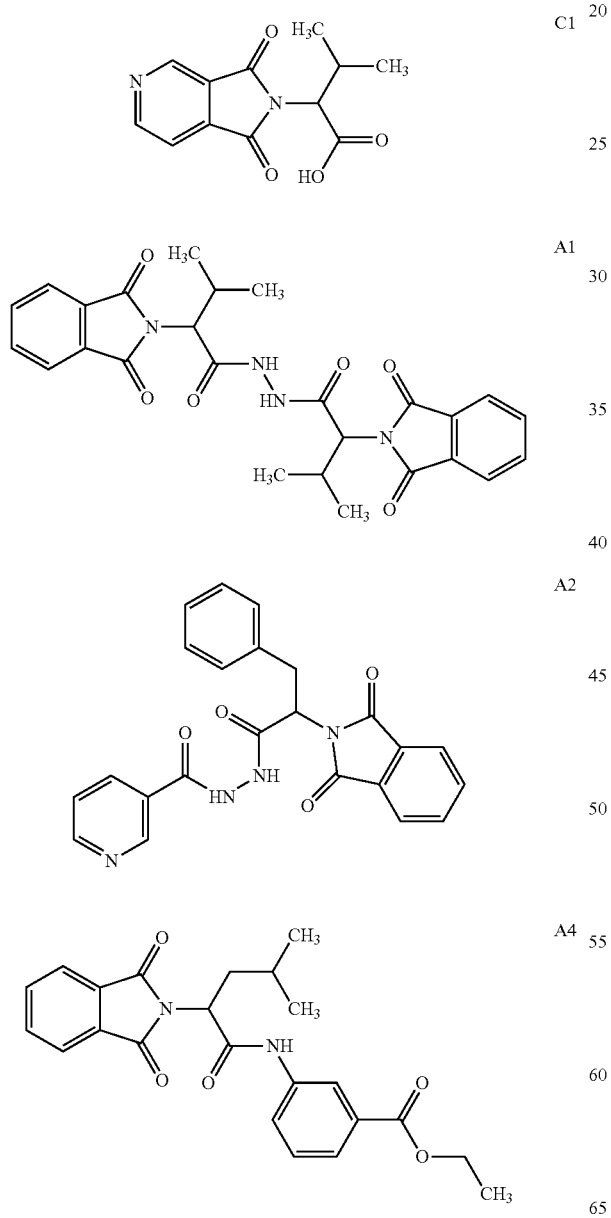

TABLE 1-continued

Structures of lead compounds and analogs.

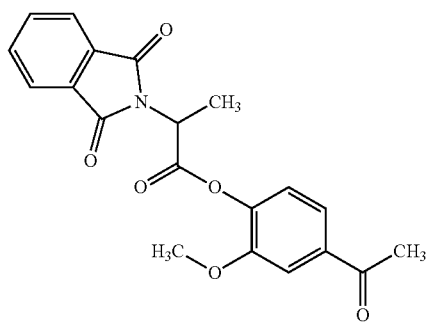 [SMILES: COc1cc(C(C)=O)ccc1OC(=O)C(C)N1C(=O)c2ccccc2C1=O]

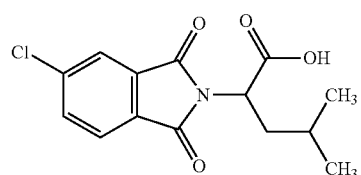

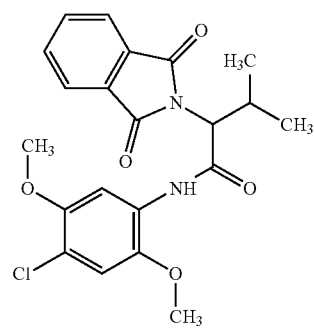 [SMILES: COc1cc(NC(=O)C(C(C)C)N2C(=O)c3ccccc3C2=O)c(OC)cc1Cl]

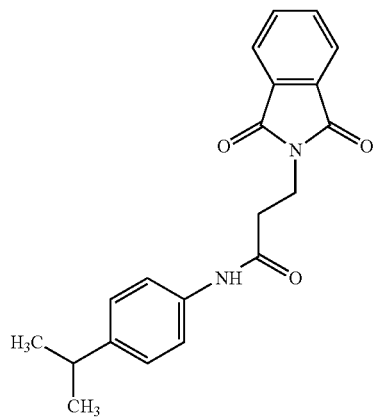 [SMILES: CC(C)c1ccc(NC(=O)CCN2C(=O)c3ccccc3C2=O)cc1]

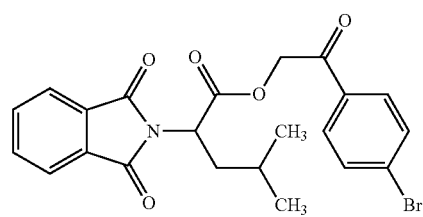 [SMILES: CC(C)CC(C(=O)OCC(=O)c1ccc(Br)cc1)N1C(=O)c2ccccc2C1=O]

TABLE 1-continued
Structures of lead compounds and analogs.
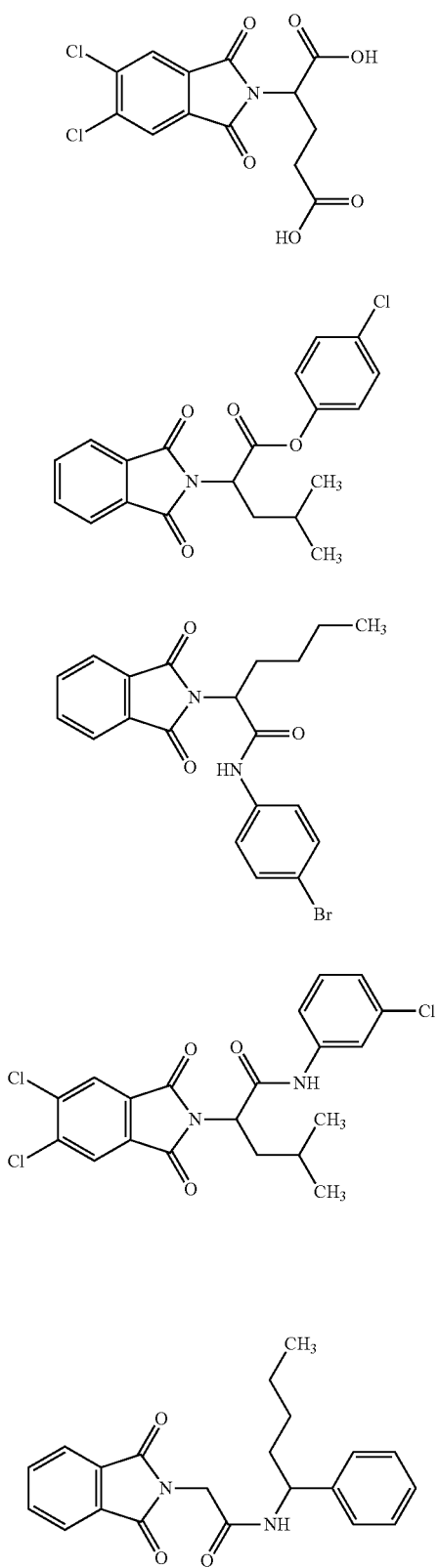
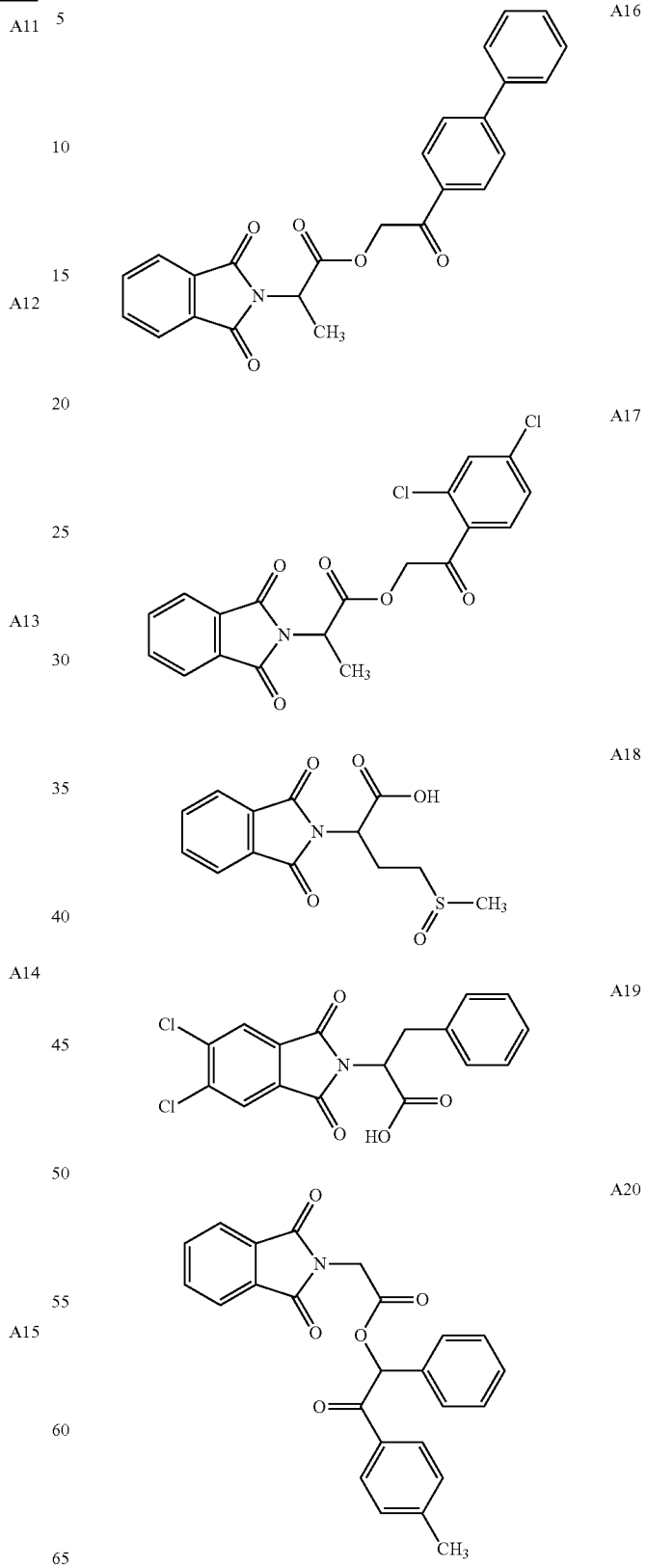

TABLE 1-continued
Structures of lead compounds and analogs.
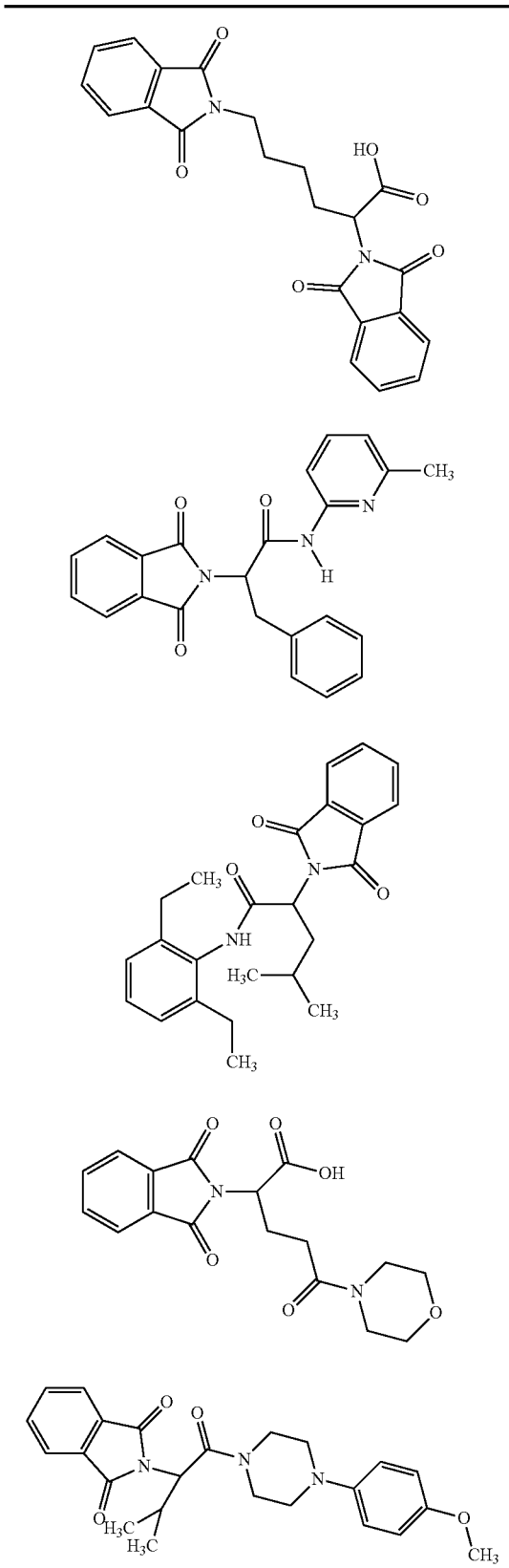
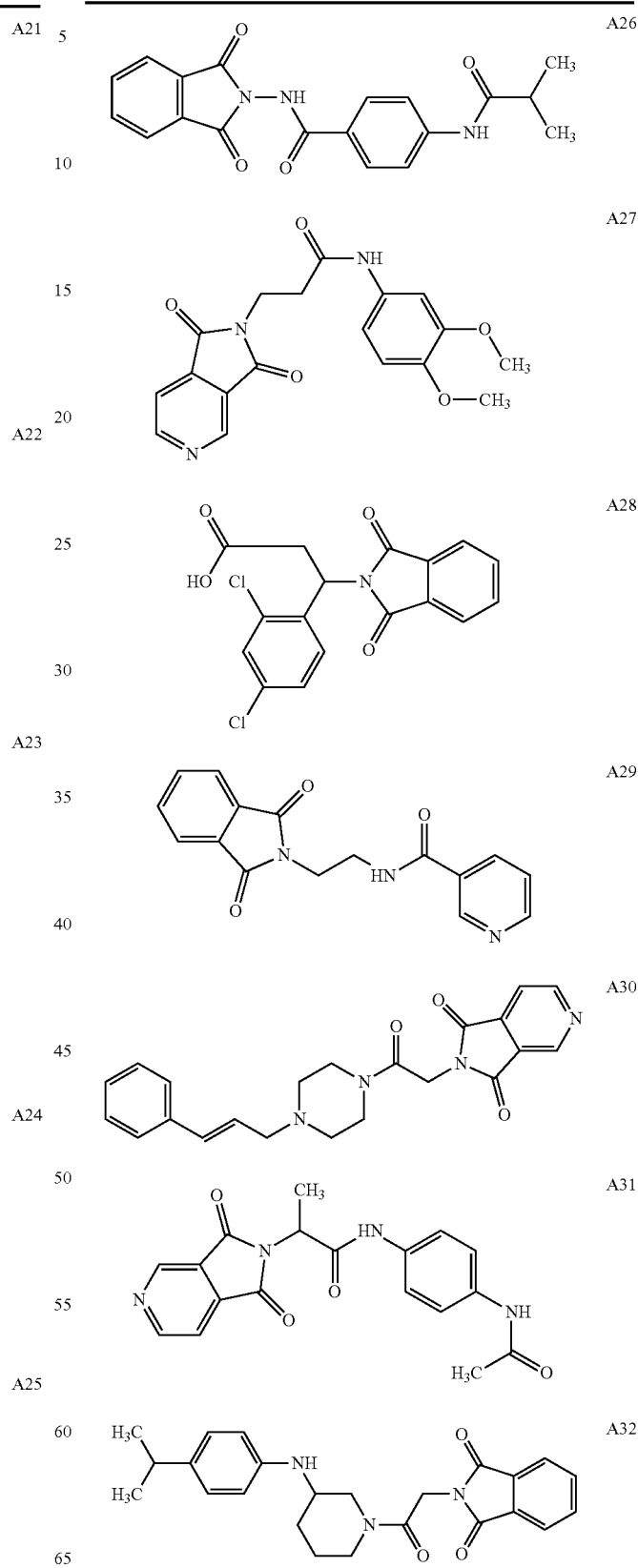

TABLE 1-continued

Structures of lead compounds and analogs.

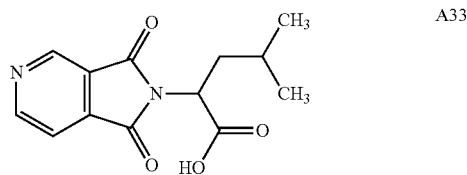

A33

Example 4: Materials and Methods

Computational protocol for identifying allosteric binding sites and small molecule inhibitors of TXNIP. Conventional high throughput virtual screening methods have shown some success in identifying small molecule binders for regular protein targets. However, these methods are inadequate for challenging targets such as TXNIP. TXNIP interacts with its partner TRX using covalent disulfide bonds, thereby making it impossible to target the protein-protein interface using small molecules. While it is possible to identify small molecules that disrupt the interaction between TXNIP and TRX by binding to a distant site in TXNIP (allosteric site), such a problem is extremely challenging due to (A) difficulty of discovering novel druggable sites over the entire protein surface, and (B) determining which of these sites will have the desired inhibitory effect on TRX interaction upon drug binding. We have addressed these challenges by developing a combination of computational in-silico methods and successfully applied them to TXNIP.

Our computational protocol for identifying small molecule inhibitors of TXNIP may be divided into three steps: A) Identification of druggable binding sites in TXNIP using the in-house program 'FindBindSite'; B) Selection of suitable binding site(s) from (A) for inhibitor screening using the in-house program 'Allosteer'; and C) Hierarchical screening of small molecule databases in the selected sites in TXNIP, enhanced by an in-house filtering algorithm based on fragment pharmacophores, and selection of the final hits.

Figure 3:
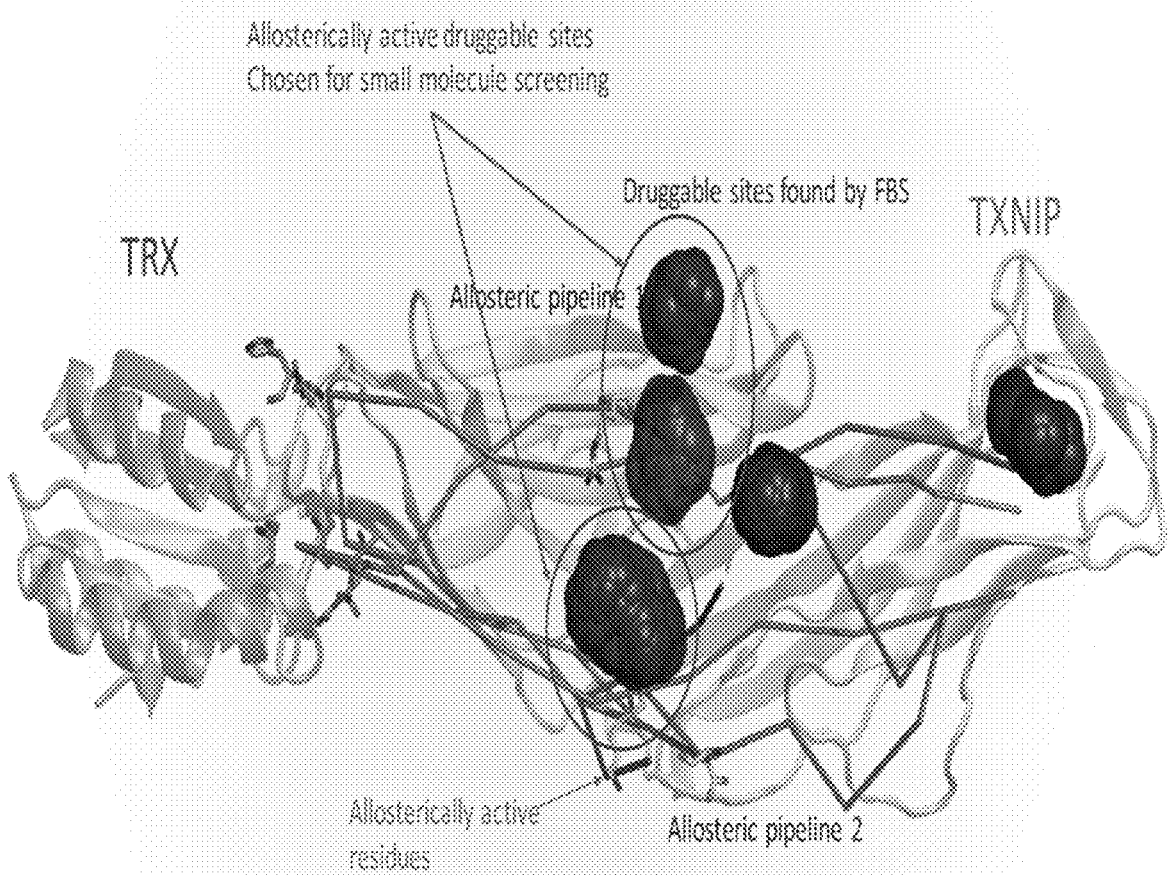
FIG. 3. Schematic TXNIP-TRX complex showing the predicted allosteric sites for small molecule design. The communication pipelines connecting the TRX site to the allosteric sites were calculated from multiple MD (molecular dynamics) simulations of TXNIP-TRX complex (computational).

FindBindSite (FBS) is a method and software developed for identifying small molecule binding sites in proteins (Li et al., 2014). FBS has been validated against multiple protein targets (Li et al., 2014). As part of the FBS procedure, we first docked a database of 10,000 chemically diverse druglike compounds to the entire protein surface of TXNIP. Then we clustered the docked compounds and analyzed the energetic and chemical properties of each cluster. The sites which docked the highest number of small molecules and showed the best overall binding energy scores were selected for further consideration. FIG. 3 shows the major druggable sites in TXNIP (clusters) as identified by FBS.

Our next challenge was to determine which of the binding sites have the desired inhibitory effect on TXNIP-TRX interaction. To this end, we calculated the allosteric communication between the druggable sites and the TRX interface using the in-house method Allosteer. The method Allosteer and the associated software were developed, and have been validated by applying to multiple protein targets including several GPCRs and the phosphotyrosine phosphatase PTPN5 (Bhattacharya et al., 2016; Bhattacharya and Vaidehi, 2014; Nivedha et al., 2018; Tautermann et al., 2019; Vaidehi and Bhattacharya, 2016). Using extensive molecular dynamics simulations starting from the crystal structure of the TXNIP-TRX complex (Hwang et al., 2014), we calculated the allosteric communication pipelines between the druggable sites and the TRX interface. Two of the sites that showed the strongest allosteric communication with the TRX interface were selected for drug design. Using Allosteer, we also identified the allosteric hotspots in each binding site (amino acid residues that play vital role in allosteric modulation of TRX binding), that would be critical in selecting the final hits. FIG. 3 shows the major allosteric pipelines as lines and the hotspot residues as sticks. The binding sites which were selected for drug design are circled.

Figure 19:
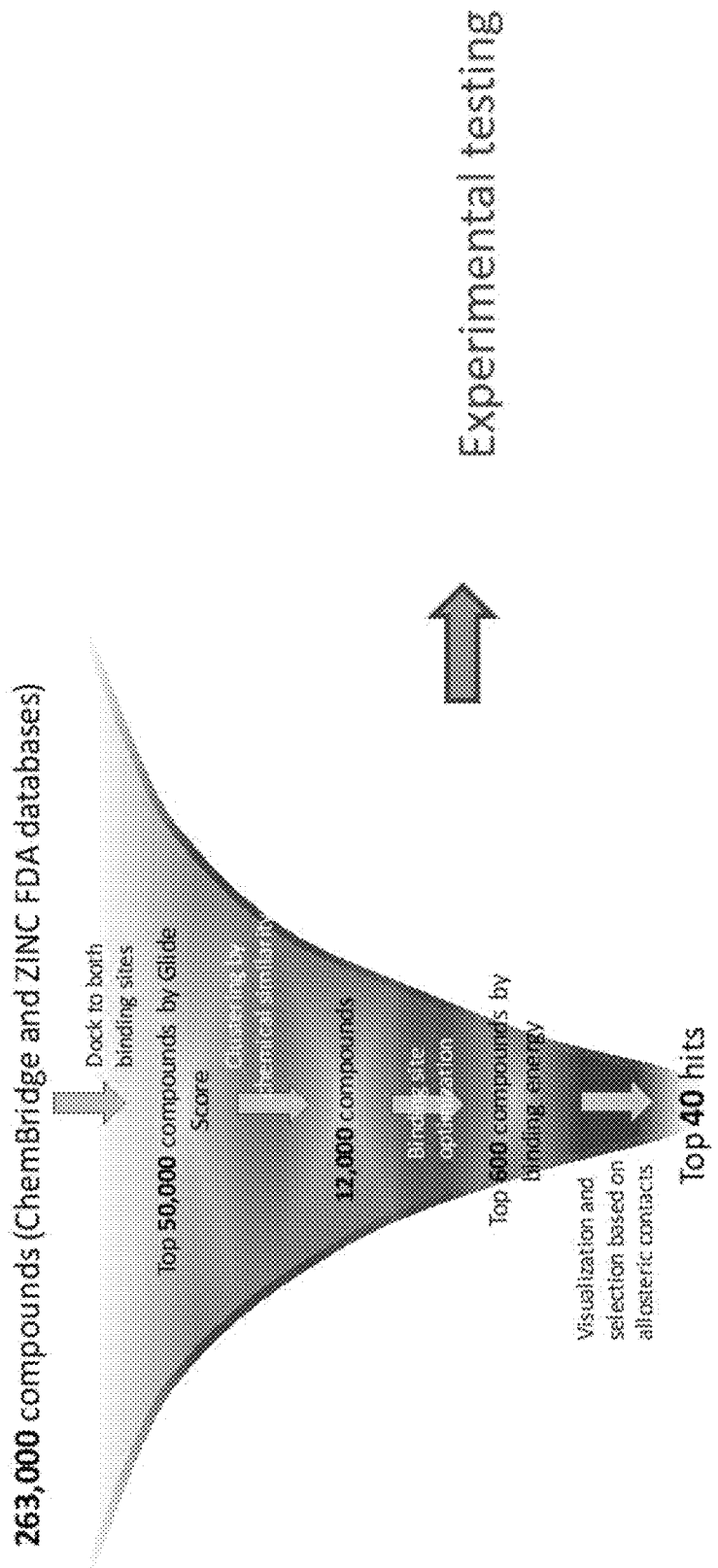
FIG. 19. Computational screening strategy.

For drug screening, we used over 250,000 compounds from two small molecule databases from the vendors ZINC and ChemBridge Inc. The screening of small molecules to TXNIP was performed in three phases using the Glide software from Schrodinger (Friesner et al., 2004; Halgren et al., 2004). In the first phase, the small molecules were docked to the two binding sites in TXNIP using the Glide Standard Precision method (Friesner et al., 2004; Halgren et al., 2004). The top 50,000 compounds from each site were selected by glide score and were clustered by chemical similarity. The top 12,000 chemically diverse compounds were retained from this step and were subjected to binding site optimization using Prime and MacroModel from the Maestro Suite (Schrodinger™) (Bell et al., 2012), followed by binding free energy calculation. The top 600 compounds by binding free energy were retained from each site. The final hits were selected based on low binding free energy, interaction with the allosteric hotspot residues, and manual visualization of bound poses. A schematic of the screening process is shown in FIG. 19. Experimental testing of the top 40 hits obtained from this phase generated one lead compound, C1 (Table 1).

Next, the chemical structure of C1 was used to search the ChemBridge online database for analogous compounds. During the search, the central aromatic moiety of C1, that makes major protein contacts, was retained and substituents around this moiety were varied in the analogs. In total, 689 analogs were obtained which were then processed using Ligprep in Maestro (Bell et al., 2012) and the probable protonation states of each compound were determined. Then, MacroModel was used to generate unique conformations of each compound (Bell et al., 2012). In total, 1637 conformations were generated for the 689 analogs. For the purpose of docking the C1 analogs, the TXNIP binding pocket was optimized in presence of the compound C1 by reassigning side-chains within 5 Å of the ligand, followed by minimization using PRIME/MMGBSA. The 1637 C1 analog conformations were then docked to the optimized TXNIP binding pocket and the resulting docked poses were optimized through combined side chain reassignment and minimization of the binding pockets using Prime/MMGBSA, followed by binding free energy calculation. Next, compounds that were chemically the most distant from C1 were discarded. Then, the compounds that scored more than 10 kcal/mol lower binding energy than that of C1 were further selected. These compounds were individually visualized and the ones where the docked pose was very different than that of C1 were rejected. Finally, the resulting 92 compounds were clustered based on chemical fingerprint and the top compound (by binding free energy) from each cluster was selected for testing. This phase resulted in 33 compounds (A1-A33, Table 1).

Western blotting. Cell extract buffer (Thermo Fisher Scientific) and protease inhibitor cocktail [Roche]) were used to lyse cells after various treatments. SDS-PAGE-resolved proteins were transferred to nitrocellulose membrane. Antibodies used were rabbit anti-TXNIP (Cell Signaling) and mouse anti-TRX (Abcam ab16965).

RNA extraction and quantitative RT-PCR. RNA was extracted using the Direct-zol™ RNA MiniPrep Plus (Zymo Research). Reverse transcription of RNA samples into cDNA was performed using the GeneAmp RNA PCR Kit (Applied Biosystems), dNTP (from Roche Applied Science), Rnase inhibitor, MULV Reverse Transcriptase and Random hexamers reagent (all from Invitrogen). Diluted cDNA was quantified using real-time PCR performed with Power SYBR Green qPCR MasterMix (Applied Biosystem) and 7500 real-time PCR system (Applied Biosystems). The HPRT1 gene was used as an internal control.

Co-immunoprecipitation. THP1 cells were treated with compounds (up to 10 uM) overnight and glucose was added to 25 mM and cells cultured at 37° C. for 3-5 days. Co-IP with mouse anti-TRX antibody was performed using standard co-IP protocols. Rabbit anti-TXNIP antibody (Cell Signaling) was used for Western blotting.

Drug affinity responsive target stability (DARTS) assay. DARTS assay was conducted according to a published protocol (Lomenick et al., 2009; Pai et al., 2015). THP1 cells were lysed with extract buffer. Lysates were incubated on ice for 10 minutes and then centrifuged at 18,000 g for 10 minutes at 4° C. and the pellet discarded. After mixing with various amounts of pronase (Roche), lysate-pronase mixtures were incubated at room temperature for 5-30 minutes, and SDS loading buffer added and the mixture heated at 950° C. for 2 minutes. 10 µg of protein lysate was applied to SDS-polyacrylamide gels for electrophoresis and Western blotting.

RNA-seq: Sequence alignment and gene counts. RNA-Seq reads were trimmed to remove sequencing adapters using Trimmomatic (Bolger et al., 2014), and polyA tails using FASTP (Chen et al., 2018). The processed reads were mapped to the human genome (hg19) using STAR software (v. 020201) (Dobin et al., 2013). The HTSeq software (v.0.6.0) (Anders and Huber, 2010) was applied to generate the count matrix, with default parameters.

Differential gene expression analyses by RNA-seq. THP1 cells were treated with High glucose (25 mM, 72 hr) with or without C1 addition, and then gene expression analysis was performed by RNA-sequencing. Differential expression analysis was conducted by adjusting read counts to normalized expression values using the TMM normalization method in edgeR package (Robinson et al., 2010). Prior to the alignment against the human genome (hg19) using STAR (Dobin et al., 2013), Trimmomatic (Bolger et al., 2014) was used to remove Illumina Sequencing adapters, while FASTP (Chen et al., 2018) was used to remove poly-A tails. Next, Raw counts for each gene in the GENCODE coding gene annotation (hg19) were measured using HTseq (Anders and Huber, 2010) with an argument of "-r pos -s reserve". Differential expression was calculated using these counts with edgeR (5, 6) version 3.0. After correcting for differences in library sizes, a fold change of >1.5 and a p-value of <0.05 were applied to select expressed genes. The corrected measures of the latter were further processed using Cluster3.0 to generate a heatmap using Java TreeView.

REFERENCES

Chen Z*, Miao F*, Paterson A D, Lachin J M, Zhang L, Riggs A D, Schones D E, Wu X, Wang J, Tompkins J D, Genuth S M, Braffett B, DCCT/EDIC Research group, Natarajan R. Epigenomic Profiling reveals an association between persistence of DNA methylation and metabolic memory in the DCCT/EDIC type 1 diabetes cohort. *Proc Natl Acad Sci USA*. 2016 May 24; 113(21):E3002-11. doi: 10.1073/pnas.1603712113. PMID: 27162351. Bhattacharya S., and Vaidehi N., 2014, Differences in allosteric communication pipelines in the inactive and active states of a GPCR, *Bio Phys. J.*, 107, 422-34. Recognized as New and Notable by the Biophysical Society. Bhattacharya S, Salomon-Ferrer R, Lee S, Vaidehi N. Conserved mechanism of conformational stability and dynamics in G-protein-coupled receptors. *J. Chemical Theory and Computation*. 2016 Oct. 17; 12(11):5575-84. Vaidehi N, Bhattacharya S. Allosteric communication pipelines in G-protein-coupled receptors. *Current Opinion in Pharmacology*. 2016 Oct. 1; 30:76-83. Anders, S., and Huber, W. (2010). Differential expression analysis for sequence count data. Genome biology 11, R106. Bell, J. A., Cao, Y., Gunn, J. R., Day, T., Gallicchio, E., Zhou, Z., Levy, R., and Farid, R. (2012). PrimeX and the Schrödinger computational chemistry suite of programs. In International Tables for Crystallography. Bhattacharya, S., Salomon-Ferrer, R., Lee, S., and Vaidehi, N. (2016). Conserved Mechanism of Conformational Stability and Dynamics in G-Protein-Coupled Receptors. J Chem Theory Comput 12, 5575-5584. Bhattacharya, S., and Vaidehi, N. (2014). Differences in Allosteric Communication Pipelines in the Inactive and Active States of a GPCR. Biophys J 107, 422-434. Bolger, A. M., Lohse, M., and Usadel, B. (2014). Trimmomatic: a flexible trimmer for Illumina sequence data. Bioinformatics 30, 2114-2120. Chen, S., Zhou, Y., Chen, Y., and Gu, J. (2018). fastp: an ultra-fast all-in-one FASTQ preprocessor. Bioinformatics 34, i884-i890. Dobin, A., Davis, C. A., Schlesinger, F., Drenkow, J., Zaleski, C., Jha, S., Batut, P., Chaisson, M., and Gingeras, T. R. (2013). STAR: ultrafast universal RNA-seq aligner. Bioinformatics 29, 15-21. Duan, J. X., Dixon, S. L., Lowrie, J. F., and Sherman, W. (2010). Analysis and comparison of 2D fingerprints: Insights into database screening performance using eight fingerprint methods. J Mol Graph Model 29, 157-170. Friesner, R. A., Banks, J. L., Murphy, R. B., Halgren, T. A., Klicic, J. J., Mainz, D. T., Repasky, M. P., Knoll, E. H., Shelley, M., Perry, J. K., et al. (2004). Glide: A new approach for rapid, accurate docking and scoring. 1. Method and assessment of docking accuracy. J Med Chem 47, 1739-1749. Halgren, T. A., Murphy, R. B., Friesner, R. A., Beard, H. S., Frye, L. L., Pollard, W. T., and Banks, J. L. (2004). Glide: A new approach for rapid, accurate docking and scoring. 2. Enrichment factors in database screening. J Med Chem 47, 1750-1759. Hwang, J., Suh, H. W., Jeon, Y. H., Hwang, E., Nguyen, L. T., Yeom, J., Lee, S. G., Lee, C., Kim, K. J., Kang, B. S., et al. (2014). The structural basis for the negative regulation of thioredoxin by thioredoxin-interacting protein. Nat Commun 5, 10-23. Li, H., Kasam, V., Tautermann, C. S., Seeliger, D., and Vaidehi, N. (2014). Computational Method To Identify Druggable Binding Sites That Target Protein-Protein Interactions. J Chem Inf Model 54, 1391-1400. Lomenick, B., Hao, R., Jonai, N., Chin, R. M., Aghajan, M., Warburton, S., Wang, J., Wu, R. P., Gomez, F., Loo, J. A., et al. (2009). Target identification using drug affinity responsive target stability (DARTS). Proceedings of the National Academy of Sciences of the United States of America 106, 21984-21989. Nivedha, A. K., Tautermann, C. S., Bhattacharya, S., Lee, S., Casarosa, P., Kollak, I., Kiechle, T., and Vaidehi, N. (2018). Identifying Functional Hotspot Residues for Biased Ligand Design in G-Protein-Coupled Receptors. Mol Pharmacol 93, 288-296. Pai, M. Y., Lomenick, B., Hwang, H., Schiestl, R., McBride, W., Loo, J. A., and Huang, J. (2015). Drug affinity responsive target stability (DARTS) for small-molecule target identification. Methods in molecular biology 1263, 287-298. Robinson, M. D., McCarthy, D. J., and Smyth, G. K. (2010). edgeR: a Bioconductor package for differential expression analysis of digital gene expression data. Bioinformatics 26, 139-140. Sastry, M., Lowrie, J. F., Dixon, S. L., and Sherman, W. (2010). Large-Scale Systematic Analysis of 2D Fingerprint Methods and Parameters to Improve Virtual Screening Enrichments. J Chem Inf Model 50, 771-784. Tautermann, C. S., Binder, F., Buttner, F. H., Eickmeier, C., Fiegen, D., Gross, U., Grundl, M. A., Heilker, R., Hobson, S., Hoerer, S., et al. (2019). Allosteric Activation of Striatal-Enriched Protein Tyrosine Phosphatase (STEP, PTPN5) by a Fragment-like Molecule. J Med Chem 62, 306-316. Vaidehi, N., and Bhattacharya, S. (2016). Allosteric communication pipelines in G-protein-coupled receptors. Curr Opin Pharmacol 30, 76-83. Waldhart, A. N., Dykstra, H., Peck, A. S., Boguslawski, E. A., Madaj, Z. B., Wen, J., Veldkamp, K., Hollowell, M., Zheng, B., Cantley, L. C., et al. (2017). Phosphorylation of TXNIP by AKT Mediates Acute Influx of Glucose in Response to Insulin. Cell reports 19, 2005-2013. Wu, N., Zheng, B., Shaywitz, A., Dagon, Y., Tower, C., Bellinger, G., Shen, C. H., Wen, J., Asara, J., McGraw, T. E., et al. (2013). AMPK-dependent degradation of TXNIP upon energy stress leads to enhanced glucose uptake via GLUT1. Molecular cell 49, 1167-1175.

Alhawiti, N. M., Al Mahri, S., Aziz, M. A., Malik, S. S., and Mohammad, S. (2017). TXNIP in Metabolic Regulation: Physiological Role and Therapeutic Outlook. Current drug targets 18, 1095-1103. Anders, S., and Huber, W. (2010). Differential expression analysis for sequence count data. Genome biology 11, R106. Bell, J. A., Cao, Y., Gunn, J. R., Day, T., Gallicchio, E., Zhou, Z., Levy, R., and Farid, R. (2012). PrimeX and the Schrödinger computational chemistry suite of programs. In International Tables for Crystallography. Bhattacharya, S., Salomon-Ferrer, R., Lee, S., and Vaidehi, N. (2016). Conserved Mechanism of Conformational Stability and Dynamics in G-Protein-Coupled Receptors. J Chem Theory Comput 12, 5575-5584. Bhattacharya, S., and Vaidehi, N. (2014). Differences in Allosteric Communication Pipelines in the Inactive and Active States of a GPCR. Biophys J 107, 422-434. Bolger, A. M., Lohse, M., and Usadel, B. (2014). Trimmomatic: a flexible trimmer for Illumina sequence data. Bioinformatics 30, 2114-2120. Chen, S., Zhou, Y., Chen, Y., and Gu, J. (2018). fastp: an ultra-fast all-in-one FASTQ preprocessor. Bioinformatics 34, i884-i890. Chen, Z., Miao, F., Paterson, A. D., Lachin, J. M., Zhang, L., Schones, D. E., Wu, X., Wang, J., Tompkins, J. D., Genuth, S., et al. (2016). Epigenomic profiling reveals an association between persistence of DNA methylation and metabolic memory in the DCCT/EDIC type 1 diabetes cohort. Proceedings of the National Academy of Sciences of the United States of America 113, E3002-3011. Chong, C. R., Chan, W. P., Nguyen, T. H., Liu, S., Procter, N. E., Ngo, D. T., Sverdlov, A. L., Chirkov, Y. Y., and Horowitz, J. D. (2014). Thioredoxin-interacting protein: pathophysiology and emerging pharmacotherapeutics in cardiovascular disease and diabetes. Cardiovascular drugs and therapy 28, 347-360. Dobin, A., Davis, C. A., Schlesinger, F., Drenkow, J., Zaleski, C., Jha, S., Batut, P., Chaisson, M., and Gingeras, T. R. (2013). STAR: ultrafast universal RNA-seq aligner. Bioinformatics 29, 15-21. Friesner, R. A., Banks, J. L., Murphy, R. B., Halgren, T. A., Klicic, J. J., Mainz, D. T., Repasky, M. P., Knoll, E. H., Shelley, M., Perry, J. K., et al. (2004). Glide: A new approach for rapid, accurate docking and scoring. 1. Method and assessment of docking accuracy. J Med Chem 47, 1739-1749. Halgren, T. A., Murphy, R. B., Friesner, R. A., Beard, H. S., Frye, L. L., Pollard, W. T., and Banks, J. L. (2004). Glide: A new approach for rapid, accurate docking and scoring. 2. Enrichment factors in database screening. J Med Chem 47, 1750-1759. Hwang, J., Suh, H. W., Jeon, Y. H., Hwang, E., Nguyen, L. T., Yeom, J., Lee, S. G., Lee, C., Kim, K. J., Kang, B. S., et al. (2014). The structural basis for the negative regulation of thioredoxin by thioredoxin-interacting protein. Nat Commun 5, 10-23. Li, H., Kasam, V., Tautermann, C. S., Seeliger, D., and Vaidehi, N. (2014). Computational Method To Identify Druggable Binding Sites That Target Protein-Protein Interactions. J Chem Inf Model 54, 1391-1400. Lomenick, B., Hao, R., Jonai, N., Chin, R. M., Aghajan, M., Warburton, S., Wang, J., Wu, R. P., Gomez, F., Loo, J. A., et al. (2009). Target identification using drug affinity responsive target stability (DARTS). Proceedings of the National Academy of Sciences of the United States of America 106, 21984-21989. Nivedha, A. K., Tautermann, C. S., Bhattacharya, S., Lee, S., Casarosa, P., Kollak, I., Kiechle, T., and Vaidehi, N. (2018). Identifying Functional Hotspot Residues for Biased Ligand Design in G-Protein-Coupled Receptors. Mol Pharmacol 93, 288-296. Pai, M. Y., Lomenick, B., Hwang, H., Schiestl, R., McBride, W., Loo, J. A., and Huang, J. (2015). Drug affinity responsive target stability (DARTS) for small-molecule target identification. Methods in molecular biology 1263, 287-298. Robinson, M. D., McCarthy, D. J., and Smyth, G. K. (2010). edgeR: a Bioconductor package for differential expression analysis of digital gene expression data. Bioinformatics 26, 139-140. Shalev, A. (2014). Minireview: Thioredoxin-interacting protein: regulation and function in the pancreatic beta-cell. Molecular endocrinology 28, 1211-1220. Tautermann, C. S., Binder, F., Buttner, F. H., Eickmeier, C., Fiegen, D., Gross, U., Grundl, M. A., Heilker, R., Hobson, S., Hoerer, S., et al. (2019). Allosteric Activation of Striatal-Enriched Protein Tyrosine Phosphatase (STEP, PTPN5) by a Fragment-like Molecule. J Med Chem 62, 306-316. Vaidehi, N., and Bhattacharya, S. (2016). Allosteric communication pipelines in G-protein-coupled receptors. Curr Opin Pharmacol 30, 76-83.

What is claimed is:

1. A method of treating diabetic nephropathy, said method comprising administering to a subject in need thereof an effective amount of a compound of formula (I), or a pharmaceutically acceptable salt thereof:

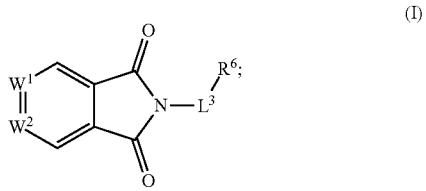

(I)

wherein
W¹ is N;
W² is CH;
L³ is substituted or unsubstituted alkylene;
R⁶ is —SOR⁶ᴰ, —C(O)R⁶ᶜ, —C(O)—OR⁶ᶜ, —C(O)NR⁶ᴬR⁶ᴮ, —NR⁶ᴬC(O)R⁶ᶜ, or —C(O)NR⁶ᶜNR⁶ᴬR⁶ᴮ; and
R⁶ᴬ, R⁶ᴮ, R⁶ᶜ, and R⁶ᴰ are each independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

2. The method of claim 1, wherein L³ is substituted or unsubstituted C₁-C₆ alkylene.

3. The method of claim 1, wherein R⁶ is -C(O)-OR⁶ᶜ; and R⁶ᶜ is hydrogen, substituted C₁-C₈ alkyl, or substituted or unsubstituted C₆-C₁₀ aryl.

4. The method of claim 1, wherein R⁶ is —C(O)NR⁶ᴬR⁶ᴮ.

5. The method of claim 4, wherein R⁶ᴬ is hydrogen.

6. The method of claim 1, wherein R⁶ is —C(O)NR⁶ᴬR⁶ᴮ, and R⁶ᴮ is substituted or unsubstituted C₁-C₆ alkyl, substituted or unsubstituted phenyl, or substituted or unsubstituted 5 to 6 membered heteroaryl.

7. The method of claim 1, wherein the compound is

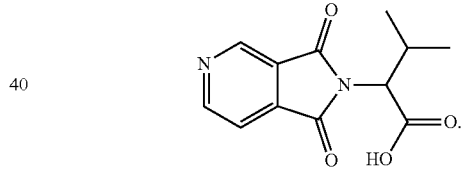

8. The method of claim 1, wherein the compound inhibits TXNIP protein activity or function.

9. The method of claim 1, wherein the compound inhibits TXNIP protein binding to TRX.

10. The method of claim 1, wherein R⁶ is —C(O)—OR⁶ᶜ.

11. The method of claim 10, wherein R⁶ᶜ is hydrogen.

12. The method of claim 1, wherein each substituted alkylene, substituted alkyl, substituted heteroalkyl, substituted cycloalkyl, substituted heterocycloalkyl, substituted aryl, and substituted heteroaryl is substituted with at least one substituent group.

13. The method of claim 1, wherein
L³ is substituted or unsubstituted C₁-C₆ alkylene;
R⁶ is —SOR⁶ᴰ, —C(O)R⁶ᶜ, —C(O)—OR⁶ᶜ, —C(O)NR⁶ᴬR⁶ᴮ, —NR⁶ᴬC(O)R⁶ᶜ, or —C(O)NR⁶ᶜNR⁶ᴬR⁶ᴮ; and
R⁶ᴬ, R⁶ᴮ, R⁶ᶜ, and R⁶ᴰ are each independently hydrogen, substituted or unsubstituted C1-C₈ alkyl, substituted or unsubstituted 2 to 8 membered heteroalkyl, substituted or unsubstituted C₃-C₈ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl.

\* \* \* \* \*

SEQUENCE LISTING

<160> NUMBER OF SEQ ID NOS: 2

<210> SEQ ID NO 1
<211> LENGTH: 105
<212> TYPE: PRT
<213> ORGANISM: Artificial Sequence

```
<220> FEATURE:
<223> OTHER INFORMATION: Synthetic polypeptide

<400> SEQUENCE: 1

Met Val Lys Gln Ile Glu Ser Lys Thr Ala Phe Gln Glu Ala Leu Asp
1               5                   10                  15

Ala Ala Gly Asp Lys Leu Val Val Asp Phe Ser Ala Thr Trp Cys
            20                  25                  30

Gly Pro Cys Lys Met Ile Lys Pro Phe Phe His Ser Leu Ser Glu Lys
            35                  40                  45

Tyr Ser Asn Val Ile Phe Leu Glu Val Asp Val Asp Asp Cys Gln Asp
            50                  55                  60

Val Ala Ser Glu Cys Glu Val Lys Cys Met Pro Thr Phe Gln Phe Phe
65                  70                  75                  80

Lys Lys Gly Gln Lys Val Gly Glu Phe Ser Gly Ala Asn Lys Glu Lys
                85                  90                  95

Leu Glu Ala Thr Ile Asn Glu Leu Val
                100                 105

<210> SEQ ID NO 2
<211> LENGTH: 391
<212> TYPE: PRT
<213> ORGANISM: Artificial Sequence
<220> FEATURE:
<223> OTHER INFORMATION: Synthetic polypeptide

<400> SEQUENCE: 2

Met Val Met Phe Lys Lys Ile Lys Ser Phe Glu Val Val Phe Asn Asp
1               5                   10                  15

Pro Glu Lys Val Tyr Gly Ser Gly Glu Lys Val Ala Gly Arg Val Ile
            20                  25                  30

Val Glu Val Cys Glu Val Thr Arg Val Lys Ala Val Arg Ile Leu Ala
            35                  40                  45

Cys Gly Val Ala Lys Val Leu Trp Met Gln Gly Ser Gln Gln Cys Lys
    50                  55                  60

Gln Thr Ser Glu Tyr Leu Arg Tyr Glu Asp Thr Leu Leu Glu Asp
65                  70                  75                  80

Gln Pro Thr Gly Glu Asn Glu Met Val Ile Met Arg Pro Gly Asn Lys
                85                  90                  95

Tyr Glu Tyr Lys Phe Gly Phe Glu Leu Pro Gln Gly Pro Leu Gly Thr
            100                 105                 110

Ser Phe Lys Gly Lys Tyr Gly Cys Val Asp Tyr Trp Val Lys Ala Phe
            115                 120                 125

Leu Asp Arg Pro Ser Gln Pro Thr Gln Glu Thr Lys Lys Asn Phe Glu
            130                 135                 140

Val Val Asp Leu Val Asp Val Asn Thr Pro Asp Leu Met Ala Pro Val
145                 150                 155                 160

Ser Ala Lys Lys Glu Lys Lys Val Ser Cys Met Phe Ile Pro Asp Gly
                165                 170                 175

Arg Val Ser Val Ser Ala Arg Ile Asp Arg Lys Gly Phe Cys Glu Gly
            180                 185                 190

Asp Glu Ile Ser Ile His Ala Asp Phe Glu Asn Thr Cys Ser Arg Ile
            195                 200                 205

Val Val Pro Lys Ala Ala Ile Val Ala Arg His Thr Tyr Leu Ala Asn
            210                 215                 220

Gly Gln Thr Lys Val Leu Thr Gln Lys Leu Ser Ser Val Arg Gly Asn
```

|     |     |     |     | 225 |     |     |     |     | 230 |     |     |     |     | 235 |     |     |     |     | 240 |
| --- | --- | --- | --- | --- | --- | --- | --- | --- | --- | --- | --- | --- | --- | --- | --- | --- | --- | --- | --- |
| His | Ile | Ile | Ser | Gly | Thr | Cys | Ala | Ser | Trp | Arg | Gly | Lys | Ser | Leu | Arg |
|     |     |     |     |     | 245 |     |     |     |     | 250 |     |     |     |     | 255 |
| Val | Gln | Lys | Ile | Arg | Pro | Ser | Ile | Leu | Gly | Cys | Asn | Ile | Leu | Arg | Val |
|     |     |     |     | 260 |     |     |     |     | 265 |     |     |     |     | 270 |     |
| Glu | Tyr | Ser | Leu | Leu | Ile | Tyr | Val | Ser | Val | Pro | Gly | Ser | Lys | Lys | Val |
|     |     |     | 275 |     |     |     |     | 280 |     |     |     |     | 285 |     |     |
| Ile | Leu | Asp | Leu | Pro | Leu | Val | Ile | Gly | Ser | Arg | Ser | Gly | Leu | Ser | Ser |
|     |     | 290 |     |     |     |     | 295 |     |     |     |     | 300 |     |     |     |
| Arg | Thr | Ser | Ser | Met | Ala | Ser | Arg | Thr | Ser | Ser | Glu | Met | Ser | Trp | Val |
| 305 |     |     |     |     | 310 |     |     |     |     | 315 |     |     |     |     | 320 |
| Asp | Leu | Asn | Ile | Pro | Asp | Thr | Pro | Glu | Ala | Pro | Pro | Cys | Tyr | Met | Asp |
|     |     |     |     | 325 |     |     |     |     | 330 |     |     |     |     | 335 |     |
| Val | Ile | Pro | Glu | Asp | His | Arg | Leu | Glu | Ser | Pro | Thr | Thr | Pro | Leu | Leu |
|     |     |     |     | 340 |     |     |     |     | 345 |     |     |     |     | 350 |     |
| Asp | Asp | Met | Asp | Gly | Ser | Gln | Asp | Ser | Pro | Ile | Phe | Met | Tyr | Ala | Pro |
|     |     |     | 355 |     |     |     |     | 360 |     |     |     |     | 365 |     |     |
| Glu | Phe | Lys | Phe | Met | Pro | Pro | Pro | Thr | Tyr | Thr | Glu | Val | Asp | Pro | Cys |
|     |     | 370 |     |     |     |     | 375 |     |     |     |     | 380 |     |     |     |
| Ile | Leu | Asn | Asn | Asn | Val | Gln |
| 385 |     |     |     |     | 390 |     |